United States Patent [19]

Freskos et al.

[11] Patent Number: 6,013,649
[45] Date of Patent: Jan. 11, 2000

[54] THIOL SULFONE METALLOPROTEASE INHIBITORS

[75] Inventors: John N. Freskos, Clayton; S. Zaheer Abbas, Chesterfield; Gary A. DeCrescenzo, St. Charles; Daniel P. Getman, Chesterfield; Robert M. Heintz, Ballwin; Brent V. Mischke, Defiance; Joseph J. McDonald, Ballwin, all of Mo.

[73] Assignee: Monsanto Company, St. Louis, Mo.

[21] Appl. No.: 08/900,028

[22] Filed: Jul. 22, 1997

Related U.S. Application Data

[60] Provisional application No. 60/022,043, Jul. 22, 1996.

[51] Int. Cl.[7] .................. A61K 31/535; A01N 43/40; A01N 43/78; A01N 43/50; A01N 37/10; A01N 37/02; A01N 37/18; A01N 41/12

[52] U.S. Cl. ...................... 514/237.8; 514/239.2; 514/345; 514/369; 514/386; 514/486; 514/543; 514/546; 514/568; 514/570; 514/571; 514/618; 514/630; 514/707; 514/709; 544/158; 544/159; 544/160; 546/290; 546/339; 548/186; 548/316.4; 560/11; 560/12; 560/254; 562/429; 568/23; 568/29; 568/31; 568/32

[58] Field of Search ...................... 544/158, 159, 544/160; 546/290, 339; 548/186, 316.4; 560/11, 12, 254; 562/429; 568/23, 29, 31, 32; 514/237.8, 239.2, 345, 369, 386, 486, 543, 546, 568, 570, 571, 618, 630, 707, 709

[56] References Cited

U.S. PATENT DOCUMENTS

| | | | |
|---|---|---|---|
| 4,595,700 | 6/1986 | Donald et al. | 514/616 |
| 5,451,676 | 9/1995 | Whittaker et al. | 546/118 |
| 5,472,978 | 12/1995 | Baker et al. | 514/443 |
| 5,475,138 | 12/1995 | Pal et al. | 564/342 |
| 5,599,994 | 2/1997 | Pal et al. | 564/355 |

FOREIGN PATENT DOCUMENTS

| | | |
|---|---|---|
| 2 263 109 | 7/1993 | United Kingdom . |
| WO 94/02466 | 2/1994 | WIPO . |
| WO 94/24140 | 10/1994 | WIPO . |
| WO 95/04720 | 2/1995 | WIPO . |
| WO 95/12389 | 5/1995 | WIPO . |
| WO 95/13064 | 5/1995 | WIPO . |
| WO 96/11209 | 4/1996 | WIPO . |
| WO 97/05865 | 2/1997 | WIPO . |
| WO 97/20824 | 6/1997 | WIPO . |

OTHER PUBLICATIONS

Database CAPLUS on STN, Acc. No. 1992:545973, Spatola et al., 'Peptide Inhibitors of Matrix Metalloproteases.' Pept.: Chem. Biol., Proc. Am. Pept. Symp., 12th (1992), Meeting Date 1991, 820–1, Ed. Smith, and Rivier, ESCOM: Leiden, Neth. abstract.
Gearing et al., *Nature*, 370:555–557 (1994).
McGeehan et al., *Nature*, 370:558–561 (1994).
Mitchell et al., *J. Clin. Invest.*, 97:761–768 (1996).
Reboul et al., *J. Clin. Invest.*, 97:2011–2019 (1996).
Knight et al., *FEBS Lett.*, 296:263–266 (1992).
Kenyon et al., *Investigative Ophtalmology & Visual Science*, 37:1625–1632 (Jul. 1996).
Fong et al., *Canada J. Chem.*, 57:1206–1213 (1979).
Field et al., *J. Org. Chem.*, 46:2771–2775 (1981).

*Primary Examiner*—Gary Geist
*Assistant Examiner*—Brian J. Davis
*Attorney, Agent, or Firm*—Welsh & Katz, Ltd.

[57] ABSTRACT

This invention is directed to proteinase (protease) inhibitors, and more particularly to thiol sulfone inhibitors for matrix metalloproteinase 13(MMP-13), compositions of proteinase inhibitors, intermediates for the syntheses of proteinase inhibitors, processes for the preparation of proteinase inhibitors and processes for treating pathological conditions associated with pathological matrix metalloproteinase activity related to MMP-13.

26 Claims, No Drawings

THIOL SULFONE METALLOPROTEASE INHIBITORS

CROSS-REFERENCE TO RELATED APPLICATION

This is a continuation of provisional application 60/022,043 filed Jul. 22, 1996.

TECHNICAL FIELD

This invention is directed to proteinase (protease) inhibitors, and more particularly to thiol sulfone inhibitors for matrix metalloproteinases, compositions of proteinase inhibitors, intermediates for the syntheses of proteinase inhibitors, processes for the preparation of proteinase inhibitors and processes for treating pathological conditions associated with pathological matrix metalloproteinase activity.

BACKGROUND OF THE INVENTION

Connective tissue, extracellular matrix constituents and basement membranes are required components of all mammals. These components are the biological materials that provide rigidity, differentiation, attachments and, in some cases, elasticity to biological systems including human beings and other mammals. Connective tissues components include, for example, collagen, elastin, proteoglycans, fibronectin and laminin. These biochemicals makeup, or are components of structures, such as skin, bone, teeth, tendon, cartilage, basement membrane, blood vessels, cornea and vitreous humor.

Under normal conditions, connective tissue turnover and/or repair processes are controlled and in equilibrium. The loss of this balance for whatever reason leads to a number of disease states. Inhibition of the enzymes responsible loss of equilibrium provides a control mechanism for this tissue decomposition and, therefore, a treatment for these diseases.

Degradation of connective tissue or connective tissue components is carried out by the action of proteinase enzymes released from resident tissue cells and/or invading inflammatory or tumor cells. A major class of enzymes involved in this function are the zinc metalloproteinases (metalloproteases).

The metalloprotease enzymes are divided into classes with some members having several different names in common use. Examples are: collagenase I (MMP-1, fibroblast collagenase; EC 3.4.24.3); collagenase II (MMP-8, neutrophil collagenase; EC 3.4.24.34), collagenase III (MMP-13), stromelysin 1 (MMP-3; EC 3.4.24.17), stromelysin 2 (MMP-10; EC 3.4.24.22), proteoglycanase, matrilysin (MMP-7), gelatinase A (MMP-2, 72 kDa gelatinase, basement membrane collagenase; EC 3.4.24.24), gelatinase B (MMP-9, 92 kDa gelatinase; EC 3.4.24.35), stromelysin 3 (MMP-11), metalloelastase (MMP-12, HME, human macrophage elastase) and membrane MMP (MMP-14) MMP is an abbreviation or acronym representing the term Matrix Metalloprotease with the attached numerals providing differentiation between specific members of the MMP group.

The uncontrolled breakdown of connective tissue by metalloproteases is a feature of many pathological conditions. Examples include rheumatoid arthritis, osteoarthritis, septic arthritis; corneal, epidermal or gastric ulceration; tumor metastasis, invasion or angiogenesis; periodontal disease; proteinuria; Alzheimers Disease; coronary thrombosis and bone disease. Defective injury repair processes also occur. This can produce improper wound healing leading to weak repairs, adhesions and scarring. These latter defects can lead to disfigurement and/or permanent disabilities as with post-surgical adhesions.

Matrix metalloproteases are also involved in the biosynthesis of tumor necrosis factor (TNF), and inhibition of the production or action of TNF and related compounds is an important clinical disease treatment mechanism. TNF-α, for example, is a cytokine that at present is thought to be produced initially as a 28 kD cell-associated molecule. It is released as an active, 17 kD form that can mediate a large number of deleterious effects in vitro and in vivo. For example, TNF can cause and/or contribute to the effects of inflammation, rheumatoid arthritis, autoimmune disease, multiple sclerosis, graft rejection, fibrotic disease, cancer, infectious diseases, malaria, mycobacterial infection, meningitis, fever, psoriasis, cardiovascular/pulmonary effects such as post-ischemic reperfusion injury, congestive heart failure, hemorrhage, coagulation, hyperoxic alveolar injury, radiation damage and acute phase responses like those seen with infections and sepsis and during shock such as septic shock and hemodynamic shock. Chronic release of active TNF can cause cachexia and anorexia. TNF can be lethal.

TNF-α convertase is a metalloprotease involved in the formation of active TNF-α. Inhibition of TNF-α convertase inhibits production of active TNF-α. Compounds that inhibit both MMPs activity and TNF-α production have been disclosed in WIPO International Publication Nos. WO 94/24140, WO 94/02466 and WO 97/20824. Compounds that inhibit MMPs such as collagenase, stromelysin and gelatinase have been shown to inhibit the release of TNF (Gearing et al. Nature 376, 555–557 (1994), McGeehan et al., Nature 376, 558–561 (1994)). There remains a need for effective MMP and TNF-α convertase inhibiting agents.

MMPs are involved in other biochemical processes in mammals as well. Included is the control of ovulation, post-partum uterine involution, possibly implantation, cleavage of APP (β-Amyloid Precursor Protein) to the amyloid plaque and inactivation of $\alpha_1$-protease inhibitor ($\alpha_1$-PI). Inhibition of these metalloproteases permits the control of fertility and the treatment or prevention of Alzheimers Disease. In addition, increasing and maintaining the levels of an endogenous or administered serine protease inhibitor drug or biochemical such as $\alpha_1$-PI supports the treatment and prevention of diseases such as emphysema, pulmonary diseases, inflammatory diseases and diseases of aging such as loss of skin or organ stretch and resiliency.

Inhibition of selected MMPs can also be desirable in other instances. Treatment of cancer and/or inhibition of metastasis and/or inhibition of angiogenesis are examples of approaches to the treatment of diseases wherein the selective inhibition of stromelysin, gelatinase, or collagenase III are the relatively most important enzyme or enzymes to inhibit especially when compared with collagenase I (MMP-1). A drug that does not inhibit collagenase I can have a superior therapeutic profile. Osteoarthritis, another prevalent disease wherein it is believed that cartilage degradation in inflamed joints is at least partially caused by MMP-13 released from cells such as stimulated chondrocytes, may be best treated by administration of drugs one of whose modes of action is inhibition of MMP-13. See, for example, Mitchell et al., J. Clin. Invest., 97:761–768 (1996) and Reboul et al., J. Clin. Invest., 97:2011–2019 (1996).

Inhibitors of metalloproteases are known. Examples include natural biochemicals such as tissue inhibitor of metalloproteinase (TIMP), $\alpha_2$-macroglobulin and their analogs or derivatives. These are high molecular weight protein molecules that form inactive complexes with metalloproteases. A number of smaller peptide-like compounds that inhibit metalloproteases have been described. Mercaptoamide peptidyl derivatives have shown ACE inhibition in vitro and in vivo. Angiotensin converting enzyme (ACE) aids in the production of angiotensin II, a potent pressor substance in mammals and inhibition of this enzyme leads to the lowering of blood pressure. Thiol group-containing amide or peptidyl amide-based metalloprotease (MMP) inhibitors are known as is shown in, for example, WO95/12389, WO96/11209 and U.S. Pat. No. 4,595,700.

It is recognized that a compound that inhibits a known member of the MMP group of enzymes can inhibit members in that group and also new, yet to be discovered, enzymes. Therefore, the skilled person will presume that the novel inhibitors of this invention can be useful in the treatment of the diseases in which known and new MMP enzymes are implicated.

SUMMARY OF THE INVENTION

The present invention is directed to a process for treating a mammal having a condition associated with pathological matrix metalloprotease (MMP) activity, as well as to molecules that particularly inhibit the activity of MMP-13.

Briefly, therefore, one embodiment of the present invention is directed to a process for treating a mammal having a condition associated with pathological matrix metalloprotease activity that comprises administering a metalloprotease inhibitor in an effective amount to a host having such a condition. The administered enzyme inhibitor corresponds in structure to one of formulas (I), (II) or (III), below

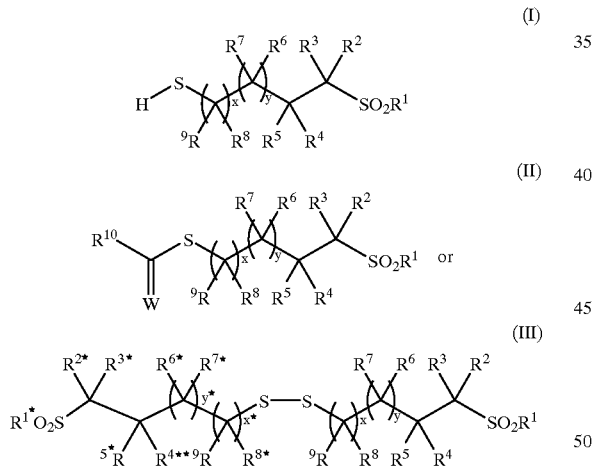

wherein
each of x and y independently is zero, 1 or 2;
W is oxygen or sulfur;
A contemplated $R^{10}$ group is an alkyl, aryl, alkoxy, cycloalkyl, aryloxy, aralkoxy, aralkyl, aminoalkyl, heteroaryl and N-monosubstituted or N,N-disubstituted aminoalkyl group wherein the substituent(s) on the nitrogen are selected from the group consisting of alkyl, aryl, aralkyl, cycloalkyl, aralkoxycarbonyl, alkoxycarbonyl, and alkanoyl, or wherein the nitrogen and two substituents attached thereto form a 5- to 8-membered heterocyclic or heteroaryl ring;
A contemplated $R^1$ group is linked to the $SO_2$ portion of an inhibitor is an aryl (carbocyclic) or heteroaryl group.

That $SO_2$-linked substituent can be an aralkanoylalkyl, arylcarbonylalkyl, aralkylaryl, aryloxyalkylaryl, aralkoxyaryl, arylazoaryl, arylhydrazinoaryl, alkylthioaryl, arylthioalkyl, alkylthioaralkyl, aralkylthioalkyl, or aralkylthioaryl group, the sulfoxide or sulfone of any of those thio substituents, alkylthioalkyl, and can have a fused ring structure comprising two or three 5- or 6-membered aryl rings that can be carbocyclic or heterocyclic rings. The $SO_2$-linked substituent is preferably aryl or heterocyclic (heteroaryl) ring having a single aromatic ring such as a single-ringed aralkyl, heteroaralkyl, aralkoxyalkyl, or aryloxyalkyl group. The aryl (carbocyclic) and heteroaryl substituents of which $R^1$ can be comprised are unsubstituted or substituted with one or two substituents independently selected from among halo, $C_1$–$C_{10}$ alkyl, $C_1$–$C_{10}$ alkoxy, nitro, cyano, perfluoroalkyl, trifluoromethylalkyl, hydroxy, thiol, hydroxycarbonyl, aryloxy, arylthio, arylamino, aralkyl, arylcarboxamido, heteroarylcarboxamido, azoaryl, azoheteroaryl, aryl, heteroaryloxy, heteroarylthio, heteroarylamino, heteroaralkyl, cycloalkyl, heterocyclooxy, heterocyclothio, heterocycloamino, cycloalkyloxy, cycloalkylthio, cycloalkylamino, heteroaralkoxy, heteroaralkylthio, heteroaralkylamino, aralkoxy, aralkylthio, aralkylamino, heterocyclic, heteroaryl, arylazo, hydroxycarbonylalkoxy, alkoxycarbonylalkoxy, alkanoyl, arylcarbonyl, aralkanoyl, alkanoyloxy, aralkanoyloxy, hydroxyalkyl, hydroxyalkoxy, alkylthio, alkoxyalkylthio, alkoxycarbonyl, aryloxyalkoxyaryl, arylthioalkylthioaryl, aryloxyalkylthioaryl, arylthioalkcxyaryl, hydroxycarbonylalkoxy, hydroxycarbonylalkylthio, alkoxycarbonylalkoxy, alkoxycarbonylalkylthio, amino, alkanoylamino, arylcarbonylamino, aralkanoylamino, heteroarylcarbonylamino, heteroaralkanoylamino, and N-monosubstituted or N,N-disubstituted aminoalkyl wherein the substituent(s) on the nitrogen are selected from the group consisting of alkyl, aryl, aralkyl, cycloalkyl, aralkoxycarbonyl, alkoxycarbonyl, and alkanoyl, or wherein the nitrogen and two substituents attached thereto together form a 5- to 8-membered heterocyclo or heteroaryl ring.

Contemplated $R^2$ and $R^3$ substituents can independently be hydrogen (hydrido), an alkyl, aryl, aralkyl, heteroaryl, heteroaralkyl, alkynylalkyl, alkenylalkyl, thioalkyl, cycloalkyl, cycloalkylalkyl, heterocycloalkylalkyl, alkoxyalkyl, aralkoxyalkyl, aminoalkyl, alkoxyalkoxyalkyl, aryloxyalkyl, hydroxyalkyl, hydroxycarbonylalkyl, hydroxycarbonylaralkyl, or N-monosubstituted or N,N-disubstituted aminoalkyl group wherein the substituent(s) on the nitrogen are selected from the group consisting of alkyl, aralkyl, cycloalkyl and alkanoyl, or wherein $R^2$ and another substituent ($R^2$ and $R^4$, or $R^2$ and $R^6$, or $R^2$ and $R^8$) together with the atoms to which they are attached form a 4- to 8-membered ring.

Contemplated $R^4$ and $R^5$ groups are independently selected. Those substituents can be hydrogen (hydrido), an alkyl, cycloalkyl, cycloalkylalkyl, alkoxyalkyl, hydroxyalkyl, aryloxyalkyl, aralkoxyalkyl, aralkyl, aryl, heteroaryl, heteroaralkyl, hydroxycarbonylalkyl, alkoxycarbonylalkyl, aralkoxycarbonylalkyl, hydroxycarbonyl, alkoxycarbonyl, perfluoroalkyl, trifluoromethylalkyl, thioalkyl, alkylthioalkyl, arylthioalkyl, aralkylthioalkyl, heteroaralkylthioalkyl, or a sulfoxide or sulfone of any of the thio substituents, aminocarbonyl, aminocarbonylalkyl, N-monosubstituted or N,N-disubstituted aminocarbonyl or aminocarbonylalkyl group wherein the substituent(s) on the nitrogen are independently selected from among alkyl, aralkyl, cycloalkyl and alkanoyl, or wherein the nitrogen and two substituents attached thereto together form a 5- to 8-membered heterocyclo or heteroaryl ring that can contain one additional heteroatom, or $R^2$ and $R^4$ together with the atoms to which they are attached form a 4- to 8-membered ring (as above), or $R^4$ and $R^5$ together with the atom to which they are attached form a 3- to 8-membered ring, or $R^4$ and $R^8$ together with the atoms to which they are attached form a 5- to 8-membered ring.

$R^6$ and $R^7$ substituents are also independently selected. $R^6$ and $R^7$ substituents can be a substitutent that constitutes $R^4$ and $R^5$, or $R^6$ and $R^4$ together with atoms to which they are attached form a 4- to 8-membered ring, or $R^6$ and $R^2$ together with the atoms to which they are attached form a 5- to 8-membered ring (as above), or $R^6$ and $R^8$ together with the atoms to which they are attached form a 4- to 8-membered ring, or $R^6$ and $R^7$ together with atom to which they are attached form a 3- to 8-membered ring.

Contemplated $R^8$ and $R^9$ substituents are also independently selected. $R^8$ and $R^9$ substituents can also be a substituent that constitutes $R^3$ and $R^4$, or $R^8$ and $R^2$ together with the atoms to which they are attached form a 6- to 8-membered ring (as above), or $R^8$ and $R^9$ together with the atom to which they are attached form a 3- to 8-membered ring, or $R^8$ and $R^4$ together with the atom to which they are attached form a 5- to 8-membered ring (as above), or $R^8$ and $R^6$ together with the atoms to which they are attached form a 4- to 8-membered ring (as above).

A provision to the above definitions is that no carbon atom is geminally substituted with more than one sulfhydryl group. Additionally, a starred substituent "R*" groups, "y*" and "x*" of formula III are the same as or different from the unstarred "R" groups, "y" and "x".

The present invention is also directed to a more preferred sub-set of molecules of formulas I, II, and III, above. Here, x is zero so that $R^8$ and $R^9$ and their bonded carbon atom are absent, y is one, the mercapto group is bonded directly to the carbon atom that bears the $R^6$ substituent radical, when present, with the $R^7$ radical of formulas I–III being hydrido, as are $R^3, R^4$ and $R^5$. Here, also, $R^1$ is a substituted aryl (carbocyclic aryl), or substituted heteroaryl group containing one 5- or 6-membered ring; i.e., $R^1$ is other than a fused ring substituted aryl or heteroaryl group, and a compound of formula III is a homodimer. These preferred compounds are depicted by formulas Ia, IIa, and IIIa, below, and the substituent "R" groups and W are discussed hereinafter.

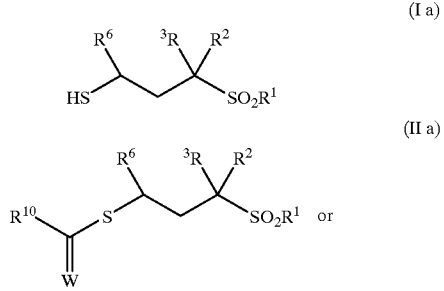

(Ia)

(IIa)

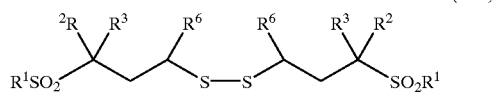

(IIIa)

In most preferred practice, a contemplated inhibitor compound constitutes another sub-set of the compounds of formulas I, II and III. Here, $R^3$, $R^4$ and $R^5$ of formulas I–III are hydrido, only one of $R^2$ and $R^6$ is present unless bonded together in a ring, the $SO_2$-linked $R^1$ subsituent is a 4-substituted phenyl group ($PhR^{11}$), and W is O. These most preferred compounds are depicted by formulas Ib, IIb and IIIb, below. Specifics of the depicted "R" groups are discussed hereinafter.

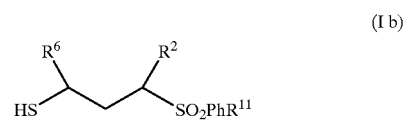

(Ib)

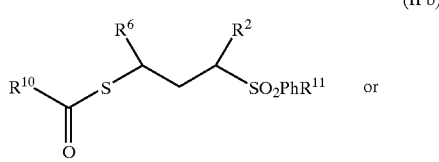

(IIb)

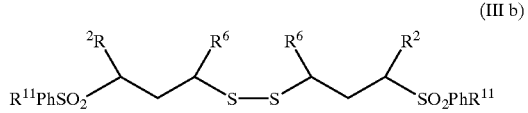

(IIIb)

Among the several benefits and advantages of the present invention are the provision of compounds and compositions effective as inhibitors of matrix metalloproteinase activity, the provision of such compounds and compositions that are effective for the inhibition of metalloproteinases implicated in diseases and disorders involving uncontrolled breakdown of connective tissue.

More particularly, a benefit of this invention is the provision of a compound and composition effective for inhibiting metalloproteinases, particularly MMP-13, associated with pathological conditions such as, for example, rheumatoid arthritis, osteoarthritis, septic arthritis, corneal, epidermal or gastric ulceration, tumor metastasis, invasion or angiogenesis, periodontal disease, proteinuria, Alzheimer's Disease, coronary thrombosis and bone disease.

An advantage of the invention is the provision of a method for preparing such compositions. Another benefit is the provision of a method for treating a pathological condition associated with abnormal matrix metalloproteinase activity.

Another advantage is the provision of compounds, compositions and methods effective for treating such pathological conditions by selective inhibition of a metalloproteinase, MMP-13, associated with such conditions with minimal side effects resulting from inhibition of other proteinases whose activity is necessary or desirable for normal body function.

Still further benefits and advantages of the invention will be apparent to the skilled worker from the disclosure that follows.

DESCRIPTION OF THE PREFERRED EMBODIMENTS

In accordance with the present invention, it has been discovered that certain thiol sulfones are effective for inhibition of matrix metalloproteinases ("MMPs") believed to be associated with uncontrolled or otherwise pathological breakdown of connective tissue. In particular, it has been found that these certain thiolsulfonamides are effective for inhibition of collagenase III (MMP-13), which can be particularly destructive to tissue if present or generated in abnormal quantities or concentrations, and thus exhibit a pathological activity.

Moreover, it has been discovered that many of these thiol sulfones are selective in the inhibition of MMP-13, as well as other MMPs associated with diseased conditions without excessive inhibition of those collagenases essential to normal bodily function such as tissue turnover and repair. More particularly, it has been found that particularly preferred the thiol sulfones useful in the invention are particularly active in inhibiting of MMP-13, while being selective for MMP-13, in having a limited or minimal effect on MMP-1. This point is discussed in detail hereinafter and is illustrated in several examples.

One embodiment of the present invention is directed to a process for treating a mammal having a condition associated with pathological matrix metalloprotease activity. That process comprises administering a metalloprotease inhibitor in an effective amount to a host having such a condition. The administered enzyme inhibitor corresponds in structure to one of formulas (I), (II) or (III), below

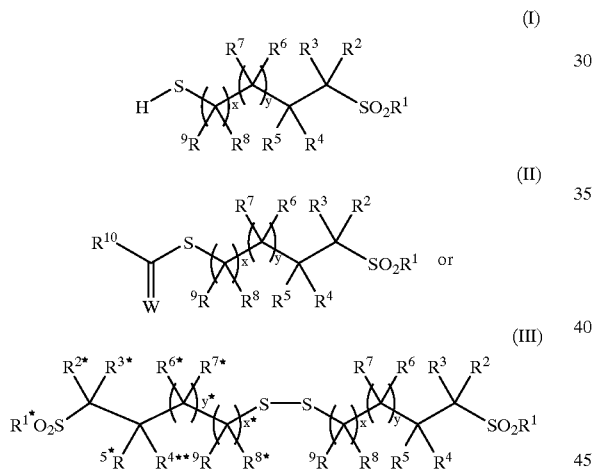

wherein
each of x and y independently is zero, 1 or 2;
W is oxygen or sulfur;
A contemplated $R^{10}$ group is an alkyl, aryl, alkoxy, cycloalkyl, aryloxy, aralkoxy, aralkyl, aminoalkyl, heteroaryl and N-monosubstituted or N,N-disubstituted aminoalkyl group wherein the substituent(s) on the nitrogen are selected from the group consisting of alkyl, aryl, aralkyl, cycloalkyl, aralkoxycarbonyl, alkoxycarbonyl, and alkanoyl, or wherein the nitrogen and two substituents attached thereto form a 5- to 8-membered heterocyclic or heteroaryl ring;
A contemplated $R^1$ group is linked to the $SO_2$ portion of an inhibitor is an aryl (carbocyclic) or heteroaryl group. That $SO_2$-linked substituent can be an aralkanoylalkyl, arylcarbonylalkyl, aralkylaryl, aryloxyalkylaryl, aralkoxyaryl, arylazoaryl, arylhydrazinoaryl, alkylthioaryl, arylthioalkyl, alkylthioaralkyl, aralkylthioalkyl, or aralkylthioaryl group, the sulfoxide or sulfone of any of those thio substituents, alkylthioalkyl, and can have a fused ring structure comprising two or three 5- or 6-membered aryl rings that can be carbocyclic or heterocyclic rings. The $SO_2$-linked substituent is preferably aryl or heterocyclic (heteroaryl) ring having a single aromatic ring such as a single-ringed aralkyl, heteroaralkyl, aralkoxyalkyl, or heteroaryloxyalkyl group. The aryl (carbocyclic) and heteroaryl substituents of which $R^1$ can be comprised are unsubstituted or substituted with one or two substituents independently selected from among halo, $C_1$–$C_{10}$ alkyl, $C_1$–$C_{10}$ alkoxy, nitro, cyano, perfluoroalkyl, trifluoromethylalkyl, hydroxy, thiol, hydroxycarbonyl, aryloxy, arylthio, arylamino, aralkyl, arylcarboxamido, heteroarylcarboxamido, azoaryl, azoheteroaryl, aryl, heteroaryloxy, heteroarylthio, heteroarylamino, heteroaralkyl, cycloalkyl, heterocyclooxy, heterocyclothio, heterocycloamino, cycloalkyloxy, cycloalkylthio, cycloalkylamino, heteroaralkoxy, heteroaralkylthio, heteroaralkylamino, aralkoxy, aralkylthio, aralkylamino, heterocyclic, heteroaryl, arylazo, hydroxycarbonylalkoxy, alkoxycarbonylalkoxy, alkanoyl, arylcarbonyl, aralkanoyl, alkanoyloxy, aralkanoyloxy, hydroxyalkyl, hydroxyalkoxy, alkylthio, alkoxyalkylthio, alkoxycarbonyl, aryloxyalkoxyaryl, arylthioalkylthioaryl, aryloxyalkylthioaryl, arylthioalkoxyaryl, hydroxycarbonylalkoxy, hydroxycarbonylalkylthio, alkoxycarbonylalkoxy, alkoxycarbonylalkylthio, amino, alkanoylamino, arylcarbonylamino, aralkanoylamino, heteroarylcarbonylamino, heteroaralkanoylamino, and N-monosubstituted or N,N-disubstituted aminoalkyl wherein the substituent(s) on the nitrogen are selected from the group consisting of alkyl, aryl, aralkyl, cycloalkyl, aralkoxycarbonyl, alkoxycarbonyl, and alkanoyl, or wherein the nitrogen and two substituents attached thereto together form a 5- to 8-membered heterocyclo or heteroaryl ring.

Contemplated $R^2$ and $R^3$ substituents can independently be hydrogen (hydrido), an alkyl, aryl, aralkyl, heteroaryl, heteroaralkyl, alkynylalkyl, alkenylalkyl, thioalkyl, cycloalkyl, cycloalkylalkyl, heterocycloalkylalkyl, alkoxyalkyl, aralkoxyalkyl, aminoalkyl, alkoxyalkoxyalkyl, aryloxyalkyl, hydroxyalkyl, hydroxycarbonylalkyl, hydroxycarbonylaralkyl, or N-monosubstituted or N,N-disubstituted aminoalkyl group wherein the substituent(s) on the nitrogen are selected from the group consisting of alkyl, aralkyl, cycloalkyl and alkanoyl, or wherein $R^2$ and another substituent ($R^2$ and $R^4$, or $R^2$ and $R^6$, or $R^2$ and $R^8$) together with the atoms to which they are attached form a 4- to 8-membered ring.

Contemplated $R^4$ and $R^5$ groups are independently selected. Those substituents can be hydrogen (hydrido), an alkyl, cycloalkyl, cycloalkylalkyl, alkoxyalkyl, hydroxyalkyl, aryloxyalkyl, aralkoxyalkyl, aralkyl, aryl, heteroaryl, heteroaralkyl, hydroxycarbonylalkyl, alkoxycarbonylalkyl, aralkoxycarbonylalkyl, hydroxycarbonyl, alkoxycarbonyl, perfluoroalkyl, trifluoromethylalkyl, thioalkyl, alkylthioalkyl, arylthioalkyl, aralkylthioalkyl, heteroaralkylthioalkyl, or a sulfoxide or sulfone of any of the thio substituents, aminocarbonyl, aminocarbonylalkyl, N-monosubstituted or N,N-disubstituted aminocarbonyl or aminocarbonylalkyl group wherein the substituent(s) on the nitrogen are independently selected from among alkyl, aralkyl, cycloalkyl and alkanoyl, or wherein the nitrogen and two substituents attached thereto together form a 5- to 8-membered heterocyclo or heteroaryl ring that can contain one additional heteroatom, or $R^2$ and $R^4$ together with the atoms to which they are attached form a 4- to 8-membered ring (as above), or $R^4$ and $R^5$ together with the atom to which they are attached form a 3- to 8-membered ring, or $R^4$ and $R^8$ together with the atoms to which they are attached form a 5- to 8-membered ring.

$R^6$ and $R^7$ substituents are also independently selected. $R^6$ and $R^7$ substituents can be a substituent that constitutes $R^4$ and $R^5$, or $R^6$ and $R^4$ together with atoms to which they are attached form a 4- to 8-membered ring, or $R^6$ and $R^2$ together with the atoms to which they are attached form a 5- to 8-membered ring (as above), or $R^6$ and $R^8$ together with the atoms to which they are attached form a 4- to 8-membered ring, or $R^6$ and $R^7$ together with atom to which they are attached form a 3- to 8-membered ring.

Contemplated $R^8$ and $R^9$ substituents are also independently selected. $R^8$ and $R^9$ substituents can also be a substituent that constitutes $R^3$ and $R^4$, or $R^8$ and $R^2$ together with the atoms to which they are attached form a 6- to 8-membered ring (as above), or $R^8$ and $R^9$ together with the atom to which they are attached form a 3- to 8-membered ring, or $R^8$ and $R^4$ together with the atom to which they are attached form a 5- to 8-membered ring (as above), or $R^8$ and $R^6$ together with the atoms to which they are attached form a 4- to 8-membered ring (as above).

A provision to the above definitions is that no carbon atom is geminally substituted with more than one sulfhydryl group. Additionally, a starred substituent groups (R*), as well as "y*" and "x*" of formula III are the same as or different from the unstarred "R" groups, "y" and "x".

In generally increasing order of preference, the following paragraphs summarize the substituents that can most $R^{10}$ advantageously constitute each of $R^1$ through $R^1$, as well as W, x and y.

$R^1$ represents a substituted aryl or heteroaryl ring that is substituted by one or more of the following substituents: $C_1$–$C_{10}$ alkyl, $C_1$–$C_{10}$ alkoxy, aryloxy, heteroaryloxy, aryl, heteroaryl, aralkoxy, heteroaralkoxy, $C_1$–$C_{10}$ alkylthio, arylthio, heteroarylthio.

$R^1$ represents a substituted aryl or heteroaryl ring that is substituted by one or more of the following substituents: $C_1$–$C_6$ alkyl, $C_1$–$C_6$ alkoxy, arylcarboxamido, heteroarylcarboxamido, arylazo, heteroarylazo, aryloxy, heteroaryloxy, aryl, heteroaryl, aralkoxy, heteroaralkoxy, $C_1$–$C_6$ alkylthio, arylthio, heteroarylthio in which each ring-containing substituent itself contains a single ring.

$R^1$ represents a 6-membered substituted aryl ring that is substituted in the para-position (4-position) by one of the following substituents: $C_1$–$C_6$ alkyl, $C_1$–$C_6$ alkoxy, arylcarboxamido, heteroarylcarbox-amido, arylazo, heteroarylazo, aryloxy, heteroaryloxy, aryloxy, heteroaryloxy, aryl, heteroaryl, aralkoxy, heteroaralkoxy, $C_1$–$C_6$ alkylthio, arylthio, heteroarylthio in which each ring-containing substituent itself contains a single ring.

$R^1$ represents a 6-membered substituted aryl ring that is substituted in the 4- or para-position by $C_1$–$C_6$ alkyl, $C_1$–$C_6$ alkoxy arylcarboxamido, arylazo, aryloxy, arylthio and aryl in which each ring-containing substituent itself contains a single ring.

$R^1$ represents substituted phenyl, wherein the phenyl ring is substituted in the para-position by n-propyl, n-butyl, n-pentyl, n-hexyl, isobutyl, isoamyl, ethoxy, n-propyloxy, n-butoxy, n-pentyloxy, n-hexyloxy, isobutoxy, phenoxy, thiophenoxy(phenylthio), phenyl, azophenyl or benzamido, in which the para-substituted $R^1$ phenyl substituent can itself optionally contain a para-substituent containing one atom or a chain of no more than five atoms other than hydrogen, or in the meta- and para-positions by a methylenedioxy moiety.

$R^2$ and $R^3$ Preferences $R^2$ and $R^3$ are independently hydrogen (hydrido), $C_1$–$C_6$ alkyl, aralkyl, heteroaralkyl, cycloalkylalkyl having 4–8 carbons in the ring and 1–3 carbons in the alkyl chain, heterocycloalkylalkyl in which 4–8 atoms are in the ring, one or two of which atoms can be nitrogen, oxygen or sulfur and in which the alkyl chain contains 1–3 carbons, $C_1$–$C_5$ alkyl substituted by hydroxycarbonyl, amino, mono-substituted amino and di-substituted amino, wherein the substituents on nitrogen are chosen from $C_1$–$C_4$ alkyl, aralkyl, $C_5$–$C_8$ cycloalkyl and $C_1$–$C_6$ alkanoyl groups, or wherein the two substituents and the nitrogen to which they are attached when taken together form a 5- to 8-membered heterocyclo or heteroaryl ring.

$R^2$ and $R^3$ are independently hydrogen (hydrido), $C_1$–$C_6$ alkyl, aralkyl, heteroaralkyl, cycloalkylalkyl having 4–8 carbons in the ring and 1– 3 carbons in the alkyl chain, heterocycloalkylalkyl in which 4–8 atoms are in the ring, one or two of which atoms can be nitrogen, oxygen or sulfur and in which the alkyl chain contains 1–3 carbons.

$R^2$ represents hydrogen (hydrido) or $C_1$–$C_6$ alkyl and $R^3$ is hydrogen.

$R^2$ represents hydrogen (hydrido), methyl, ethyl, n-propyl, n-butyl, or isobutyl and $R^3$ is hydrogen.

$R^2$ represents hydrogen (hydrido) benzyl, 2-pyridylmethyl, 3-pyridylmethyl, 4-pyridylmethyl, 2-thiazolylmethyl, 4-thiazolylmethyl, or 5-thiazolylmethyl and $R^3$ is hydrogen.

$R^4$ and $R^5$ Preferences $R^4$ and $R^5$ independently are hydrogen (hydrido) hydroxy, amino, alkanoylamino, aralkanoylamino, arylcarbonylamino, heteroarylcarbonylamino, hydroxycarbonyl, aminocarbonyl, $C_1$–$C_6$ alkyl, aralkyl aryl heteroaryl, cycloalkyl, heteroaralkyl, or alkylcycloalkyl.

$R^4$ and $R^5$ independently are hydrogen (hydrido) hydroxy, amino, hydroxycarbonyl, aminocarbonyl, or C1–C6 alkyl.

$R^4$ and $R^5$ independently are hydrogen (hydrido) hydroxy, or amino.

$R^4$ and $R^5$ independently are hydrogen (hydrido) methyl, ethyl, propyl or butyl.

$R^4$ and $R^5$ independently are hydrogen (hydrido) aryl or heteroaryl.

$R^4$ and $R^5$ independently are hydrogen (hydrido) benzyl, 2-pyridylmethyl, 3-pyridylmethyl, 4-pyridylmethyl, 2-thiazolylmethyl, 4-thiazolylmethyl or 5-thiazolylmethyl.

$R^4$ and $R^5$ independently are hydrogen (hydrido) alkanoylamino, aralkanoylamino, or heteroarylcarbonylamino.

$R^4$ and $R^5$ are both hydrogen (hydrido).

$R^6$ and $R^7$ Preferences $R^6$ and $R^7$ independently are hydrido or a radical selected from the group consisting of an cycloalkyl, aryl, heteroaryl, aralkyl, heteroaralkyl, $C_1$–$C_6$ alkyl group, a carboxyl group, a $C_1$–$C_6$ alkoxy carbonyl group, an amino $C_1$–$C_6$ alkanoyl group, a carboxamide group where the amido nitrogen is (i) unsubstituted or substituted with (ii) a $C_1$–$C_4$ alkyl substituted by amino, mono-substituted amino or di-substituted amino, wherein the substituent on the amino nitrogen is selected from the group consisting of $C_1$–$C_6$ alkyl, $C_5$–$C_8$ cycloalkyl and $C_1$–$C_6$ alkanoyl groups, or wherein two amino nitrogen substitutents and the nitrogen to which they are bonded together form a 5- to 8-membered heterocyclic or heteroaryl ring containing zero or one additional hetero atoms that are nitrogen, oxygen or sulfur or (iii) the amido nitrogen is the amine of an amino acid.

$R^6$ and $R^7$ independently are hydrogen and hydroxycarbonyl.

$R^6$ and $R^7$ independently are hydrogen, aryl, and heteroaryl.

$R^6$ and $R^7$ independently are hydrogen, aralkyl, and heteroaralkyl.

$R^6$ and $R^7$ independently are hydrogen, benzyl, 2-pyridylmethyl, 3-pyridylmethyl, 4-pyridylmethyl, 2-thiazolylmethyl, 4-thiazolylmethyl or 5-thiazolylmethyl.

$R^6$ and $R^7$ are both hydrogen.

$R^7$ is hydrogen (hydrido) and $R^6$ is a $C_1$–$C_6$ alkyl group, a carboxyl group, a carboxamide group where the amido nitrogen is (i) unsubstituted or substituted with (ii) a $C_1$–$C_4$ alkyl substituted by amino, mono-substituted amino or di-substituted amino, wherein the substituents on nitrogen are chosen from $C_1$–$C_6$ alkyl, $C_5$–$C_8$ cycloalkyl and $C_1$–$C_6$ alkanoyl, or wherein the two substitutents and the nitrogen to which they are attached when taken together form a 5- to 8-membered heterocyclo or heterozryl ring containing zero or one additional hetero atoms that are nitrogen, oxygen or sulfur or (iii) the amido nitrogen is the amine of an amino acid, $C_1$–$C_6$ alkoxy carbonyl or an amino $C_1$–$C_6$ alkanoyl group, or $R^2$ and $R^6$ together with the atoms to which theare bonded form a 5- or 6-membered ring. These latter ring compounds are discussed separately hereinafter.

$R^8$ and $R^9$ Preferences $R^8$ and $R^9$ independently are hydrogen, hydroxycarbonyl, $C_1$–$C_6$ alkyl, aryl, heteroaryl, aralkyl, or heteroaralkyl.

$R^8$ and $R^9$ independently are hydrogen and hydroxycarbonyl.

$R^8$ and $R^9$ independently are hydrogen hydrogen and $C_1$–$C_6$ alkyl.

$R^8$ and $R^9$ independently are hydrogen, aryl, or heteroaryl.

$R^8$ and $R^9$ independently are hydrogen, aralkyl, or heteroaralkyl.

$R^8$ and $R^9$ independently are hydrogen, benzyl, 2-pyridylmethyl, 3-pyridylmethyl, 4-pyridylmethyl, 2-thiazolylmethyl, 4-thiazolylmethyl, or 5-thiazolylmethyl.

$R^8$ and $R^9$ are both hydrogen.

$R^{10}$ Preferences $R^{10}$ is alkyl, cycloalkyl, aryl, alkoxy, heteroaryl, aminoalkyl, N-monosubstituted aminoalkyl and N,N-disubstituted aminoalkyl, wherein the substituents on nitrogen are selected from the group consisting of alkyl, aralkyl, cycloalkyl and alkanoyl, or wherein the two substituents and the nitrogen to which they are attached when taken together form a 5- to 8-membered heterocyclo or heteroaryl ring.

$R^{10}$ is alkyl, aryl, alkoxy, heteroaryl, aminoalkyl, N-monosubstitued aminoalkyl, and N,N-disubstituted aminoalkyl, wherein the substituents on nitrogen are selected from the group consisting of alkyl, aralkyl, cycloalkyl and alkanoyl, or wherein the two substituents and the nitrogen to which they are attached when taken together form a 5- to 8-membered heterocyclo or heteroaryl ring.

$R^{10}$ is $C_1$–$C_6$ alkyl, aryl, alkoxy, or heteroaryl.

$R^{10}$ is methyl, ethyl, n-propyl, n-butyl, isopropyl, or isobutyl.

$R^{10}$ is a 3- to 8-membered cycloalkyl ring $R^{10}$ is cyclohexyl and cyclopentyl.

$R^{10}$ is aryl or heteroaryl having a single ring.

$R^{10}$ is phenyl, 2-pyridyl, 3-pyridyl, 4-pyridyl, thiophene-2-yl, or 3-thiophene-3-yl.

$R^{10}$ is $C_1$–$C_6$ alkoxy.

$R^{10}$ is methoxy and ethoxy.

Starred substituents, R*, y* and x* are preferably the same as unstarred substituents, R, y and x so that a compound of formula III is homodimer.

In particularly preferred practice, a chain of three carbon atoms separates the $SO_2$ portion of a $SO_2$-linked $R^1$ substituent and the mercapto group so that x is zero and y is 1. An $SO_2$-linked $R^1$ substituent is a substituted aryl or heteroaryl group that is a 5- or 6-membered single-ring; i.e., the aryl or heteroaryl group is not a fused ring radical, and is itself substituted with one other single-ringed aryl or heteroaryl group or, with an alkyl or alkoxy group containing an chain of 2 to about 7 carbon atoms, a phenoxy group, a thiophenoxy $[C_6H_5$—S—$]$ group, a phenylazido $[C_6H_5$—$N_2$—$]$ group or a benzamido $[$—$NHC(O)C_6H_5]$ group. The $SO_2$-linked single-ringed aryl or heteroaryl $R^1$ group is substituted at its own 4-position when a 6-membered ring, and at its own 3-position when a 5-membered ring.

The $R^1$ group's substituent single-ringed aryl or heteroaryl, phenoxy, thienyl, thiophenoxy, phenylazo or benzamido group is unsubstituted or can itself be substituted at the 4-position, and sometimes at both the 3- and 4-positions, when a 6-membered ring or the 3-position when a 5-membered ring. The 4- and 3-positions of rings discussed here are numbered from the sites of substituent bonding as compared to formalized ring numbering positions used in heteroaryl nomenclature. Here, single atoms such as halogen moieties or substituents that contain one to a chain of about five atoms other than hydrogen such as $C_1$–$C_4$ alkyl, $C_1$–$C_4$ alkoxy or carboxyethyl groups can be used. Exemplary substituted $SO_2$-linked $R^1$ substituents include biphenyl, 4-phenoxyphenyl, 4-thiophenoxyphenyl, 4-butoxyphenyl, 4-methoxyphenyl, 4-pentylphenyl, 4-(4'-dimethylaminophenyl)azophenyl, 4-(3,4-methylenedioxy)phenoxy and 2-[(2-pyridyl)-5-thienyl].

When examined along its longest chain of atoms, an $R^1$ substituent including its own substituent has a total length of greater than a saturated chain of six carbon atoms and less than a saturated chain of about 18 and preferably about 12 carbon atoms, even though many more atoms may be present in ring structures or substituents. This length requirement is discussed further below.

Looked at more generally, and aside from specific moieties from which it is constructed, a particularly preferred $R^1$ radical (group or moiety) has a length greater than about that of a pentyl group, e.g., 4-ethylphenyl or 4-methoxyphenyl. Such an $R^1$ radical also has a length that is less than that of a stearyl(octadecyl) group. That is to say that a particularly preferred $R^1$ group is a radical having a length greater than about that of a saturated six carbon chain, and shorter than that of a saturated eighteen carbon chain. More preferably, the radical has a length greater than that of a hexyl group and less than that of a lauryl group.

The radical chain lengths are measured along the longest linear atom chain in the radical, and each atom in the chain is presumed to be carbon for ease in calculation. Such lengths can be readily determined by using published bond angles, bond lengths and atomic radii, as needed, to draw and measure a staggered chain, or by building models using commercially available kits whose bond angles, lengths and atomic radii are in accord with accepted, published values. For example, a phenyl group has a length of about a butyl group. Radical lengths can also be determined somewhat less exactly by assuming that all atoms have bond lengths of saturated carbon, that unsaturated bonds have the same lengths as saturated bonds and that bond angles for unsaturated bonds are the same as those for saturated bonds, although the above-mentioned modes of measurement are preferred.

In addition, a particularly preferred $R^1$ group when rotated about an axis drawn through the $SO_2$-bonded 1-position and the 4-position of a 6-membered ring, or the $SO_2$-bonded position and substituent-bonded 3- or 5-position of a 5-membered ring defines a three-dimensional volume whose widest dimension has the width of about one phenyl ring to about three phenyl rings in a direction transverse to that axis to rotation.

As a consequence of these length and width requirements, $R^1$ substituents such as 4-(phenyl)phenyl[biphenyl], 4-(4'-methoxyphenyl)phenyl, 4-(phenoxy)phenyl, 4-(thiophenyl)phenyl[4-(phenylthio)phenyl], 4-(azophenyl)phenyl and 4-(benzamido)phenyl are particularly preferred $R^1$ substituents. Those substituents can themselves also be substituted in the second ring from the $SO_2$ group at the meta- or para-position or both with a single atom or a substituent containing a longest chain of up to five atoms, excluding hydrogen.

One sub-set of particularly preferred MMP-13 inhibitor compounds useful in a before-described process has structures depicted by formulas Ia, IIa and IIIa, below.

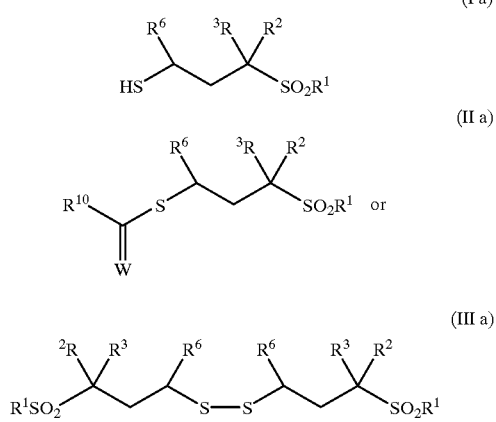

In the above particularly preferred MMP-13 inhibitor compounds useful herein, $R^1$ is as described immediately above. W is preferably oxygen (O) in these compounds, but can be sulfur (S). $R^{10}$ is as discussed before, but is preferably aryl or heteroaryl having a single ring or $C_1$–$C_6$ alkoxy.

$R^2$ and $R^3$ are radicals that are independently selected from the group consisting of hydrido, $C_1$–$C_6$ alkyl, single-ringed aralkyl or heteroaralkyl having 1–3 carbons in the alkyl chain, cycloalkylalkyl having 4–8 carbons in the ring and 1–3 carbons in the alkyl chain, and heterocycloalkylalkyl in which 4–8 atoms are in the ring, one or two of which atoms are nitrogen, oxygen or sulfur and in which the alkyl chain contains 1–3 carbons, or wherein $R^2$ and $R^6$ together with the atoms to which they are bonded form a 5- or 6-membered ring.

$R^6$ is a radical selected from the group consisting of an $C_1$–$C_6$ alkyl group, a carboxyl group, a $C_1$–$C_6$ alkoxy carbonyl group, an amino $C_1$–$C_6$ alkanoyl group, a carboxamide group where the amido nitrogen is (i) unsubstituted or substituted with (ii) a $C_1$–$C_4$ alkyl substituted by amino, mono-substituted amino or di-substituted amino, wherein the substituent on the amino nitrogen is selected from the group consisting of $C_1$–$C_6$ alkyl, $C_5$–$C_8$ cycloalkyl and $C_1$–$C_6$ alkanoyl groups, or wherein two amino nitrogen substitutents and the nitrogen to which they are bonded together form a 5- to 8-membered heterocyclic or heteroaryl ring containing zero or one additional hetero atoms that are nitrogen, oxygen or sulfur or (iii) the amido nitrogen is the amine of an amino acid. $R^2$ and $R^6$ can also form a 5- or 6-membered ring together with the atoms to which they are bonded, as noted above. A 6-membered ring is preferred and that ring can be aromatic.

A most preferred MMP-13 inhibitor sub-set of compounds useful in a before-described process corresponds to the structures depicted by formulas Ib, IIb and IIIb, below.

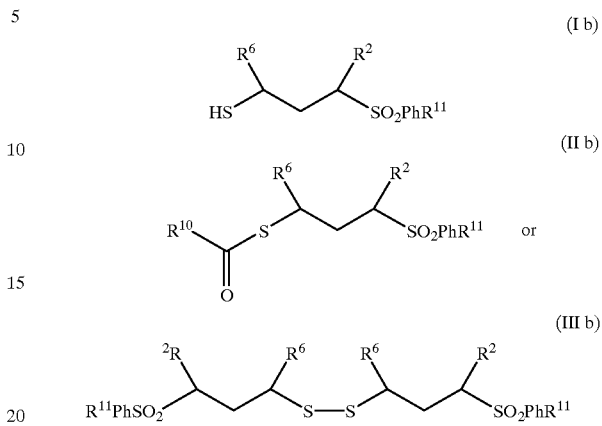

In an inhibitor compound of formulas Ib, IIb, or IIIb, $R^2$ and $R^6$ are as discussed immediately above, except that only one of $R^2$ or $R^6$ is present, unless $R^2$ and $R^6$ together with the atoms to which they are bonded form a 5- or 6-membered ring. $R^{10}$ is also as discussed immediately above. The phenyl ring (Ph) of a $PhR^{11}$ group is substituted at its para-position by an $R^{11}$ group that can be another single-ringed aryl or heteroaryl group or, with a $C_2$–$C_6$ alkyl group, a $C_1$–$C_6$ alkoxy group, a phenoxy group, a thiophenoxy [$C_6H_5$—S—] group, a phenylazido [$C_6H_5$—$N_2$—] group or a benzamido [—$NHC(O)C_6H_5$] group. In one embodiment of a most preferred inhibitor compound, an $R^{11}$ substituent is phenoxy and is itself substituted at its own para-position with a moiety that is selected from the group consisting of a halogen, a $C_1$–$C_4$ alkoxy group, a $C_1$–$C_4$ alkyl group, a dimethylamino group, a $C_1$–$C_3$ alkyl carboxyl group, a $C_1$–$C_3$ alkylcarbonyl $C_1$–$C_4$ alkoxy group and a $C_1$–$C_3$ alkyl carboxamido group, or is substituted at the meta- and para-positions by a methylenedioxy group.

Compounds in which $R^2$ and $R^6$ together with the atoms to which they are bonded form a 5- or a 6-membered ring correspond to formulas IVa, IVb, Va, and Vb, below:

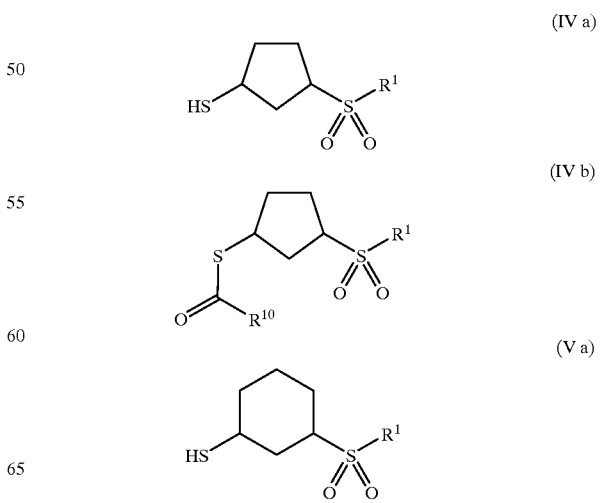

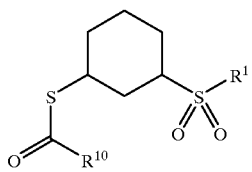

(IV b)

The following preferences apply to the inhibitor compounds of formulas IVa, IVb, Va and Vb:

$R^1$ Preferences $R^1$ is a radical that is selected from the group consisting of aryl, heteroaryl, alkyl, alkylthioalkyl, arylthioalkyl, heteroarylthioalkyl, aralkylthioalkyl, heteroaralkylthioalkyl; the sulfone or sulfoxide of any of those thio substituents. The aryl or heteroaryl groups can be substituted at one, two, or three positions by a radical selected from the group consisting of $C_1$–$C_{10}$ alkyl, $C_1$–$C_{10}$ alkoxy, aryloxy, heteroaryloxy, aryl, heteroaryl, aralkoxy, heteroaralkoxy, $C_1$–$C_{10}$ alkylthio, arylthio, heteroarylthio, cycloalkylthio, heterocyclo, cycloalkyl, amino, alkanoylamino, aralkanoylamino, arylcarbonylamino, heteroaralkanoyl, heteroarylcarbonylamino.

$R^1$ represents, $C_1$–$C_{10}$ alkyl, aryl, heteroaryl, wherein the aryl or heteroaryl can optionally be substituted by one or more of the following substituents: $C_1$–$C_{10}$ alkyl, $C_1$–$C_{10}$ alkoxy, aryloxy, heteroaryloxy, aryl, heteroaryl, aralkoxy, heteroaralkoxy, $C_1$–$C_{10}$ alkylthio, arylthio, heteroarylthio, arylamino, heteroarylamino.

$R^1$ represents aryl, wherein the aryl can optionally be substituted by one or more of the following substituents; $C_1$–$C_6$ alkyl, $C_1$–$C_6$ alkoxy, aryloxy, heteroaryloxy, aryl, heteroaryl, aralkoxy, heteroaralkoxy, $C_1$–$C_6$ alkylthio, arylthio, heteroarylthio.

$R^1$ represents aryl, wherein the aryl is optionally substituted in the para-position by one of the following substituents; $C_1$–$C_6$ alkyl, $C_1$–$C_6$ alkoxy, aryloxy, heteroaryloxy, aryl, heteroaryl, aralkoxy, heteroaralkoxy $C_1$–$C_6$ alkylthio, arylthio, heteroarylthio or benzamido.

$R^1$ represents aryl, wherein the aryl is substituted in the para-position by $C_1$–$C_6$ alkyl or $C_1$–$C_6$ alkoxy.

$R^1$ represents aryl, wherein the aryl is substituted in the para-position by n-propyl, n-butyl, n-pentyl, n-hexyl, isobutyl, isoamyl, thoxy, n-propyloxy, n-butoxy, n-pentyloxy, n-hexyloxy, isobutoxy.

$R^1$ represents aryl, wherein the aryl is substituted in the para-position by n-butyl, n-pentyl, n-hexyl, n-butoxy, n-pentyloxy, isobutoxy.

$R^1$ represents single-ringed aryl, wherein the aryl is substituted in the para-position by aryloxy, phenyl, phenylazo, benzamido or heteroaryloxy.

$R^1$ represents single-ringed aryl, wherein the aryl is substituted in the para-position by a phenoxy group.

$R^1$ represents single-ringed aryl, wherein the aryl is substituted in the para-position by aryl or heteroaryl.

$R^1$ represents single-ringed aryl, wherein the aryl is substituted in the para-position by phenyl, 2-pyridyl, 3-pyridyl, 4-pyridyl.

$R^1$ represents single-ringed aryl, wherein the aryl is substituted in the para-position by phenyl.

$R^1$ represents single-ringed aryl, wherein the aryl is substituted in the para-position by $C_1$–$C_6$ alkylthio.

$R^1$ represents single-ringed aryl, wherein the aryl is substituted in the para-position by methylthio, n-propylthio, n-butylthio.

$R^1$ represents single-ringed aryl, wherein the aryl is substituted in the para-position by arylthio and heteroarylthio.

$R^1$ represents single-ringed aryl, wherein the aryl is substituted in the para-position by phenylthio.

$R^{10}$ Preferences $R^{10}$ is a radical selected from the group consisting of alkyl, aryl, alkoxy, heteroaryl, cycloalkyl, aminoalkyl, N-monosubstituted aminoalkyl and N,N-disubstituted aminoalkyl, wherein the substituents on nitrogen are chosen from alkyl, aralkyl, cycloalkyl and alkanoyl, or wherein the two substituents and the nitrogen to which they are attached together form a 5 to 8 membered heterocyclo or heteroaryl ring.

$R^{10}$ represents $C_1$–$C_6$ alkyl, aryl, $C_1$–$C_6$ alkoxy, or heteroaryl.

$R^{10}$ represents methyl, ethyl, n-propyl, n-butyl, isopropyl, or isobutyl.

$R^{10}$ represents a 3- to 8-membered cycloalkyl ring.

$R^{10}$ represents cyclohexyl and cyclopentyl.

$R^{10}$ represents aryl or heteroaryl.

$R^{10}$ represents phenyl, 2-pyridyl, 3-pyridyl, 4-pyridyl, thiophene-2-yl, 3-thiophene-3-yl.

$R^{10}$ represents $C_1$–$C_6$ alkoxy.

$R^{10}$ represents methoxy and ethoxy.

Particularly preferred and most preferred $R^1$ and $R^{10}$ substituents of inhibitor compounds of formulas IVa, IVb, Va and Vb are as discussed before for compounds of formulas Ia–IIIa and Ib–IIIb, respectively.

Another group of compounds in which $R^4$ and $R^6$ or $R^6$ and $R^8$ together with the atoms to which they are bonded form a 6-membered ring are those in which the formed ring is aromatic. Exemplary compounds correspond to formulas VIa, VIb, VIIa, and VIIb, below. In those formulas, it is seen that inhibitor compounds of formulas VIa and VIb are compounds of formulas I and II in which y is zero and x is one, whereas compounds of formulas VIIa and VIIb are compounds of formulas I and II in which y is one and x is one.

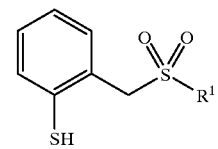

(VI a)

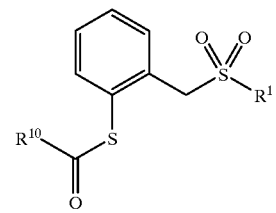

(VI b)

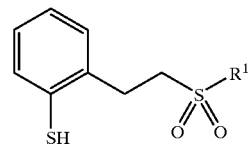

(VII a)

-continued

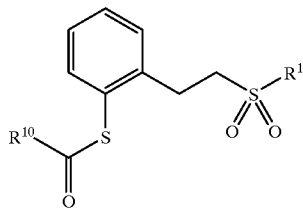

(VIIb)

The following preferences apply for preferred compounds of the above formulas.

$R^1$ Preferences $R^1$ is a radical that is selected from the group consisting of aryl, heteroaryl, alkyl, alkylthioalkyl, arylthioalkyl, heteroarylthioalkyl, aralkylthioalkyl, heteroaralkylthioalkyl; the sulfone or sulfoxide of any of said thio substituents. The aryl or heteroaryl groups can be substituted at one, two, or three positions by a radical selected from the group consisting of $C_1$–$C_{10}$ alkyl, $C_1$–$C_{10}$, aryloxy, heteroaryloxy, aryl, heteroaryl, aralkoxy, heteroaralkoxy, $C_1$–$C_{10}$ alkylthio, arylthio, heteroarylthio, cycloalkylthio, heterocyclo, cycloalkyl, amino, alkanoylamino, aralkanoylamino, arylcarbonylamino, heteroaralkanoyl, heteroarylcarbonylamino.

$R^1$ is a radical that is aryl, heteroaryl, $C_1$–$C_{10}$ alkyl, wherein the aryl or heteroaryl can optionally be substituted by one or more of the following substituents: $C_1$–$C_{10}$ alkyl, $C_1$–$C_{10}$ alkoxy, aryloxy, heteroaryloxy, aryl, heteroaryl, aralkoxy, heteroaralkoxy, $C_1$–$C_{10}$ alkylthio, arylthio, heteroarylthio, arylamino, heteroarylamino.

$R^1$ is a radical that is aryl, wherein the aryl can optionally be substituted by one or more of the following substituents: $C_1$–$C_6$ alkyl, $C_1$–$C_6$ alkoxy, aryloxy, heteroaryloxy, aryl, heteroaryl, aralkoxy, heteroaralkoxy, $C_1$–$C_6$ alkylthio, arylthio, heteroarylthio.

$R^1$ is a radical that is single-ringed aryl, wherein the aryl is optionally substituted in the para-position by one of the following substituents: $C_1$–$C_6$ alkyl, $C_1$–$C_6$ alkoxy, aryloxy heteroaryloxy, aryl, heteroaryl, aralkoxy, heteroaralkoxy, $C_1$–$C_6$ alkylthio, arylthio, heteroarylthio.

$R^1$ is a radical that is single-ringed aryl, wherein the aryl is substituted in the para-position by $C_1$–$C_6$ alkyl or $C_1$–$C_6$ alkoxy.

$R^1$ is a radical that is single-ringed aryl, wherein the aryl is substituted in the para-position by n-propyl, n-butyl, n-pentyl, n-hexyl, isobutyl, isoamyl, t-butoxy, n-propyloxy, n-butoxy, n-pentyloxy, n-hexyloxy, isobutoxy.

$R^1$ is a radical that is single-ringed aryl, wherein the aryl is substituted in the para-position by n-butyl, n-pentyl, n-hexyl, n-butoxy, n-pentyloxy, isobutoxy.

$R^1$ is a radical that is single-ringed aryl, wherein the aryl is substituted in the para-position by aryloxy or heteroaryloxy.

$R^1$ is a radical that is single-ringed aryl, wherein the aryl is substituted in the para-position by a phenoxy group.

$R^1$ is a radical that is single-ringed aryl, wherein the aryl is substituted in the para-position by aryl or heteroaryl.

$R^1$ is a radical that is single-ringed aryl, wherein the aryl is substituted in the para-position by phenyl, 2-pyridyl, 3-pyridyl, 4-pyridyl.

$R^1$ is a radical that is single-ringed aryl, wherein the aryl is substituted in the para-position by phenyl.

$R^1$ is a radical that is single-ringed aryl, wherein the aryl is substituted in the para-position by C1 to C6 alkylthio.

$R^1$ is a radical that is single-ringed aryl, wherein the aryl is substituted in the para-position by methylthio, n-propylthio, n-butylthio.

$R^1$ is a radical that is single-ringed aryl, wherein the aryl is substituted in the para-position by arylthio and heteroarylthio.

$R^1$ is a radical that is single-ringed aryl, wherein the aryl is substituted in the para-position by phenylthio.

$R^{10}$ Preferences $R^{10}$ is a radical that is selected from the group consisting of alkyl, aryl, alkoxy, heteroaryl, cycloalkyl, aminoalkyl, N-monosubstituted aminoalkyl and N,N-disubstituted aminoalkyl, wherein the substituents on nitrogen are chosen from alkyl, aralkyl, cycloalkyl and alkanoyl, or wherein the two substituents and the nitrogen to which they are attached when taken together form a 5 to 8 membered heterocyclo or heteroaryl ring.

$R^{10}$ is a radical that is $C_1$–$C_6$ alkyl, aryl, $C_1$–$C_6$ alkoxy, or heteroaryl.

$R^{10}$ is a radical that is methyl, ethyl, n-propyl, n-butyl, isopropyl, or isobutyl.

$R^{10}$ is a radical that is a 3- to 8-membered cycloalkyl ring.

$R^{10}$ is a radical that is cyclohexyl or cyclopentyl.

$R^{10}$ is a radical that is aryl or heteroaryl.

$R^{10}$ is a radical that is phenyl, 2-pyridyl, 3-pyridyl, 4-pyridyl, thiophene-2-yl, or 3-thiophene-3-yl.

$R^{10}$ is a radical that is $C_1$–$C_6$ alkoxy.

$R^{10}$ is a radical that is methoxy and ethoxy.

Particularly preferred and most preferred $R^1$ and $R^{10}$ substituents of inhibitor compounds of formulas VIa, VIb, VIIa and VIIb are as discussed before for compounds of formulas Ia–IIIa and Ib–IIIb, respectively.

The compounds described herein are useful in a process described herein in that such compounds can inhibit the activity of MMP-13. A particularly preferred compound inhibits the enzyme with an $IC_{50}$ value of about 1000 nm or less in the in vitro assay discussed hereinafter. A most preferred compound exhibits an $IC_{50}$ value in that assay of about 30 nm or less, with some compounds exhibiting values of about 1 nm or less.

In addition, while being highly active against MMP-13, selectivity of inhibitory activity toward MMP-1 is also exhibited by many of these particularly preferred and most preferred compounds. That is, many compounds exhibit little or no inhibition in the in vitro assay against MMP-1 so that $IC_{50}$ values are often found to be several thousand to greater than 10,000 nm toward MMP-1. Exemplary ratios of $IC_{50}$ values toward MMP-1 and MMP-13 ($IC_{50}$ MMP-1/$IC_{50}$ MMP-13) can range from about 5 to about 25,000, with most preferred compounds exhibiting ratios of about 500 to about 25,000. Inhibition data for several exemplary compounds are provided in a table hereinafter.

A contemplated inhibitor compound is used for treating a host mammal such as a mouse, rat, rabbit, dog, horse, primate such as a monkey, chimpanzee or human that has a condition associated with pathological matrix metalloprotease activity.

Also contemplated is use of a contemplated metalloprotease inhibitor compound in the treatment of a disease states that can be affected by the activity of metalloproteases. An example of such disease states is those affected by the activity of TNF-α convertase. Exemplary of such disease status are the acute phase responses of shock and sepsis, coagulation responses, hemorrhage and cardiovascular effects, fever and inflammation, anorexia and cachexia.

In treating a disease condition associated with pathological matrix metalloproteinase activity, a contemplated MMP inhibitor compound can be used in the form of an amine salt derived from an inorganic or organic acid. Exemplary salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate and undecanoate.

Also, a basic nitrogen-containing group can be quaternized with such agents as lower alkyl halides, such as methyl, ethyl, propyl, and butyl chloride, bromides, and iodides; dialkyl sulfates like dimethyl, diethyl, dibuytl, and diamyl sulfates, long chain halides such as decyl, lauryl, myristyl and stearyl chlorides, bromides and iodides, aralkyl halides like benzyl and phenethyl bromides, and others to provide enhanced water-solubility. Water or oil-soluble or dispersible products are thereby obtained as desired. The salts are formed by combining the basic compounds with the desired acid.

Other compounds useful in this invention that are acids can also form salts. Examples include salts with alkali metals or alkaline earth metals, such as sodium, potassium, calcium or magnesium or with organic bases or basic quaternary ammonium salts.

In some cases, the salts can also be used as an aid in the isolation, purification or resolution of the compounds of this invention.

Total daily dose administered to a host mammal in single or divided doses can be in amounts, for example, for 0.001 to 30 mg/kg body weight daily and more usually 0.01 to 10 mg. Dosage unit compositions can contain such amounts or submultiples thereof to make up the daily dose. A suitable dose can be administered, in multiple sub-doses per day. Multiple doses per day can also increase the total daily dose should this be desired by the person prescribing the drug.

The dosage regimen for treating a disease condition with a compound and/or composition of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed can vary widely and therefore can deviate from the preferred dosage regimen set forth above.

A compound useful in the present invention can be formulated as a pharmaceutical composition. Such a composition can then be administered orally, parenterally, by inhalation spray, rectally, or topically in dosage unit formulations containing conventional nontoxic pharmaceutically acceptable carriers, adjuvants, and vehicles as desired. Topical administration can also involve the use of transdermal administration such as transdermal patches or iontophoresis devices. The term parenteral as used herein includes subcutaneous injections, intravenous, intramuscular, intrasternal injection, or infusion techniques. Formulation of drugs is discussed in, for example, Hoover, John E., *Remington's Pharmaceutical Sciences*, Mack Publishing Co., Easton, Pa.; 1975 and Liberman, H. A. and Lachman, L., Eds., *Pharmaceutical Dosage Forms*, Marcel Decker, New York, N.Y., 1980.

Injectable preparations, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables. Dimethyl acetamide, surfactants including ionic and nonionic detergents, polyethylene glycols can be used. Mixtures of solvents and wetting agents such as those discussed above are also useful.

Suppositories for rectal administration of the drug can be prepared by mixing the drug with a suitable nonirritating excipient such as cocoa butter, synthetic mono- di- or triglycerides, fatty acids and polyethylene glycols that are sold at ordinary temperatures but liquid at the rectal temperature and will therefore melt in the rectum and release the drug.

Solid dosage forms for oral administration can include capsules, tablets, pills, powders, and granules. In such solid dosage forms, the compounds of this invention are ordinarily combined with one or more adjuvants appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. The compounds can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The amount of active ingredient that can be combined with the carrier materials to produce a single dosage form varies depending upon the mammalian host treated and the particular mode of administration.

Certain compounds of this invention can serve as prodrugs to other compounds of this invention. Prodrugs are drugs that can be chemically converted in vivo or in vitro by biological systems into an active derivative or derivatives. An example from this invention are drugs of formula II (IIa or IIb) where the acyl group is hydrolyzed to a compound of formula I (Ia or Ib). An additional example is where a disulfide of this invention is reduced to its thiol product or, in some cases, converted into an active mixed disulfide.

Table 1 through Table 40, below, show several compounds useful in a process of this invention. Each group of compounds is illustrated by a generic formula, or formulae, followed by a series of preferred moieties or groups that constitute various substituents that can be attached at the position clearly shown in the generic structure. The generic symbols, e.g., $R^1$, $R^2$ and the like, are as defined before. This system is well known in the chemical communication arts and is widely used in scientific papers and presentations. For example in Table 2, $R^1$ is the variable group with the structural variables that can substitute for $R^1$ shown in the balance of the table. There are 30 $R^1$ groups (including hydrogen) shown that are used to represent, in a non-limiting manner, 30 distinct compounds that can be prepared for use in the invention.

TABLE 1

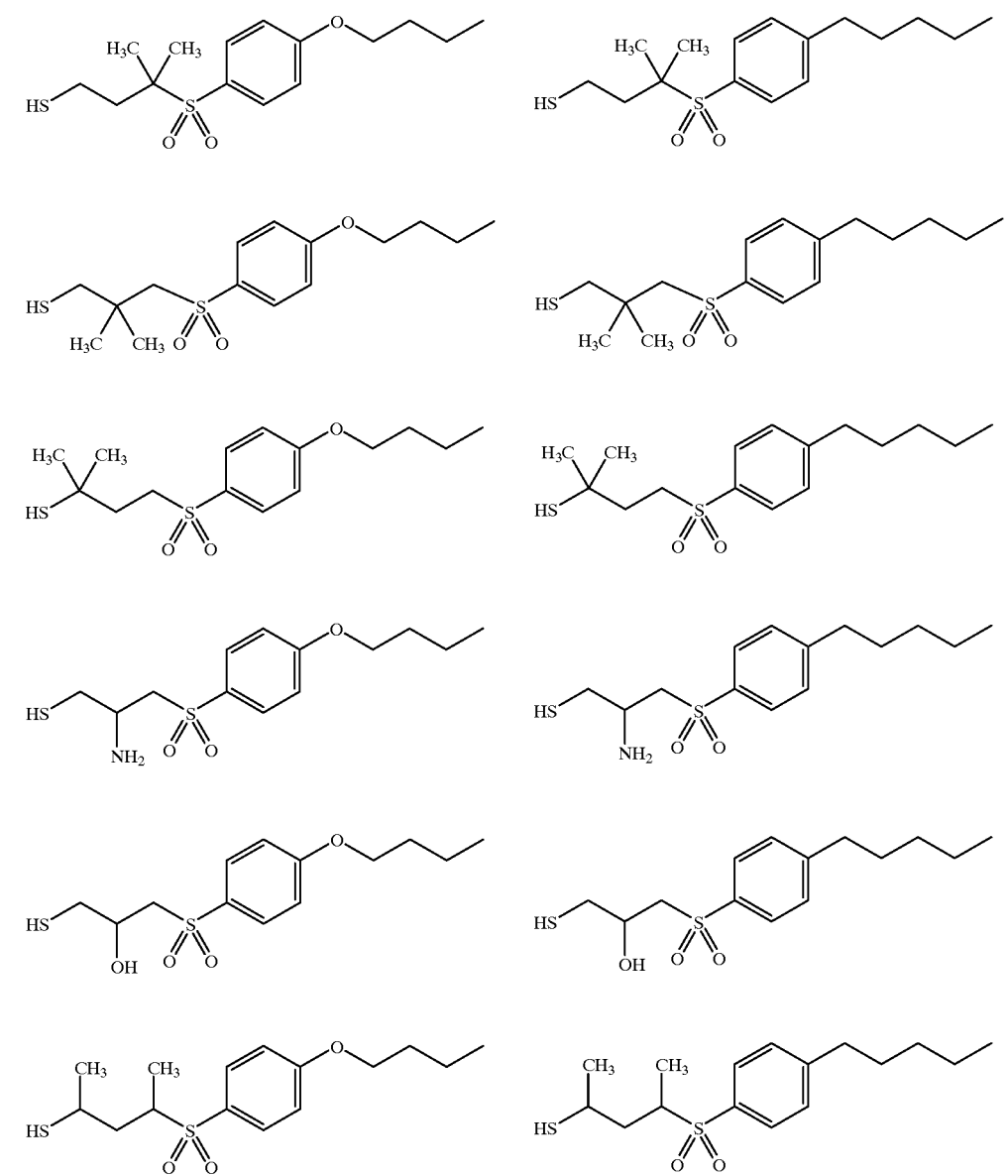

TABLE 2
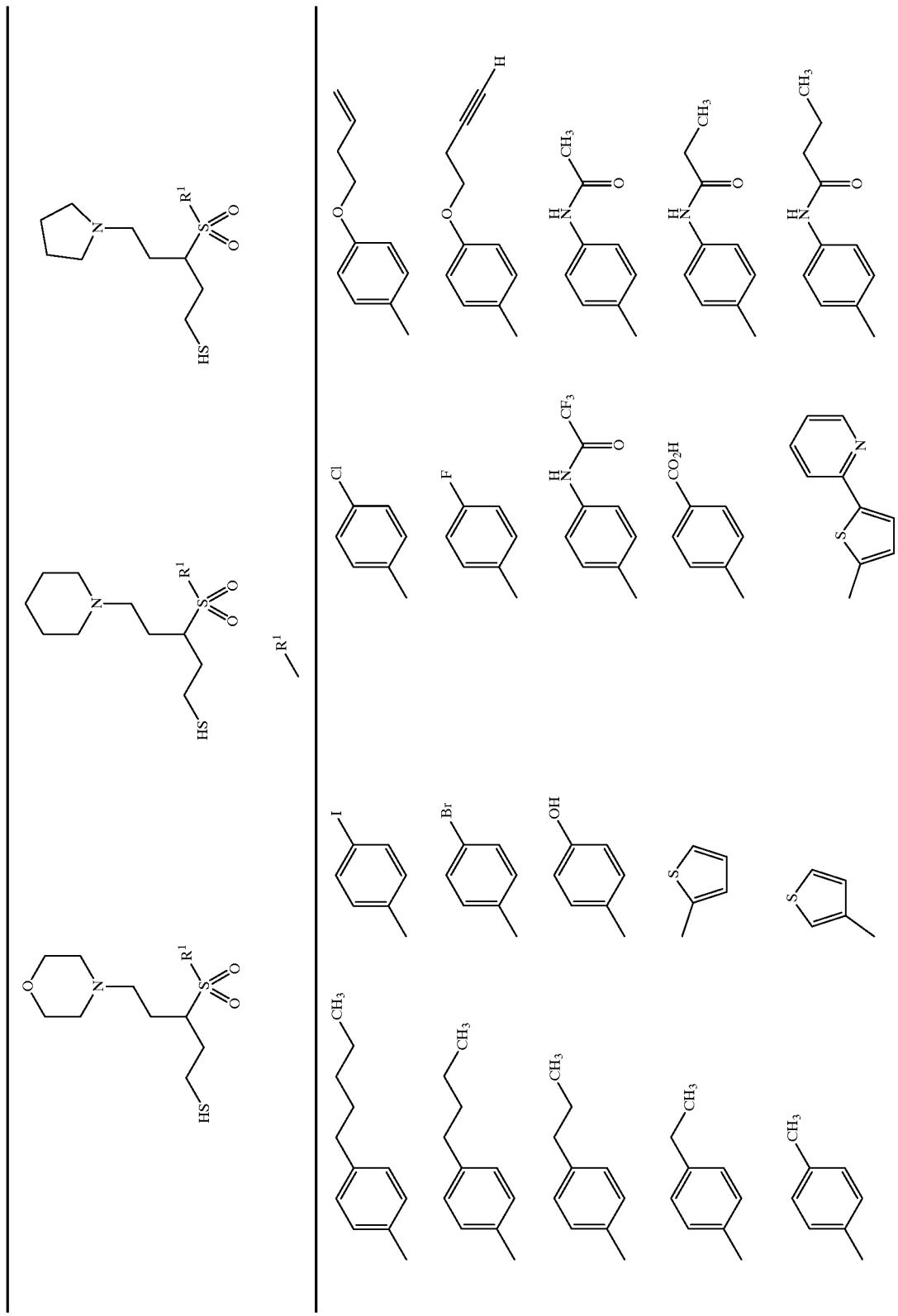

TABLE 2-continued
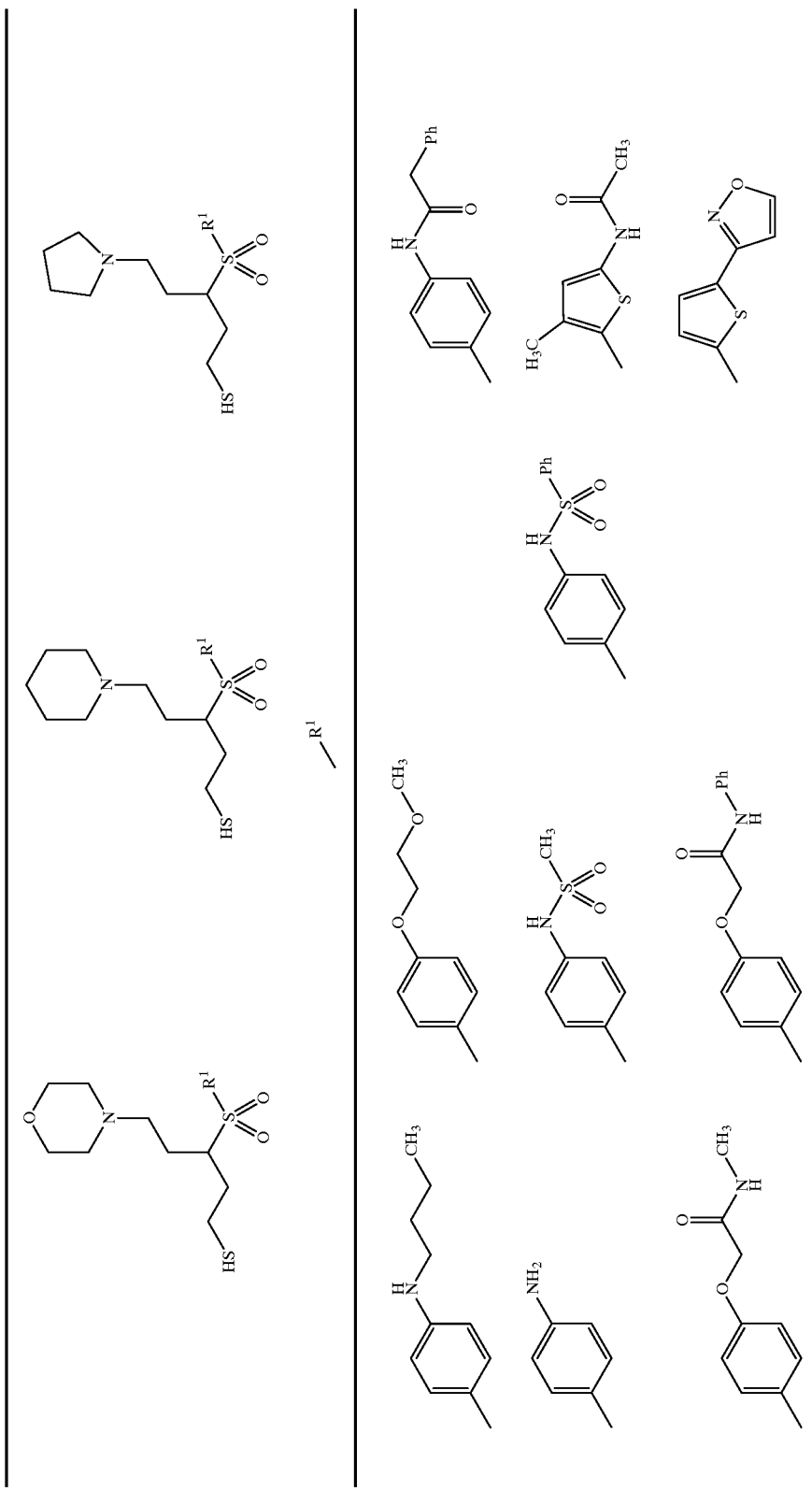

TABLE 3
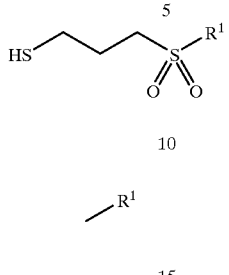
—R¹
| 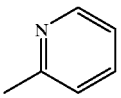 | 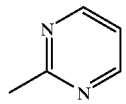 | 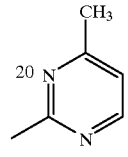 | 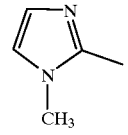 |
|---|---|---|---|
| 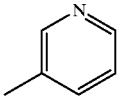 | 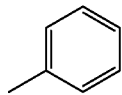 | 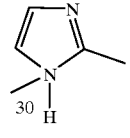 | 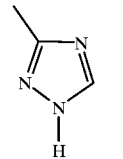 |
| 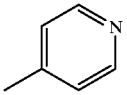 | 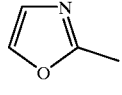 | 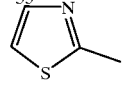 | 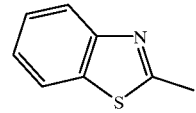 |
| 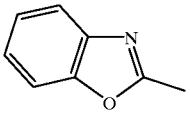 | 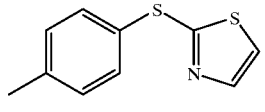 |  | 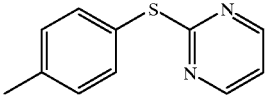 |
| 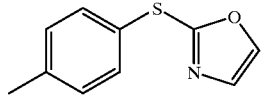 |  |  |  |
|  | 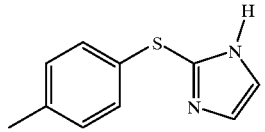 |  | 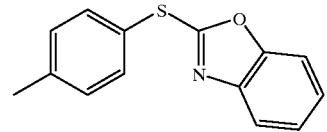 |

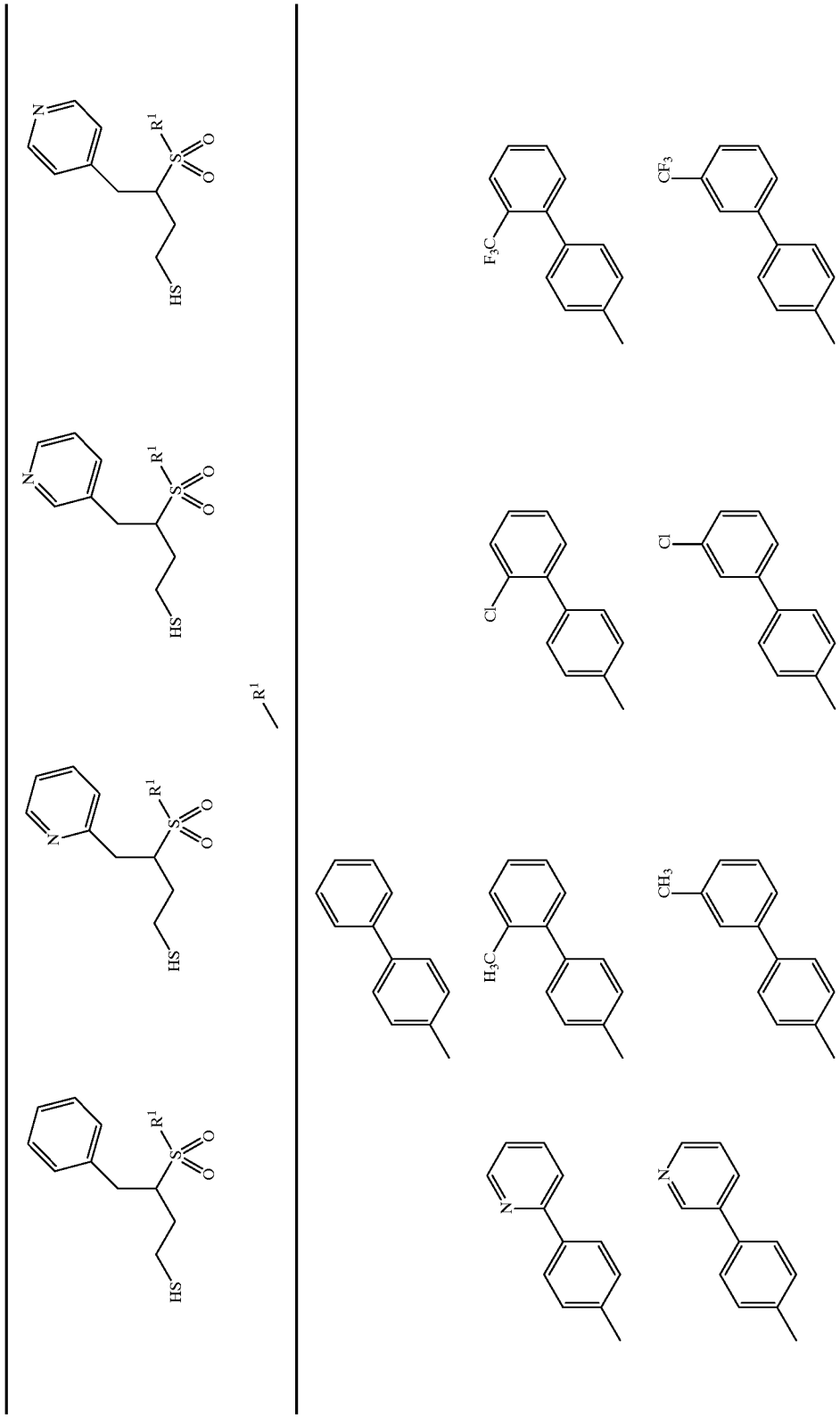

TABLE 4-continued
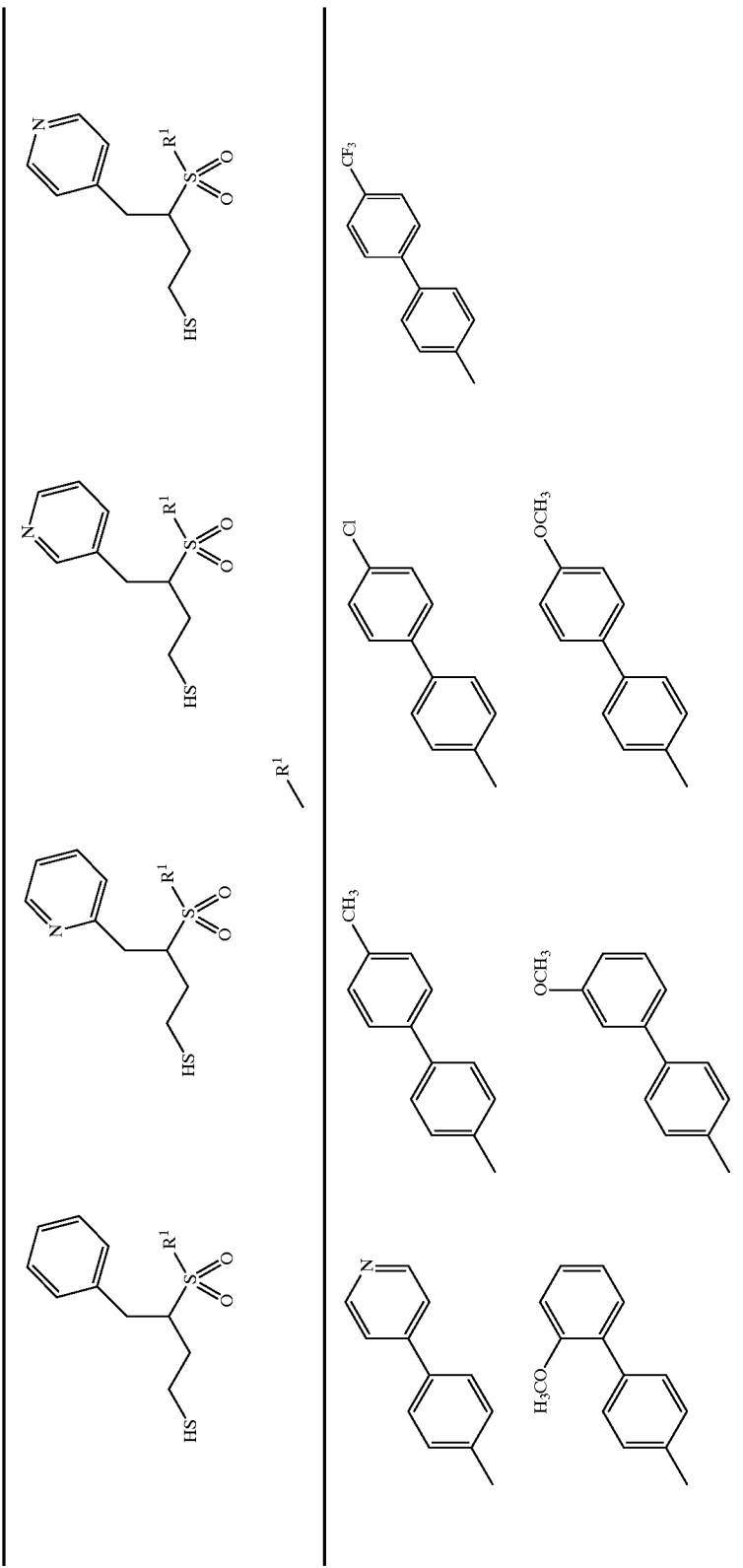

TABLE 5
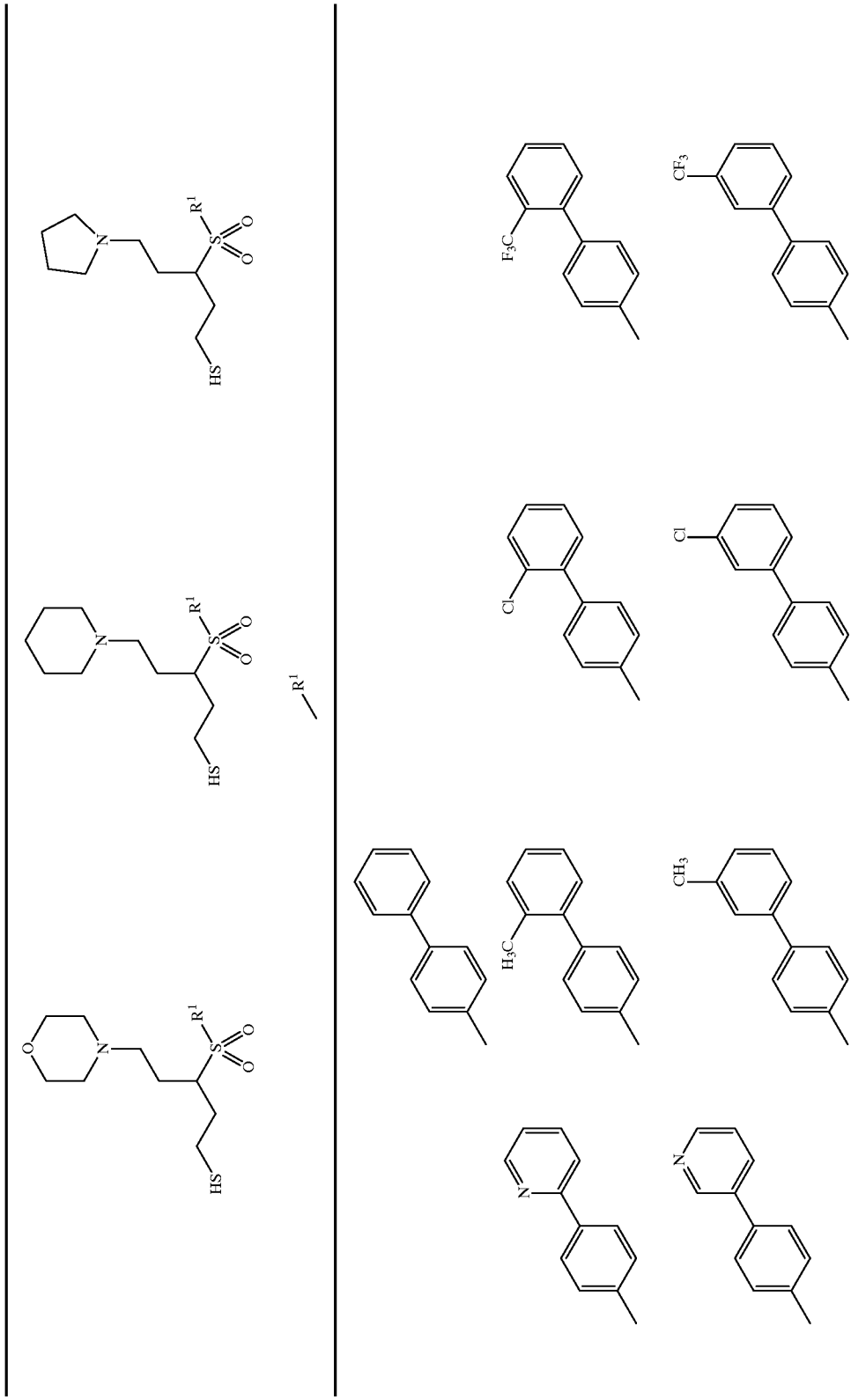

TABLE 5-continued
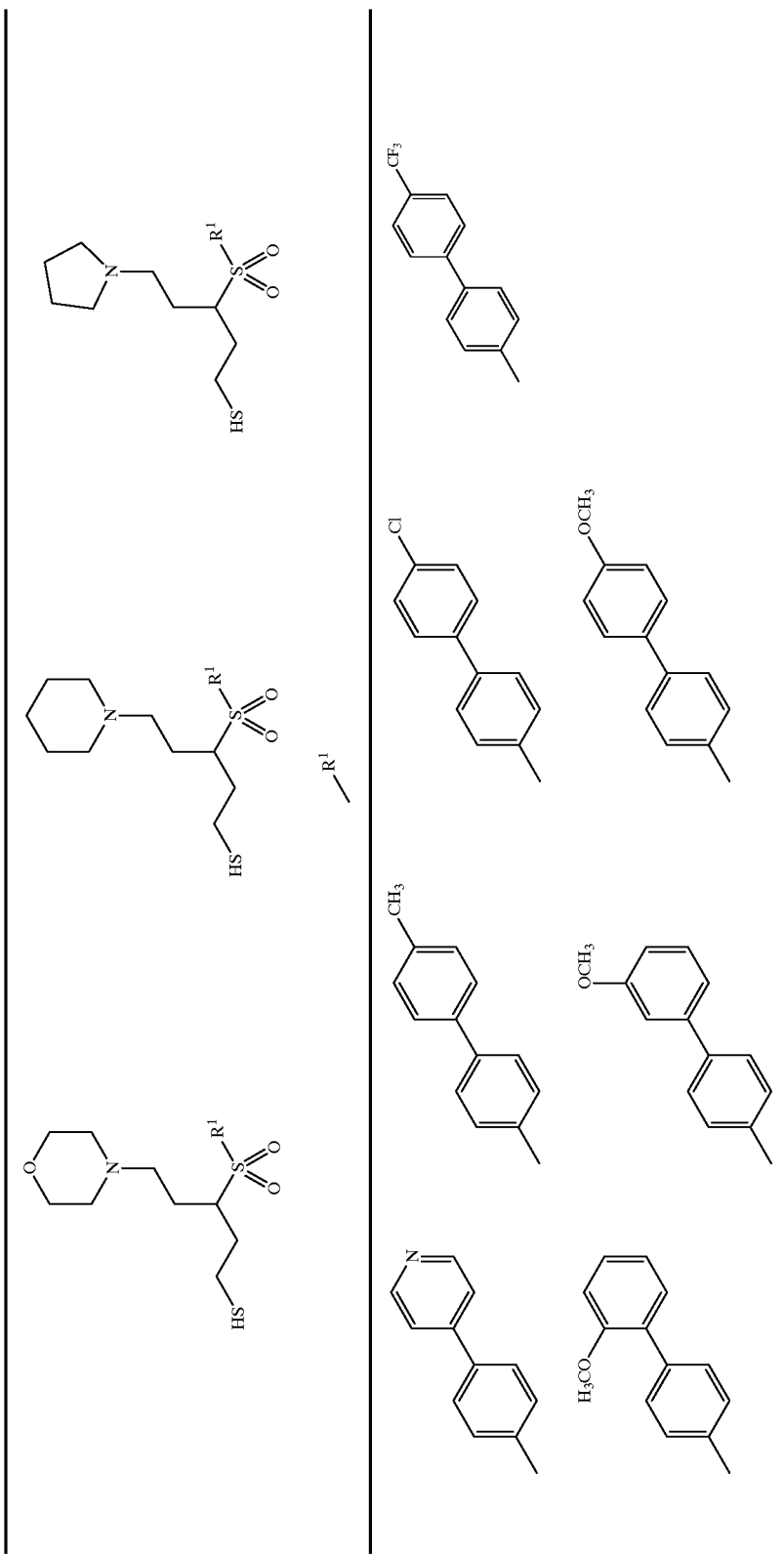

TABLE 6
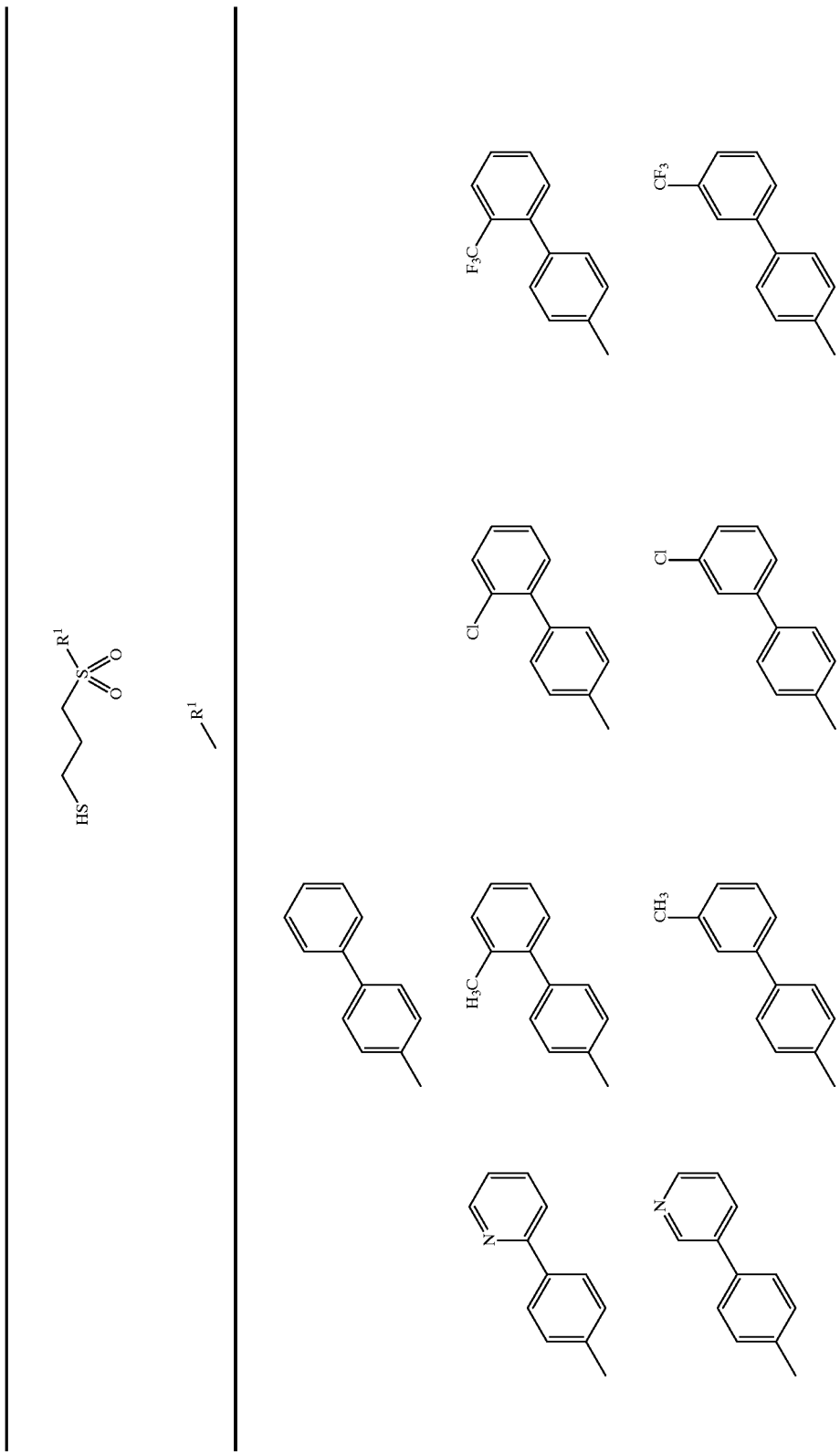

TABLE 6-continued
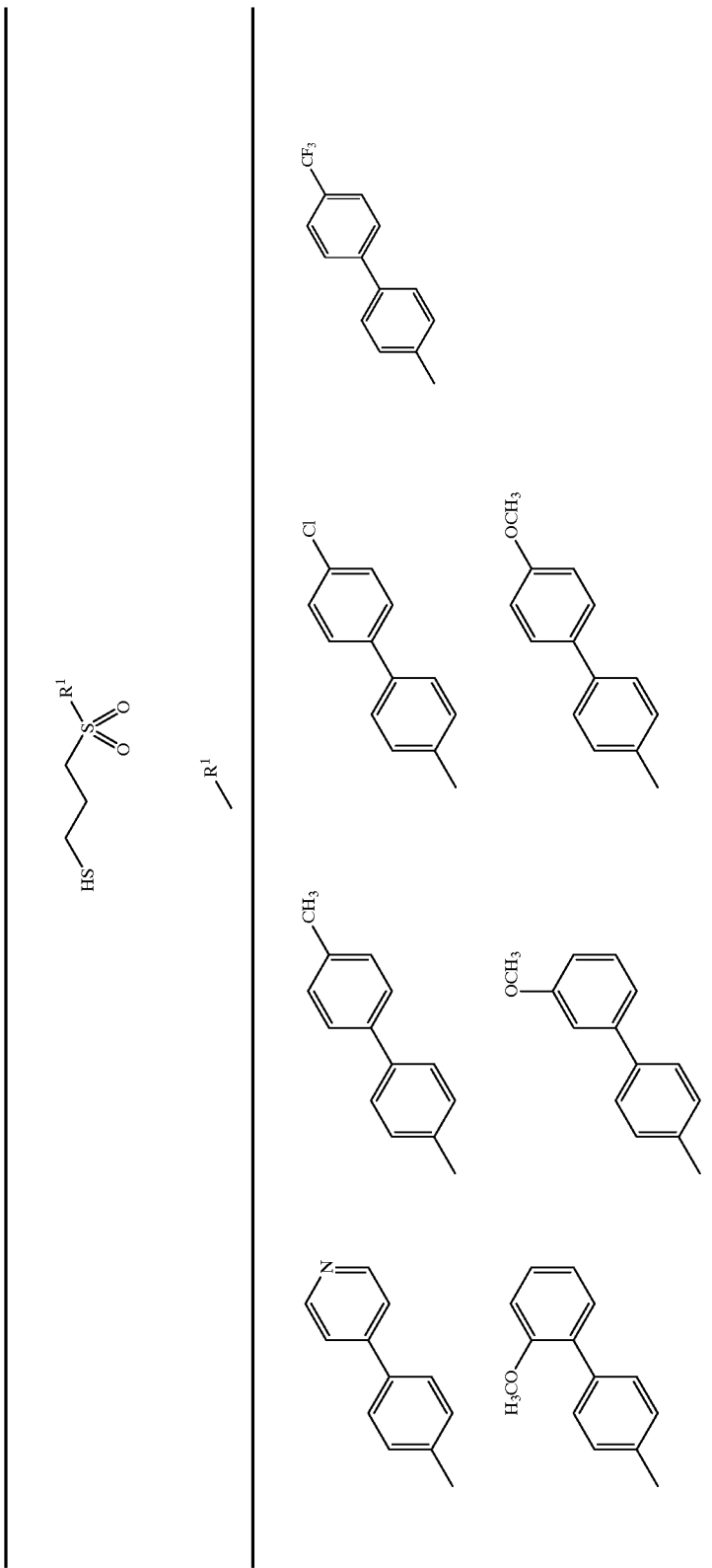

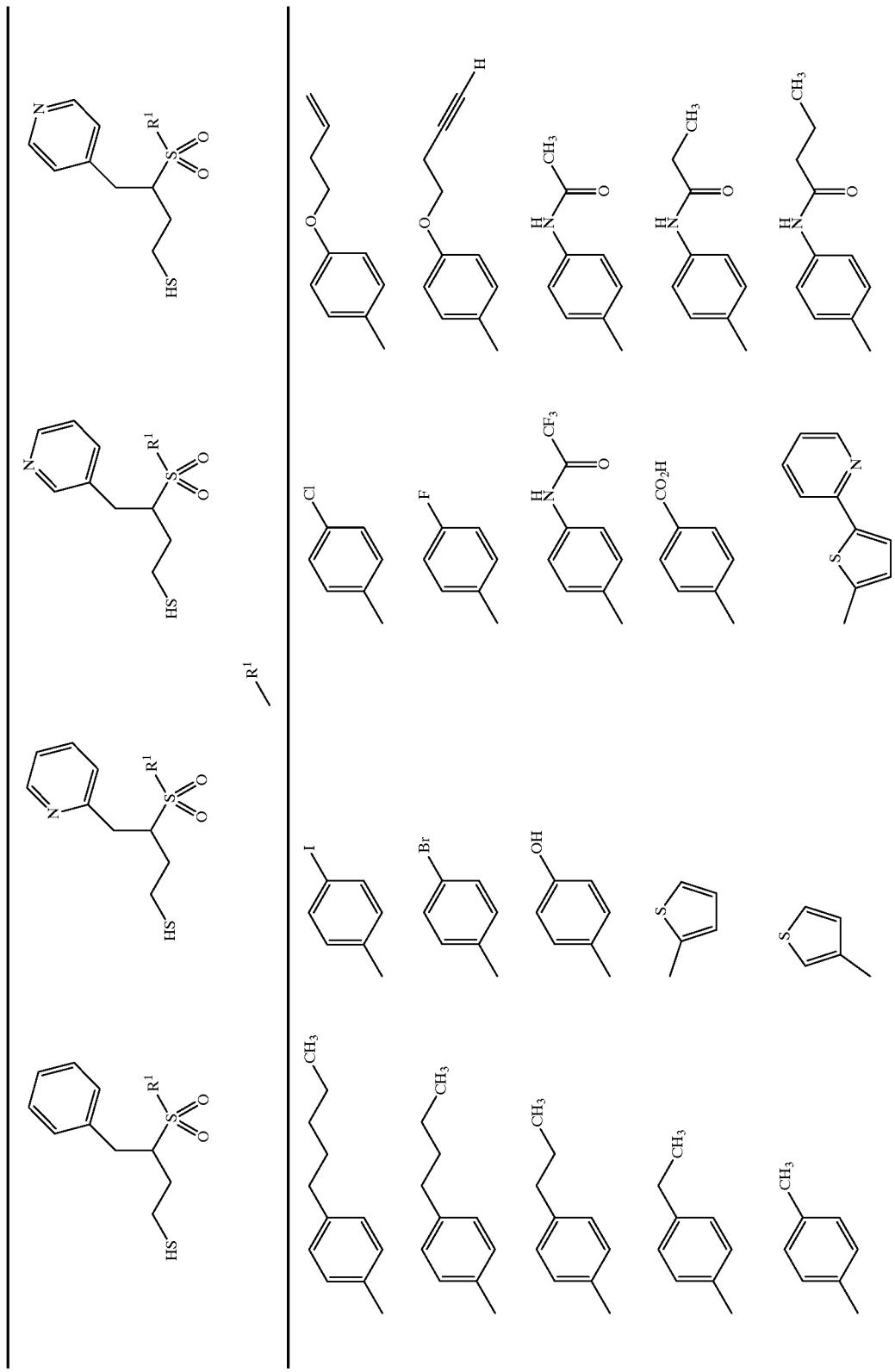

TABLE 7-continued
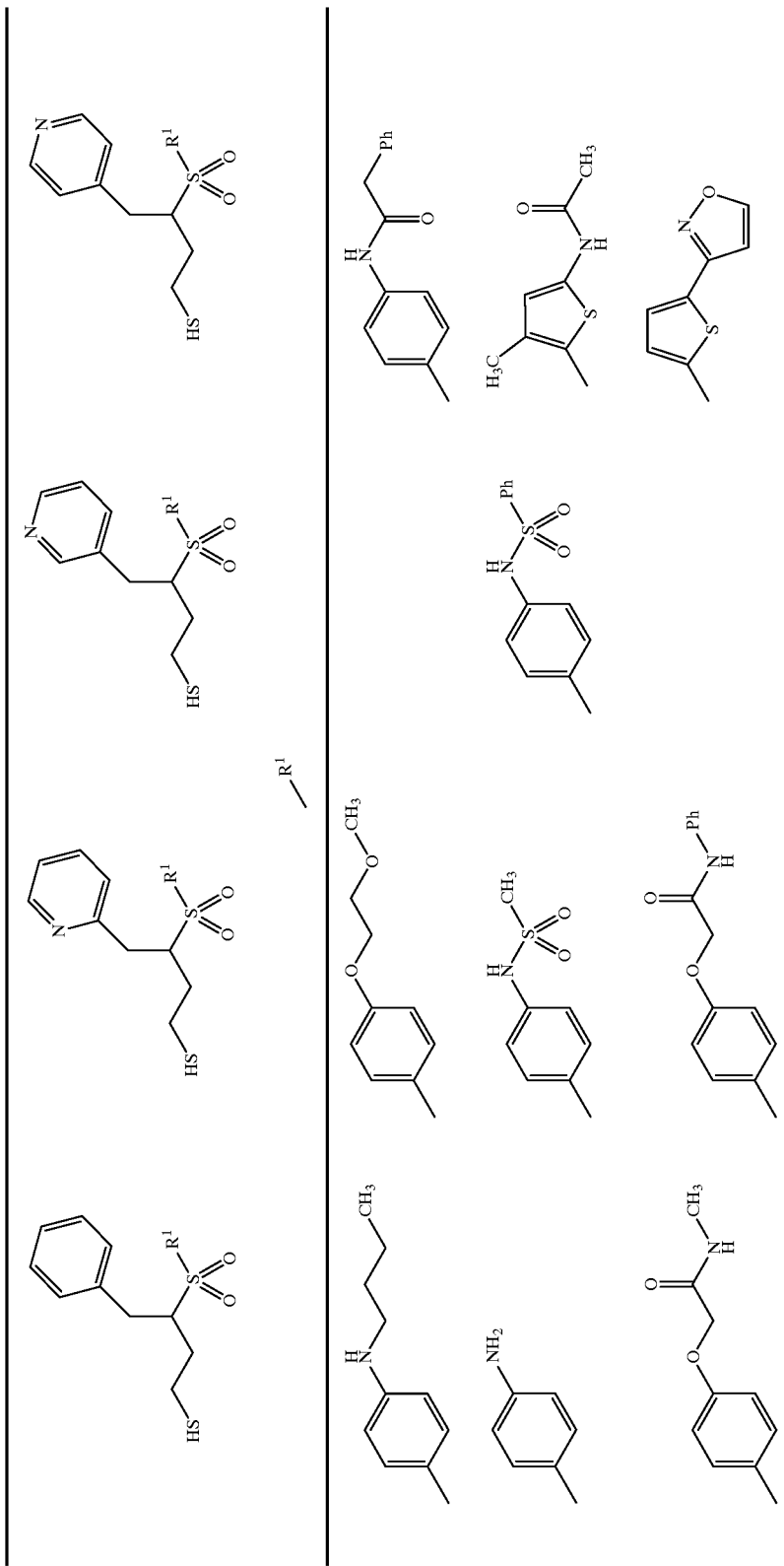

TABLE 8
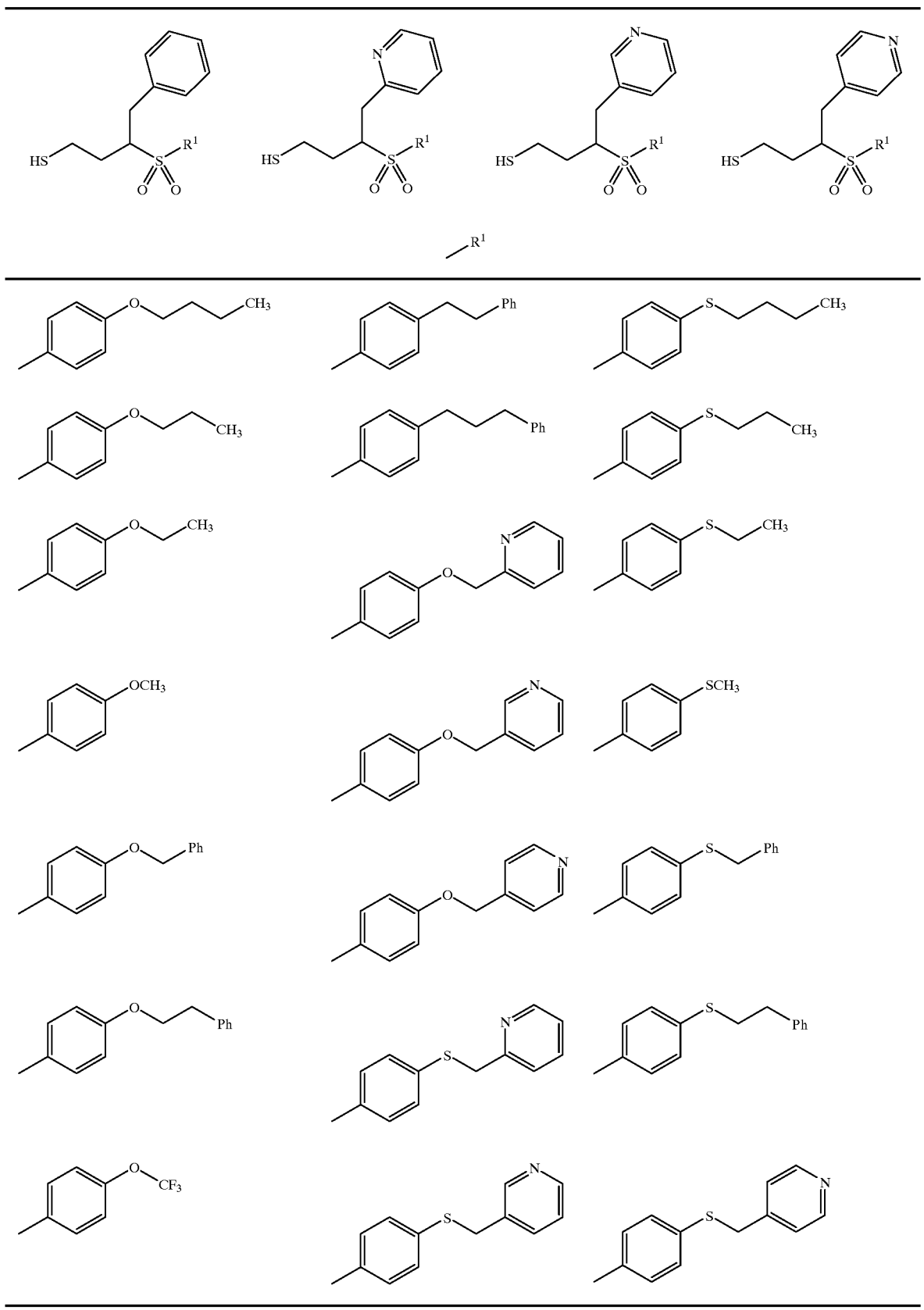

TABLE 9
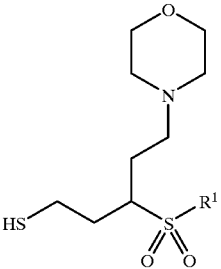 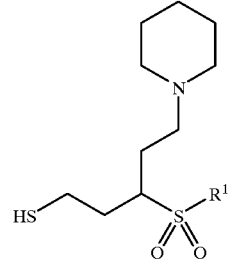 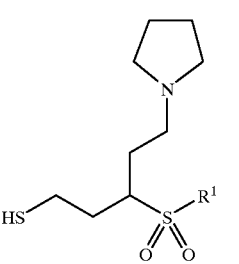
—R¹
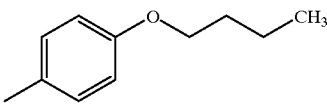 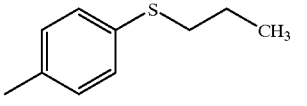 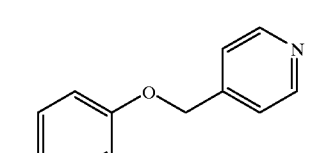
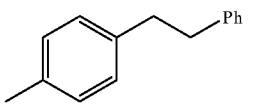 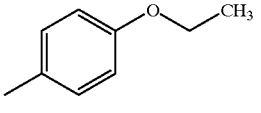 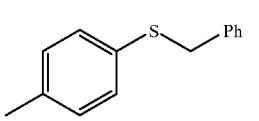
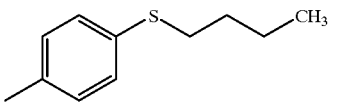 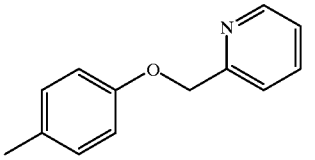 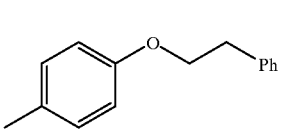
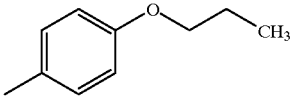 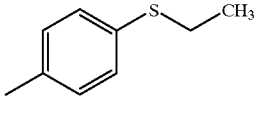 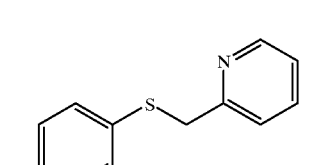
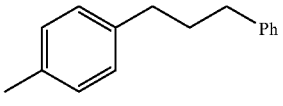 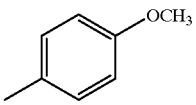 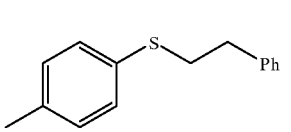
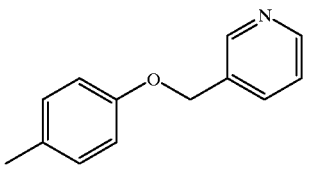 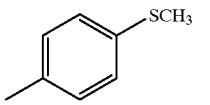 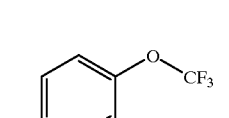
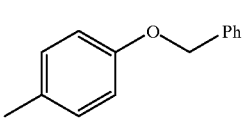 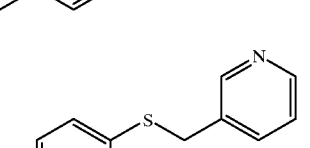 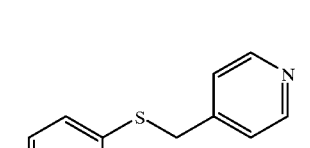

TABLE 10
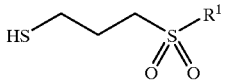
—R¹
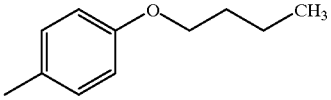 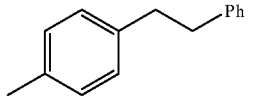 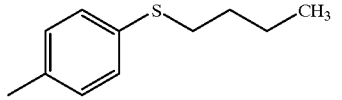
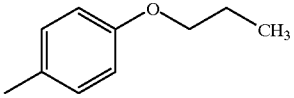 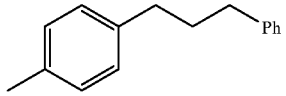 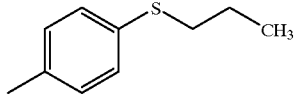
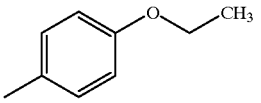 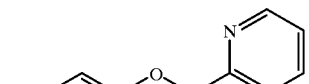 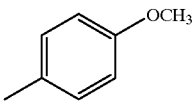
 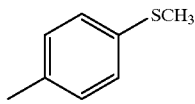 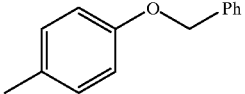
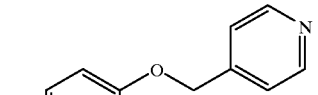 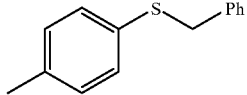 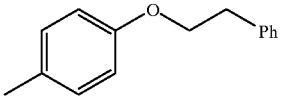
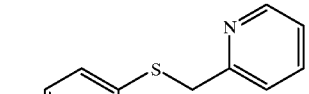 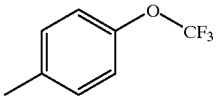 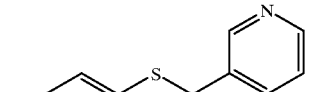
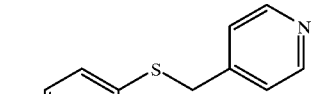

TABLE 11
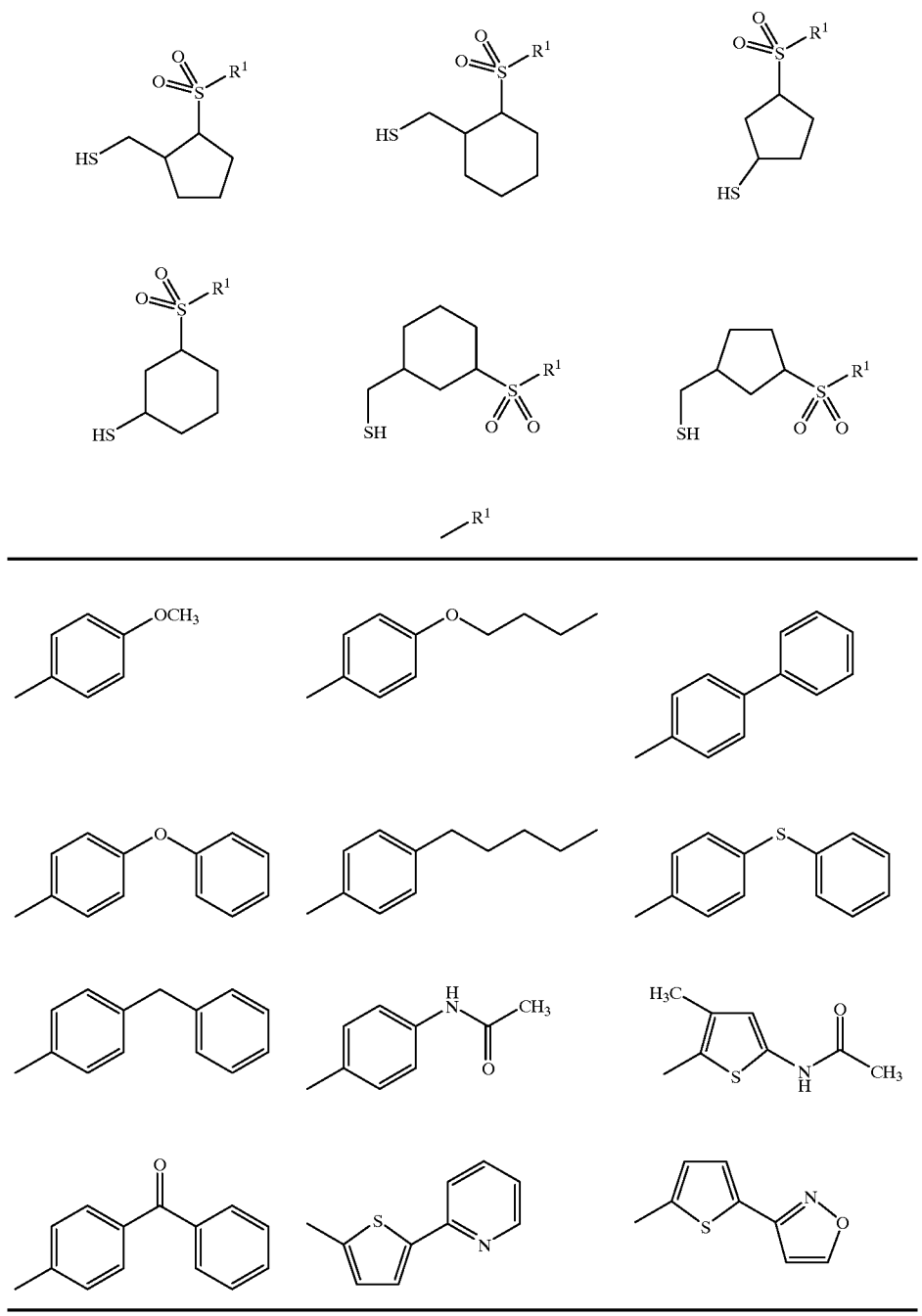

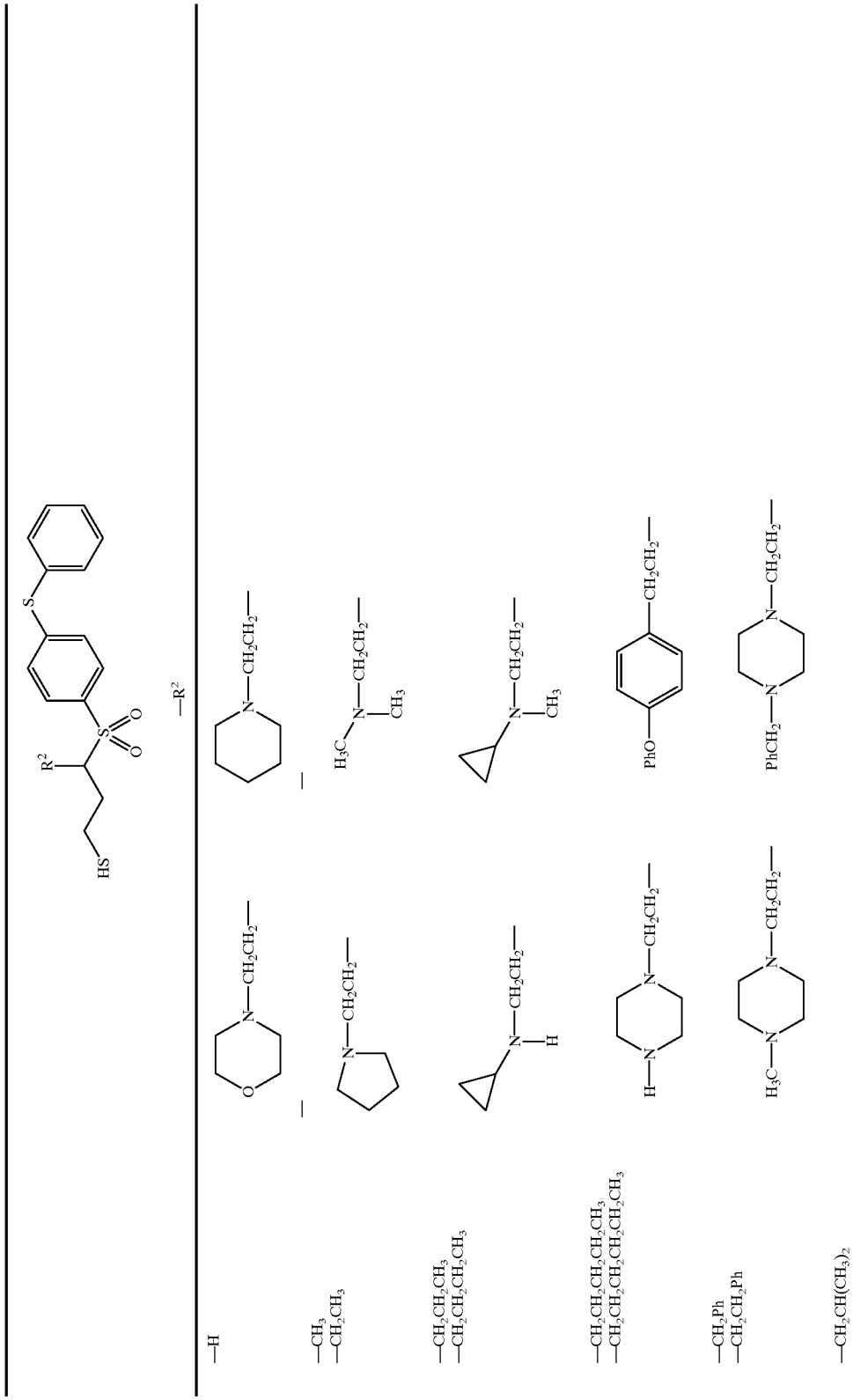

TABLE 12-continued
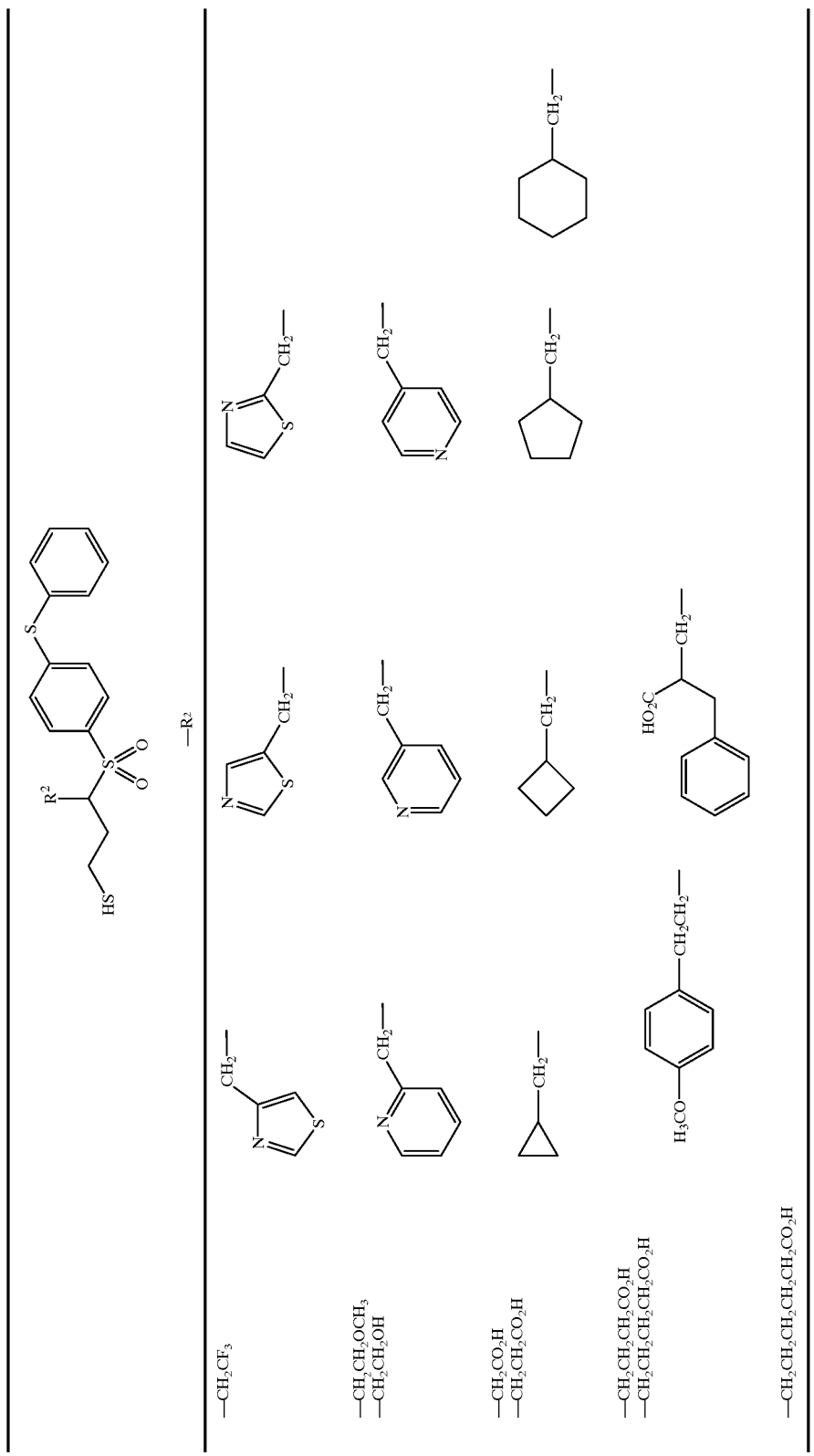

TABLE 13
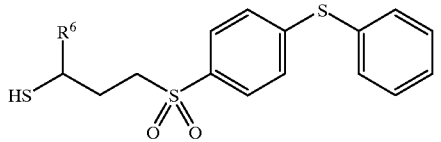
| $R^6$ | | | | | |
|---|---|---|---|---|---|

TABLE 14
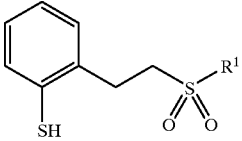
—R¹
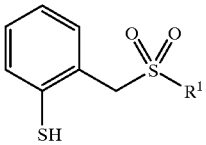

TABLE 15
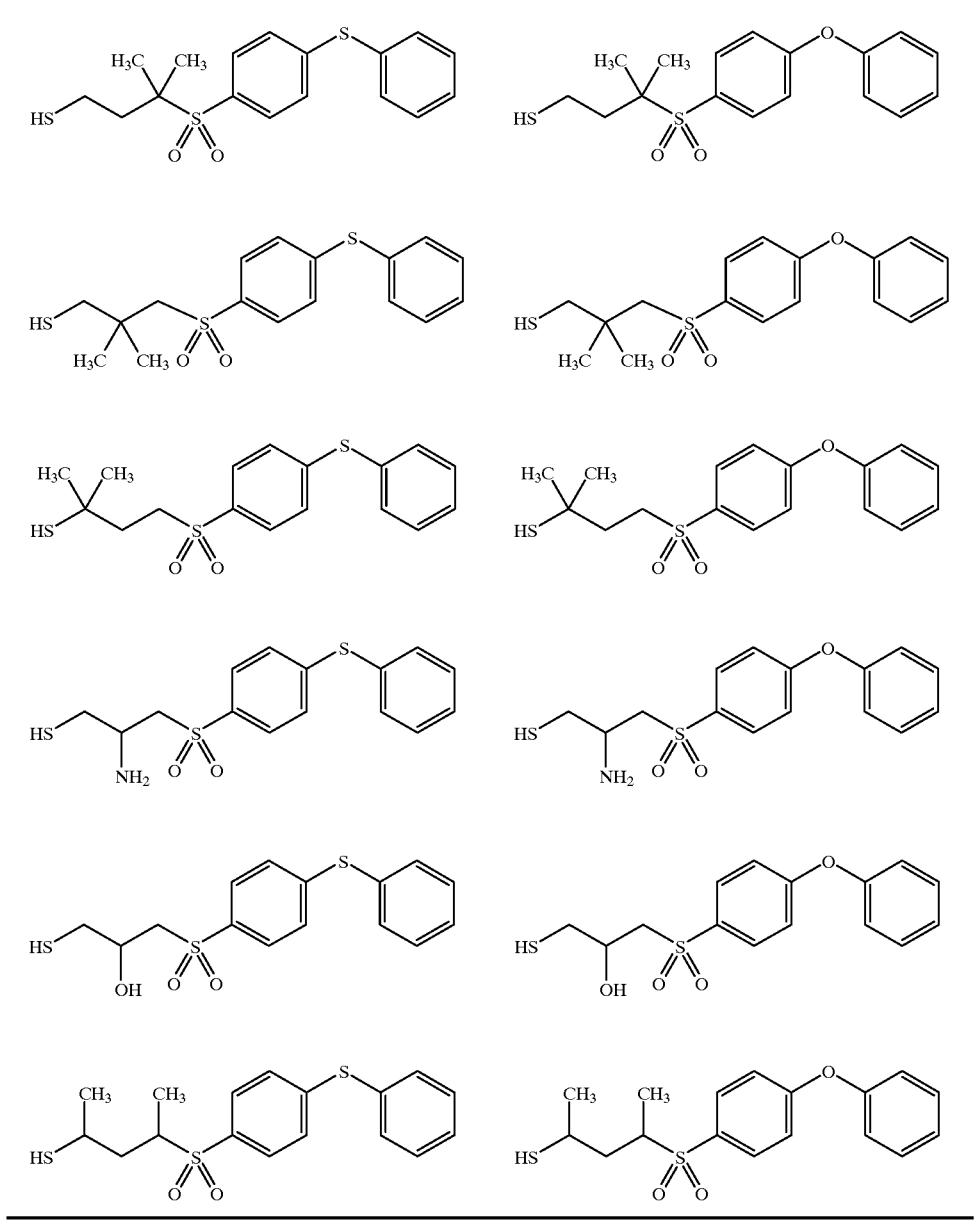

TABLE 16

(structures shown: 3-mercaptocyclohexyl sulfonyl-R¹; 3-mercaptocyclopentyl sulfonyl-R¹)

—R¹

| | | |
|---|---|---|
| 4-methoxyphenyl | 4-butoxyphenyl | 4-biphenyl |
| 4-phenoxyphenyl | 4-pentylphenyl | 4-(phenylthio)phenyl |
| 4-benzylphenyl | 4-(acetylamino)phenyl | 4,5-dimethyl-2-(acetylamino)thienyl |
| 4-benzoylphenyl | 5-(pyridin-2-yl)thien-2-yl | 5-(isoxazol-3-yl)thien-2-yl |
| 4-(3-methylphenoxy)phenyl | 4-(4-trifluoromethylphenoxy)phenyl | 4-(pyridin-2-ylthio)phenyl |
| 4-(4-methylphenoxy)phenyl | 4-(3-chlorophenoxy)phenyl | 4-(pyridin-3-ylthio)phenyl |
| 4-(3-trifluoromethylphenoxy)phenyl | 4-(4-chlorophenoxy)phenyl | 4-(pyridin-4-ylthio)phenyl |

TABLE 17
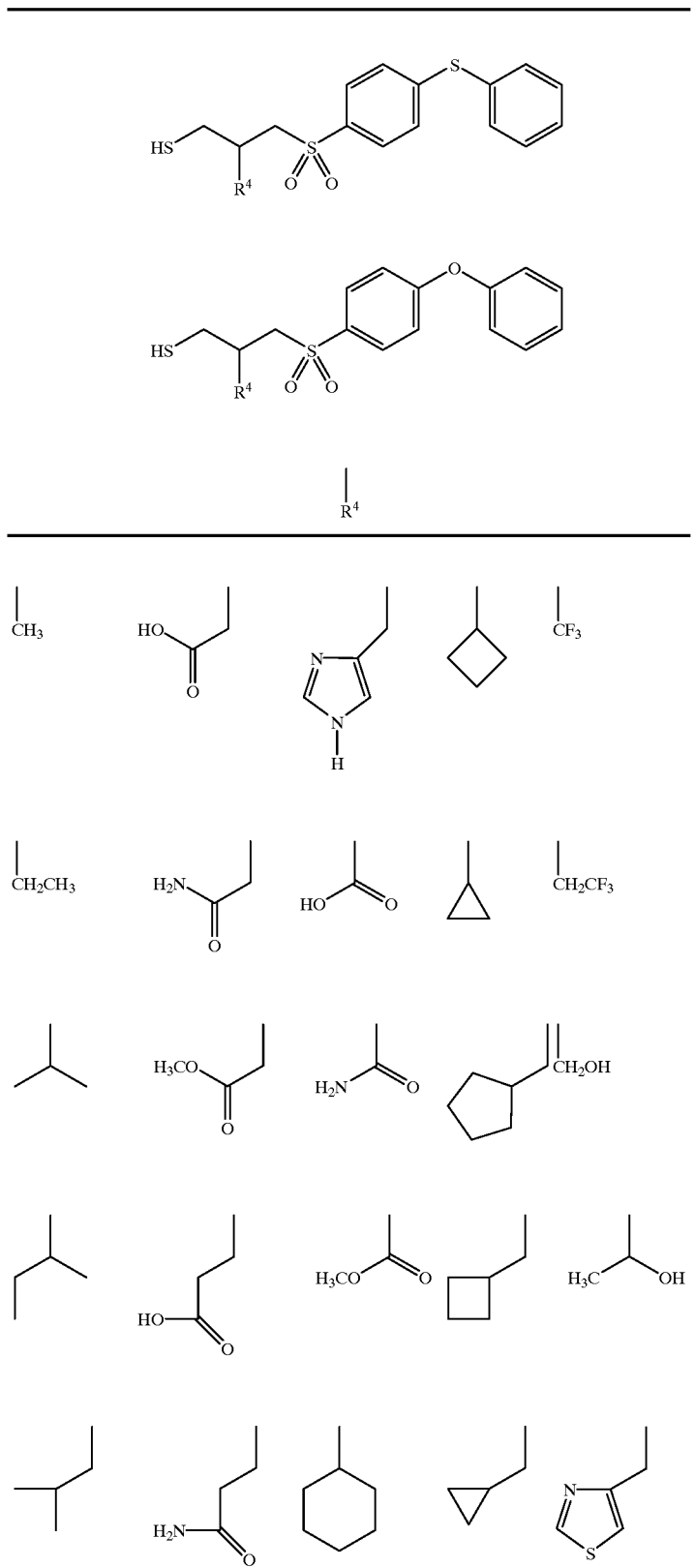

TABLE 17-continued
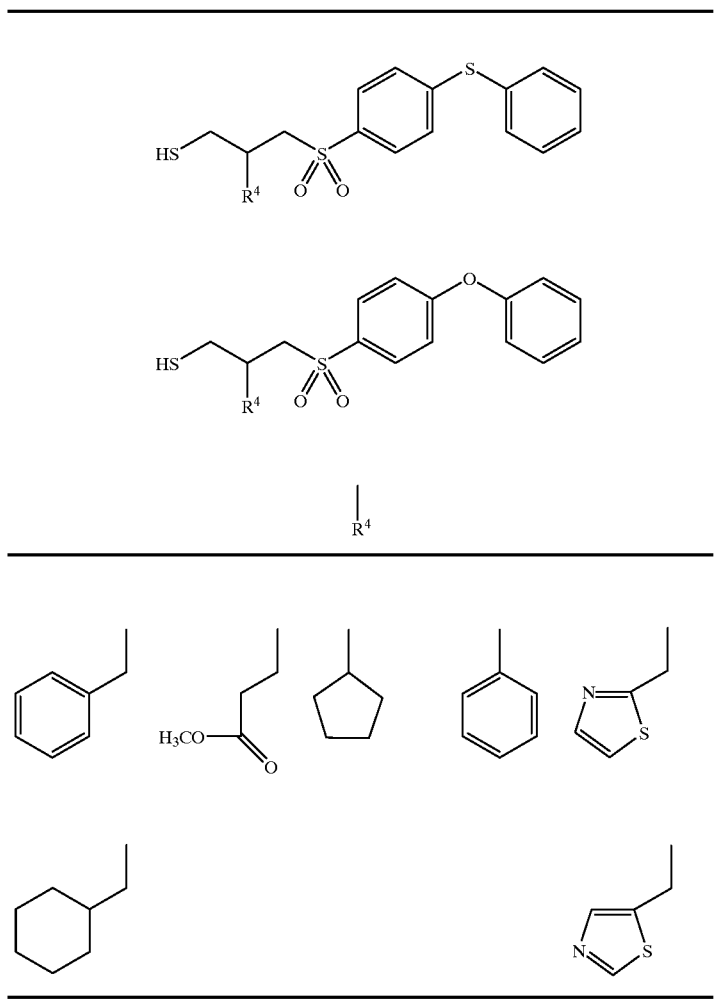

TABLE 18

[Structure: 4-butoxyphenyl-sulfonyl compound with R² substituent and thiol side chain]

| —R² | |
|---|---|
| —H | |
| —CH₃ | —CH₂CH₂-morpholine |
| —CH₂CH₃ | —CH₂CH₂-piperidine |
| —CH₂CH₂CH₃ | —CH₂CH₂-pyrrolidine |
| —CH₂CH₂CH₂CH₃ | —N(CH₃)(CH(CH₃)₂) via CH₂CH₂ |
| | —N(H)(cyclopropyl) via CH₂CH₂ |
| —CH₂CH₂CH₂CH₂CH₃ | —N(CH₃)(cyclopropyl) via CH₂CH₂ |
| —CH₂CH₂CH₂CH₂CH₂CH₃ | —CH₂CH₂-piperazine (NH) |
| —CH₂Ph | —CH₂CH₂-(4-PhO-phenyl) |
| —CH₂CH₂Ph | —CH₂CH₂-(4-methylpiperazine) |
| | —CH₂CH₂-(4-benzylpiperazine) |

TABLE 18-continued
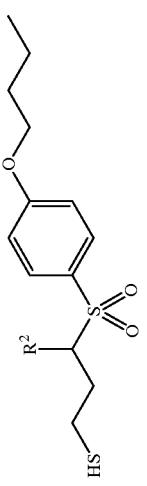
—R²
| —R² |
|---|
| —CH²CH(CH₃)₂ |
| —CH₂CF₃ |
| —CH₂CH₂OCH₃ |
| —CH₂CH₂OH |
| —CH₂CO₂H |
| —CH₂CH₂CO₂H |
| —CH₂CH₂CH₂CO₂H |
| —CH₂CH₂CH₂CH₂CO₂H |
| —CH₂CH₂CH₂CH₂CH₂CO₂H |
  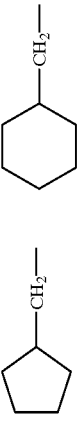 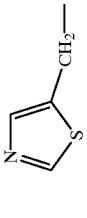
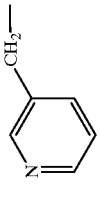 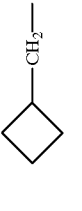 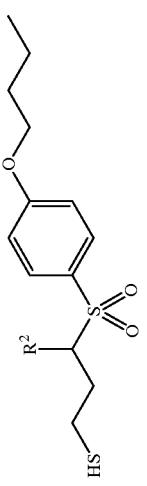
  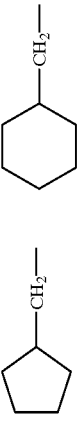 
 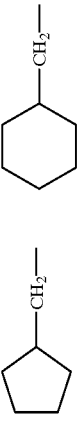

TABLE 19
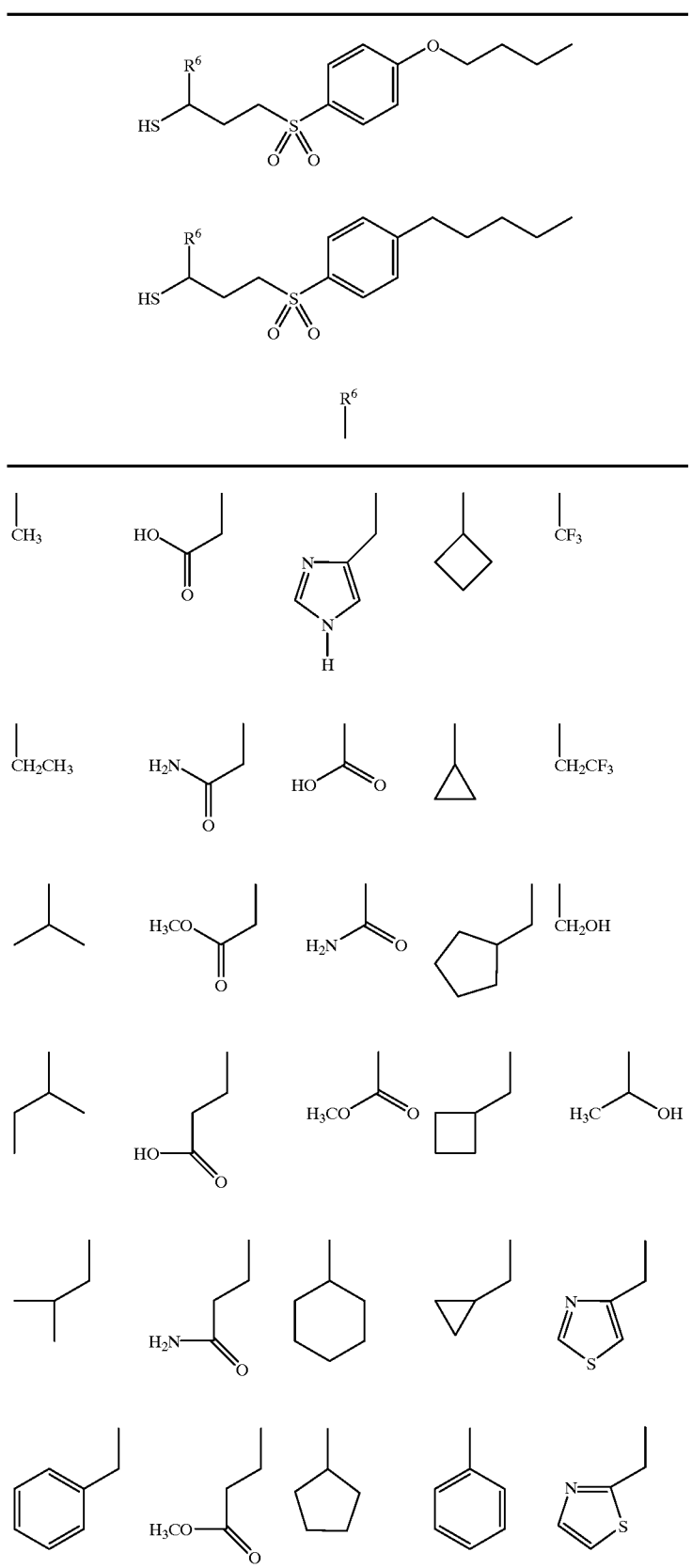

TABLE 19-continued
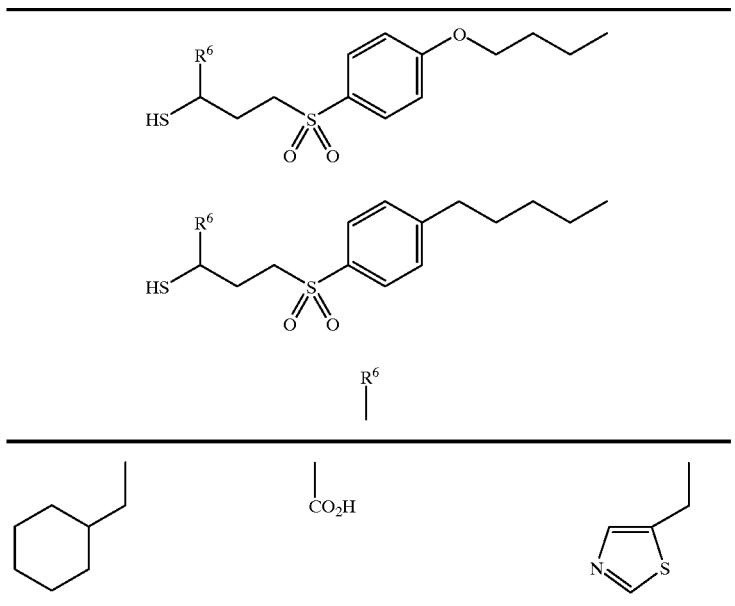
TBLE 20
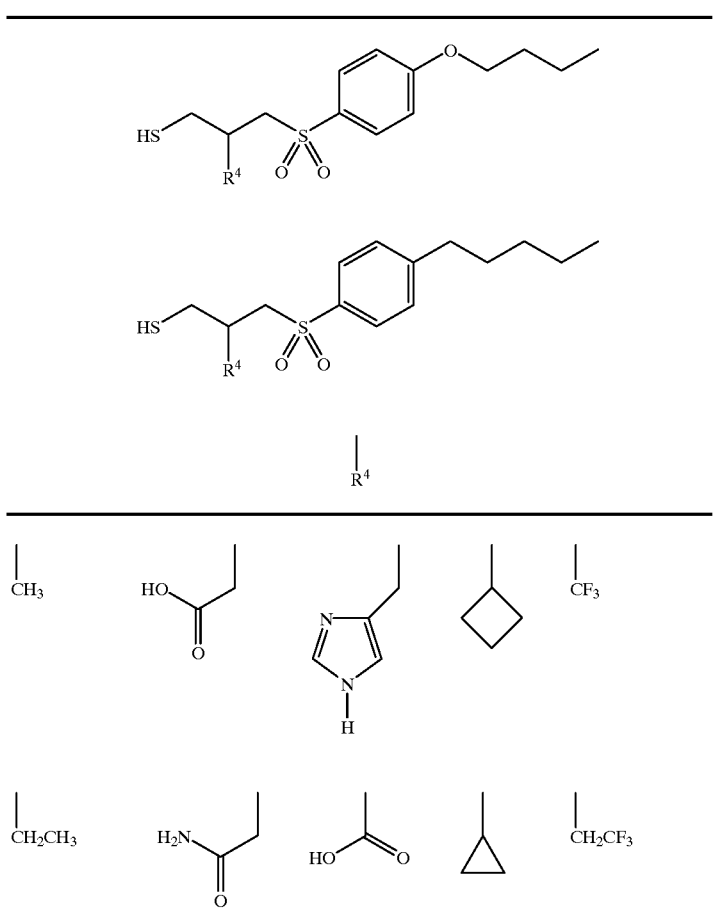

TBLE 20-continued
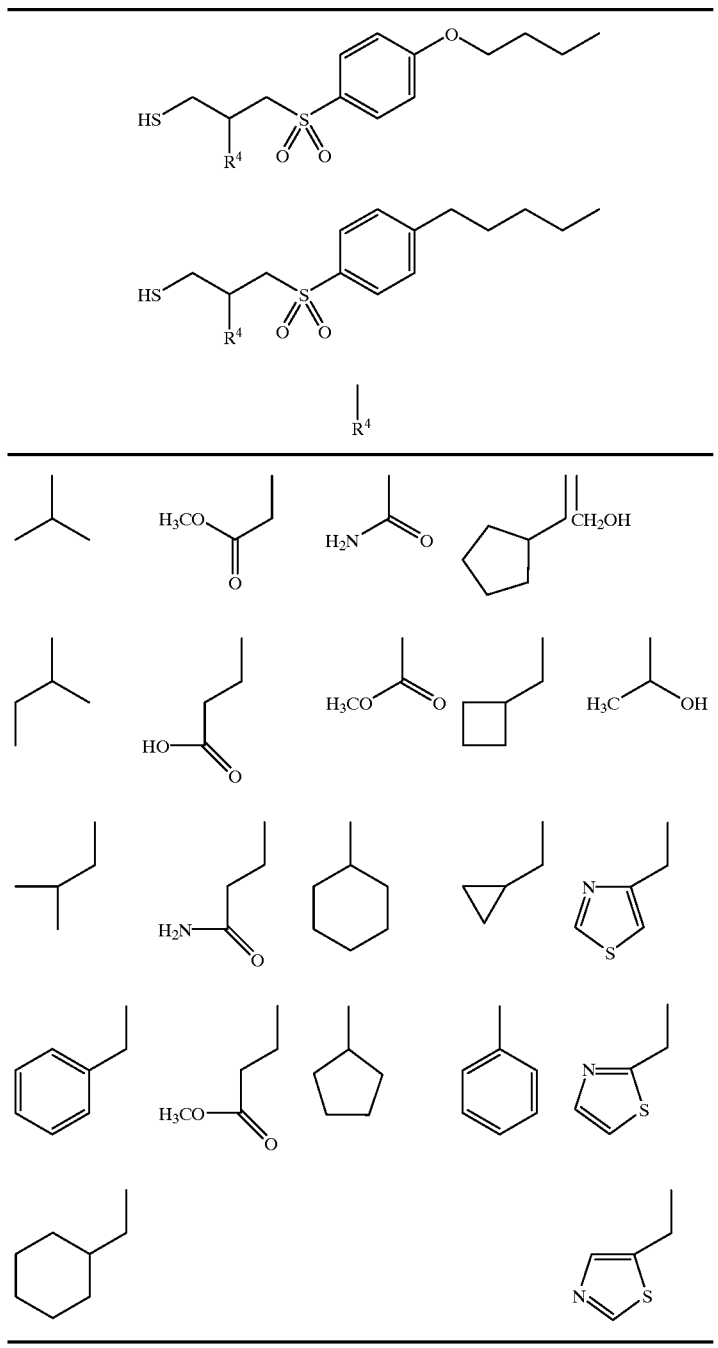

TABLE 21
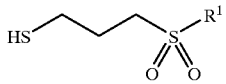
—R¹
| 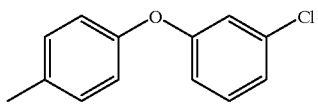 | 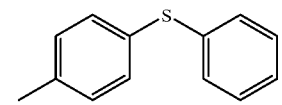 | 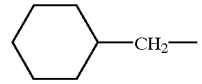 |
| 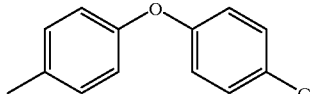 | 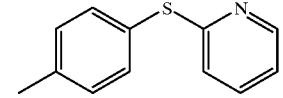 | 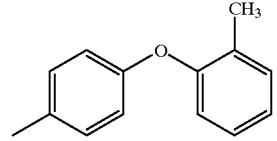 |
| 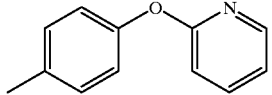 | 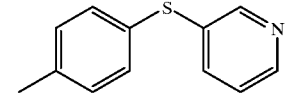 | 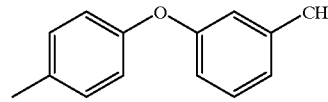 |
| 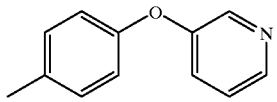 | 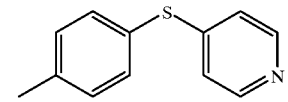 | 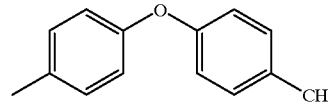 |
| 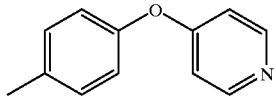 | 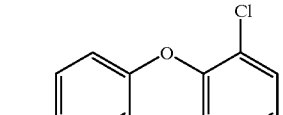 | 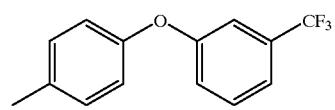 |
| 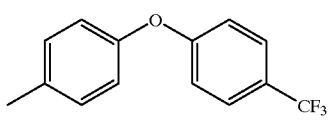 | | |

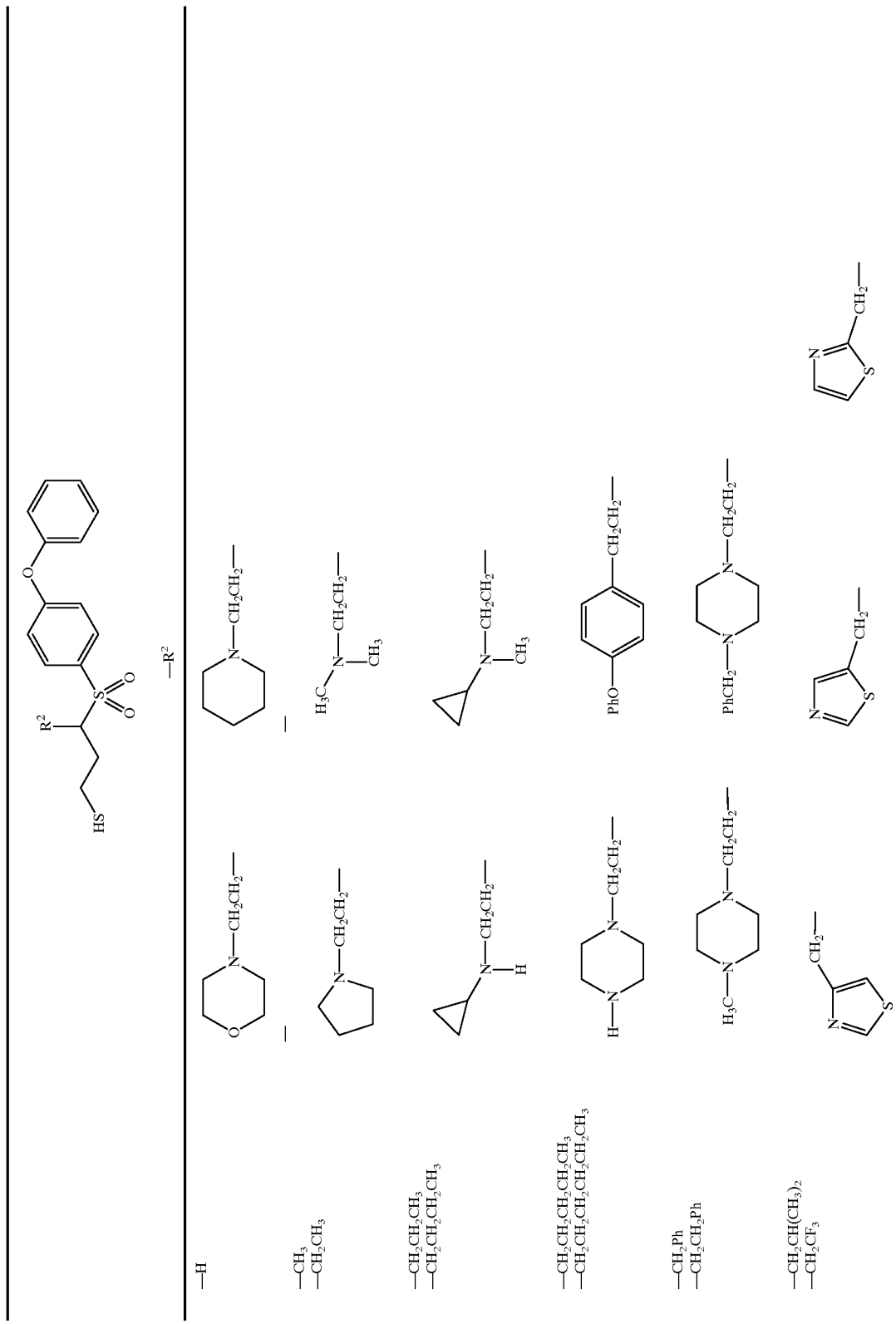

TABLE 22-continued
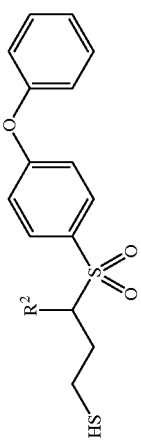
—R²
| | | | |
|---|---|---|---|
| —CH₂CH₂OCH₃ —CH₂CH₂OH | —CH₂CO₂H —CH₂CH₂CO₂H | —CH₂CH₂CH₂CO₂H —CH₂CH₂CH₂CH₂CO₂H | —CH₂CH₂CH₂CH₂CH₂CO₂H |

TABLE 23
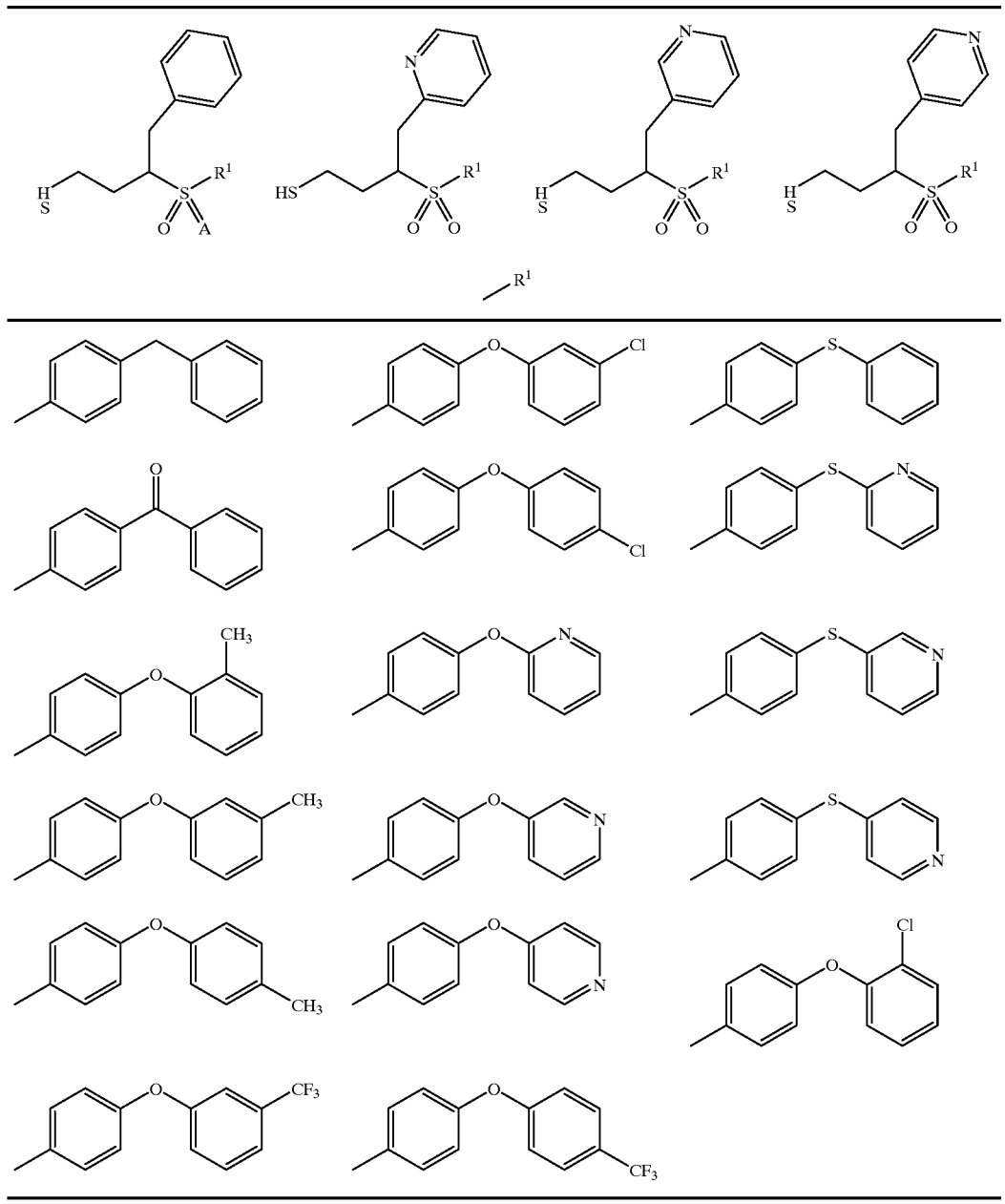

TABLE 24
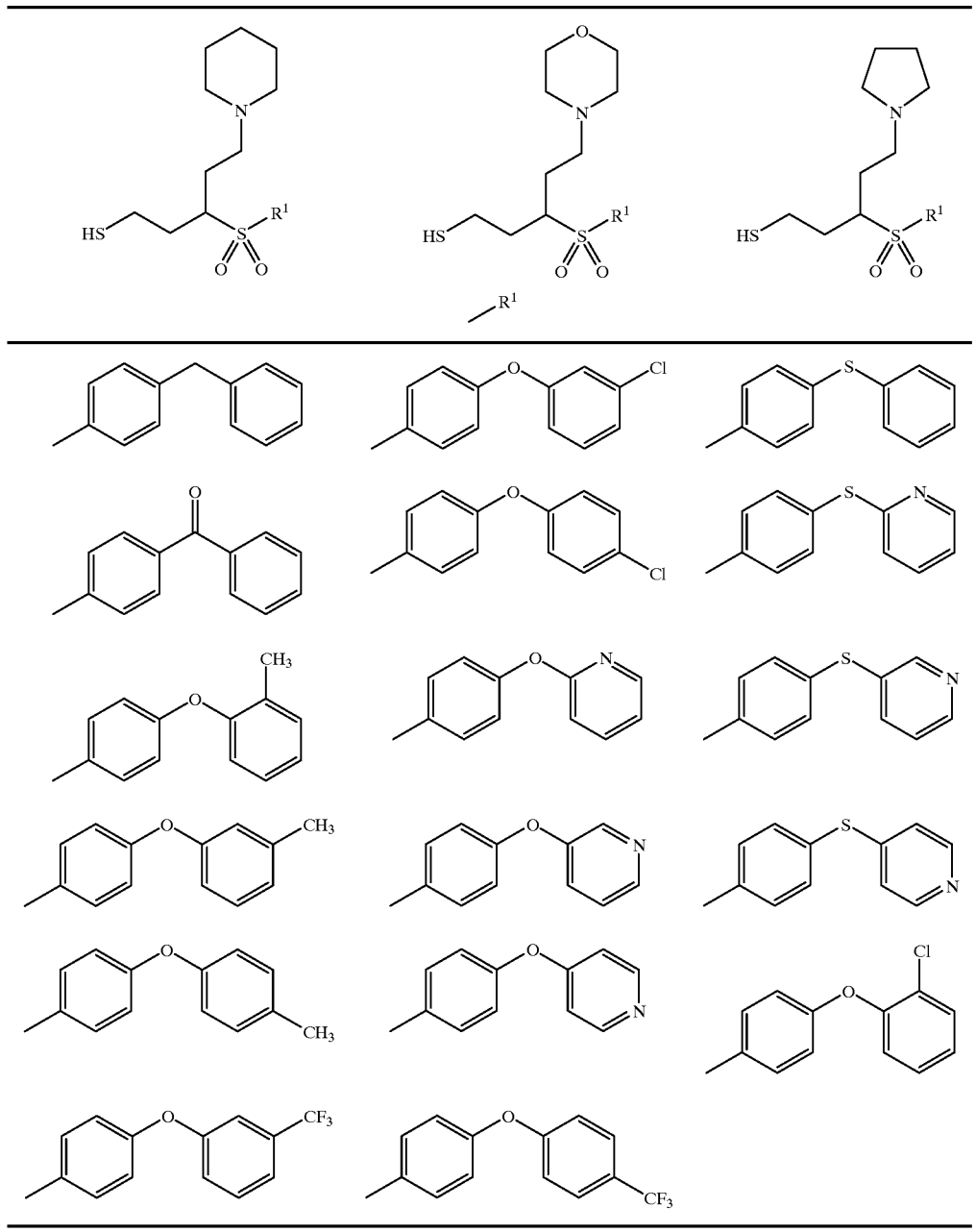

TABLE 25
| | —R² | |
|---|---|---|
| —H | 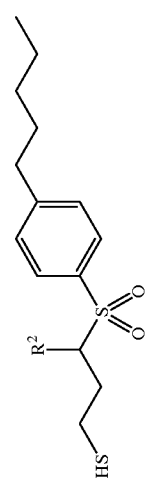 | 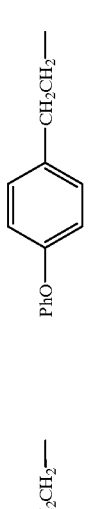 |
| —CH₃ | | |
| —CH₂CH₃ |  |  |
| —CH₂CH₂CH₃ | | |
| —CH₂CH₂CH₂CH₃ |  |  |
| —CH₂CH₂CH₂CH₂CH₃ | | |
| —CH₂CH₂CH₂CH₂CH₂CH₃ |  |  |
| —CH₂Ph | | |
| —CH₂CH₂Ph |  |  |

TABLE 25-continued

[Structure: R² group attached to CH(R²)-CH₂-CH₂-SH with sulfonyl linked to 4-pentylphenyl]

—R²

| 4-thiazolyl-CH₂— | 2-thiazolyl-CH₂— | |
| 2-pyridyl-CH₂— | 3-pyridyl-CH₂— | 4-pyridyl-CH₂— |
| cyclopropyl-CH₂— | cyclobutyl-CH₂— | cyclopentyl-CH₂— cyclohexyl-CH₂— |
| 4-methoxyphenyl-CH₂CH₂— | HO₂C-CH(CH₂Ph)-CH₂— | |

—CH₂CH(CH₃)₂
—CH₂CF₃

—CH₂CH₂OCH₃
—CH₂CH₂OH

—CH₂CO₂H
—CH₂CH₂CO₂H

—CH₂CH₂CH₂CO₂H
—CH₂CH₂CH₂CH₂CO₂H

—CH₂CH₂CH₂CH₂CH₂CO₂H

TABLE 26
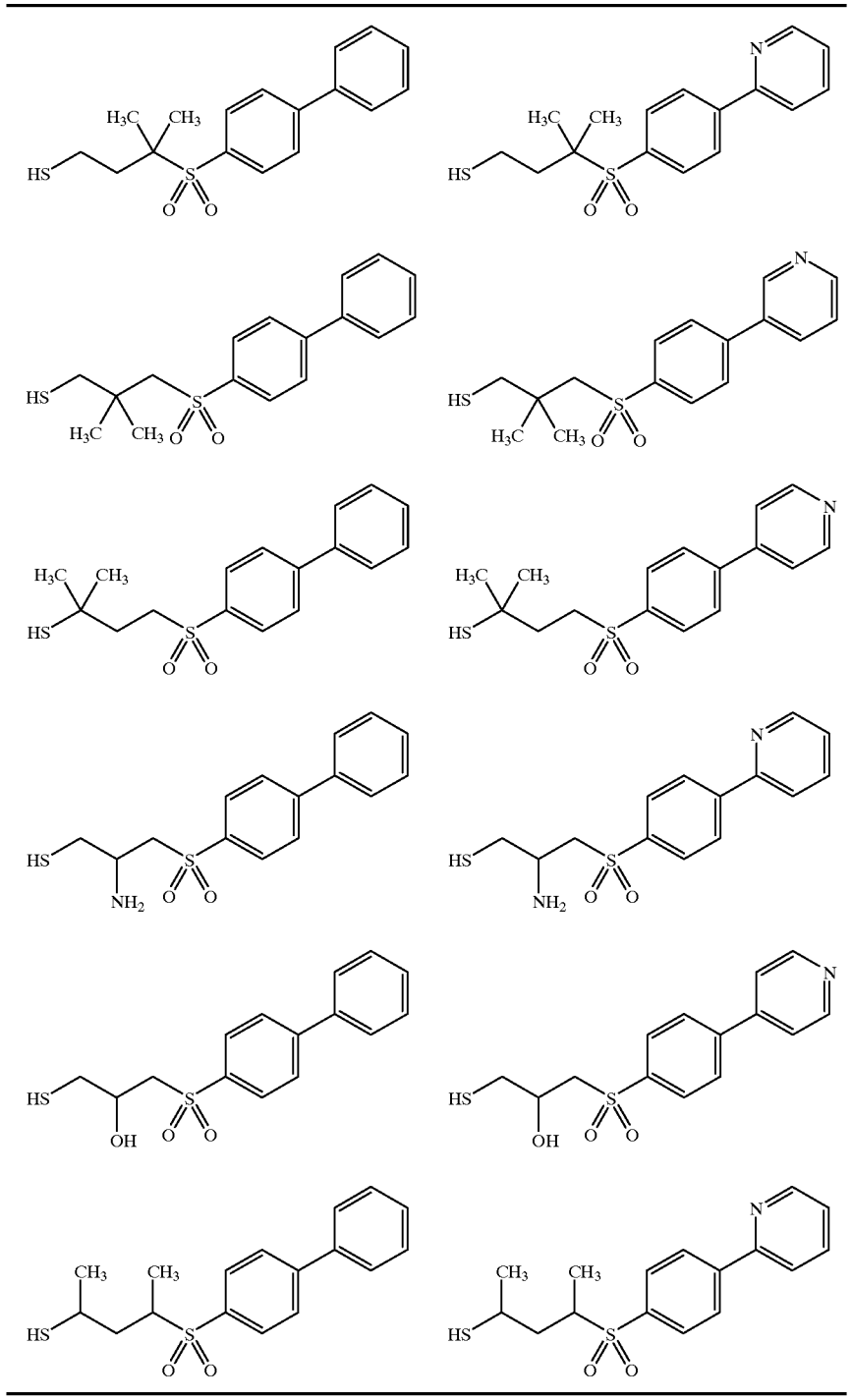

TABLE 27
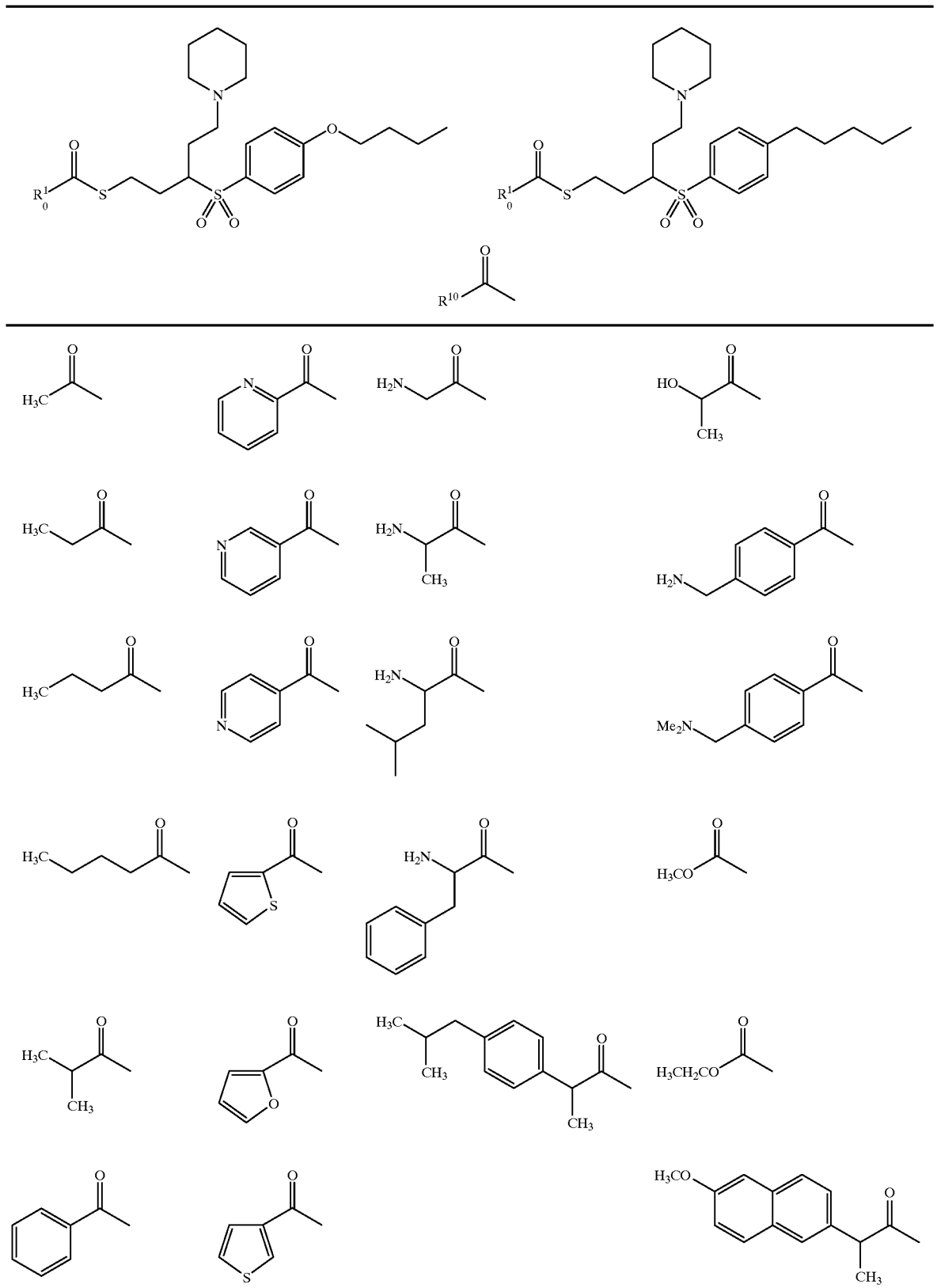

TABLE 27-continued
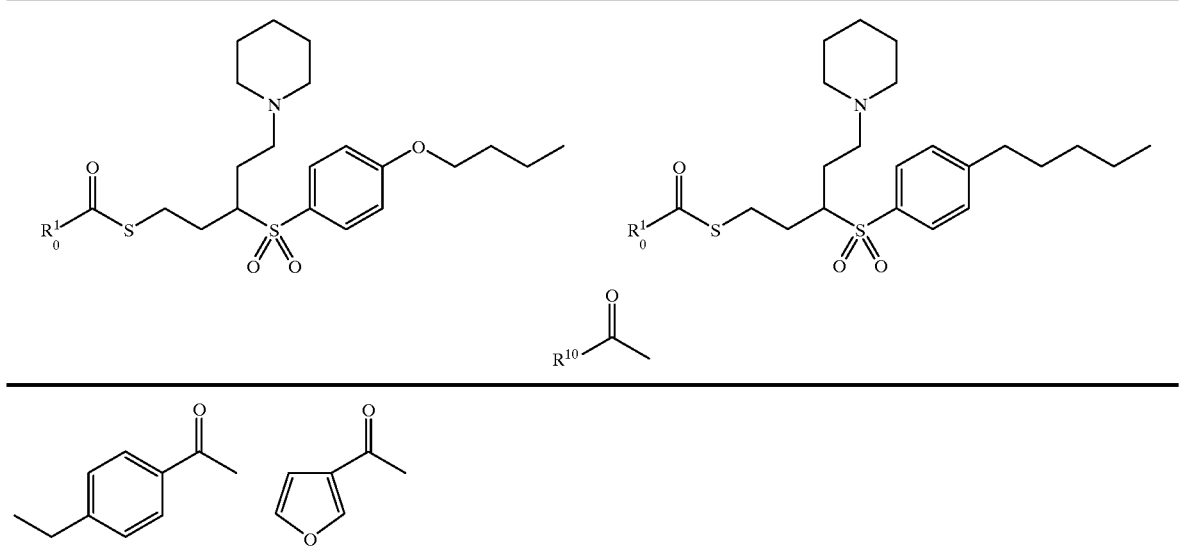
25
TABLE 28
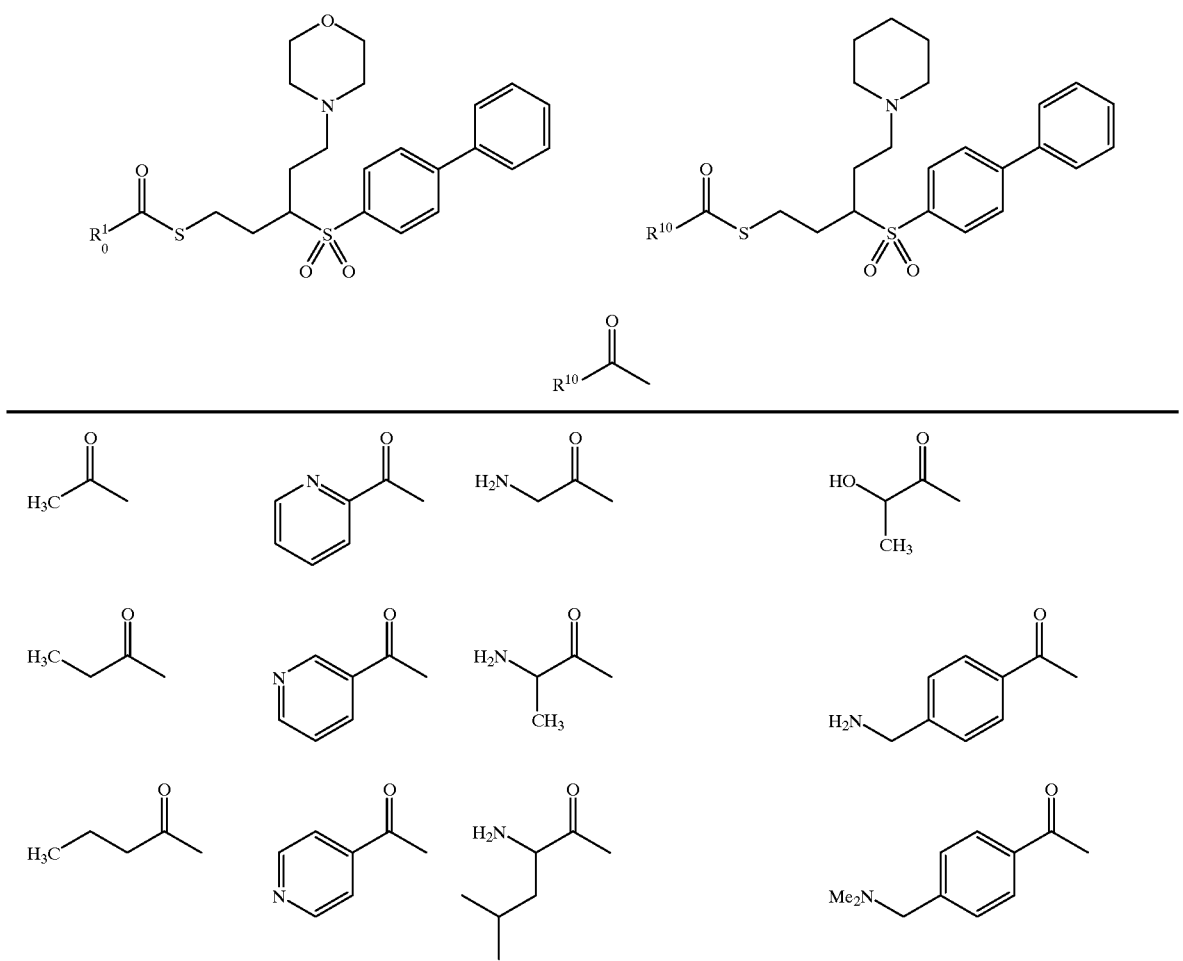

TABLE 28-continued
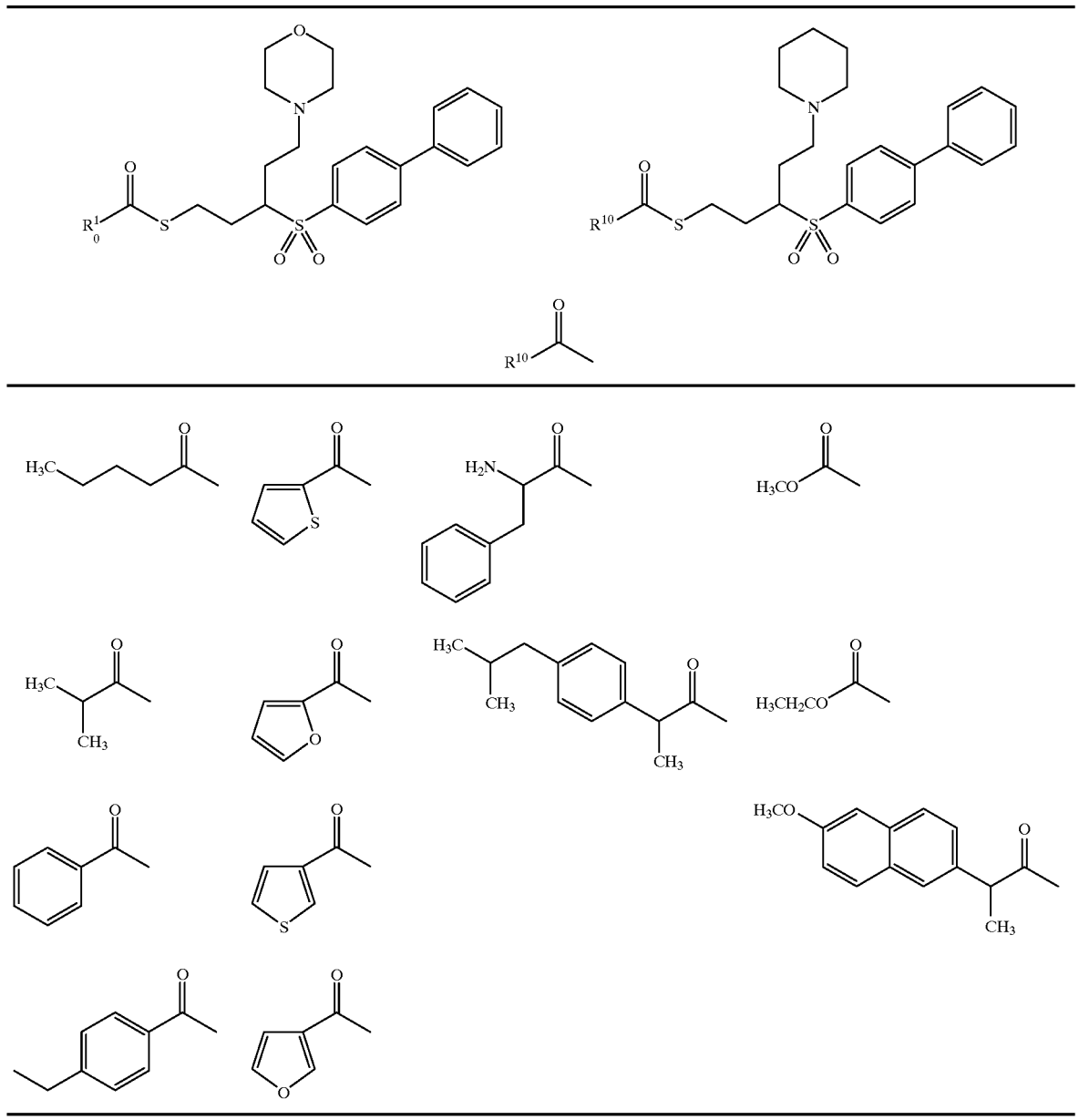

TABLE 29
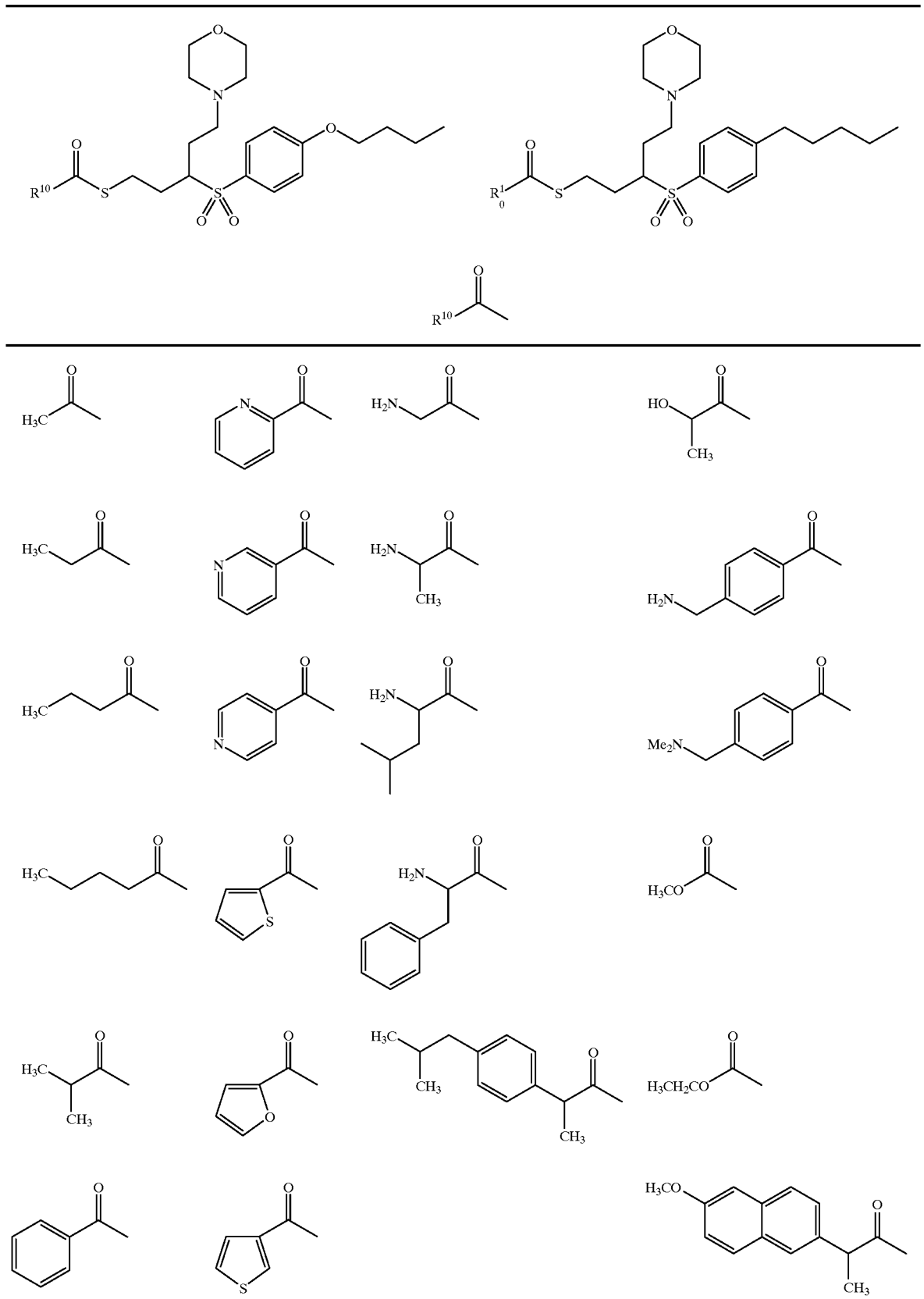

TABLE 29-continued
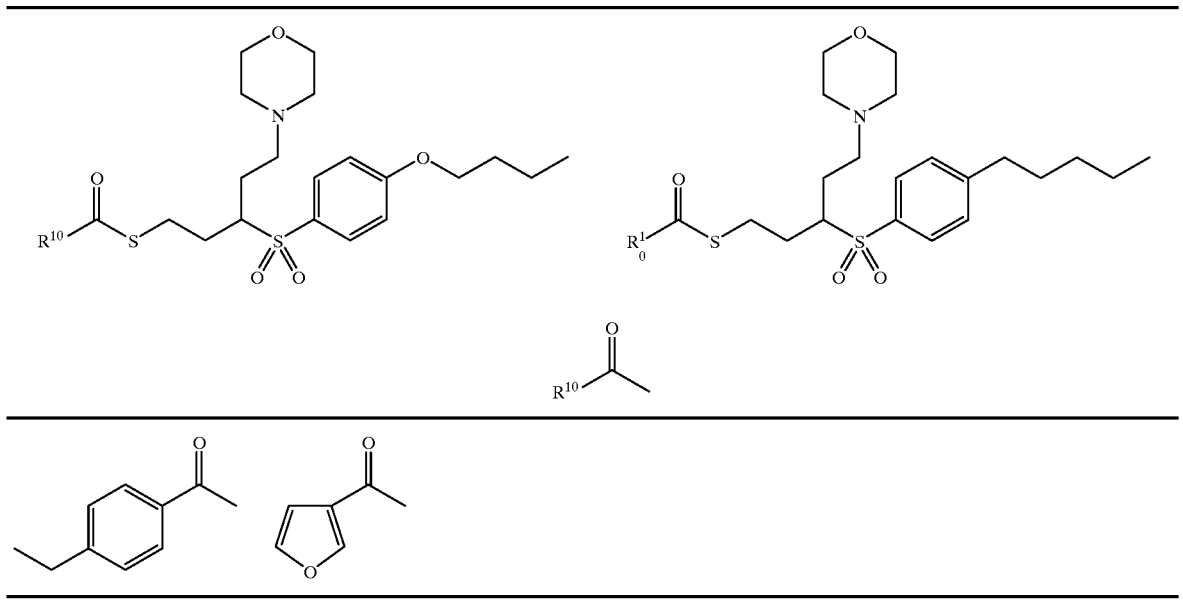
TABLE 30

TABLE 30-continued
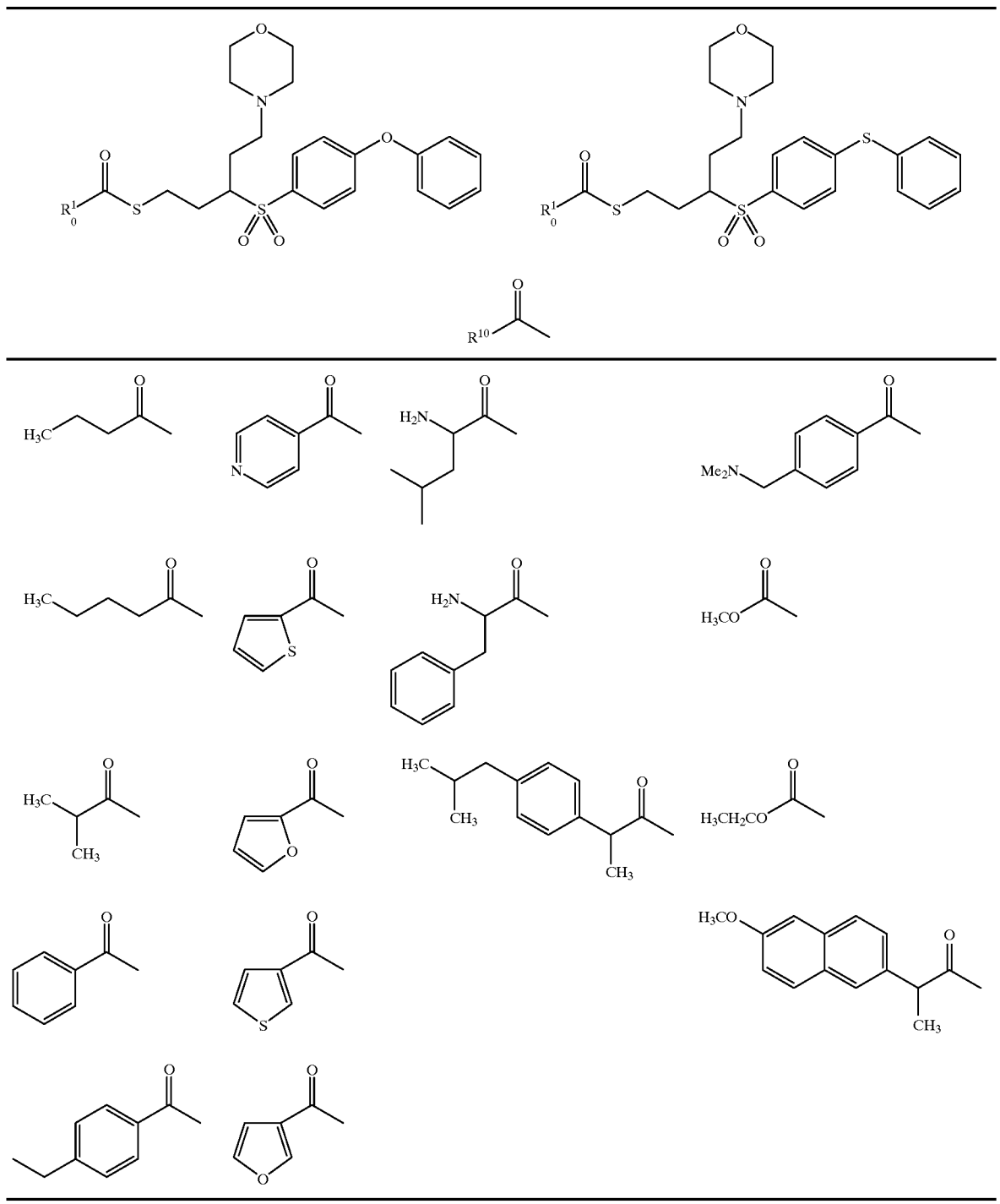

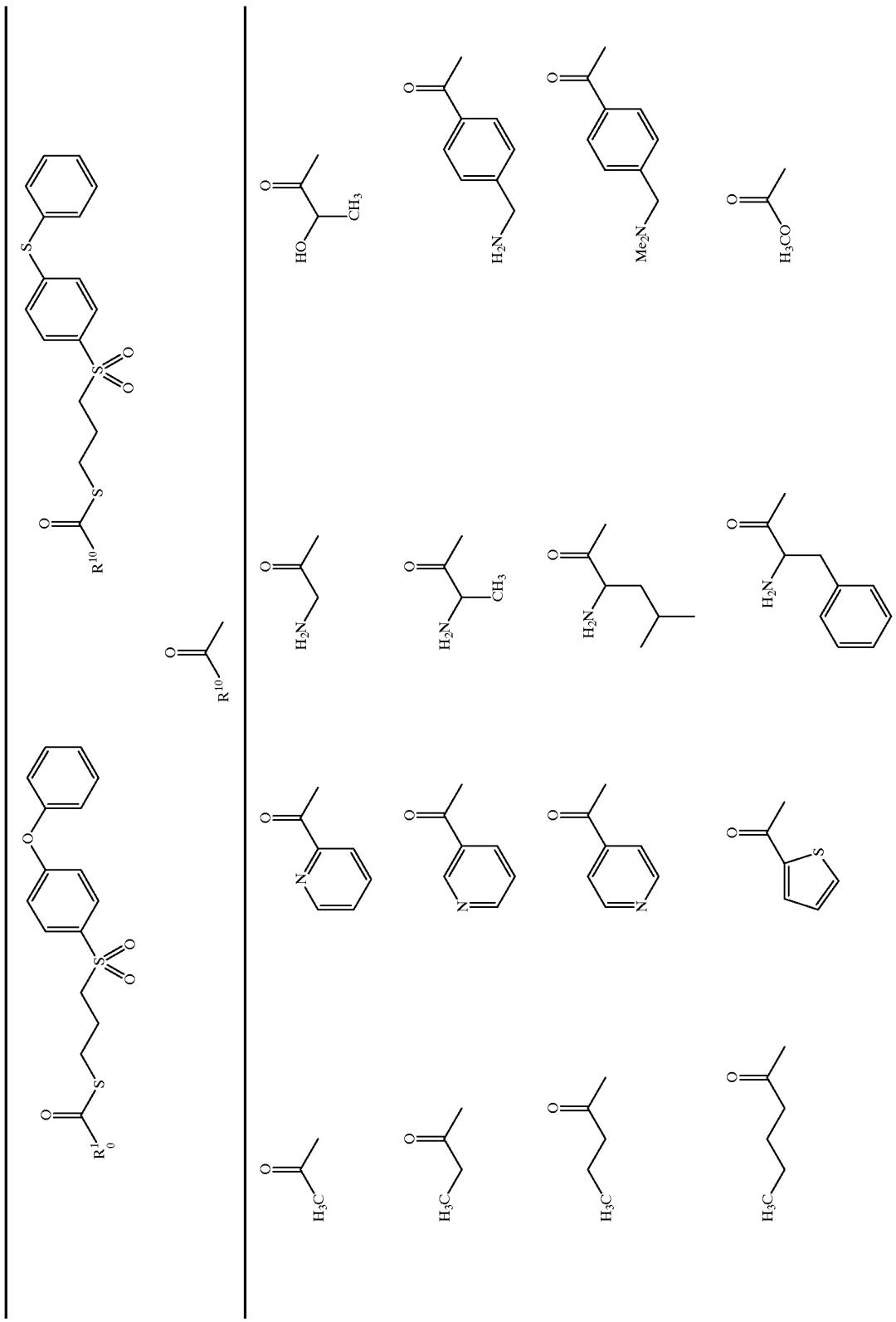
TABLE 31

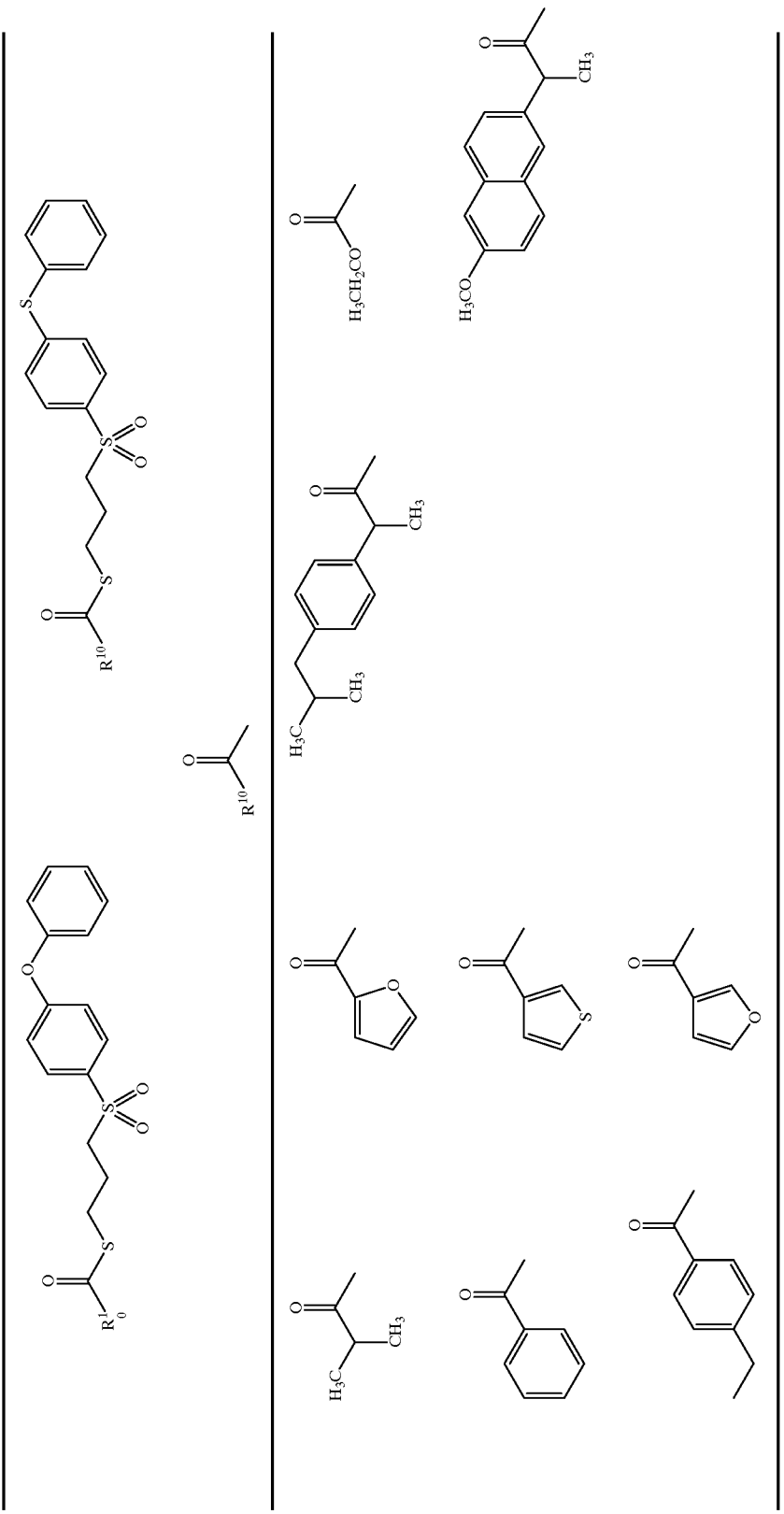

TABLE 32
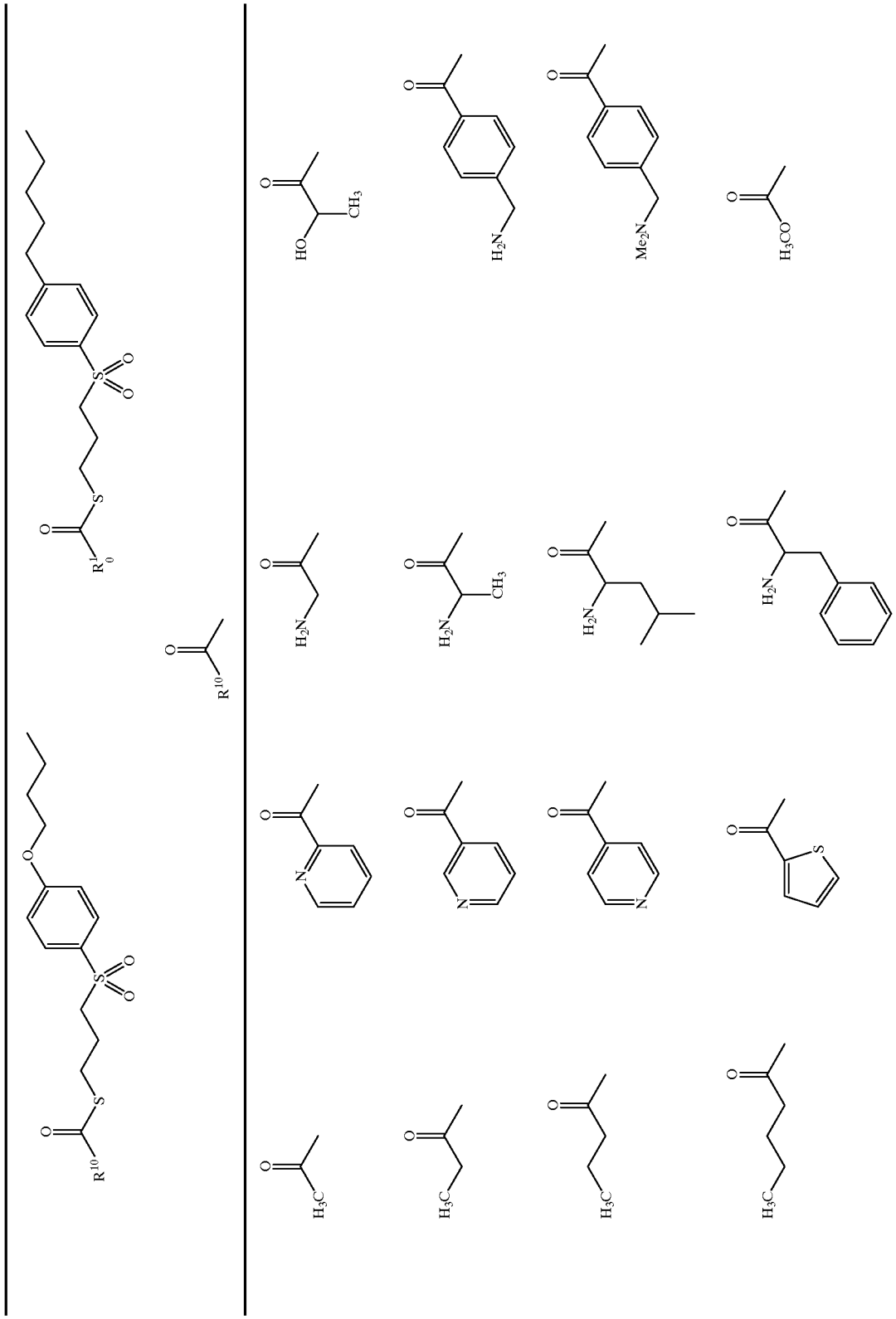

TABLE 32-continued
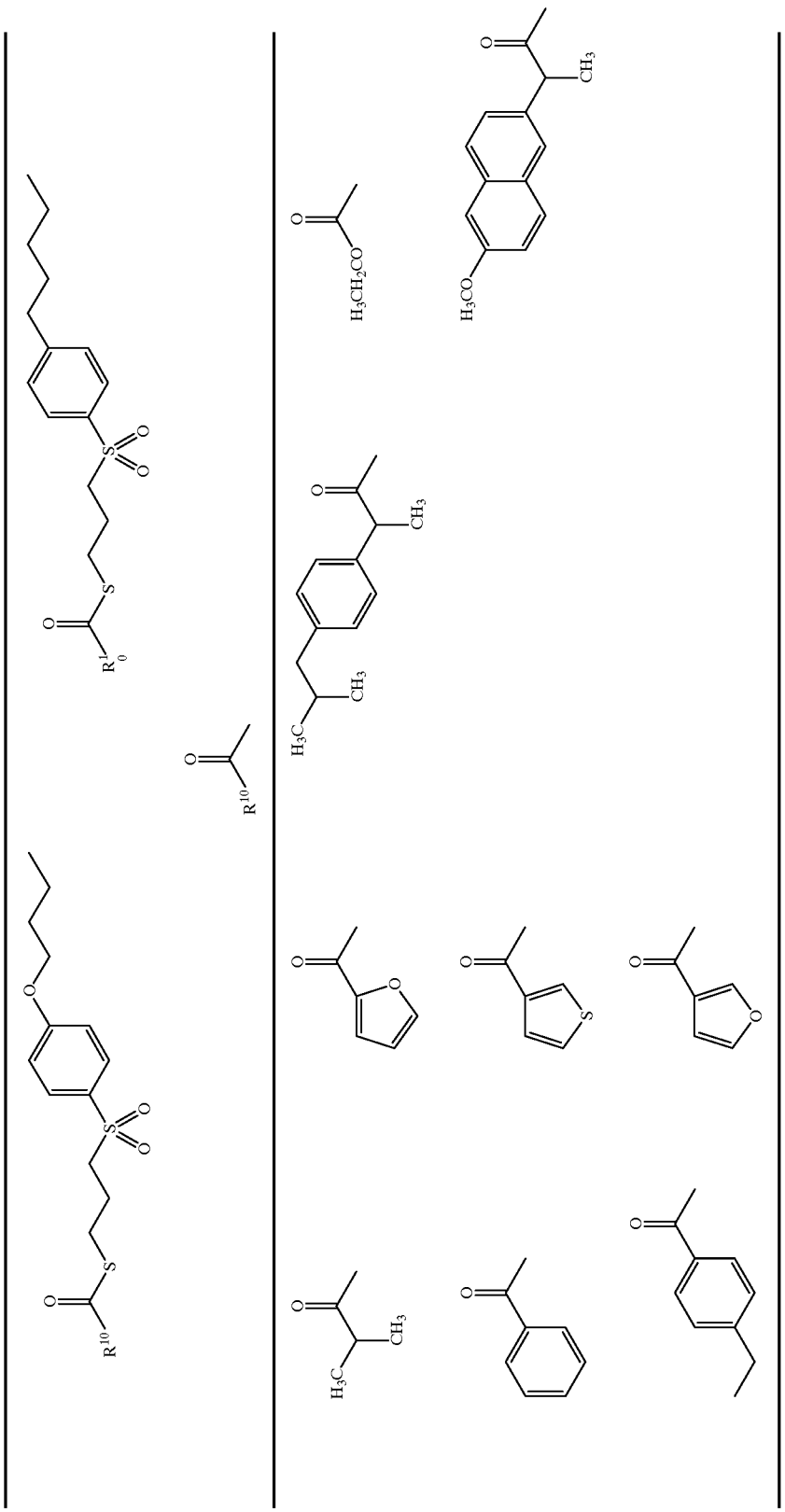

TABLE 33

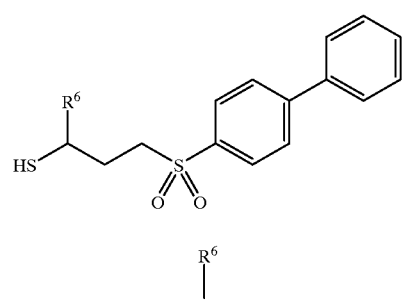

| R⁶ | | | | | |
|---|---|---|---|---|---|
| CH₃ | HO–CH₂–C(O)– | imidazol-4-ylmethyl | cyclobutyl | CF₃ | CO₂H |
| CH₂CH₃ | H₂N–C(O)–CH₂– | HO–CH₂–C(O)– (HOCH-) | cyclopropyl | CH₂CF₃ | |
| isobutyl | H₃CO–C(O)–CH₂– | H₂N–C(O)– | cyclopentylmethyl | CH₂OH | |
| sec-butyl | HOOC–CH₂CH₂– | H₃CO–C(O)–CH₂– | cyclobutylmethyl | CH(CH₃)OH | |
| isobutyl | H₂N–C(O)–CH₂CH₂– | cyclohexyl | cyclopropylmethyl | thiazol-4-ylmethyl | |
| benzyl | H₃CO–C(O)–CH₂CH₂– | cyclopentyl | phenyl | thiazol-2-ylmethyl | |
| cyclohexylmethyl | | | | thiazol-5-ylmethyl | |

TABLE 34
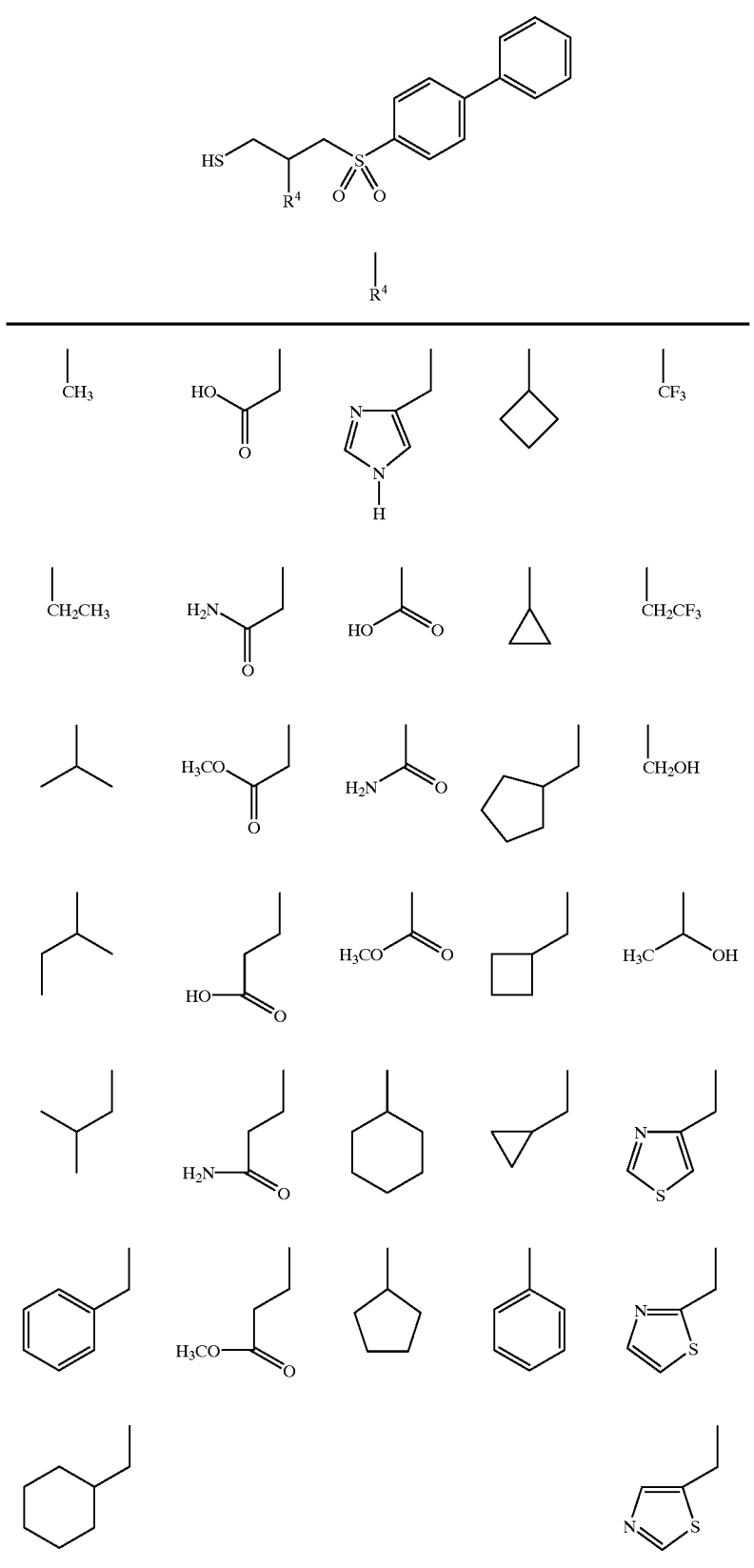

TABLE 35
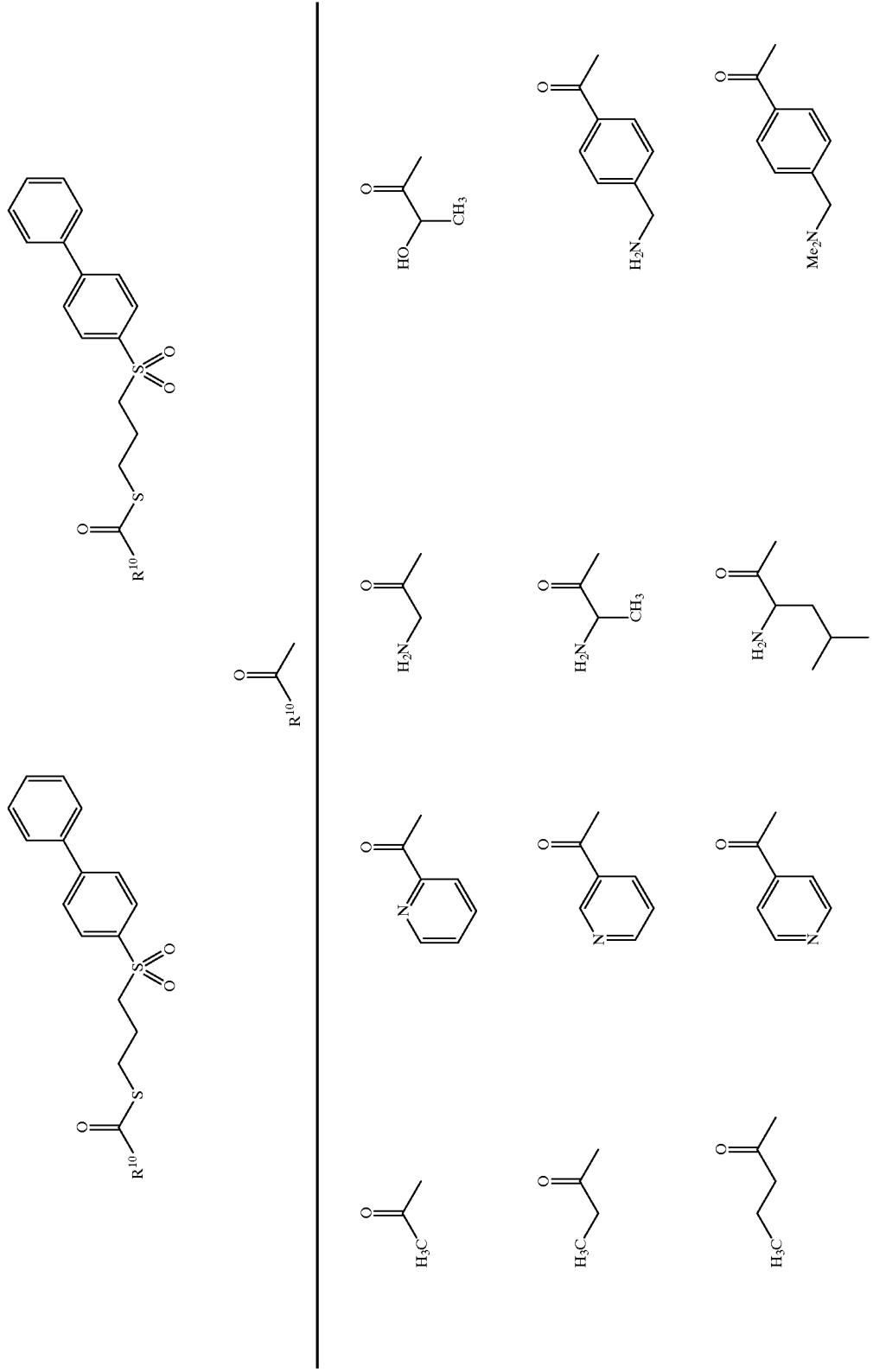

TABLE 35-continued
| 121 | 122 |
|---|---|
|  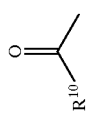 | 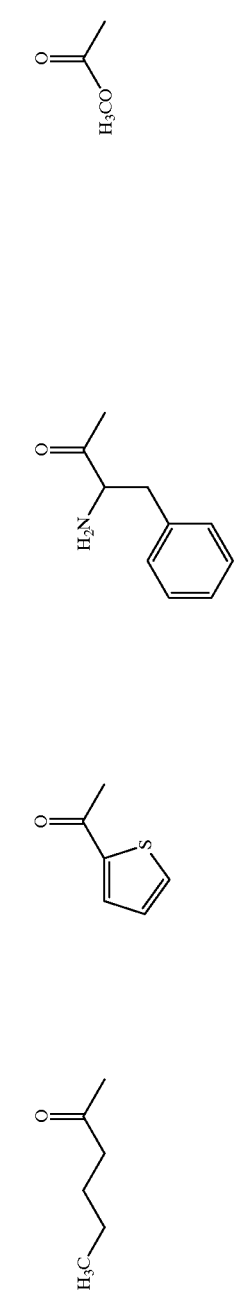  |

TABLE 35-continued
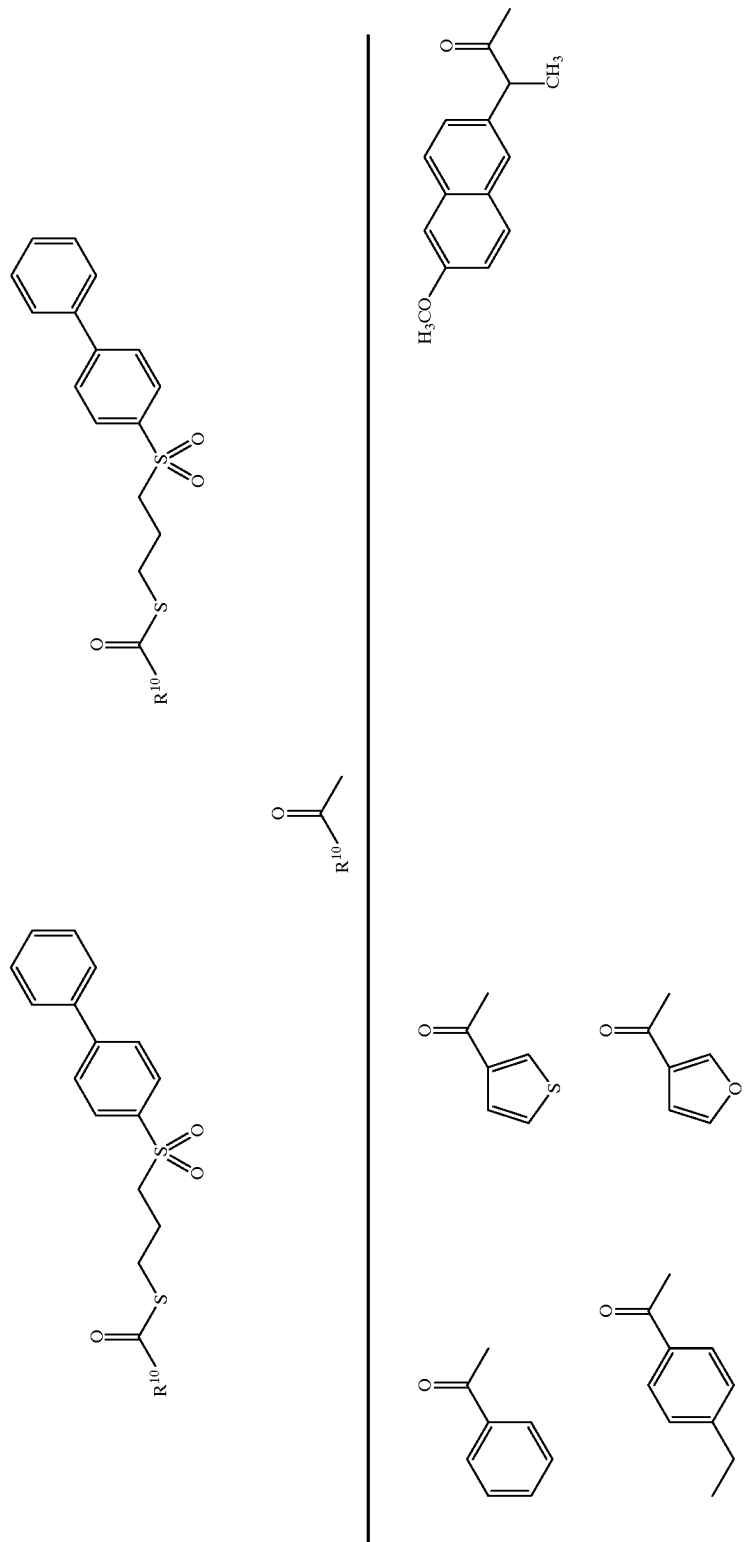

TABLE 36
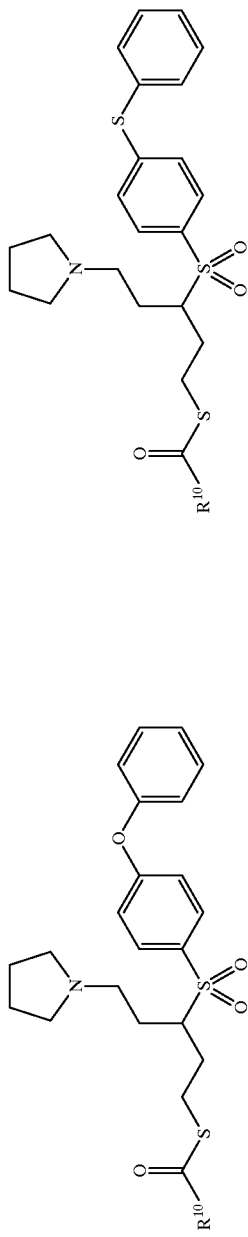
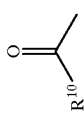
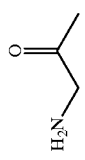
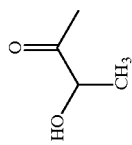
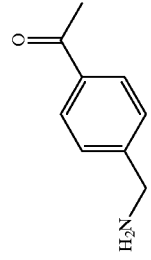
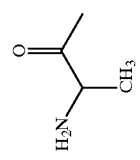
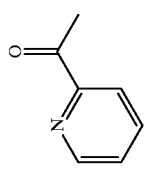
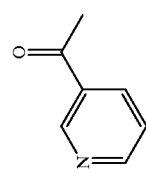
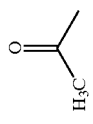

TABLE 36-continued
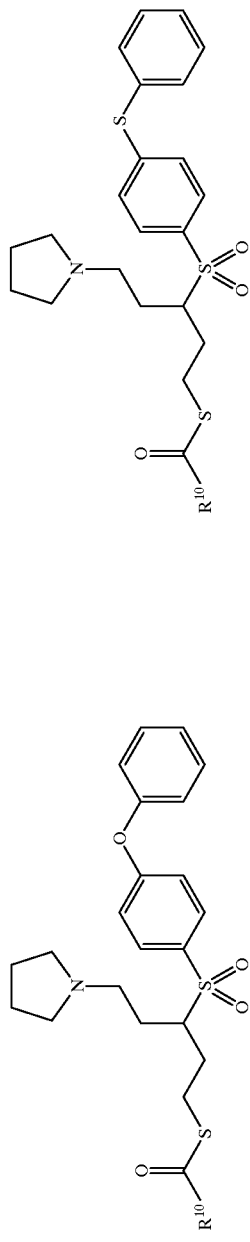
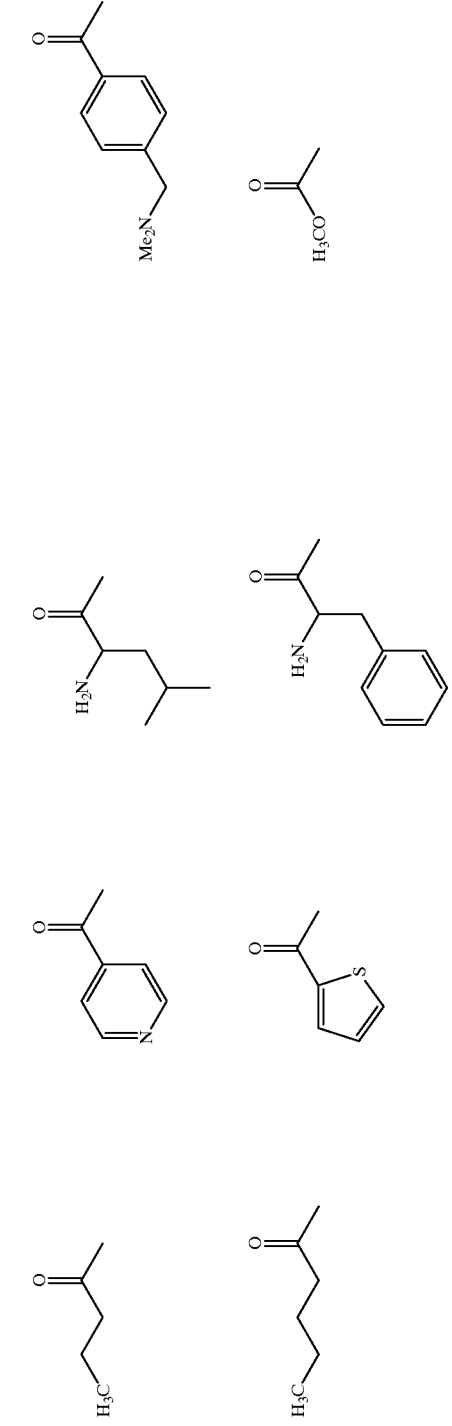

TABLE 36-continued
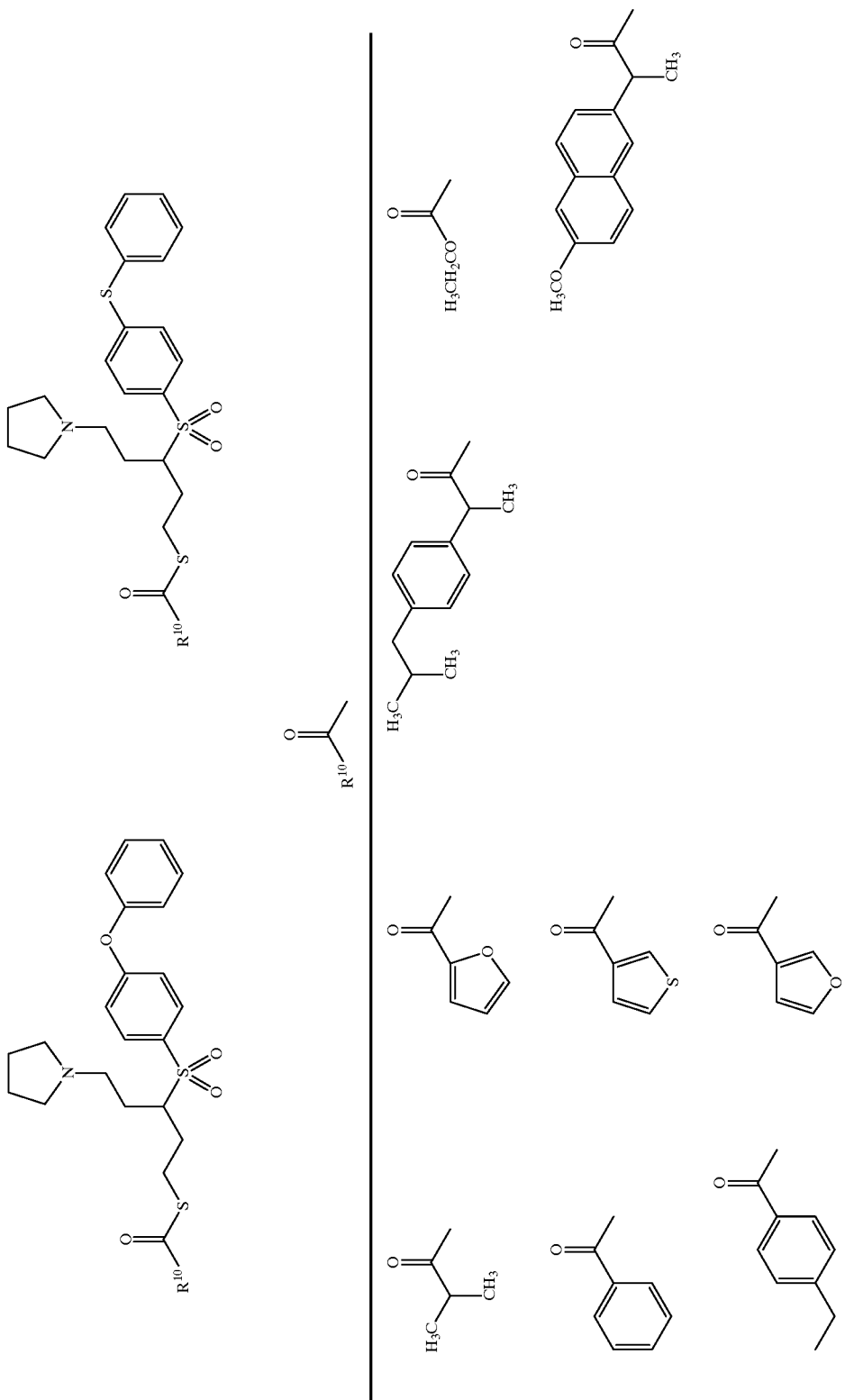

TABLE 37
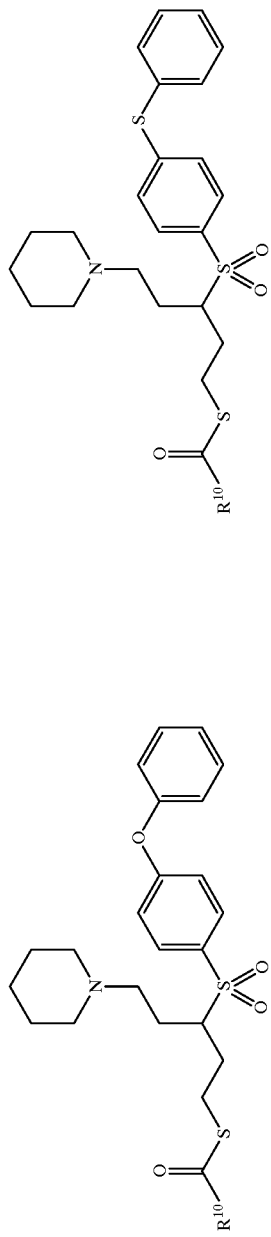
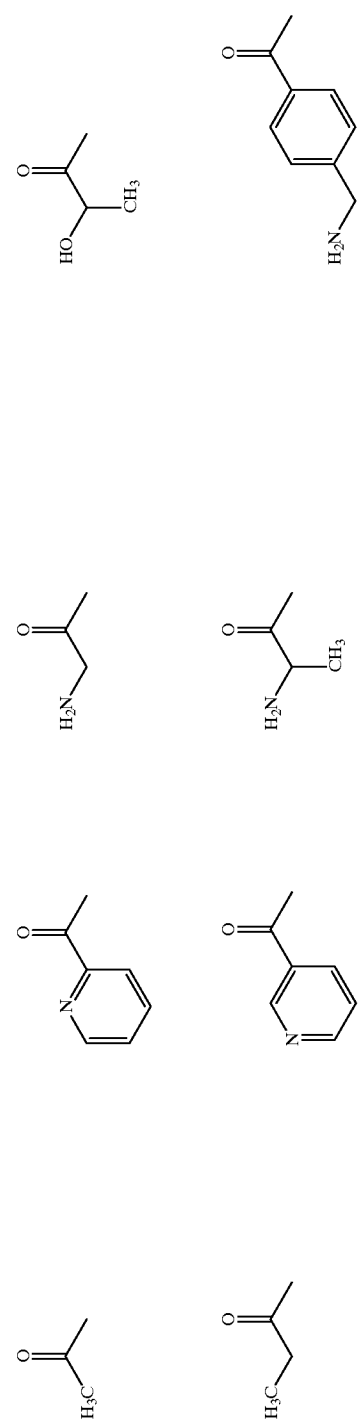

TABLE 37-continued
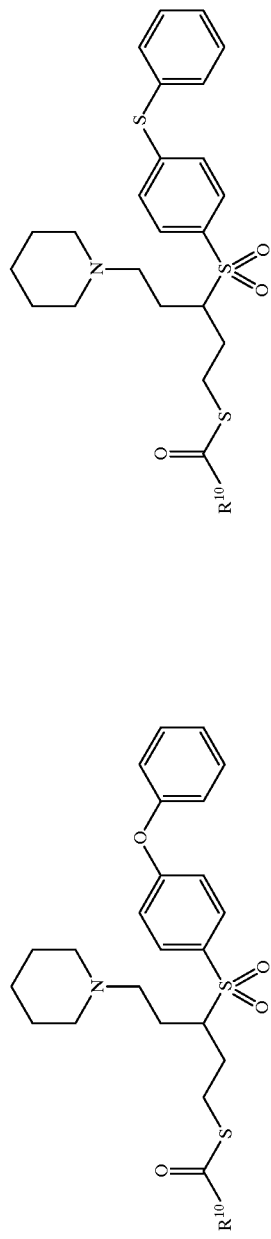
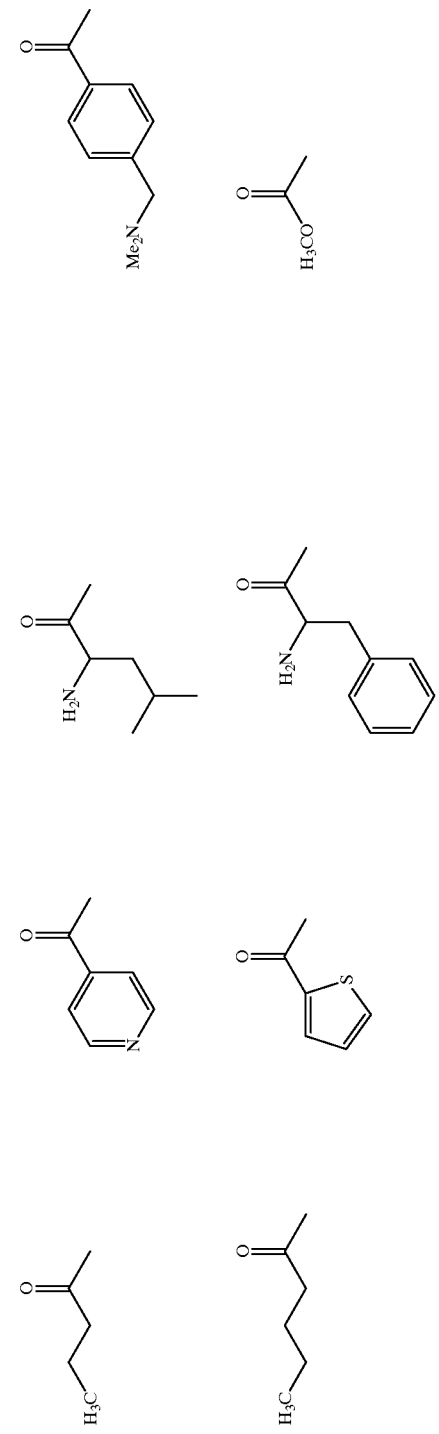

TABLE 37-continued
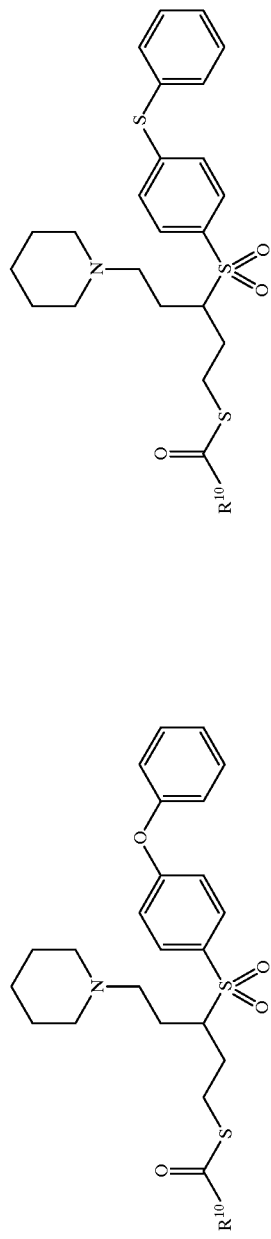
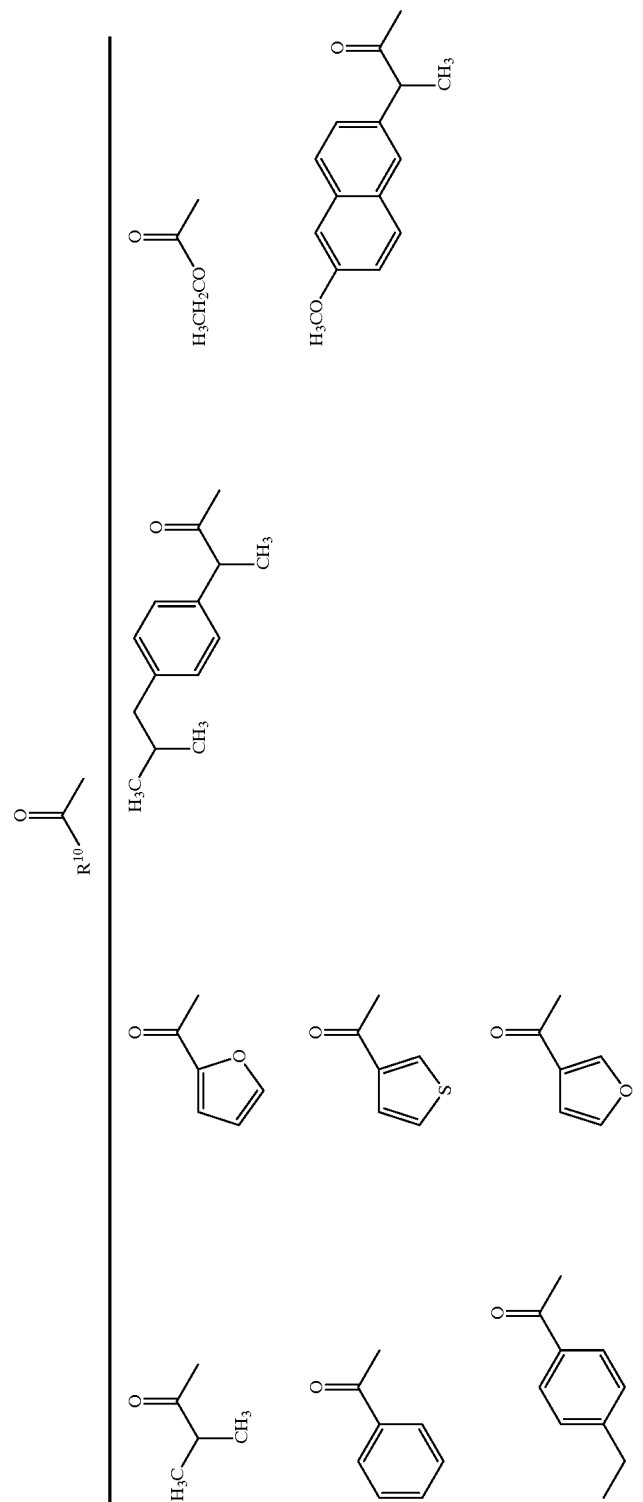

TABLE 38
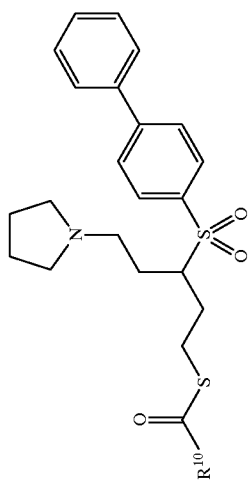 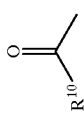
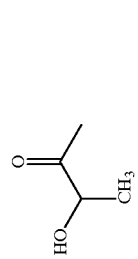 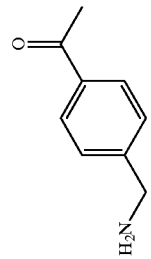
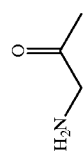 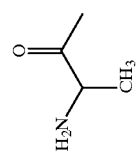
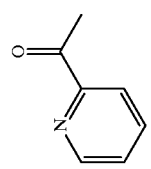 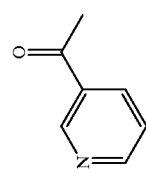
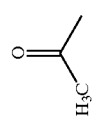 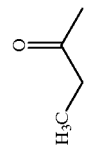

TABLE 38-continued
| | |
|---|---|
| 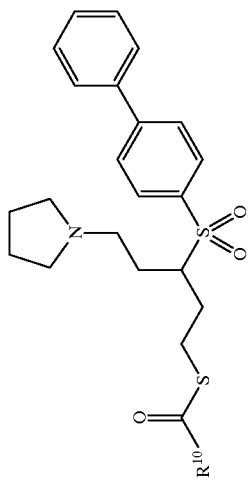 | 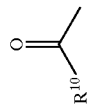 |
| | 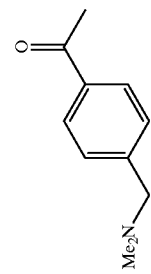 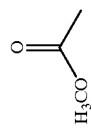 |
| | 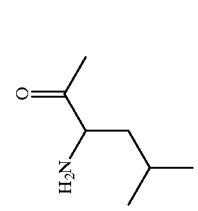 |
| | 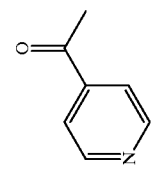 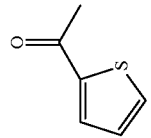 |
| | 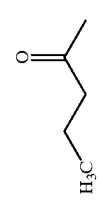  |

TABLE 38-continued
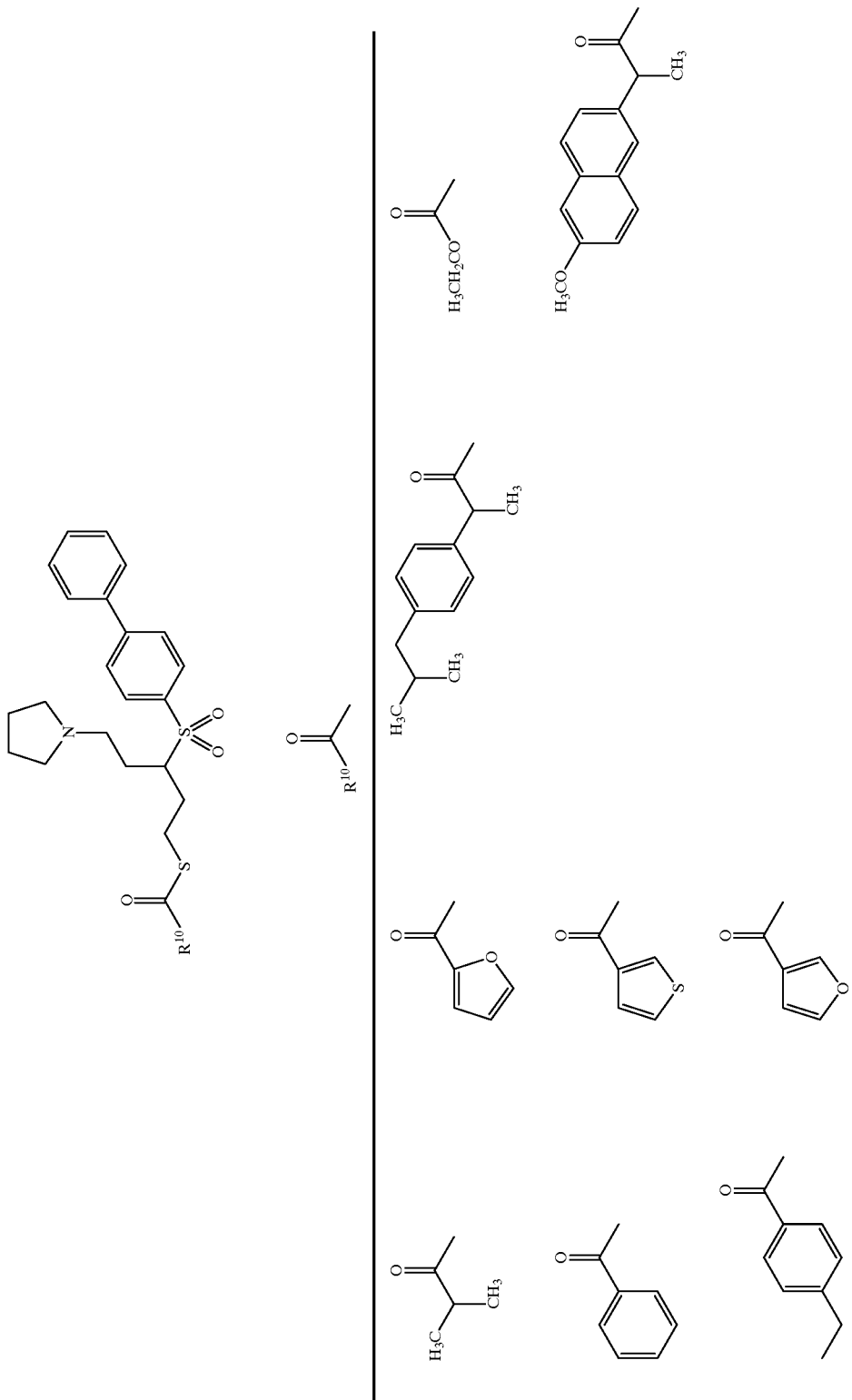

TABLE 39
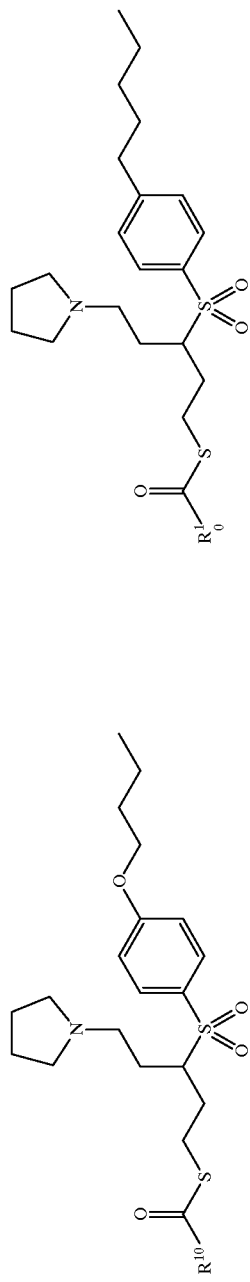
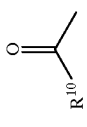
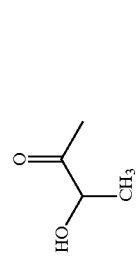
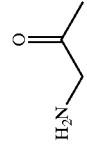
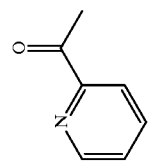
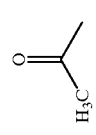
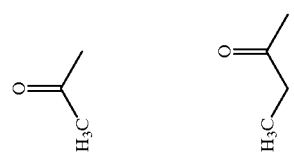

TABLE 39-continued
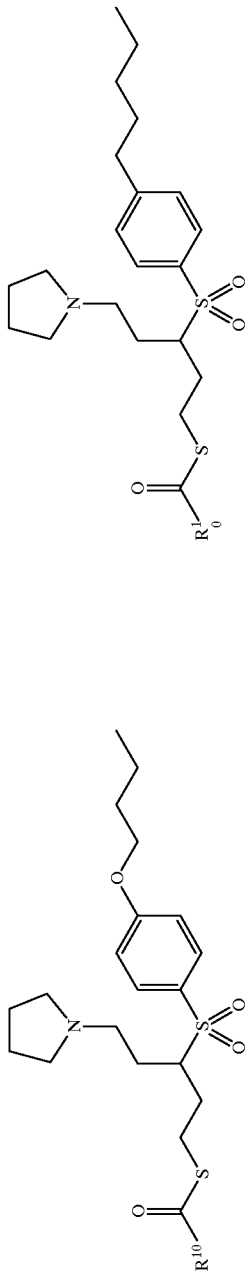
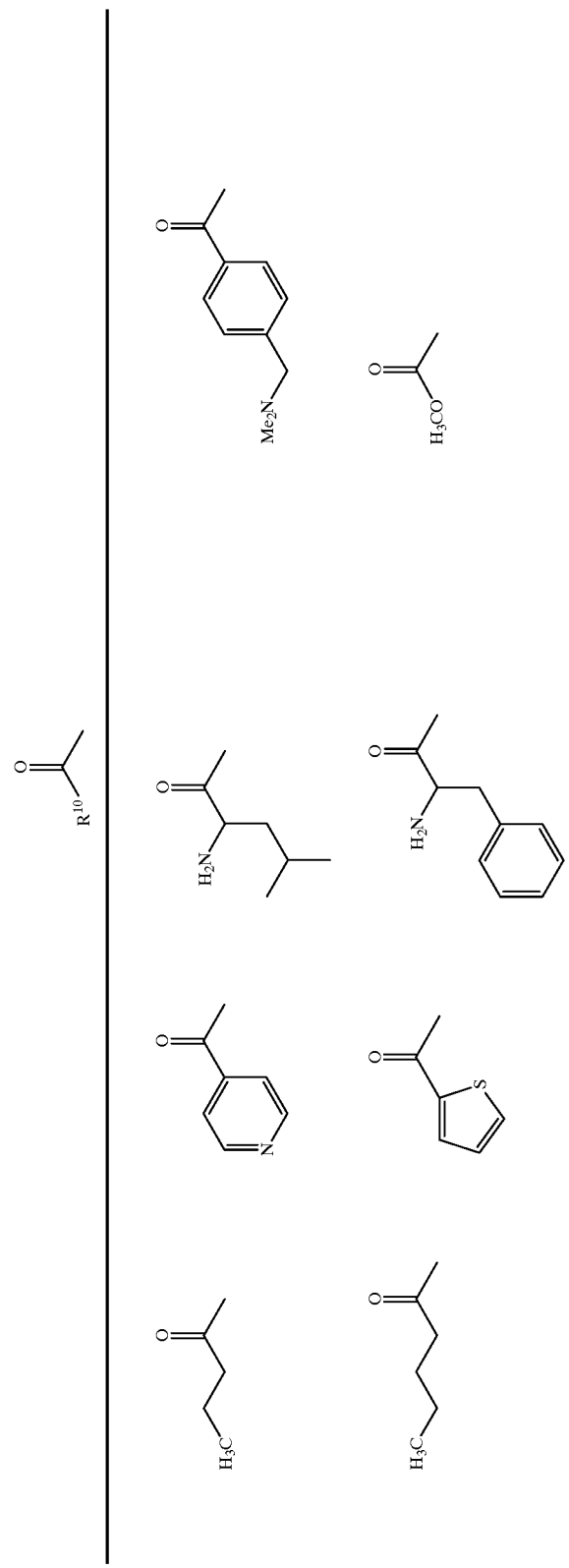

TABLE 39-continued
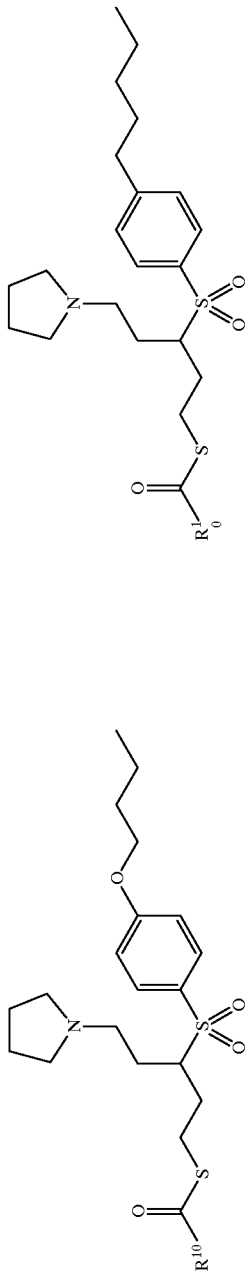
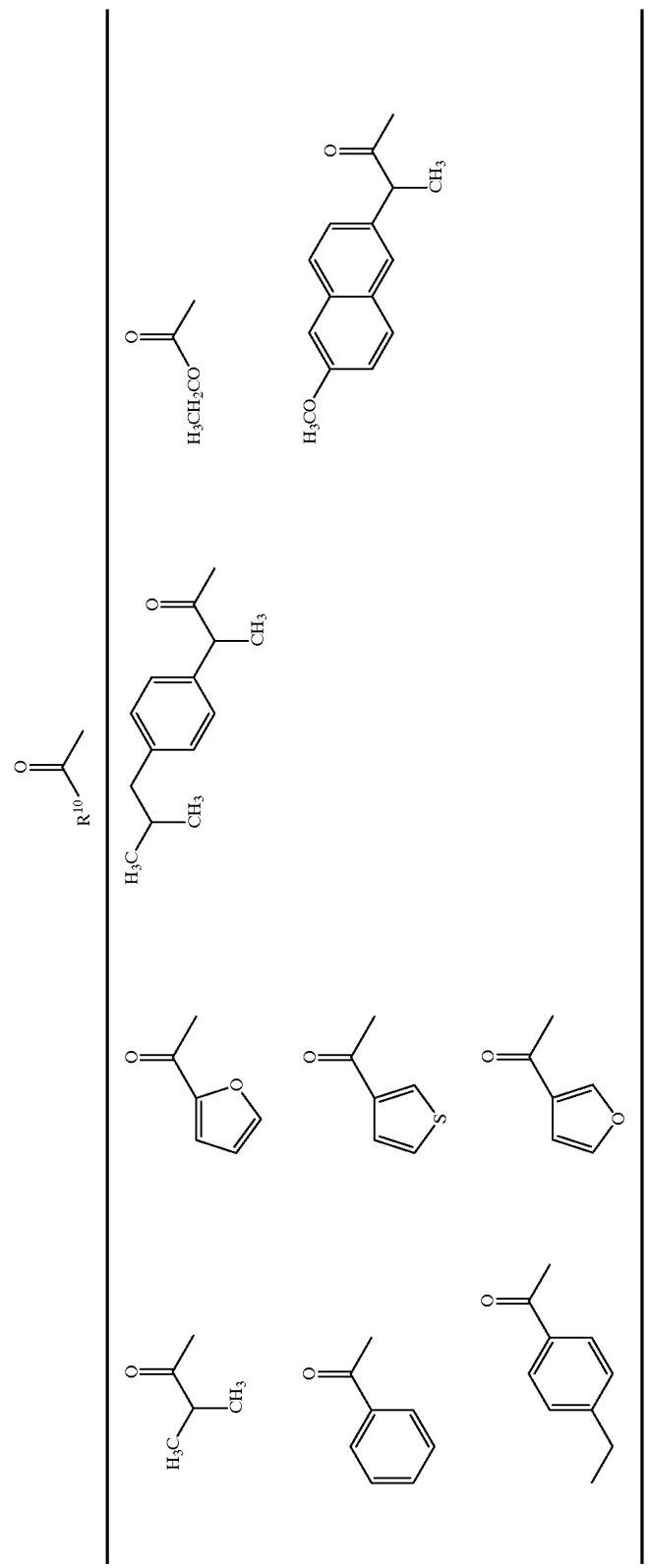

TABLE 40
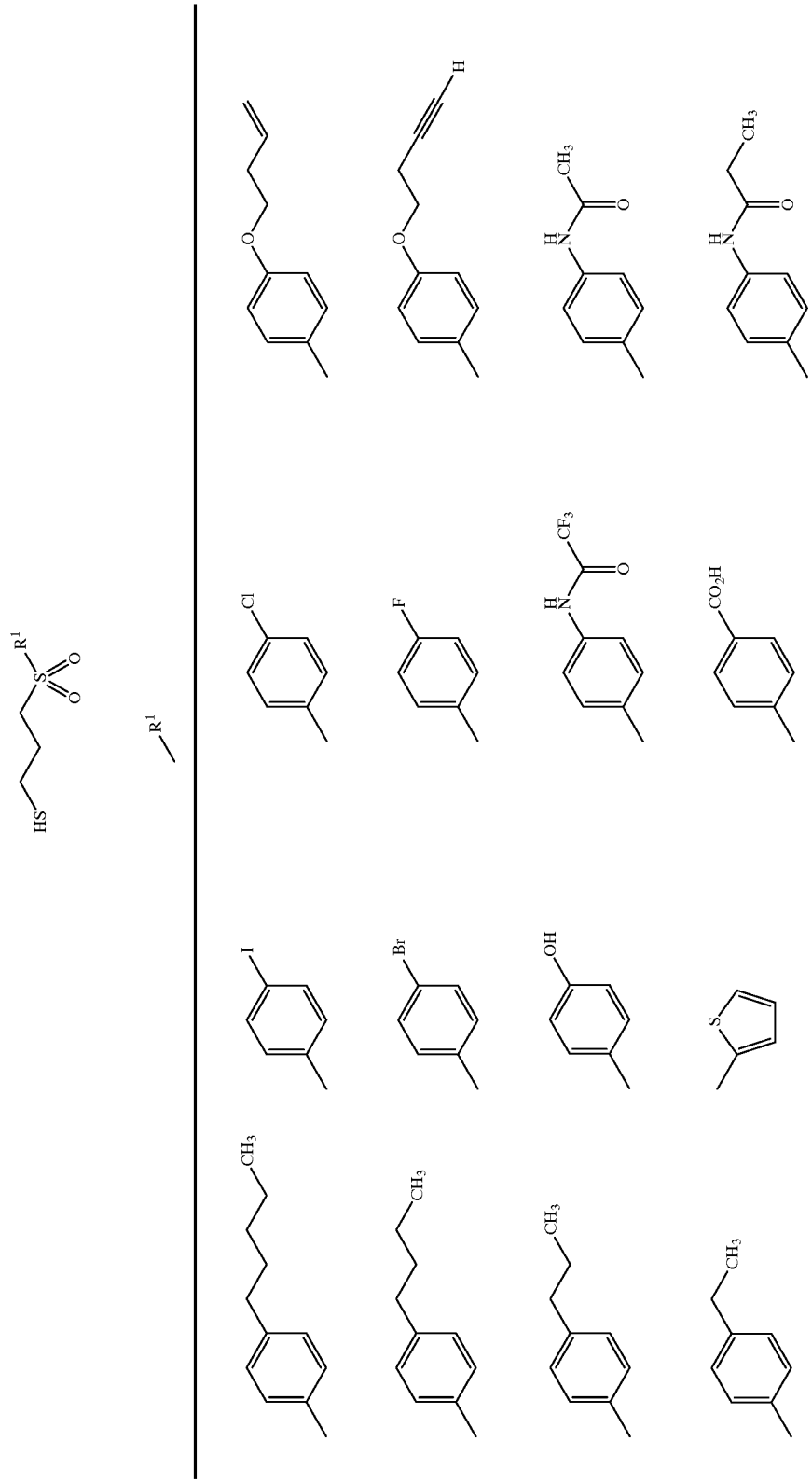

TABLE 40-continued
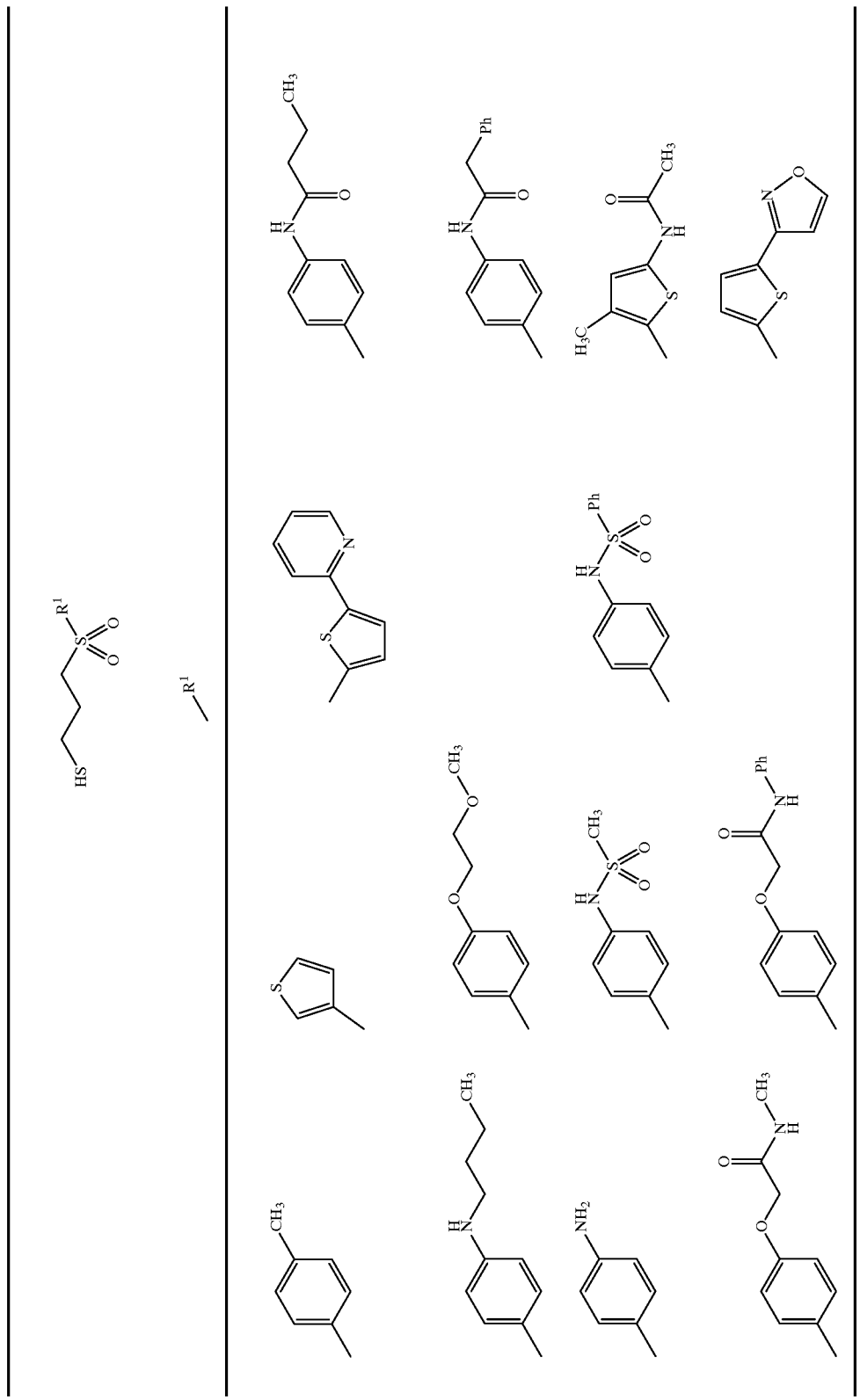

In the written descriptions of molecules and groups, molecular descriptors can be combined to produce words or phrases that describe structural groups or are combined to describe structural groups. Such descriptors are used in this document. Common illustrative examples include such terms as aralkyl (or arylalkyl), heteroaralkyl, heterocycloalkyl, cycloalkylalkyl, aralkoxyalkoxycarbonyl and the like. A specific example of a compound encompassed with the latter descriptor aralkoxyalkoxycarbonyl is $C_6H_5$—$CH_2$—$CH_2$—O—$CH_2$—O—(C=O)— wherein $C_6H_5$— is phenyl. It is also to be noted that a structural group can have more than one descriptive word or phrase in the art, for example, heteroaryloxyalkylcarbonyl can also be termed heteroaryloxyalkanoyl. Such combinations are used above in the description of the compounds and compositions of this invention and further examples are described below. The following list is not intended to be exhaustive or drawn out but provide further illustrative examples of such words or phrases.

As utilized herein, the term "alkyl", alone or in combination, means a straight-chain or branched-chain alkyl radical containing 1 to about 12 carbon atoms, preferably 1 to about 10 carbon atoms, and more preferably 1 to about 6 carbon atoms.

Examples of such radicals include methyl, ethyl, n-propyl, isopropyl, n-butyl, isobutyl, sec-butyl, tert-butyl, pentyl, iso-amyl, hexyl, octyl and the like.

The term "alkenyl", alone or in combination, means a straight-chain or branched-chain hydrocarbon radical having one or more double bonds and containing 2 to about 12 carbon atoms preferably 2 to about 10 carbon atoms, and more preferably, 2 to about 6 carbon atoms. Examples of suitable alkenyl radicals include ethenyl(vinyl), 2-propenyl, 3-propenyl, 1,4-pentadienyl, 1,4-butadienyl, 1-butenyl, 2-butenyl, 3-butenyl, decenyl and the like.

The term "alkynyl", alone or in combination, means a straight-chain hydrocarbon radical having one or more triple bonds and containing 2 to about 12 carbon atoms, preferably 2 to about 10 carbon atoms, and more preferably, 2 to about 6 carbon atoms. Examples of alkynyl radicals include ethynyl, 2-propynyl, 3-propynyl, decynyl, 1-butynyl, 2-butynyl, 3-butynyl, and the like.

The term "carbonyl", alone or in combination, means a —C(=O)— group wherein the remaining two bonds (valences) can be independently substituted. The term "thiol" or "sulfhydryl", alone or in combination, means a —SH group. The term "thio" or "thia", alone or in combination, means a thiaether group; i.e., an ether group wherein the ether oxygen is replaced by a sulfur atom.

The term "amino", alone or in combinations means an amine or —$NH_2$ group whereas the term mono-substituted amino, alone or in combination, means a substituted amine —N(H)(substituent) group wherein one hydrogen atom is replaced with a substituent, and disubstituted amine means a —N(substituent)$_2$ wherein two hydrogen atoms of the amino group are replaced with independently selected substituent groups.

Amines, amino groups and amides are compounds that can be designated as primary (I°), secondary (II°) or tertiary (III°) or unsubstituted, mono-substituted or di-substituted depending on the degree of substitution of the amino nitrogen.

Quaternary amine (ammonium)(IV°) means a nitrogen with four substituents [—$N^+$(substituent)$_4$] that is positively charged and accompanied by a counter ions whereas N-oxide means one substituent is oxygen and the group is represented as [—$N^+$(substituent)$_3$—$O^-$]; i.e., the charges are internally compensated.

The term "cyano", alone or in combination, means a —C-triple bond-N (—C≡N) group. The term "azido", alone or in combination, means a —N-triple bond-N (—N≡N) group. The term "hydroxyl", alone or in combination, means a —OH group. The term "nitro", alone or in combination, means a —$NO_2$ group. The term "azo", alone or in combination, means a —N=N— group wherein the bonds at the terminal positions can be independently substituted.

The term "hydrazino", alone or in combination, means a —NH—NH— group wherein the depicted remaining two bonds (valences) can be independently substituted. The hydrogen atoms of the hydrazino group can be replaced, independently, with substituents and the nitrogen atoms can form acid addition salts or be quaternized.

The term "sulfonyl", alone or in combination, means a —$SO_2$— group wherein the depicted remaining two bonds (valences) can be independently substituted. The term "sulfoxido", alone or in combination, means a —SO— group wherein the remaining two bonds (valences) can be independently substituted.

The term "sulfone", alone or in combination, means a —$SO_2$— group wherein the depicted remaining two bonds (valences) can be independently substituted. The term "sulfide", alone or in combination, means a —SON= group wherein the remaining three depicted bonds (valences) can be independently substituted. The term "sulfenamide", alone or in combination, means a —S— group wherein the remaining two bonds (valences) can be independently substituted.

The term "alkoxyl", alone or in combination, means an alkyl ether radical wherein the term alkyl is as defined above. Examples of suitable alkyl ether radicals include methoxy, ethoxy, n-propoxy, isopropoxy, n-butoxy, iso-butoxy, sec-butoxy, tert-butoxy and the like.

The term "cycloalkyl", alone or in combination, means a cyclic alkyl radical that contains 3 to about 8 carbon atoms. The term "cycloalkylalkyl" means an alkyl radical as defined above that is substituted by a cycloalkyl radical containing 3 to about 8, preferably 3 to about 6, carbon atoms. Examples of such cycloalkyl radicals include cyclopropyl, cyclobutyl, cyclopentyl, cyclohexyl and the like.

The term "aryl", alone or in combination, means a 5- or 6-membered aromatic ring-containing moiety or a fused ring system containing two or three rings that have all carbon atoms in the ring; i.e., a carbocyclic aryl radical, or a heteroaryl radical containing one or more heteroatoms such as sulfur, oxygen and nitrogen in the ring(s). Exemplary carbocyclic aryl radicals include phenyl, indenyl and naphthyl radicals. Examples of such heterocyclic or heteroaryl groups are pyrrolidinyl, piperidinyl, piperazinyl, morpholinyl, thiamorpholinyl, pyrrolyl, imidazolyl (e.g., imidazol-4-yl, 1-benzyloxycarbonylimidazol-4-yl, and the like), pyrazolyl, pyridyl, pyrazinyl, pyrimidinyl, furyl, tetrahydrofuryl, thienyl, triazolyl, oxazolyl, oxadiazoyl, thiazolyl, thiadiazoyl, indolyl (e.g., 2-indolyl, and the like), quinolinyl, (e.g., 2-quinolinyl, 3-quinolinyl, 1-oxido-2-quinolinyl, and the like), isoquinolinyl (e.g., 1-isoquinolinyl, 3-isoquinolinyl, and the like), tetrahydroquinolinyl (e.g., 1,2,3,4-tetrahydro-2-quinolyl, and the like), 1,2,3,4-tetrahydroisoquinolinyl (e.g., 1,2,3,4-tetrahydro- 1-oxo-isoquinolinyl, and the like), quinoxalinyl, β-carbolinyl, 2-benzofurancarbonyl, benzothiophenyl, 1-, 2-, 4- or 5-benzimidazolyl, and the like.

An aryl ring group optionally carries one or more substituents selected from alkyl, alkoxy, halogen, hydroxy, amino, nitro and the like, such as phenyl, p-tolyl, 4-methoxyphenyl, 4-(tert-butoxy)phenyl, 4-fluorophenyl, 4-chlorophenyl, 4-hydroxyphenyl, 1-naphthyl, 2-naphthyl, and the like.

The term "aralkyl", alone or in combination, means an alkyl radical as defined above in which one hydrogen atom is replaced by an aryl radical as defined above, such as benzyl, 2-phenylethyl and the like.

The term "aralkoxycarbonyl", alone or in combination, means a radical of the formula —C(O)—O-aralkyl in which the term "aralkyl" has the significance given above. An example of an aralkoxycarbonyl radical is benzyloxycarbonyl.

The term "aryloxy" means a radical of the formula aryl-O— in which the term aryl has the significance given above.

The terms "alkanoyl" or "alkylcarbonyl", alone or in combination, means an acyl radical derived from an alkanecarboxylic acid, examples of which include acetyl, propionyl, butyryl, valeryl, 4-methylvaleryl, and the like.

The term "cycloalkylcarbonyl" means an acyl group derived from a monocyclic or bridged cycloalkanecarboxylic acid such as cyclopropanecarbonyl, cyclohexanecarbonyl, adamantanecarbonyl, and the like, or from a benz-fused monocyclic cycloalkanecarboxylic acid that is optionally substituted by, for example, alkanoylamino, such as 1,2,3,4-tetrahydro-2-naphthoyl, 2-acetamido-1,2,3,4-tetrahydro-2-naphthoyl.

The terms "aralkanoyl" or "aralkylcarbonyl", mean an acyl radical derived from an aryl-substituted alkanecarboxylic acid such as phenylacetyl, 3-phenylpropionyl(hydrocinnamoyl), 4-phenylbutyryl, (2-naphthyl)acetyl, 4-chlorohydrocinnamoyl, 4-aminohydrocinnamoyl, 4-methoxyhydrocinnamoyl and the like.

The terms "aroyl" or "arylcarbonyl" means an acyl radical derived from an aromatic carboxylic acid. Examples of such radicals include aromatic carboxylic acids, an optionally substituted benzoic or naphthoic acid such as benzoyl, 4-chlorobenzoyl, 4-carboxybenzoyl, 4-(benzyloxycarbonyl)benzoyl, 1-naphthoyl, 2-naphthoyl, 6-carboxy-2 naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like.

The heterocyclic (heterocyclo) or heterocycloalkyl portion of a heterocyclocarbonyl, heterocyclooxycarbonyl, heterocycloalkoxycarbonyl, or heterocycloalkyl group or the like is a saturated or partially unsaturated monocyclic, bicyclic or tricyclic heterocycle that contains one or more hetero atoms selected from nitrogen, oxygen and sulphur. Such a moiety can be optionally substituted on one or more carbon atoms by halogen, alkyl, alkoxy, oxo, and the like, and/or on a secondary nitrogen atom (i.e., —NH—) by alkyl, aralkoxycarbonyl, alkanoyl, aryl or arylalkyl or on a tertiary nitrogen atom (i.e., =N—) by oxido and that is attached via a carbon atom. The tertiary nitrogen atom with three substituents can also attached to form a N-oxide [=N(O)—] group.

The term "cycloalkylalkoxycarbonyl" means an acyl group of the formula cycloalkylalkyl-O—CO— wherein cycloalkylalkyl has the significance given above. The term "aryloxyalkanoyl" means an acyl radical of the formula aryl-O-alkanoyl wherein aryl and alkanoyl have the significance given above. The term "heterocyclooxycarbonyl" means an acyl group having the formula heterocyclo-O—CO— wherein heterocyclo is as defined above.

The term "heterocycloalkanoyl" is an acyl radical of the formula heterocyclo-substituted alkane carboxylic acid wherein heterocyclo has the significance given above. The term "heterocycloalkoxycarbonyl" means an acyl radical of the formula heterocyclo-substituted alkane-O—CO— wherein heterocyclo has the significance given above. The term "heteroaryloxycarbonyl" means an acyl radical represented by the formula heteroaryl-O—CO— wherein heteroaryl has the significance given above.

The term "aminocarbonyl" alone or in combination, means an amino-substituted carbonyl (carbamoyl) group derived from an amino-substituted carboxylic acid (carboxamide) wherein the amino (amido nitrogen) group can be a primary or secondary amino group containing substituents selected from hydrogen, and alkyl, aryl, aralkyl, cycloalkyl, cycloalkylalkyl radicals and the like.

The term "aminoalkanoyl" means an acyl group derived from an amino-substituted alkanecarboxylic acid wherein the amino group can be a primary or secondary amino group containing substituents independently selected from hydrogen, alkyl, aryl, aralkyl, cycloalkyl, cycloalkylalkyl radicals and the like.

The term "halogen" means fluoride, chloride, bromide or iodide. The term "haloalkyl" means an alkyl radical having the significance as defined above wherein one or more hydrogens are replaced with a halogen. Examples of such haloalkyl radicals include chloromethyl, 1-bromoethyl, fluoromethyl, difluoromethyl, trifluoromethyl, 1,1,1-trifluoroethyl and the like.

The term perfluoroalkyl means an alkyl group wherein each hydrogen has been replaced by a fluorine atom. Examples of such perfluoroalkyl groups, in addition to trifluoromethyl above, are perfluorobutyl, perfluoroisopropyl, perfluorododecyl and perfluorodecyl.

The term "aromatic ring" in combinations such as substituted-aromatic ring sulfone or substituted-aromatic ring sulfoxide means aryl or heteroaryl as defined above.

M utilized in the reaction schemes that follow represents a leaving group such as halogen, phosphate ester or sulfate ester.

Preparation of Useful Compounds

Schemes 1 through 7 illustrate procedures with examples of chemical transformations that can be used for the preparation of compounds useful in this invention, e.g., compounds of formulas I–III, Ia–IIIa, or Ib–IIIb. The $R^1$ through $R^{10}$ groups shown in the schemes have been defined previously in this document.

This discussion is not intended to be exhaustive as is readily noted that additional or alternative methods, conditions, reactions or systems can be identified and used by a chemist of ordinary skill to obtain the compounds shown. Optically active as well as non-optically active isomers are included, e.g., $R^1$ isomers, enantiomers, diastereomers, racemates, E isomers, Z isomers, syn-isomers, anti-isomers and the like.

These syntheses, as with all of the reactions discussed herein, can be carried out under a dry inert atmosphere such a nitrogen or argon if desired. Selected reactions known to those skilled in the art are carried out under a dry atmosphere such as dry air, whereas other synthetic steps, for example, aqueous acid or base ester or amide hydrolyses are carried out with a reaction solution in contact with laboratory air.

Scheme 1

The first reaction in Scheme 1 is a Michael reaction of a thiol, compound 1, with an unsaturated aldehyde (when $R^6$ is H) or ketone, compound 2, to form a sulfide aldehyde or ketone, compound 3. Unsaturated esters, amides and acids are also substrates for the Michael reaction wherein the corresponding sulfide esters, amides or acids are prepared.

A Michael reaction can be base-mediated by the use of catalytic amounts of some bases, carried out with an equivalent or more of a base, or by the use of an additional reagent. Alternatively, the thiol reagent can be a preformed thiol base salt.

Bases that can be used include, for example, metal hydroxides such as sodium, potassium, lithium or magnesium hydroxide; oxides such as those of sodium, potassium, lithium, calcium or magnesium; metal carbonates such as those of sodium, potassium, lithium, calcium or magnesium; metal bicarbonates such as sodium bicarbonate or potassium bicarbonate; hindered primary organic amines or secondary tertiary organic amines such as alkyl amines, arylalkyl amines, alkylarylalkyl amines, heterocyclic amines or heteroaryl amines; ammonium hydroxide or quaternary ammonium hydroxides.

As non-limiting examples, such amines that can be used as a base mediator of the Michael reaction in Scheme 1 can include triethylamine, trimethylamine, diisopropylamine, methyldiisopropylamine, diazabicyclononane, tribenzylamine, dimethylbenzylamine, N-methylmorpholine, N,N'-dimethylpiperazine, N-ethylpiperidine, 2,2,6,6-tetramethylpiperidine, dimethylaminopyridine, pyridine, quinoline, tetramethylethylenediamine, diazabicyclononane and the like.

Non-limiting examples of ammonium hydroxides, (usually made from amines and water) that can be used as a base mediator, can include ammonium hydroxide, triethylammonium hydroxide, trimethylammonium hydroxide, methyldiiospropylammonium hydroxide, tribenzylammonium hydroxide, dimethylbenzylammonium hydroxide, N-methylmorpholinium hydroxide, N,N'-dimethylpiperazinium hydroxide, N-ethylpiperidinium hydroxide, and the like.

Non-limiting examples of quaternary ammonium hydroxides that can be used as a base mediator include tetraethylammonium hydroxide, tetramethylammonium hydroxide, dimethyldiiospropylammonium hydroxide, benzylmethyldiisopropylammonium hydroxide, methyldiazabicyclononylammonium hydroxide, methyltribenzylammonium hydroxide, N,N-dimethylmorpholinium hydroxide, N,N,N',N',-tetramethylpiperazinium hydroxide, and N-ethyl-N'-hexylpiperidinium hydroxide and the like.

Metal hydrides, amide or alcoholates such as calcium hydride, sodium hydride, potassium hydride, lithium hydride, sodium methoxide, potassium tert-butoxide, calcium ethoxide, magnesium ethoxide, sodium amide, potassium diisopropyl amide and the like may also be suitable reagents for use as a base mediator.

Organometallic deprotonating agents such as alkyl or aryl lithium reagents such as methyl lithium, phenyl lithium, tert-butyl lithium, lithium acetylide or butyl lithium, Grignard reagents such as methylmagnesium bromide or methylmagnesium chloride, organocadium reagents such as dimethylcadium and the like can also serve as bases for causing thiolate salt formation or catalyzing the reaction.

Quaternary ammonium hydroxides or mixed salts are also useful for aiding phase transfer couplings or serving as phase transfer reagents.

The reaction medium can be a single solvent, mixed solvents of the same or different classes or serve as a reagent in a single or mixed solvent system. The solvents can be protic, non-protic or dipolar aprotic.

Non-limiting examples of protic solvents for the Michael reaction include water, methanol (MeOH), ethanol (EtOH; denatured, 95% or absolute) isopropanol and the like. Typical non-protic solvents include acetone, tetrahydrofuran (THF), dioxane, diethyl ether, tert-butylmethyl ether (TBME), aromatic solvents such as xylene, toluene, or benzene, ethyl acetate (EA), methyl acetate, butyl acetate, trichloroethane, methylene chloride, ethylenedichloride (EDC), hexane, heptane, isooctane, cyclohexane and the like. Dipolar aprotic solvents include compounds such as dimethylformamide (DMF), dimethylacetamide (DMAc), acetonitrile, dimethylsulfoxide (DMSO), hexamethylphosphoric triamide (HMPA), nitromethane, tetramethylurea, N-methylpyrrolidone and the like.

Non-limiting examples of reagents that can be used as solvents or as part of a mixed solvent system for the Michael reaction include organic or inorganic mono- or multi-protic acids or bases such as hydrochloric acid, phosphoric acid, sulfuric acid, acetic acid, formic acid, citric acid, succinic acid, triethylamine, morpholine, N-methylmorpholine, piperidine, pyrazine, piperazine, pyridine, potassium hydroxide, sodium hydroxide, alcohols or amines for making esters or amides or thiols for making the products of this invention and the like.

Room temperature or less, or moderate warming (−10° C. to 60° C.) are the preferred temperatures of the Michael reaction. If desired, the reaction temperature can be about −76° C. to the reflux point of the reaction solvent or solvents.

The sulfide compound 3, an electrophile that is the product of the Michael reaction, can be oxidized to a sulfone, compound 7, in one step using two equivalents of oxidizing agent. Oxidizing agents for this process, in a non-limiting example, include peroxymonosulfate (OXONE®), hydrogen peroxide, meta-chloroperbenzoic acid, perbenzoic acid, percamphoric acid, peracetic acid, perlactic acid, tert-butyl peroxide, tert-butyl hydroperoxide, tert-butyl hypochlorite, sodium hypochlorite, hypochlorous acid, sodium meta-periodate, periodic acid, and the like.

Protic, non-protic, dipolar aprotic solvents, either pure or mixed, can be used for the oxidation reaction, such as methanol/water.

The oxidation can be carried out at temperature of about −78° to about 50° degrees centigrade and preferable about −10° C. to about 40° C.

Preparation of the sulfone can also be carried out via a two-step process wherein a sulfoxide, compound 6, is prepared in the first step. The synthesis of a sulfoxide starting with a sulfide requires the use of only about one equivalent of one of the above oxidizing agents with a preferred temperature of about zero° C.

The use of a protected thiol group can be desired by one skilled in the art as an aid in selectivity and as a supplement to the exploitation of the usual steric and electronic factors. The solvents listed above for use with the Michael reaction can be used with these selective sulfoxide preparations with, for example, methanol or methanol/water being preferred along with a reaction temperature of about −10° C. to about 30° C. It can be desirable in the case of more active oxidizing agents, but not required, that the reactions be carried out under an inert gas atmosphere with or without degassed solvents.

A formed sulfoxide, compound 6 or compound 9, can then be oxidized to a sulfone, if desired, and with or without prior isolation and characterization of the sulfoxide by the use of the oxidation procedures discussed above. In addition, optically active sulfoxides can be prepared using optically active oxidizing agents such as per-camphoric acid.

Scheme 1 also illustrates the conversion of compound 3, into an alcohol compound 4. Compound 3 can be an aldehyde (when $R^6$ is H) or ketone, or in some instances an acid (when $R^6$ is O), ester (when $R^6$ is OR), or amide (where $R^6$ is N). The useful process for this conversion is treatment of the electrophile compound 3 with an organometallic reagent such as a lithium reagent, magnesium reagent (Grignard reagent), zinc reagent, cadium reagent, sodium reagent or potassium reagent. Where H is required on the oxygen, the carbonyl compound can be reduced by well known methods such as the use of sodium borohydride, lithium aluminum hydride or the like. Such reactions of carbonyl compounds with organometallic reagents are well known in the art to produce alcohols such as compound 4 or, depending on reagent and starting material, new carbonyl compounds.

These conversion reactions are usually carried out under an inert atmosphere such as $N_2$ or Ar at a temperature of about −80° C. to about 50° C. in a inert non-polar or dipolar aprotic solvent or mixture of solvents. The alcohol compound 4 can be oxidized to a sulfone such as compound 7 or a sulfoxide such as compound 6 using methods as outline above. The alcohol can also converted into a sulfide derivative such as compound 5 wherein W is oxygen or sulfur. Non-limiting examples of such are the thioacetate [—S(C=O)CH$_3$] or dithioacetate groups [—S(C=S)CH$_3$].

Conversion of compounds 7 to 8, 6 to 9 or 4 to 5 in Scheme 1 can be carried out by an activated azo process wherein a phosphine such as triphenyl phosphine and an azo compound such as diisopropyl azodicarboxylate (DIAD) or diethyl azodicarboxylate (DEAD) and the starting alcohol are treated with a thiolcarboxylic acid or dithiocarboxylic acid. The reaction is usually carried out under an inert atmosphere at about −40° C. to about room temperature in an inert solvent such as methylene chloride, THF or others listed above.

Scheme 2

Scheme 2 shows the same overall conversion of compounds 7 to 8, 6 to 9 or 4 to 5 using an alternative process that proceeds through via hydroxyl activation or replacement to provide intermediate compounds 10 (sulfide), 11 (sulfone) or 12 (sulfoxide).

In the Schemes, M represents groups such as halides (Cl, Br, I), fluorides (aromatic), tosylate (OTs), mesylate (OMs) and triflate (OTf) groups and the like. M can also represent groups such as —SH (thiol) or, following treatment with base or as a pre-formed salt, an —S$^-$ (thiolate) group. The nonthiols are prepared from alcohols by standard methods such as treatment with HCl, HBr, thionyl chloride or bromide, phosphorus trihalide, phosphorus pentahalide, tosylchloride or methanesulfonyl chloride and the like.

The hydroxyl activation or replacement reactions are usually carried out at a temperature of about −25° C. to solvent reflux under an inert atmosphere such as nitrogen or argon.

The solvent or solvent mixture can vary widely depending upon reagents and other conditions and can include polar or dipolar aprotic solvents as listed before or mixtures of those solvents. In some cases, bases such as triethyl amine, pyridine or other non-reactive bases can serve as reagents and/or solvents and/or cosolvents. The preparations of sulfate esters and/or organic halides are well known in the art.

In some instances, in the reactions in these Schemes, protecting groups are used in other parts of a molecule(s) at locations that is(are) not desired to be reactive centers. Such protecting groups can include acyl groups, carbamoyl groups, ethers, alkoxyalkyl ethers, cycloalkyloxy ethers, arylalkyl groups, silyl groups as well as trisubstituted silyl groups and the like. Examples of such protecting groups include acetyl, THP, benzyl, benzoyl, tert-butyldimethylsilyl (TBDMS) or MEM groups. The preparation of such protected compounds as well as removal of the protecting groups are well known in the art.

Reaction of compounds 10, 11 and 12 in Scheme 2 shows the second step in the preparation of compounds 5, 8 and 9. This method of synthesis of sulfur-containing compounds; i.e., use of the $SN_2$ class of reactions, is commonly called nucleophilic substitution.

A bimolecular nucleophilic substitution ($SN_2$) reaction is illustrated in the step so named wherein group M is displaced by a thiol compound or the salt of a thiol compound producing compounds of formula I or formula II or a compound of formula I via conversion of formula II to I. The opposite procedure is also possible. Compounds of formulas I and II are also intermediates in the preparation of compounds of formula III. Compounds of formula III can also be converted into those of formulas I or II.

Non-limiting examples of thiol compounds or their salts are hydrogen sulfide ($H_2S$), sodium sulfide (NaSH), thiolacetic acid [HS(C=O)CH$_3$], sodium thiolacetate [NaS(C=O)CH$_3$], dithioacetic acid [HS(C=S)CH$_3$] and sodium dithiolacetate [NaS(C=S)CH$_3$]. Thiols are shown at other points in the Schemes.

As with the Michael reaction discussed along with Scheme 1, the thiol anion can be derived from a preformed salt or the salt can be formed in situ via addition of a base. The bases and solvents discussed with regard to Scheme 1, the Michael reaction, are applicable to this step. Preferred bases are those that are hindered such as tertiary amines so that competition with thiolate anion in a two stage reaction is minimized. The solvents, solvent mixtures or solvent/reagent mixtures discussed above are satisfactory but non-protic or dipolar aprotic solvents such as acetone, acetonitrile, DMF, acetonitrile and the like are examples of a preferred class. Bases can also be used as solvents as well as reagents. Mixtures of the above solvents or with a solvent and a base such as pyridine or triethylamine are also useful. Again, procedures involving nucleophilic substitution reactions are well know in the art.

The generalized oxidation/reduction sequence illustrated in Scheme 2 is also well known in the art. Hydrolysis by base, preferably aqueous as discussed above, reaction of the C=W group with a organometallic reagent or its reductive removal can provide an —SH (thiol) compound of formula I. This thiol compound that is not shown per se in Schemes 1 or 2 can then be oxidized, if desired, using, for example, air, oxygen, hypohalide reagents, sodium plumbite, or oxidation agents listed above. Non-oxidizable solvents and a basic or slightly basic pH value are preferred and the atmosphere of the reaction can be air or another gas mentioned above. Preferred temperature is zero° C. to 40° C. but lower or higher temperatures can be used. Mixed disulfides can be made if the starting materials have different structures.

Reversal of the oxidation process ex vivo requires reduction of the disulfide bond to the thiol of formula II followed by acylation with a reagent such as a derivative of HO(C=W)R$^{10}$. Such a derivative can be an activated carbonyl compound prepared using activation reagents well known in the art including the peptide and protein synthesis and amino acid coupling or conjugation art. Examples of such activation reagents are thionyl chloride, oxalyl chloride, phosphorus oxychloride, HOBT (hydroxybenzotriazole), isobutylchloroformate, carbodiimide, azodicarboxylate compounds and the like all of which are well known and established in the art. Reduction of the disulfide to the corresponding thiol can be carried out by, for example, treatment with hydride reagents such as lithium aluminum hydride, aluminum hydride, metal borohydrides, sodium cyanoborohydride and the like.

Scheme 3

Scheme 3 illustrates an alternative sequence for the preparation of intermediates and products of this invention. A thiol such as compound 1 can be reacted with an alpha-substituted aldehyde, ketone, acid, acid salt, ester or amide, wherein M is the alpha substituent. This $SN_2$ reaction is carried out as previously discussed preferably at the lower end of the permissible temperature range. This reaction produces the sulfide compound 17, which can be reduced or treated with an organometallic reagent to produce alcohol compound 18. Both processes have been discussed above.

Compound 18 can also be made via a double bond containing feedstock that is, for example, converted into an epoxide compound 19 that can be ring-opened via the $SN_2$ process using a thiolate anion ($R^1S^-$) In this case, the reagent can be a hydrogen sulfide anion ($HS^-$) and the product can then be reacted with, for example, a $R^1$—M reagent to form compound 18 in a two step procedure. These processes have been presented in association with earlier Schemes.

Step 4 shows the conversion of an alcohol into a sulfoxide or sulfone followed by the preparation of the activated intermediate compounds 23 and 24. These two compounds can then be converted into the compounds of formula I (Ia or Ib) (M converted into —SH) or formula II (IIa or IIb) directly or into formula II (IIa or IIb) thence back into formula I (Ia or Ib) via a hydrolysis or reduction [—S(C=W)$R^{10}$ group reduction to —SH] procedure. These procedures were presented earlier. Note the same processes can be used with the sulfides such as compounds 22 and 25 to produce the sulfone compounds 26 or sulfoxides compound 27 by oxidation (discussed above) as indicated by the reaction arrows.

Scheme 4

Scheme 4 illustrates methods that can be used to create a compound of this invention from the thiol function. Compound 28 and compound 33 both contain a double bond. The double bond can be converted into an epoxide that can be used as discussed above.

Reagents such as hydrogen peroxide, peracetic acid, pertrifluoroacetic acid can accomplish the conversion to an epoxide directly, whereas halohydrins such as sodium hypochlorite, hypochlorus acid can be used to produce an intermediate hydroxyhalide that can be converted into the epoxide with a hindered base if desired. Hypohalide compounds can be converted into hydroxy sulfide compounds first if desired. The halides can then be converted into organometallic reagents if the hydroxy group is first either protected or converted into a protected thiol function.

Step 2 shows the conversion of an epoxide into a protected thiol directly using, for example, the methods of Step 3 in Scheme 3. The hydroxy function can be converted into a halide (M group) as discussed earlier, and thence to an organometallic reagent. Addition of the organometallic reagent to the intermediate epoxide compound 34, prepared as discussed above, provides the hydroxide derivative compound 35.

The former conversions are repeated in Steps 7 through 9 to give as products of compounds of this invention of formula II and, following hydrolysis and oxidation, compounds of formula I and/or III. Preparation of the M derivatives compound 36, formation of the $R^1S$— bonds and oxidation to a sulfoxide compound 38 (n=1) or sulfone compound 38 (n=2) are processes presented in several places above.

Scheme 5

Compound 22, which can be prepared by the methods shown in Scheme 3, serves as a starting material in Scheme 5 that illustrates further alternative synthetic pathways starting from the $R^1S$— bond side of compounds of formulas I–III, Ia–IIIa or Ib–IIIb. In one process, the activated M-carbon bond is converted into an organometallic reagent compound 39 that is reacted with an epoxide compound 29. The product alcohol compound 40 containing the two additional backbone carbon atoms is converted into an activated intermediate compound 41 (carbon-M bond formed) that is reacted in an $SN_2$ manner with, for example sodium sulfide or sodium thioacetate or other reagents discussed above, to provide compound 37. This intermediate or pro-drug can then be oxidized, in one step or two steps, as shown on the continuation of Scheme 5 to the protected compound 38. Compound 38 can be hydrolyzed or reduced to a compound of formula I, Ia or Ib.

It is noted that one skilled in the art can also choose to preform conversions into sulfoxides or sulfones as is shown on the left side of this scheme.

In this instance, the oxidized sulfur- and M-containing intermediate compound 42 is converted in to an organometallic reagent compound 43 that is reacted with the epoxide compound 29. The resulting compound, 44, is then converted into another M-containing intermediate, compound 45, that is reacted via an $SN_2$ reaction as before to form compound 38.

Scheme 6

Scheme 6 illustrates further the preparation of the compounds of formulas I–III, Ia–IIIa or Ib–IIIb that are useful in this invention. $R^1$, $R^3$, $R^4$, $R^5$, $R^6$, $R^7$, $R^8$, $R^9$, $R^{10}$, M, W and -METAL are as defined hereinbefore. $R^2$ is defined as before with $R^2$-$M^2$ being a subset of R2 wherein the R2 group is part of an electrophilic reagent. In an electrophilic reagent $M^2$ serves as an halide (F, Cl, Br, I) or organosulfate such as tosylate, triflate or mesylate. Another type of $M^2$ electrophilic reagent is represented by esters, amides, anhydrides, acid halides, mixed anhydrides, aldehydes, ketones, carbonates, carbamates, ureas, sulfonyl halides, sulfonic esters and the like.

Step 1 represents a nucleophilic substitution ($SN_2$) reaction as discussed in, for example, Scheme 2. A formed sulfide such as compound 46 can be readily oxidized in one or two steps as discussed in earlier Schemes to form the sulfone compound 47 shown here. Removal of a hydrogen alpha to a sulfonyl group provides an anion intermediate such as compound 48. Hydrogen removal is accomplished through the use of a strong base such as those discussed above. Such bases are usually organometallic bases or hydride bases such as hindered Grignard reagents, lithium alkyls such as tert-butyl lithium, hydrides such as potassium hydride, metal amides such as sodium amide and the like. Anion formation is usually carried out under an inert atmosphere such as nitrogen or argon at temperature of about −100° C. to about 30° C. A preferred temperature range is from about −80° C. to about zero° C.

The solvent for such reactions are usually neutral nonprotic solvents, dipolar aprotic solvents or as mixtures or parts of mixtures. Ammonia or amines can be used also especially with, for example, sodium amide or sodium diisopropyl amide.

Once the anion is available, Step 4 can be carried out to provide compound 50. The type of $SN_2$ or electrophilic addition reaction shown in Step 4 has been discussed above. Alkylating agents include epoxides, halides, sulfate esters and the like. Aryl fluoro compounds can be in this class also. Electrophilic addition to various double bond compounds is also a common method of adding groups as is well known in the art. Reagents can include esters, amides, anhydrides, acid halides, mixed anhydrides, ketones, aldehydes, carbonates, carbamates, ureas, sulfonyl halides, sulfonic acid esters and the like as discussed above. Generally, these reactions are carried out in the same solvent as anion formation under the same atmosphere and at the same temperature. As is known in the art, it can be desirable to carry out anion formation at a higher or lower temperature than the reaction with an electrophilic reagent. One skilled in the art chooses the temperature for anion formation and that for reaction electrophilic reagent depending upon the characteristics of the starting material, the acidity of the proton being removed and activity of the electrophilic reagent as is well known. Ammonia and amines are solvents that are often removed following anion preparation.

Compound 50 can then be transformed into compound 51 following the procedures discussed before for transforming a hydroxyl group into a thiol or thiolate. Thus, compound 50 can be transform into compound 52 as described in Scheme 2 for transforming compounds 6 or 7 into compounds 12 or 11. Reaction of compound 52 with sodium sulfide or sodium hydrogen sulfide can be used to form compound 55. Similarly, activated azo coupling can be used to transform compound 50 into compound 51. The product compounds 51 and 53 are subsets of the compounds of formulas II, IIa or IIb and I, Ia or Ib, respectively.

Scheme 7

Thiol sulfones having $R^6$ substituents of the type shown in Tables 13 and 19 hereinabove can be synthesized via a ring-opening addition reaction, as shown in Scheme 7. A thiol compound 1 is reacted with a 2,4-dihydroxybutanoic acid anhydride (α-hydroxy-γ-butyrolactone) 51 to produce a sulfide having a hydroxy group 3 carbons away from the sulfide group and an $R^6$ substituent —COOH, compound 52. The reaction can be base-mediated by the use of catalytic or equivalent amounts of a base-mediator described as useful for the Michael reaction of Scheme 1, using substantially identical solvent and reaction conditions to the Michael reaction. Oxidation of the sulfide compound 52 to the sulfone compound 53 can be carried out by the one-step or two-step process, as described for the Michael reaction product in Scheme I hereinabove.

The alpha hydroxyl group can be converted to a thiol group using the hydroxyl activation or replacement process as shown in Scheme 2, where the leaving group M is substituted by a thiol group in a nucleophilic substitution reaction. The —COOH $R^6$ substituent compound 53 can be derivitized before or after conversion of the alpha hydroxyl group to a thiol group. Derivitization prior to forming the thiol is shown in Scheme 7. The —COOH $R^6$ substituent can be derivitized by esterification or amidation by methods well known in the art, preferably using base mediation. Amidation of compound 53 to compound 54 with N-(2-aminoethyl)morpholine is shown in Scheme 7, followed by hydroxyl activation or replacement to form compound 55. A compound of the invention can be made by nucleophilic substitution of compound 55 followed by hydrolysis of the product to form compound 56.

In an exemplary synthesis of a compound prepared by the reaction sequence shown in Scheme 7, the initial thiol-containing compound 1 can be prepared as illustrated below where $R^1$ of the thiol compound 1 is 4-(benzamido)-phenyl.

To a solution of chlorotriphenylmethane (trityl chloride; 5.00 g, 39.94 mmol) in 5% trifluoroacetic acid/dichloromethane was added a solution of 4-aminothiophenol (9.28 g, 33.28 mmol) dropwise, at room temperature. The resulting mixture is stirred at room temperature for 0.5 hours. The mixture is then diluted with water, neutralized with 2.5 N NaOH. The organic layer is washed further with water, dried, filtered and concentrated. The yellow solid is then triturated with diethyl ether to give a trityl-protected 4-aminothiophenolate (10.2 g, 69%) as an off-white solid, m/z=368 (M+H).

To a solution of the trityl-protected 4-aminothiophenolate (10.2 g, 27.70 mmol) and triethylamine (5.70 mL, 41.55 mmol) in dichloromethane are added benzoyl chloride (3.54 mL, 30.47 mmol). After 1 hour at room temperature, the mixture is diluted with dichloromethane. The reaction mixture is then washed with water, dried, filtered and concentrated. The resulting solid is triturated with diethyl ether to give a trityl-protected 4-(benzamido)-thiophenolate (23.9 g, 99%) as a white solid, m/z=472 (M+H).

To a solution of the trityl-protected 4-(benzamido)-thiophenolate (7.82 g, 16.58 mmol) in dichloromethane are added triisopropylsilane (16.98 mL, 82.91 mmol) and trifluoroacetic acid (25 mL). The mixture is stirred at room temperature for 0.5 hour and then concentrated. Hexanes are added and the resulting solid was collected to give the deprotected 4-(benzamido)-thiophenol (3.69 g, 97%) as a yellow solid, m/z=230 (M+H). The 4-(phenoxy)-thiophenol can be made in a similar manner.

The foregoing steps have been presented as part of Scheme 1 through Scheme 7. The terms and reactions ACTIVATED AZO COUPLING, ELECTROPHILIC SUBSTITUTION, NUCLEOPHILIC SUBSTITUTION and HYDROLYSIS utilized in those schemes are well known steps in the art.

The chemical reactions described above are generally disclosed in terms of their broadest application to the preparation of the compounds of this invention. Occasionally, the reactions may not be applicable as described to each compound included within the disclosed scope or may be unsafe in a particular instance. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

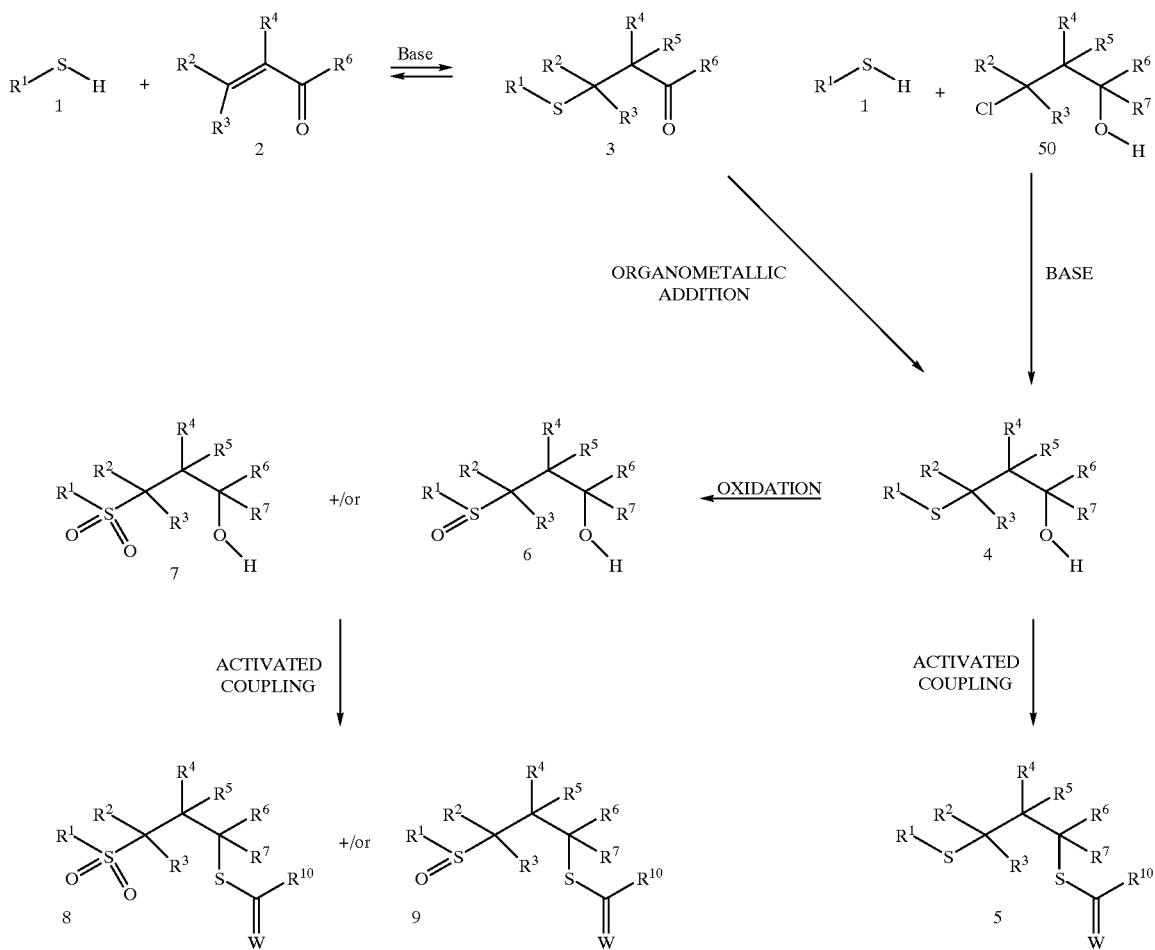
SCHEME 1
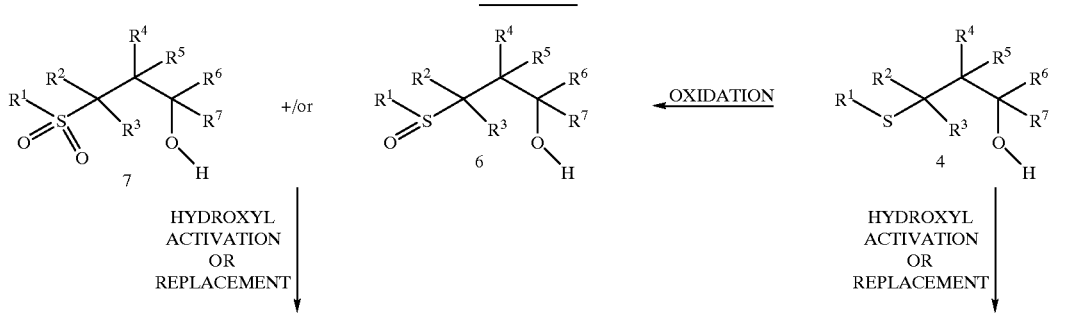
SCHEME 2

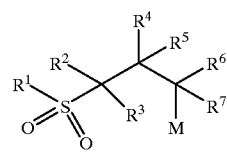
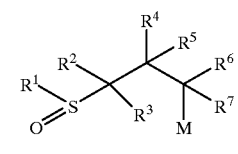
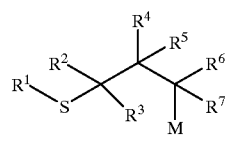
↓ NUCLEOPHILIC SUBSTITUTION     ↓ NUCLEOPHILIC SUBSTITUTION
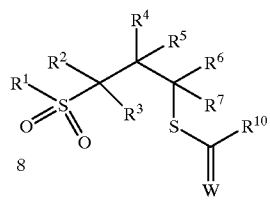
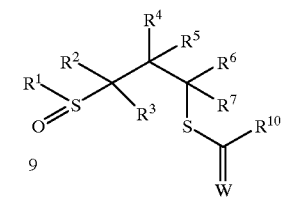
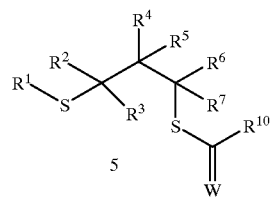
HYDROLYSIS / OXIDATION ⇅ REDUCTION / ACYLATION     HYDROLYSIS / OXIDATION ⇅ REDUCTION / ACYLATION
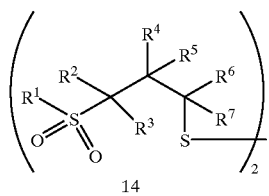
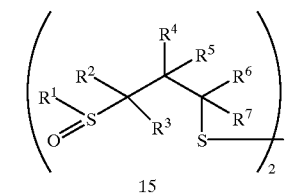
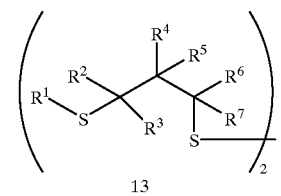
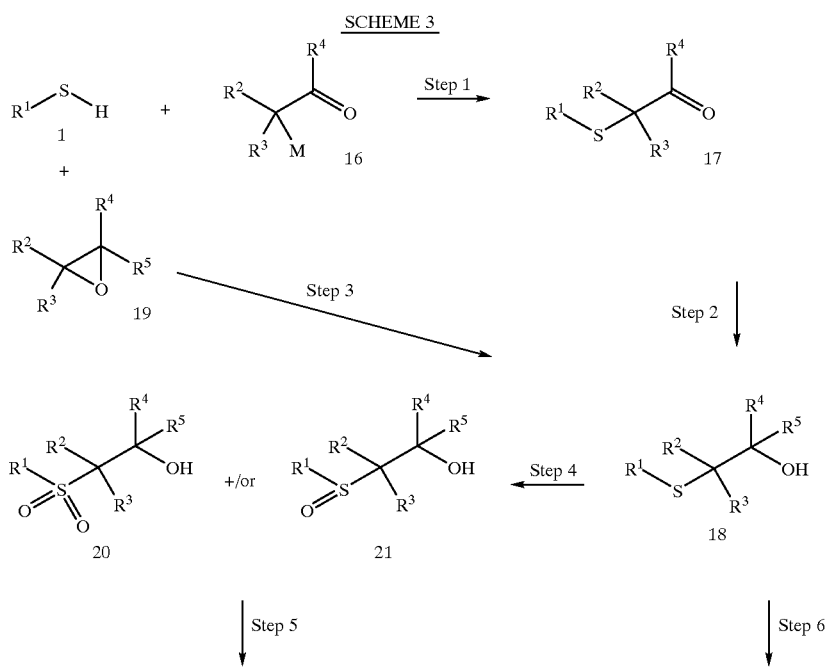
SCHEME 3

-continued
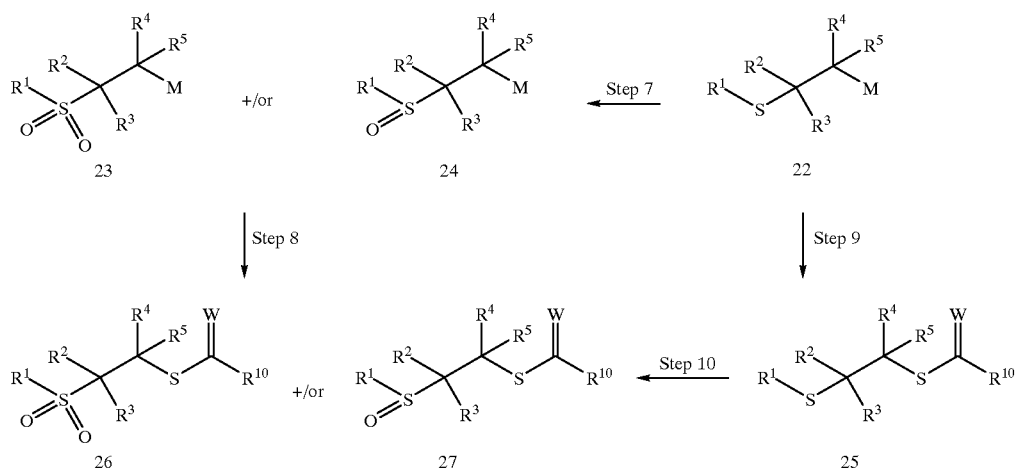
SCHEME 4
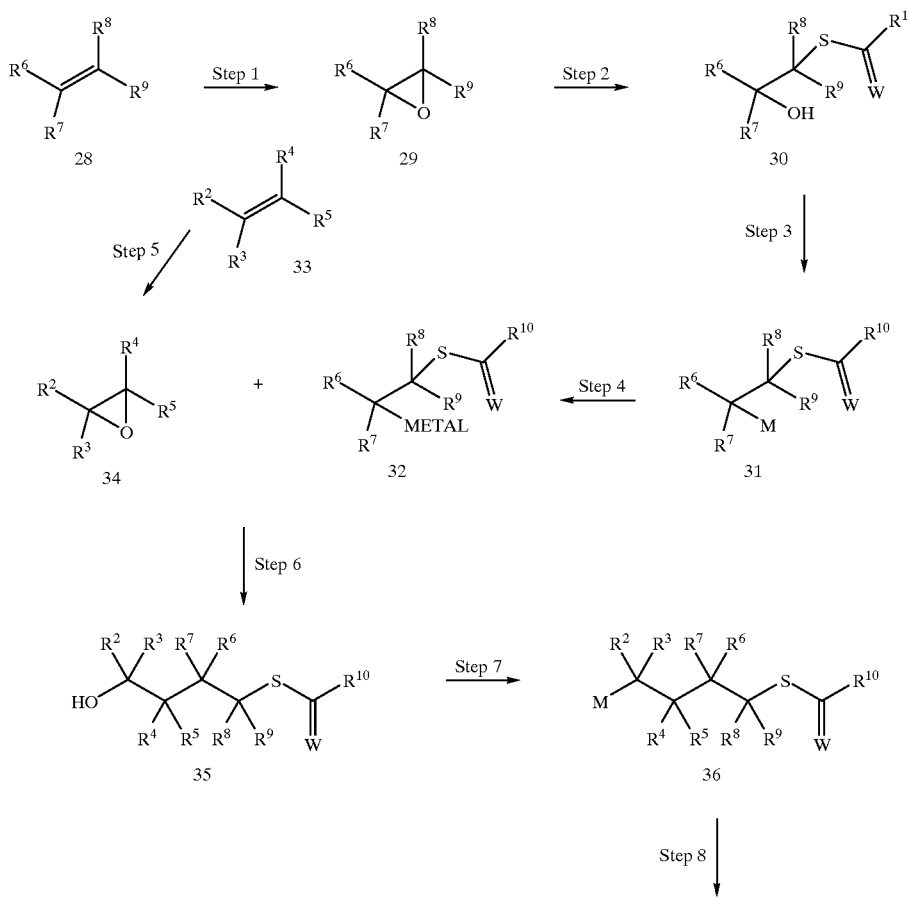

-continued
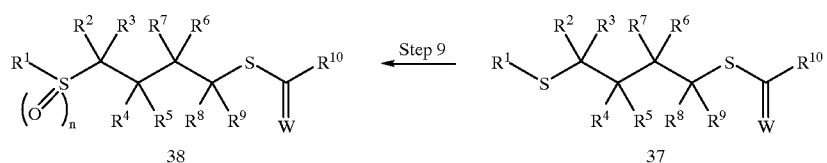
SCHEME 5
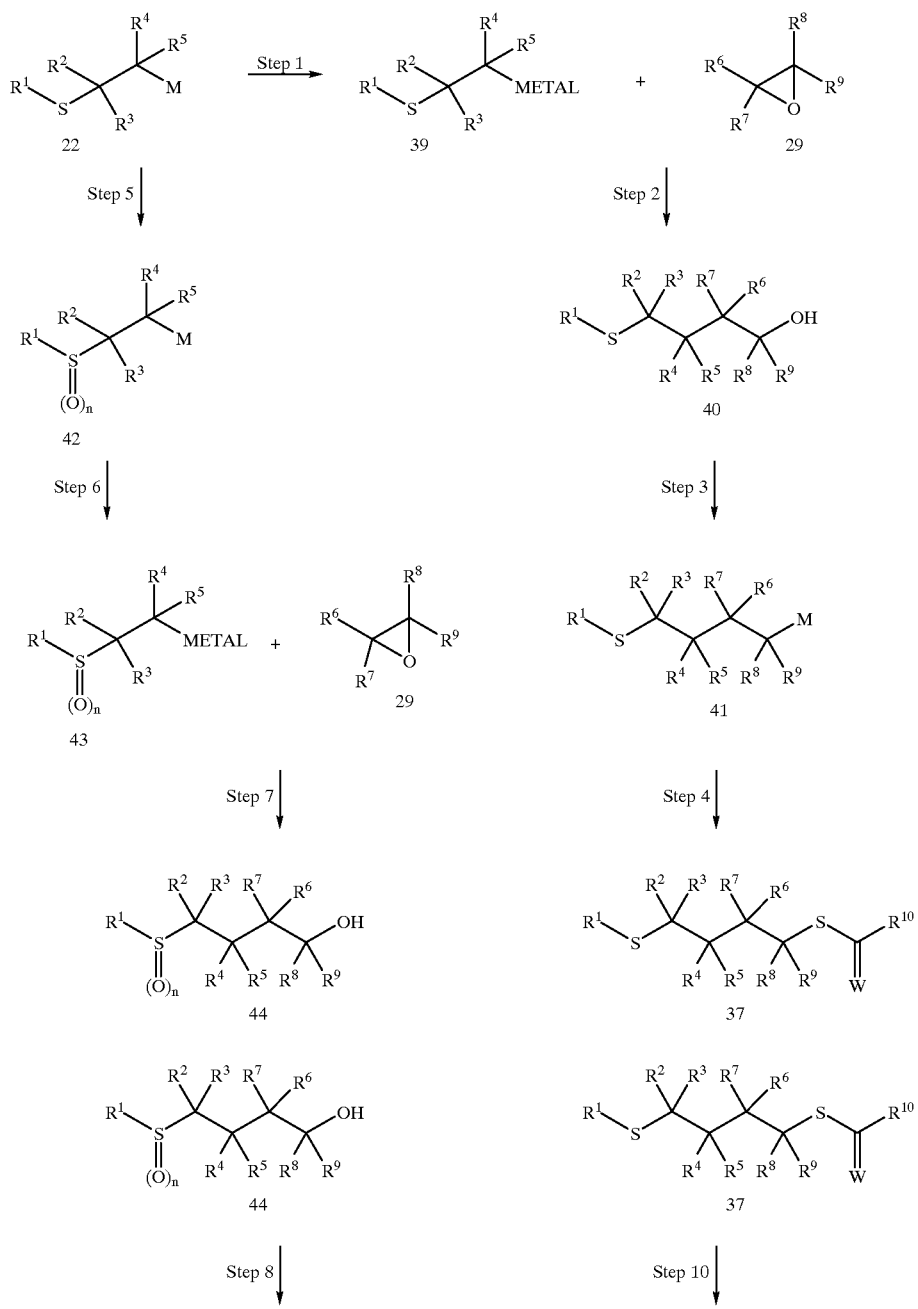

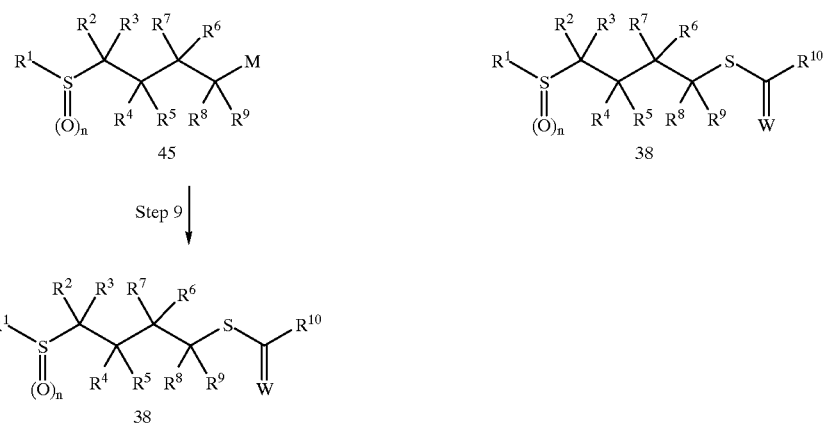
SCHEME 6
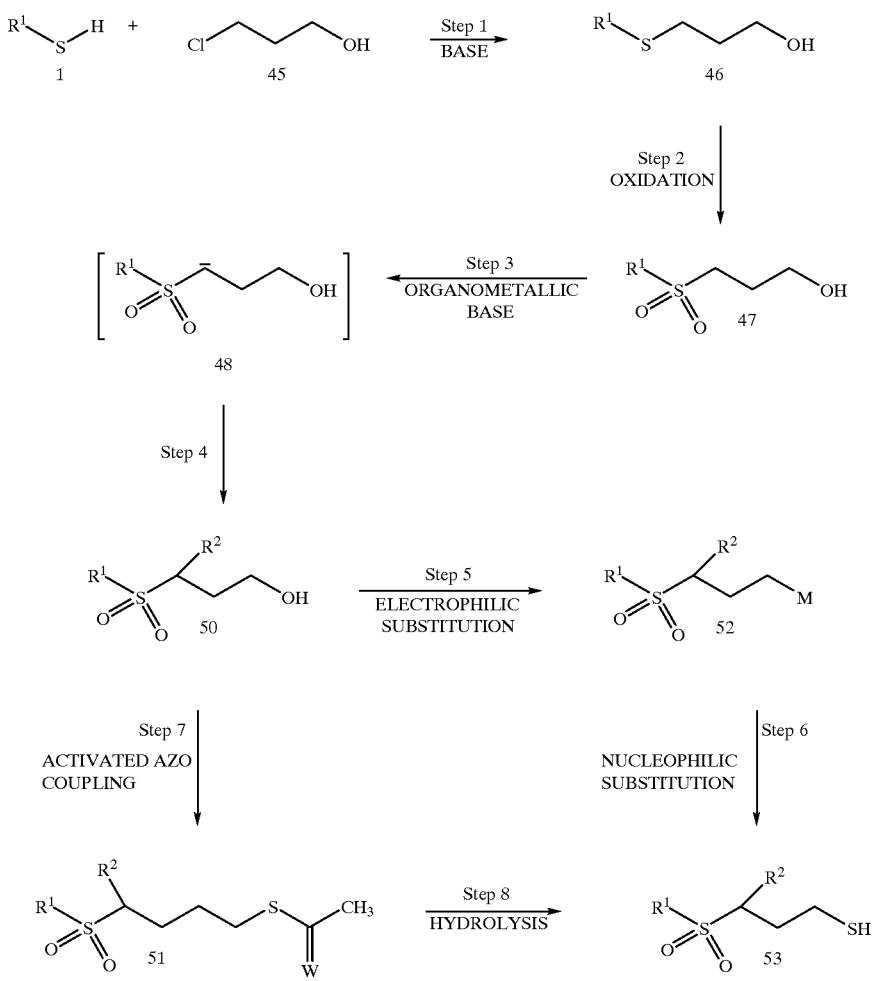

SCHEME 7

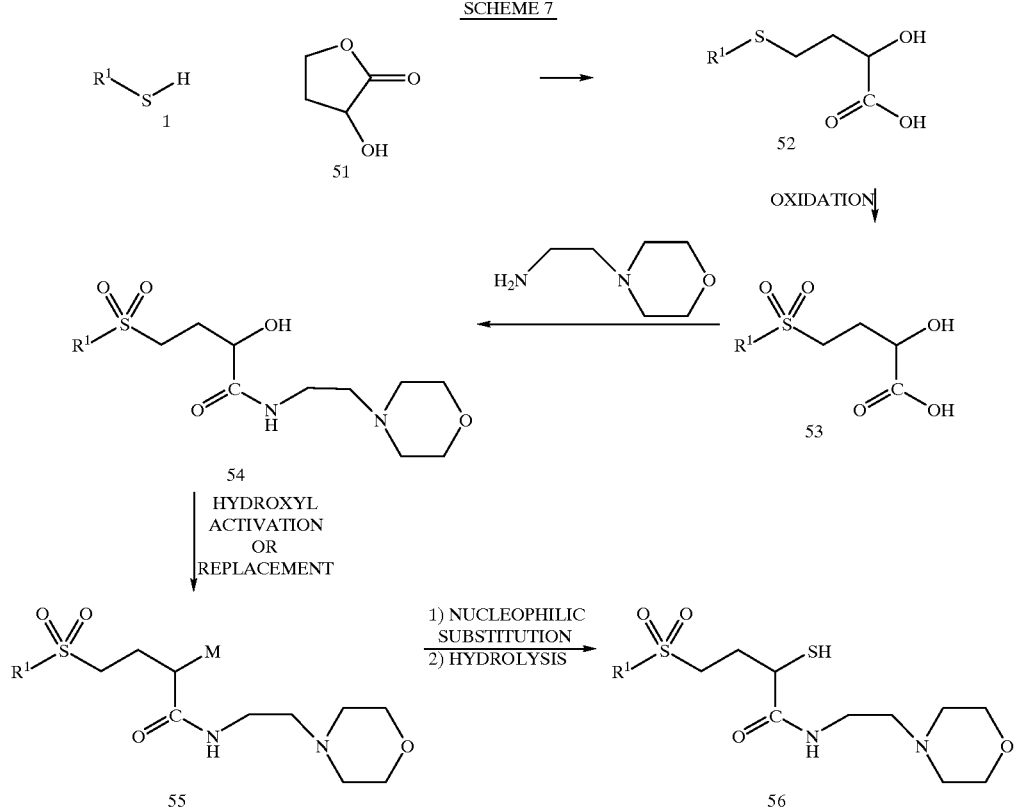

BEST MODE FOR CARRYING OUT THE INVENTION

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

Preparation of (R,S)1-[(4-methoxyphenyl)-sulfonyl] propane-2-thiol

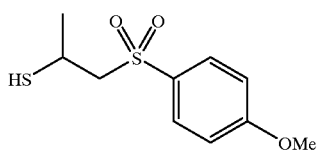

Part A: A 250 mL round bottom flask equipped with magnetic stir bar and $N_2$ inlet was charged with 3.4 g p-methoxybenzenethiol, 1.95 mL (R,S)-propylene oxide (1.15 eq), 370 mg potassium carbonate (1.15 eq) in 60 mL MeOH. The reaction was stirred 30 minutes at room temperature at this point HPLC analysis showed no starting material. The reaction was filtered and the filtrate was concentrated in vacuo. The crude sulfide was dissolved in 125 mL MeOH and 100 mL $H_2O$ and reacted with 45 g (3.0 eq) OXONE®. The reaction was stirred overnight, filtered, and the filtrate was concentrated to ½ the original volume. The reaction mixture was partitioned between ethyl acetate and water and the organic phase was washed with water, brine, dried over sodium sulfate and then concentrated in vacuo to 5.0 g of (R,S)1-[(4-methoxyphenyl)sulfonyl] propane-2-ol.

Part B: A 250 mL round bottom flask equipped with magnetic stir bar and $N_2$ inlet was charged with 1.3 g alcohol, 1.63 g triphenylphosphine (1.1 eq) in 40 mL THF. The reaction mixture was cooled to zero° C. and 1.25 mL DIAD was added. After 2 minutes 0.42 mL thioacetic acid was added and the reaction was stirred 1 hour. After standard work up the crude reaction mixture was chromatographed on silica gel (30% ethyl acetate/hexanes, 50% ethyl acetate/hexanes) to afford mostly the olefin and a fraction of 100 mg of desired alcohol contaminated with olefin. This material was used without further purification.

Part C: A 100 mL round bottom flask equipped with magnetic stir bar and $N_2$ inlet was charged with the crude product from part B in 15 mL MeOH. To this was added 1.5 mL 25% aqueous ammonium hydroxide. The reaction was stirred 2 hours then quenched with dry ice. The reaction mixture was partitioned between ethyl acetate/water and the organic phase was concentrated in vacuo to afford 75 mg crude oil. Flash chromatography on silica gel (100% MeCl) yielded 15 mg pure (R,S)1-[{4-methoxyphenyl}sulfonyl] propane-2-thiol.

EXAMPLE 2

Preparation of (R,S)-4-[(4-methoxyphenyl)-sulfonyl]butane-2-thiol

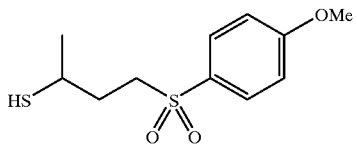

Part A: To a solution of 25.0 g (178 mmol) of 4-methoxybenzenethiol in 250 mL of anhydrous DMF, was added 16.4 mL (18.5 g, 196 mmol) of 3-chloro-1-propanol. After nitrogen gas was bubbled through the solution for 15 min., 74.0 g (535 mM) of powdered potassium carbonate was added. After 16 hours, the DMF was removed in vacuo, ethyl acetate and water were added, the organic layer separated and washed 3xs with brine, dried with magnesium sulfate, filtered and concentrated to afford 36.0 g of crude sulfide suitable for use in the next reaction.

Part B: To a solution of 36.0 g (181 mmol) of sulfide from Part A in 800 mL of methanol and 160 mL of water, was added 351 g (571 mmol) of potassium peroxymonosulfate (OXONE®). After 15 hours, the reaction was filtered, the filter cake was washed with methanol and the filtrate concentrated in vacuo, ethyl acetate and water were added, the layers were separated and the aqueous layer was extracted 2xs with ethyl acetate. The 3 organic extracts were combined and washed with saturated sodium bicarbonate solution and brine, dried with magnesium sulfate, filtered and concentrated to afford 40.0 g of crude product, identified as 3-[(4-methoxyphenyl)sulfonyl]propan-1-ol, m/e=?? (M+H).

Part C: To a solution of 5.0 g (22 mmol) of 4-[(4-methoxyphenyl)sulfonyl]propan-1-ol from part B and 12.1 mL (8.8 g, 87 mmole) of triethylamine in 25 mL of methylene chloride at zero° C., was added a solution of 13.8 g (87 mmol) of sulfur trioxidepyridine complex in 25 mL of DMSO. After 1 hour, the reaction mixture was added to 300 mL of ice, ethyl acetate was added, the organic layer was separated and washed with water, 5% potassium hydrogen sulfate solution and brine, dried with magnesium sulfate, filtered and concentrated to afford 4.1 g of 3-[(4-methoxyphenyl)sulfonyl]propan-1-al suitable for the next reaction.

Part D: A 100 mL round bottom flask equipped with magnetic stir bar, addition funnel, and $N_2$ inlet was charged with 2.87 mL of 3.0 M MeMgBr in Et2O (2.0 eq) in 15 mL THF. The reaction mixture was cooled to 0° C. and a solution of 1.0 g crude aldehyde from part C in 5 mL THF was added dropwise. After 1 hour at zero° C. the reaction was quenched with aqueous saturated ammonium chloride. The reaction mixture was partitioned between ethyl acetate/aq $KHSO_4$ and the organic phase was washed with saturated sodium bicarbonate, brine then concentrated in vacuo to afford the crude alcohol. Flash chromatography on silica gel (50% ethyl acetate-hexanes, 100% ethyl acetate) yielded 360 mg pure (R,S)-4-[(4-methoxyphenyl)-sulfonyl]butane-2-ol.

Part E: A 100 mL round bottom flask equipped with magnetic stir bar and $N_2$ inlet was charged with 360 mg alcohol from part D in 5 mL THF. The solution was cooled to zero° C. and reacted with 444 mg triphenylphosphine (1.15 eq) then 0.27 mL DEAD (1.15 eq). After stirring 5 minutes the reaction was treated with 0.12 mL thioacetic acid. The reaction was stirred 1 hour then concentrated in vacuo. The residue was slurried in 5 mL $MeCl_2$ at −78° C. filtered to remove impurities, and the filtrate was chromatographed on silica gel (30% ethyl acetatehexanes) 200 mg of 90% pure thioacetate that was used without further purification.

Part F: A 100 mL round bottom flask equipped with magnetic stir bar and $N_2$ inlet was charged with 200 mg crude thioacetate from part E in 20 mL MeOH. The solution was cooled to zero° C. and 2.0 eq NaOMe was added. After 20 minutes the reaction was partitioned between ethyl acetate and $H_2O$. The organic phase was dried and concentrated in vacuo to crude product. Chromatography on silica gel (100% $MeCl_2$ to 10% ethyl acetate-$MeCl_2$) yielded 87 mg pure (R,S)-4-[(4-methoxyphenyl)-sulfonyl]butane-2-thiol.

EXAMPLE 3

Preparation of 3-[(4-methoxyphenyl)sulfonyl]-2(S)-methylpropanethiol

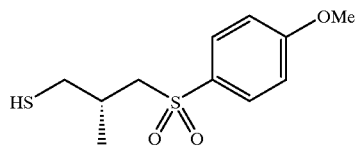

Part A: A 250 mL round bottom flask equipped with magnetic stir bar and $N_2$ inlet was charged with 1.3 g 3-bromo-2(S)-methylpropanol, 2.28 mL p-methoxybenzenethiol, 7.7 g potassium carbonate (3.0 eq) in 60 mL MeOH. After 6 hours at room temperature HPLC analysis indicated complete reaction. The reaction mixture was filtered and the filtrate was concentrated in vacuo and the residue was partitioned between ethyl acetate-$H_2O$.

The organic phase was washed with brine, dried and concentrated in vacuo to yield the crude sulfide. The sulfide was dissolved in 150 mL MeOH and added to a slurry of 36 g (3.0 eq) OXONE® in a 150 mL $H_2O$. The reaction was stirred overnight at room temperature then filtered and concentrated to ½ original volume. After ethyl acetate extraction followed by concentration in vacuo afforded 2.9 g pure 3-[(4-methoxyphenyl)sulfonyl]-2(S)-methylpropanol.

Part B: A 250 mL round bottom flask equipped with magnetic stir bar and $N_2$ inlet was charged with 2.9 g 3-[{4-methoxyphenyl}sulfonyl]-2(S)-methylpropanol in 50 mL THF. The solution was cooled to zero° C. and 3.42 g triphenylphosphine (1.15 eq) then 2.1 mL DEAD (1.15 eq). After stirring 5 minutes the reaction was treated with 0.85 mL thioacetic acid. The reaction was stirred 1 hour then concentrated in vacuo. The residue was slurried in 25 mL $MeCl_2$ at −78° C. then filtered to remove impurities and the filtrate was chromatographed on silica gel (50% $Et_2O$—H/ 80% $Et_2O$—H) to yield 2.0 g pure thioacetate.

Part C: A 250 mL round bottom flask equipped with magnetic stir bar and $N_2$ inlet was charged with 1.2 g thioacetate in 35 mL MeOH. The reaction mixture was treated with 1.0 mL 25% NaOMe in MeOH. After 30 minutes the reaction was quenched with 1N HCl and partitioned between ethyl acetate-$H_2O$. The organic phase was dried and concentrated in vacuo to crude product. Chromatography on silica gel (50% ethyl acetate-hexanes) yielded 400 mg of 3-[(4-methoxyphenyl)sulfonyl]-2(S)-methylpropane-thiol.

EXAMPLE 4

Preparation of 3-[(4-{3-phenylpropyloxy)phenyl}sulfonyl]-propanethiol

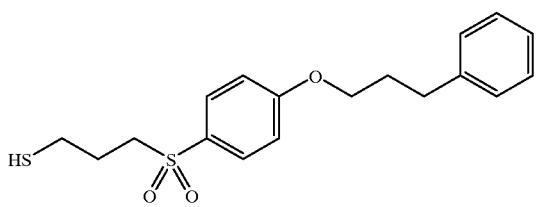

Part A: To a solution of 10.0 g (79 mmol) of 4-hydroxybenzenethiol in 100 mL, of anhydrous DMF, was added 7.3 mL (8.2 g, 87 mmol) of 3-chloro-1-propanol. After nitrogen gas was bubbled through the solution for 15 min., 33.0 g (238 mM) of powdered potassium carbonate was added. After 17 hours, the DMF was removed in vacuo, ethyl acetate and water were added, the organic layer separated and washed 3×s with brine, dried with magnesium sulfate, filtered and concentrated to afford 16 g of crude product, m/z=183 (M−H).

Part B: To a solution of 2 g (10.6 mmol) of product from Part A in 20 mL ol anhydrous DMF, was added 4.5 g (31.8 mmol) of powdered potassium carbonate, followed by 2.1 g (10.6 mM) of 1-bromo-3-phenylpropane. After 24 hours, ethyl acetate and water were added, the organic layer separated and washed 3×s with brine, dried with magnesium sulfate, filtered and concentrated to afford 3.3 g of crude product that was dissolved in 100 mL MeOH and added to 20 g OXONE® in 80 mL H$_2$O. The reaction was stirred overnight at room temperature, filtered and concentrated to ½ volume. Extraction with ethyl acetate followed by drying and concentration in vacuo gave 3.3 g of the sulfone alcohol.

Part C: A 250 mL round bottom flask equipped with magnetic stir bar and N$_2$ inlet was charged with 3.6 g alcohol from part B in 50 mL THF. The solution was cooled to zero° C. and 2.8 g triphenylphosphine then 1.7 mL DEAD. After stirring 5 minutes the reaction was treated with 0.8 mL thioacetic acid. The reaction was stirred 1 hour then concentrated in vacuo. The residue was slurried in 25 mL MeCl$_2$ at −78° C. then filtered to remove impurities and the filtrate was chromatographed on silica gel (30% ethyl acetate-hexanes/50% ethyl acetate-hexanes) to yield 1.4 g pure thioacetate.

Part D: A 100 mL round bottom flask equipped with magnetic stir bar and N$_2$ inlet was charged with 655 mg thioacetate in 50 mL MeOH. The reaction mixture was treated with 1.1 mL 25% NaOMe in MeOH. After 30 minutes the reaction was quenched with 1N HCl and partitioned between ethyl acetate-H$_2$O. The organic phase was dried and concentrated in vacuo to crude product. Chromatography on silica gel (50% ethyl acetate-hexanes) yielded 420 mg pure 3-[(4-(3-phenylpropyloxy)phenyl)sulfonyl]-propanethiol.

EXAMPLE 5

Preparation of

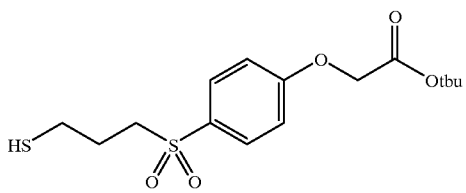

Part A: To a solution of 2.1 g of product from Ex. 4 Part A in 50 mL of anhydrous DMF, was added 4.75 g (3 eq) of powdered potassium carbonates followed by 2.25 g of t-butyl bromoacetate. After 4 hours, ethyl acetate and water were added, the organic layer separated and washed 3×s with brine, dried with magnesium sulfate, filtered and concentrated to afford 3.4 g of crude product that was dissolved in 80 mL MeCl$_2$ and reacted with 8.2 g MCPBA (2.5 eq). The reaction was stirred overnight at room temperature, quenched with sodium sulfite, and washed 2×S with saturated sodium bicarbonate. The organic phase was filtered thru CELITE®, dried and concentrated in vacuo gave 3.9 g of the crude sulfone alcohol which was filtered thru a short plug of alumina (10% ethanol-ethyl acetate) to remove MCPBA to yield 3.5 g pure product.

Part B: A 250 mL round bottom flask equipped with magnetic stir bar and N$_2$ inlet was charged with 3.5 g alcohol from part A in 50 mL THF. The solution was cooled to zero° C. and 2.8 g triphenylphosphine, then 1.67 mL DEAD. After stirring 5 minutes, the reaction was treated with 0.76 mL thioacetic acid. The reaction was stirred 1 hour then concentrated in vacuo. The residue was slurried in 15 mL MeCl$_2$ at −78° C. then filtered to remove impurities and the filtrate was chromatographed on silica gel (30% ethyl acetate-hexanes/50% ethyl acetate-hexanes) to yield 2.1 g pure thioacetate.

Part C: A 100 mL round bottom flask equipped with magnetic stir bar and N$_2$ inlet was charged with 382 mg thioacetate in 15 mL MeOH. The reaction mixture was treated with 0.46 mL 25% NaOMe in MeOH. After 30 minutes the reaction was quenched with 1N HCl and partitioned between ethyl acetate-H$_2$O. The organic phase was dried and concentrated in vacuo to crude product. Chromatography on silica gel (50% ethyl acetate-hexanes) yielded 250 mg pure product.

EXAMPLE 6

Preparation of

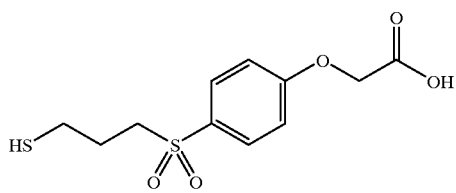

Part A: A 100 mL round bottom flask equipped with magnetic stir bar and N$_2$ inlet was charged with 1.65 g thioacetate from Ex.5 part B in 10 mL 4NHCl-Dioxane. The reaction was stirred at room temperature overnight. Concentration in vacuo followed by Et$_2$O trituration yielded 1.0 g pure acid.

Part B: A 100 mL round bottom flask equipped with magnetic stir bar and $N_2$ inlet was charged with 382 mg thioacetate in 15 mL MeOH. The reaction mixture was treated with 0.39 mL (3.0 eq) 25% NaOMe in MeOH. After 15 minutes the reaction was quenched with 1N HCl and partitioned between ethyl acetate-$H_2O$. The organic phase was dried and concentrated in vacuo to crude product that was a 65-35 mixture of thiol to disulfide.

EXAMPLE 7

Preparation of (R,S)trans-3-[(4-methoxyphenyl) sulfonyl]cyclohexanethiol

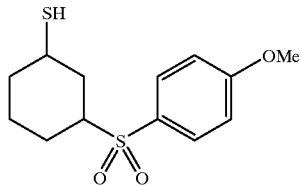

Part A: A 250 mL round bottom flask equipped with magnetic stir bar and $N_2$ inlet was charged with 4.6 g cyclohexenone, 6.7 g p-methoxy benzenethiol in 50 mL degassed MeOH. To the stirring solution was added 6.8 g triethylamine. The reaction was stirred 30 minutes then concentrated in vacuo to remove triethylamine. The crude product was dissolved in 65 mL MeOH, cooled to zero° and treated with 3.6 g $NaBH_4$ cautiously. The reaction was stirred 90 minutes at zero° C. then quenched with 1N HCl and partitioned between ethyl acetate-$H_2O$. The combined organics were washed with brine, dried, and concentrated in vacuo to crude product that was dissolved in 200 mL MeOH and added to a slurry of 86 g OXONE® in 200 mL $H_2O$. After 4 hours HPLC analysis indicated complete reaction and the reaction mixture was filtered and concentrated in vacuo to ½ original volume. After extraction with ethyl acetate the organic phase was washed with $H_2O$, brine, dried, and concentrated in vacuo to yield 8.9 g of a 3:1 diastereomeric mixture of alcohols.

Part B: A 250 mL round bottom flask equipped with magnetic stir bar and $N_2$ inlet was charged with 1.2 g alcohol from part A in 20 mL THF. The solution was cooled to zero° C. and 1.16 g triphenylphosphine then 0.7 mL DEAD. After stirring 5 minutes the reaction was treated with 0.35 mL thioacetic acid. The reaction was stirred 1 hour then concentrated in vacuo. HPLC analysis indicated a 6:1 ratio of diastereomers. The residue was slurried in 10 mL $MeCl_2$ at −78° C. then filtered to remove impurities and the filtrate was chromatographed on silica gel (30% ethyl acetate-hexanes/50% ethyl acetate-hexanes) to yield 0.4 g pure thioacetate which was analysised by HPLC and found to be >30:1 ratio of diastereomers.

Part C: A 100 mL round bottom flask equipped with magnetic stir bar and $N_2$ inlet was charged with 395 mg thioacetate in 15 mL MeOH. The reaction mixture was treated with 0.78 mL 25% NaOMe in MeOH. After 30 minutes the reaction was quenched with 1N HCl and partitioned between ethyl acetate-H $_2$O. The organic phase was dried and concentrated in vacuo to yield 320 mg pure (R,S)-3-[(4-methoxyphenyl)sulfonyl]cyclohexanethiol, whose 300 MHz proton NMR was suggestive of a trans relationship between the sulfone and thiol.

EXAMPLE 8

Preparation of (R,S)3-butyl-3-[(4-methoxyphenyl) sulfonyl]cyclohexanethiol

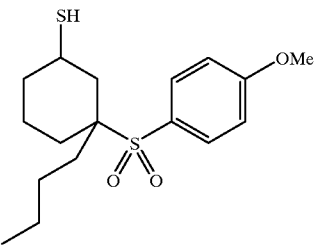

Part A: A 100 mL round bottom flask equipped with magnetic stir bar and $N_2$ inlet was charged with 2.5 g of alcohol from Example 7 part A in 25 mL THF.

The solution was cooled to −78° C. and treated with 2.65 mL (2.5 eq) DMPU, then 1.93 mL (2.2 eq) 10M nBuLi in Hexanes. The dianion was stirred 30 minutes at −78° C. then reacted with 0.94 mL butyl bromide. The reaction was stirred at room temperature overnight then quenched with saturated ammonium chloride. The reaction was partitioned between ethyl acetate-$H_2O$. The organic phase was dried and concentrated in vacuo to crude product that was chromatographed (70% ethyl acetate-hexanes) to yield 120 mg faster moving isomer and 480 mg slower moving isomer.

Part B: A 100 mL round bottom flask equipped with magnetic stir bar and $N_2$ inlet was charged with 0.48 g alcohol from part A in 8 mL THF. The solution was cooled to zero° C. and 0.41 g triphenylphosphine then 0.25 mL DEAD. After stirring 5 minutes the reaction was treated with 0.12 mL thioacetic acid. The reaction was stirred 1 hour then concentrated in vacuo. The residue was slurried in 5 mL $MeCl_2$ at −78° C. then filtered to remove impurities and the filtrate was chromatographed on silica gel (25% ethyl acetate-hexanes/50% ethyl acetate-hexanes) to yield 132 mg thioacetate contaminated with olefin. The crude thioacetate was used without further purification.

Part C: A 100 mL round bottom flask equipped with magnetic stir bar and $N_2$ inlet was charged with 132 mg crude thioacetate in 4 mL MeOH. The reaction mixture was treated with 0.14 mL 25% NaOMe in MeOH. After 30 minutes the reaction was quenched with 1N HCl and partitioned between ethyl acetate-$H_2O$. The organic phase was dried and concentrated in vacuo to a crude product that was chromatographed (25% ethyl acetate-hexanes) to yield 55 mg thiol.

EXAMPLE 9

Preparation of

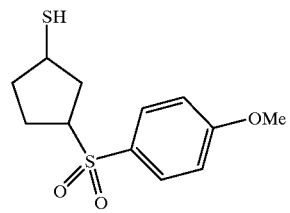

Part A: A 250 mL round bottom flask equipped with magnetic stir bar and $N_2$ inlet was charged with 5.2 g cyclopentenenone, 8.9 g p-methoxy benzenethiol in 75 mL degassed MeOH. To the stirring solution was added 8.9 mL triethylamine. The reaction was stirred 30 minutes then concentrated in vacuo to remove triethylamine. The crude product was dissolved in 100 mL MeOH, cooled to zero° C. and treated with 4.8 g NaBH4 cautiously. The reaction was stirred 90 minutes at zero° C. then quenched with 1N HCl and partitioned between ethyl acetate-H₂O. The combined organics were washed with brine, dried, and concentrated in vacuo to 14.8 g crude product that was dissolved in 250 mL MeOH and added to a slurry of 117 g OXONE® in 250 mL H₂O. After 12 hours HPLC analysis indicated complete reaction and the reaction mixture was filtered and concentrated in vacuo to ½ original volume. After extraction with ethyl acetate the organic phase was washed with H₂O, brine, dried, and concentrated in vacuo to yield 15.5 g of a 3:1 diastereomeric mixture of alcohols.

Part B: A 250 mL round bottom flask equipped with magnetic stir bar and N₂ inlet was charged with 3.0 g alcohol from part A in 50 mL THF. The solution was cooled to zero° C. and 3.0 g triphenylphosphine then 1.78 mL DEAD. After stirring 5 minutes the reaction was treated with 0.98 mL thioacetic acid. The reaction was stirred 1 hour then concentrated in vacuo. The residue was slurried in 20 mL MeCl₂ at −78° C. then filtered to remove impurities and the filtrate was chromatographed on silica gel (30% ethyl acetate-hexanes/50% ethyl acetate-hexanes) to yield 780 mg thioacetate which was analysised by HPLC and found to be 2.6:1 ratio of diastereomers.

Part C: A 100 mL round bottom flask equipped with magnetic stir bar and N₂ inlet was charged with 780 mg thioacetate in 15 mL MeOH. The reaction mixture was treated with 0.78 mL 25% NaOMe in MeOH. After 30 minutes the reaction was quenched with 1N HCl and partitioned between ethyl acetate-H₂O. The organic phase was dried and concentrated in vacuo to yield 500 mg crude thiol that was submitted without further purification.

EXAMPLE 10

Preparation of (R,S)-Methyl-4-[(4-methoxyphenyl)sulfonyl]-2-mercaptobutanoate

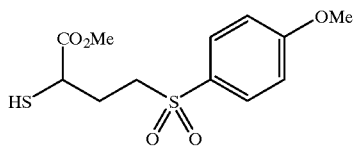

Part A: A 100 mL round bottom flask equipped with magnetic stir bar and N₂ inlet was charged with 1.0 g 3-[(4-methoxyphenyl)sulfonyl] propan-1-al in 35 mL MeCl₂. The reaction was cooled to zero° C. and charged with 700 mg (1.2 eq) trimethylsilyl cyanide and 1.1 g (1.1 eq) zinc bromide and stirred at room temperature overnight. The reaction mixture was concentrated in vacuo and partitioned between ethyl acetate-H₂O. The residue was treated with 5 mL acetic acid and 15 mL 6N HCl and heated to reflux for 3 hours. The reaction mixture was concentrated in vacuo and partitioned between ethyl acetate-H₂O. The crude hydroxy acid (435 mg) was dissolved in 15 mL MeOH and treated with 0.18 mL thionyl chloride and stirred at room temperature overnight. The reaction mixture was concentrated in vacuo and partitioned between ethyl acetate-H₂O. The crude ester was chromatographed on silica gel (50% ethyl acetate-hexanes/100% ethyl acetate) to yield 360 mg pure (R,S)-methyl-4-[(4-methoxyphenyl)sulfonyl]-2-hydroxybutanoate.

Part B: A 100 mL round bottom flask equipped with magnetic stir bar and N₂ inlet was charged with 250 mg alcohol from part A in 5 mL THF. The solution was cooled to zero° C. and 250 mg triphenylphosphine then 0.14 mL DEAD. After stirring 5 minutes the reaction was treated with 0.1 mL thioacetic acid. The reaction was stirred 1 hour then concentrated in vacuo. The residue was slurried in 5 mL MeCl₂ at −78° C. then filtered to remove impurities and the filtrate was chromatographed on silica gel (30% ethyl acetate-hexanes/50% ethyl acetate-hexanes) to yield 100 mg clear oil.

Part C: A 100 mL round bottom flask equipped with magnetic stir bar and N₂ inlet was charged with 100 mg thioacetate in 10 mL MeOH. The reaction mixture was treated with 0.2 mL 25% NaOMe in MeOH. After 30 minutes the reaction was quenched with 1N HCl and partitioned between ethyl acetate-H₂O. The organic phase was dried and concentrated in vacuo to yield 70 mg crude thiol that was filtered thru a plug of silica gel with MeCl₂ to yield 45 mg pure (R,S)-methyl-4-[(4-methoxyphenyl)-sulfonyl]-2-mercaptobutanoate.

EXAMPLE 11

Preparation of (R,S)-3-[(4-methoxybenzyl)-sulfonyl]propane thiol

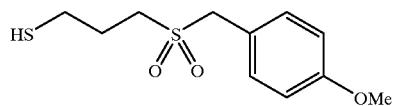

Part A: To a solution of 4.1 g of benzyl mercaptan in 40 mL of anhydrous DMF, was added 3.0 g of 3-chloro-1-propanol. After nitrogen gas was bubbled through the solution for 15 min., 8.7 g of powdered potassium carbonate was added. After 16 hours, the DMF was removed in vacuo, ethyl acetate and water were added, the organic layer separated and washed 3xs with brine, dried with magnesium sulfate, filtered and concentrated to afford 5.6 g of a rose colored liquid that was dissolved in 100 mL MeOH and added to a slurry of 58 g (3.0 eq) OXONE® in 100 mL H₂O. The reaction was stirred 3 hours and the reaction mixture was filtered and concentrated in vacuo to ½ original volume. After extraction with ethyl acetate the organic phase was washed with H₂O, brine, dried, and concentrated in vacuo to yield 3.55 g white solid.

Part B: A 100 mL round bottom flask equipped with magnetic stir bar and N₂ inlet was charged with 1.0 g alcohol from part A in 10 mL THF. The solution was cooled to zero° C. and 1.25 g triphenylphosphine then 82 mL DEAD. After stirring 5 minutes the reaction was treated with 0.36 mL thioacetic acid. The reaction was stirred 1 hour then concentrated in vacuo. The residue was slurried in 10 mL MeCl₂ at −78° C. then filtered to remove impurities and the filtrate was chromatographed on silica gel (50% ethyl acetate-hexanes) to yield 210 mg clear oil.

Part C: A 100 mL round bottom flask equipped with magnetic stir bar and N₂ inlet was charged with 210 mg thioacetate in 3 mL MeOH. The reaction mixture was treated with 0.5 mL NH₄OH in MeOH. After 60 minutes the reaction was quenched with 1N HCl and partitioned between ethyl acetate-H₂O. The organic phase was dried and concentrated in vacuo to yield 170 mg crude thiol that was triturated with Et₂O to yield 150 mg pure thiol.

EXAMPLE 12

Preparation of 3-[(4-methoxyphenyl)sulfonyl]propan-1-ol

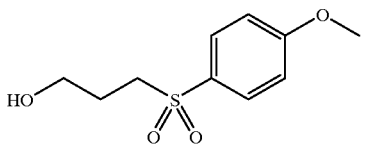

Part A: To a solution of 7.1 g (50 mmol) of 4-methoxybenzenethiol in 100 mL of anhydrous DMF, was added 4.4 mL (5.0 g, 53 mmol) of 3-chloro-1-propanol. After nitrogen gas was bubbled through the solution for 15 min., 21.0 g (151 mM) of powdered potassium carbonate was added. After 30 minutes, the DMF was removed in vacuo, ethyl acetate and water were added, the organic layer separated and washed 3×s with brine, dried with magnesium sulfate, filtered and concentrated to afford 10.3 g of product suitable for the next reaction.

Part B: To a solution of 10.0 g (50 mmol) of product from Part A in 200 mL of methanol and 20 mL of water, was added 93 g (151 mmol) of potassium peroxymonosulfate (OXONE®). After 2 hours, the reaction was filtered, the filter cake was washed with methanol and the filtrate concentrated in vacuo, ethyl acetate and water were added, the layers were separated and the aqueous layer was extracted 2×s with ethyl acetate. The 3 organic extracts were combined and washed with saturated sodium bicarbonate solution and brine, dried with magnesium sulfate, filtered and concentrated to afford 11.8 g of pure 3-[(4-methoxyphenyl)sulfonyl]-propan-1-ol, m/z=237 (M+Li).

EXAMPLE 13

Preparation of 3-[(4-methoxyphenyl)sulfonyl]propane-1-thiol

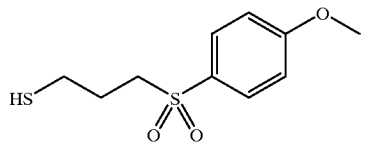

Part A: To a solution of 2.8 g (9 mmol) of 3-[(4-methoxyphenyl)sulfonyl]propan-1-ol from Example 13 in 20 mL of methylene chloride at zero° C., was added 1.3 mL (1.0 g, 9 mmol) of triethylamine, followed by 0.7 mL (1.0 g, 9 mM) of methanesulfonyl chloride. After 16 hours, the reaction was concentrated in vacuo, ethyl acetate and water were added, the organic layer was separated and washed with 5% potassium hydrogen sulfate solution, saturated sodium bicarbonate solution and brine, dried with magnesium sulfate, filtered and concentrated to yield 2.7 g of product suitable for the next reaction.

Part B: To a solution of 2.8 g (9 mmol) of product from Part A in 20 mL of anhydrous DMF, was added 1.4 mL (1.0 g, 10 mmol) of triethylamine, and 0.7 mL (0.8 g, 10 mM) of thiolacetic acid. After 16 hours, the reaction was concentrated in vacuo, ethyl acetate and water were added, the organic layer was separated and washed with 5% potassium hydrogen sulfate solution, saturated sodium bicarbonate solution and brine, dried with magnesium sulfate, filtered and concentrated to yield 2.6 g of crude product. This was chromatographed on silica gel using 20%–40% ethyl acetate/hexane to yield 1.8 g of pure thioacetate, m/z=295 (M+Li).

Part C: To a solution of 0.9 g (3 mmol) of thioacetate, from Part B, in 20 mL of anhydrous methanol, was added 0.3 g (12 mmol) of sodium metal. After 1 hour, the reaction was quenched with dry ice, ethyl acetate and 5% potassium hydrogen sulfate were added, the organic layer was separated and washed with saturated sodium bicarbonate solution and brine, dried with magnesium sulfate, filtered and concentrated to afford 0.5 g of crude product. This was chromatographed on silica gel using 20%–30% ethyl acetate/hexane to yield 0.4 g of pure 3-[(4-methoxyphenyl)sulfonyl]-propane-1-thiol, m/z=253 (M+Li).

EXAMPLE 14

Preparation of 3-[(4-methoxyphenyl)sulfonyl]-2R-methylpropane-1-thiol

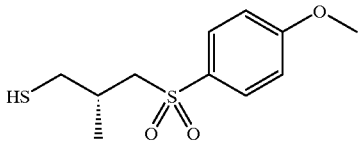

Part A: To a solution of 4.4 g (31 mmol) of 4-methoxybenzenethiol in 100 mL of anhydrous DMF, was added 3.4 mL (5.0 g, 33 mmol) of (R)-(−)-3-bromo-2-methyl-1-propanol. After nitrogen gas was bubbled through the solution for 15 min., 12.9 g (93 mM) of powdered potassium carbonate was added. After 1 hour, the DMF was removed in vacuo, ethyl acetate and water were added, the organic layer separated and washed 3×s with brine, dried with magnesium sulfate, filtered and concentrated to afford 7.4 g of product suitable for the next reaction.

Part B: To a solution of 6.6 g (31 mmol) of product from Part A in 150 mL of methanol and 15 mL of water, was added 67 g (108 mmol) of potassium peroxymonosulfate (OXONE®). After 3 hours, the reaction was filtered, the filter cake was washed with methanol and the filtrate concentrated in vacuo, ethyl acetate and water were added, the layers were separated and the aqueous layer was extracted 2×s with ethyl acetate. The 3 organic extracts were combined and washed with saturated sodium bicarbonate solution and brine, dried with magnesium sulfate, filtered and concentrated to afford 7.3 g of the crude product. This was chromatographed on silica gel using 20%–60% ethyl acetate/hexane to yield 5.9 g of pure 3-[(4-methoxyphenyl)sulfonyl]-2R-methylpropan-1-ol, m/z=251 (M+Li).

Part C: To a solution of 5.9 g (24 mmol) of 3-[(4-methoxyphenyl)sulfonyl]-2R-methylpropan-1-ol from Part B and 6.9 g (26 mmole) of triphenylphosphine in 100 mL of anhydrous THF at zero° C., was added 4.2 mL (4.3 g, 21 mmol) of diisopropylazodicarboxylate, followed after 5 min. by 1.9 mL (2.0 g, 26 mM) of thiolacetic acid. After 1 hour, the reaction was concentrated and the residue was chromatographed on silica gel using 20%–30% ethyl acetate/hexane to yield 8.6 g which was chromatographed again on silica gel using methylene chloride to yield 4.0 g of pure thioacetate, m/z=309 (M+Li).

Part D: To a solution of 1.4 g (5 mmol) of thioacetate, from Part C, in 40 mL of anhydrous methanol, was added 0.4 g (17 mmol) of sodium metal After 1 hour, the reaction was cooled, 1N HCl solution was added, followed by ethyl acetate and water, the organic layer was separated and washed with saturated sodium bicarbonate solution and brine, dried with magnesium sulfate, filtered and concentrated to afford the crude product. This was chromatographed on silica gel using 15%–25% ethyl acetate/hexane to yield 0.6 g of pure 3-[(4-methoxyphenyl)sulfonyl]-2R-methylpropane-1-thiol, m/z=267 (M+Li).

EXAMPLE 15

Preparation of 3-[(4-methoxyphenyl)sulfonyl]-2,2-dimethylpropane-1-thiol

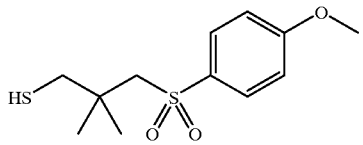

Part A: To a solution of 5.0 g (36 mmol) of 4-methoxybenzenethiol in 50 mL of anhydrous DMF, was added 4.6 mL (6.3 g, 37 mmol) of 3-bromo-2,2-dimethyl-1-propanol. After nitrogen gas was bubbled through the solution for 15 min., 14.8 g (107 mM) of powdered potassium carbonate was added. After 67 hours, the DMF was removed in vacuo, ethyl acetate and water were added, the organic layer separated and washed 3xs with brine, dried with magnesium sulfate, filtered and concentrated to afford 8.4 g of product suitable for the next reaction.

Part B: To a solution of 8.1 g (36 mmol) of product from Part A in 150 mL of methanol and 15 mL of water, was added 77 g (125 mmol) of potassium peroxymonosulfate (OXONE®). After 3 hours, the reaction was filtered, the filter cake was washed with methanol and the filtrate concentrated in vacuo, ethyl acetate and water were added, the layers were separated and the aqueous layer was extracted 2xs with ethyl acetate. The 3 organic extracts were combined and washed with saturated sodium bicarbonate solution and brine, dried with magnesium sulfate, filtered and concentrated to afford 8.3 g of the crude product. This was chromatographed on silica gel using 20%–50% ethyl acetate/hexane to yield 6.6 g of pure 3-[(4-methoxyphenyl)sulfonyl]-2,2-dimethylpropan-1-ol, m/z=265 (M+Li).

Part C: To a solution of 5.0 g (19 mmol) of 3-[(4-methoxyphenyl)sulfonyl]-2,2-dimethylpropan-1-ol from Part B and 5.6 g (21 mmole) of triphenylphosphine in 80 mL of anhydrous THF at zero° C., was added 3.4 mL (3.7 g, 21 mmol) of diethylazodicarboxylate, followed after 5 min. by 1.5 mL (1.6 g, 21 mM) of thiolacetic acid. After 16 hours, the reaction was concentrated and the residue was chromatographed on silica gel using 15%–25% ethyl acetate/hexane to yield 3.9 g of pure thioacetate, m/z=334 (M+NH₄).

Part D: To a solution of 2.0 g (6 mmol) of thioacetate from Part C in 60 mL of anhydrous methanol, was added 0.5 g (23 mmol) of sodium metal. After 1 hour, the reaction was cooled, 1N HCl solution was added, followed by ethyl acetate and water, the organic layer was separated and washed with saturated sodium bicarbonate solution and brine, dried with magnesium sulfate, filtered and concentrated to afford 1.7 g of crude product. This was chromatographed on silica gel using 10%–20% ethyl acetate/hexane to yield 1.3 g of pure 3-[(4-methoxyphenyl)sulfonyl]-2,2-dimethylpropane-1-thiol, m/z=292 (M+NH₄).

EXAMPLE 16

Preparation of 3-[(4-methoxyphenyl)sulfonyl]-pentane-1-thiol

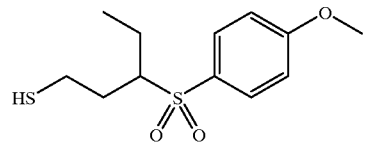

Part A: To a solution of 4.6 g (20 mmol) of 3-[(4-methoxyphenyl)sulfonyl]propane-1-ol from example 13 and 6 mL of DMPU in 60 mL of anhydrous THF at −70° C. under nitrogen, was added 5.8 mL (2.8 g, 44 mmol) of a 10.0 M solution of n-butyllithium in hexane. After stirring for 30 min. at −70° C., 1.6 mL (2.4 g, 22 mmole) of 1-bromoethane was added. After 2 hours, the reaction mixture was cooled to zero° C. and 25 mL of saturated ammonium chloride solution was added, followed by ethyl acetate and water, the layers were separated and the aqueous layer was extracted 2 xs with ethyl acetate. The 3 organic layers were combined and washed with brine, dried with magnesium sulfate, filtered and concentrated to afford 4 g of crude product. This was chromatographed on silica gel using 40%–55% ethyl acetate/hexane to yield 2.4 g of pure 3-[(4-methoxyphenyl)sulfonyl]-pentan-1-ol, m/z=265 (M+Li).

Part B: To a solution of 3.1 g (12 mmole) of triphenylphosphine in 100 mL of anhydrous THF at zero C., was added 1.9 mL (2.0 g, 12 mmol) of diethylazodicarboxylate, followed after 15 min. by a solution of 2.4 g (9 mmol) of 3-[(4-methoxyphenyl)sulfonyl]-pentan-1-ol from Part A and 0.9 mL (0.9 g, 12 mM) of thiolacetic acid. After 1 hour, the reaction was concentrated and the residue was chromatographed on silica gel using 15%–25% ethyl acetate/hexane to yield 1.5 g of pure thioacetate, m/z=323 (M+Li).

Part C: To a solution of 1.5 g (5 mmol) of thioacetate from Part B in 20 mL of anhydrous methanol, was added 0.4 g (18 mmol) of sodium metal. After 1 hour, the reaction was cooled, 1N HCl solution was added, followed by ethyl acetate and water, the organic layer was separated and washed with water and brine, dried with magnesium sulfate, filtered and concentrated to afford 1.4 g of crude product. This was chromatographed on silica gel using 10%–20% ethyl acetate/hexane to yield 0.6 g of pure 3-[(4-methoxyphenyl)sulfonyl]-pentane-1-thiol, m/z=281 (M+Li).

EXAMPLE 17

Preparation of 3-[(4-methoxyphenyl)sulfonyl]-dodecane-1-thiol

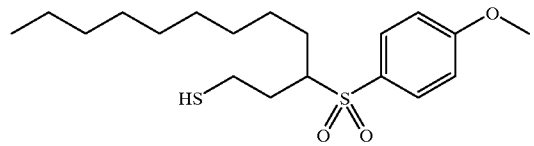

Part A: To a solution of 4.7 g (20 mmol) of 3-[(4-methoxyphenyl)sulfonyl]propan-1-ol from example 13 and 6 mL of DMPU in 100 mL of anhydrous THF at −70° C. under nitrogen, was added 5.9 mL (2.9 g, 45 mmol) of a 10.0 M solution of n-butyllithium in hexane. After stirring for 30 min. at −70° C., 4.3 mL (4.7 g, 22 mmole) of 1-bromononane was added. After 16 hours, the reaction mixture was cooled to zero° C. and 25 mL of saturated ammonium chloride solution was added, followed by ethyl acetate and water, the layers were separated and the aqueous layer was extracted 2xs with ethyl acetate. The 3 organic layers were combined and washed with brine, dried with magnesium sulfate, filtered and concentrated to afford 11 g of crude product. This was chromatographed on silica gel using 30%–50% ethyl acetate/hexane to yield 4.2 g of pure 3-[(4-ethoxyphenyl)sulfonyl]-dodecan-1-ol, m/z=363 (M+Li).

Part B: To a solution of 4.2 g (12 mmol) of 3-[(4-methoxyphenyl)sulfonyl]-dodecan-1-ol from Part A and 4.6 g (18 mmole) of triphenylphosphine in 100 mL of anhydrous THF at 0° C., was added 2.8 mL (3.1 g, 18 mmol) of diethylazodicarboxylate, followed after 15 min. by 1.3 mL (1.3 g, 18 mM) of thiolacetic acid. After 1 hour, the reaction was concentrated and the residue was chromatographed on silica gel using 5%–15% ethyl acetate/hexane to yield 4.3 g of pure thioacetate, m/z=421 (M+Li).

Part C: To a solution of 2.0 g (5 mmol) of thioacetate from Part B in 25 mL of anhydrous methanol, was added 0.4 g (18 mmol) of sodium metal. After 1 hour, the reaction was cooled, 1N HCl solution was added, followed by ethyl acetate and water, the organic layer was separated and washed with water and brine, dried with magnesium sulfate, filtered and concentrated to afford 1.7 g of crude product. This was chromatographed on silica gel using 5%–20% ethyl acetate/hexane to yield 1.2 g of pure 3-[(4-methoxyphenyl)sulfonyl]-dodecane-1-thiol, m/z=379 (M+Li).

EXAMPLE 18

Preparation of 3-[(4-methoxyphenyl)sulfonyl]-4-phenylbutane-1-thiol

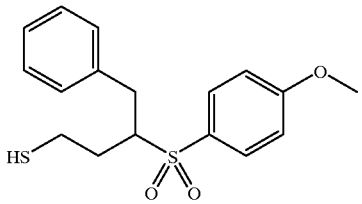

Part A: To a solution of 5.0 g (22 mmol) of 3-[(4-methoxyphenyl)sulfonyl]propan-1-ol from example 13 and 6 mL of DMPU in 100 mL of anhydrous THF at −70° C. under nitrogen, was added 5.7 mL (2.8 g, 43 mmol) of a 10.0 M solution of n-butyllithium in hexane. After stirring for 30 min. at −70° C., 2.3 mL (3.3 g, 20 mmole) of benzyl bromide was added. After 18 hours, the reaction mixture was cooled to zero° C. and 25 mL of saturated ammonium chloride solution was added, followed by ethyl acetate and water, the layers were separated and the aqueous layer was extracted 2xs with ethyl acetate. The 3 organic layers were combined and washed with brine, dried with magnesium sulfate, filtered and concentrated to afford the crude product. This was chromatographed on silica gel using 35%–45% ethyl acetate/hexane to yield 5.3 g of pure 3-[(4-methoxyphenyl) sulfonyl]-4-phenylbutan-1-ol, m/z=327 (M+Li).

Part B: To a solution of 5.3 g (17 mmol) of 3-[(4-methoxyphenyl)sulfonyl]-4-phenylbutan-1-ol from Part A and 6.5 g (25 mmole) of triphenylphosphine in 100 mL of anhydrous THF at zero° C., was added 3.9 mL (4.3 g, 25 mmol) of diethylazodicarboxylate, followed after 15 min. by 1.8 mL (1.9 g, 25 mM) of thiolacetic acid. After 1 hour, the reaction was concentrated and the residue was chromatographed on silica gel using 15%–30% ethyl acetate/hexane to yield 5.5 g of pure thioacetate, m/z=385 (M+Li).

Part C: To a solution of 2.9 g (8 mmol) of thioacetate, from Part B, in 35 mL of anhydrous methanol, was added 0.7 g (29 mmol) of sodium metal. After 1 hour, the reaction was cooled, 1N HCl solution was added, followed by ethyl acetate and water, the organic layer was separated and washed with water and brine, dried with magnesium sulfate, filtered and concentrated to afford 1.9 g of crude product. This was chromatographed on silica gel using 10%–20% ethyl acetate/hexane to yield 1.6 g of pure 3-[(4-methoxyphenyl)sulfonyl]-4-phenylbutane-1-thiol, m/z=343 (M+Li).

EXAMPLE 19

Preparation of 3-[(4-methoxyphenyl)sulfonyl]-butane-1-thiol

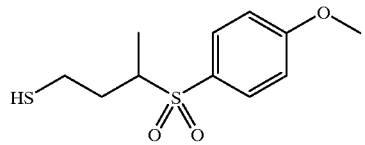

Part A: To a solution of 2.6 g (18 mmol) of 4-methoxybenzenethiol in 30 ml of methanol at zero° C., was added 2.2 mL (2.0 g, 20 mmol) of methyl methacrylate. After nitrogen gas was bubbled through the solution for 15 min., 2.8 mL (2.1 g, 20 mmole) of triethylamine was added. After 4.5 hours, 20 mL of methanol and 10 mL of water were added, followed by 36 g (59 mmol) of potassium peroxymonosulfate (OXONE®). After 65 hours, the reaction was filtered, the filter cake was washed with methanol and the filtrate concentrated in vacuo, ethyl acetate and water were added, the layers were separated and the aqueous layer was extracted 2xs with ethyl acetate. The 3 organic extracts were combined and washed with saturated sodium bicarbonate solution and brine, dried with magnesium sulfate, filtered and concentrated to afford 4.1 g of crude product. This was chromatographed on silica gel using 25%–35% ethyl acetate/hexane to yield 3.5 g of pure methyl 3-[(4-methoxyphenyl)sulfonyl]-butanoic acid, m/z=279 (M+Li).

Part B: To a solution of 3.5 g (13 mmol) of methyl 3-[(4-methoxyphenyl)sulfonyl]-butanoic acid from Part A in 50 mL of anhydrous THF at zero° C. under nitrogen, was added 14.2 mL (0.5 g, 13 mmol) of a 1.0 M solution of lithium aluminum hydride in THF. After 1.5 hours, the reaction mixture was cooled to zero° C. and z0.6 mL of water was added, followed by 0.6 mL of 2.5 N sodium hydroxide solution and 1.8 mL of water, the reaction was filtered, the filtrate concentrated in vacuo, ethyl acetate and 5% citric acid solution were added, the organic layer was separated and washed with saturated sodium bicarbonate solution and brine, dried with magnesium sulfate, filtered and concentrated to afford 2.7 grams of pure 3-[(4-methoxyphenyl)-sulfonyl]butan-1-ol, m/z=251 (M+Li).

Part C: To a solution of 2.7 g (11 mmol) of 3-[(4-methoxyphenyl)sulfonyl]butan-1-ol from Part B and 3.6 g (14 mmole) of triphenylphosphine in 50 mL of anhydrous THF at zero° C., was added 2.2 mL (2.4 g, 14 mmol) of diethylazodicarboxylate, followed after 15 min. by 1.0 mL (1.1 g, 14 mM) of thiolacetic acid. After 18 hours, the reaction was concentrated and the residue was chromatographed on silica gel using 15%–30% ethyl acetate/hexane to yield 2.8 g of pure 3-[(4-methoxyphenyl)sulfonyl]butane-1-thioacetate, m/z=303 (M+H).

Part D: To a solution of 2.8 g (9 mmol) of 3-[(4-methoxyphenyl)sulfonyl]butane-1-thioacetate from Part C in 40 mL of anhydrous methanol, was added 0.8 g (34 mmol) of sodium metal. After 1 hour, the reaction was cooled, 1N HCl solution was added, followed by ethyl acetate and water, the organic layer was separated and washed with saturated sodium bicarbonate solution and brine, dried with magnesium sulfate, filtered and concentrated to afford the crude product. This was chromatographed on silica gel using 10%–20% ethyl acetate/hexane to yield 1.8 g of pure 3-[(4-methoxyphenyl)sulfonyl]butane-1-thiol, m/z=261 (M+H).

EXAMPLE 20

Preparation of 3-[(4-methoxyphenyl)sulfonyl]hexane-1-thiol

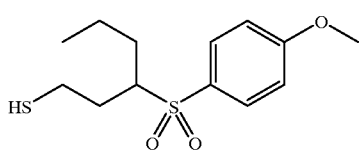

Part A: To a solution of 2.8 g (20 mmol) of 4-methoxybenzenethiol in 40 mL of methanol at zero° C., was added 2.6 g (20 mmol) of methyl trans-2-hexenoate. After nitrogen gas was bubbled through the solution for 15 min., 3.0 mL (2.2 g, 21 mmole) of triethylamine was added. The reaction was heated at the reflux temperature for 16 hours, then concentrated in vacuo, ethyl acetate and water were added, the organic layer was separated and washed with 5% citric acid solution, saturated sodium bicarbonate solution and brine, dried with magnesium sulfate, filtered and concentrated to afford 5.1 g of product suitable for the next reaction.

Part B: To a solution of 5.1 g (17 mmol) of product from Part A in 50 mL of methanol and 10 mL of water, was added 40 g (65 mmol) of potassium peroxymonosulfate (OXONE®). After 2 hours, the reaction was filtered, the filter cake was washed with methanol and the filtrate concentrated in vacuo, ethyl acetate and water were added, the layers were separated and the aqueous layer was extracted 2xs with ethyl acetate. The 3 organic extracts were combined and washed with saturated sodium bicarbonate solution and brine, dried with magnesium sulfate, filtered and concentrated to afford 5.8 g of crude product. This was chromatographed on silica gel using 15%–25% ethyl acetate/hexane to yield 4.4 g of pure methyl 3-[(4-methoxyphenyl)sulfonyl]hexanoic acid, m/z=307 (M+Li).

Part C: To a solution of 4.4 g (15 mmol) of methyl 3-[(4-methoxyphenyl)sulfonyl]hexanoic acid from Part B in 50 mL of anhydrous THF at zero° C. under nitrogen, was added 16.2 mL (0.6 g, 15 mmol) of a 1.0 M solution of lithium aluminum hydride in THF. After 1 hour, the reaction mixture was cooled to zero° C. and 0.6 mL of water was added, followed by 0.6 mL of 2.5 N sodium hydroxide solution and 1.8 mL of water, the reaction was filtered, the filtrate concentrated in vacuo, ethyl acetate and 5% citric acid solution were added, the organic layer was separated and washed with saturated sodium bicarbonate solution and brine, dried with magnesium sulfate, filtered and concentrated to afford 3.6 grams of pure 3-[(4-methoxyphenyl)sulfonyl]hexan-1-ol, m/z=273 (M+H).

Part D: To a solution of 3.6 g (12 mmol) of 3-[(4methoxyphenyl)sulfonyl]hexan-1-ol, from Part C and 3.8 g (15 mmole) of triphenylphosphine in 50 mL of anhydrous THF at zero° C., was added 2.3 mL (2.6 g, 15 mmol) of diethylazodicarboxylate, followed after 15 min. by 1.1 mL (1.1 g, 15 mM) of thiolacetic acid. After 15 hours, the reaction was concentrated and the residue was chromatographed on silica gel using 10%–25% ethyl acetate/hexane to yield 3.3 g of pure thioacetate, m/z=331 (M+H).

Part E: To a solution of 2.0 g (6 mmol) of thioacetate, from Part D, in 40 mL of anhydrous methanol, was added 0.5 g (23 mmol) of sodium metal.

After 2 hours, the reaction was cooled, 1N HCl solution was added, followed by ethyl acetate and water, the organic layer was separated and washed with water and brine, dried with magnesium sulfate, filtered and concentrated to afford the crude product. This was chromatographed on silica gel using 5%–20% ethyl acetate/hexane to yield 1.0 g of pure 3-[(4-methoxyphenyl)sulfonyl]hexane-1-thiol, m/z=289 (M+H).

EXAMPLE 21

Preparation of 3-[(4-methoxyphenyl)sulfonyl]-3-phenylpropane-1-thiol

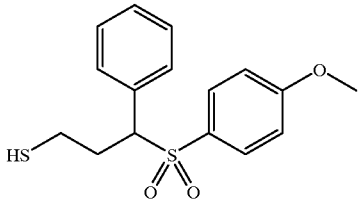

Part A: To a solution of 3.0 g (21 mmol) of 4-methoxybenzenethiol in 40 mL of methanol at zero° C., was added 3.5 g (21 mmol) of methyl transcinnamate. After nitrogen gas was bubbled through the solution for 15 min., 3.1 mL (2.3 g, 22 mM) of triethylamine was added. The reaction was heated at the reflux temperature for 16 hours, then concentrated in vacuo, ethyl acetate and 5% citric acid solution were added, the organic layer was separated and washed with saturated sodium bicarbonate solution and brine, dried with magnesium sulfate, filtered and concentrated to afford 6.5 g of product suitable for the next reaction.

Part B: To a solution of 6.5 g (21 mmol) of product from Part A in 100 mL of methanol and 20 mL of water, was added 42 g (68 mmol) of potassium peroxymonosulfate (OXONE®). After 19 hours, the reaction was filtered, the filter cake was washed with methanol and the filtrate concentrated in vacuo, ethyl acetate and water were added, the layers were separated and the aqueous layer was extracted 2xs with ethyl acetate. The 3 organic extracts were combined and washed with saturated sodium bicarbonate solution and brine, dried with magnesium sulfate, filtered and concentrated to afford 6.5 g of crude product. This was chromatographed on silica gel using 20%–35% ethyl acetate/hexane to yield 6.1 g of pure methyl 3-[(4-methoxyphenyl)sulfonyl]-3-phenylpropanoic acid, m/z=341 (M+Li).

Part C: To a solution of 5.0 g (15 mmol) of methyl 3-[(4-methoxyphenyl)sulfonyl]-3-phenylpropanoic acid, from Part B in 60 mL of anhydrous THF at zero° C. under nitrogen, was added 16.4 mL (0.6 g, 15 mmol) of a 1.0 M solution of lithium aluminum hydride in THF. After 2 hours, the reaction mixture was cooled to zero° C. and 1.2 mL of water was added, followed by 1.2 mL of 2.5 N sodium hydroxide solution and 3.6 mL of water, the reaction was filtered, the filtrate concentrated in vacuo, ethyl acetate and 5% citric acid solution were added, the organic layer was separated and washed with saturated sodium bicarbonate solution and brine, dried with magnesium sulfate, filtered and concentrated to afford 3.9 grams of pure 3-[(4-methoxyphenyl)sulfonyl]-3-phenylpropan-1-ol, m/z=313 (M+Li).

Part D: To a solution of 3.7 g (14 mmole) of triphenylphosphine in 50 mL of anhydrous THF at zero° C., was added 2.2 mL (2.4 g, 14 mmol) of diethylazodicarboxylate, followed after 30 min. by a solution of 3.9 g (13 mmol) of 3-[(4-methoxyphenyl)sulfonyl]-3-phenylpropan-1-ol from Part C and 1.0 mL (1.1 g, 14 mM) of thiolacetic acid. After 1 hour, the reaction was concentrated and the residue was chromatographed on silica gel using 15%–30% ethyl acetate/hexane to yield 2.9 g of pure thioacetate, m/z=371 (M+Li).

Part E: To a solution of 2.0 g (5 mmol) of thioacetate, from Part D, in 60 mL of anhydrous methanol, was added 0.5 g (21 mmol) of sodium metal. After 1 hour, the reaction was cooled, 1N HCl solution was added, followed by ethyl acetate and water, the organic layer was separated and washed with water and brine, dried with magnesium sulfate, filtered and concentrated to afford 1.8 g of crude product. This was chromatographed on silica gel using 15%–20% ethyl acetate/hexane to yield 1.1 g of pure 3-[(4-methoxyphenyl)sulfonyl]-3-phenylpropane-1-thiol, m/z= 329 (M+Li).

EXAMPLE 22

Preparation of 3-[(4-methoxyphenyl)sulfonyl]-octane-1-thiol

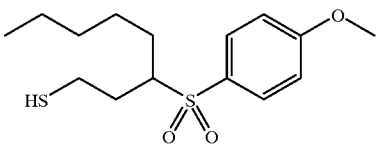

Part A: To a solution of 2.7 g (19 mmol) of 4-methoxybenzenethiol in 40 mL of methanol at zero° C., was added 3.0 g (19 mmol) of methyl trans-2-octenoate. After nitrogen gas was bubbled through the solution for 15 min., 2.8 mL (2.0 g, 20 mM) of triethylamine was added. The reaction was heated at the reflux temperature for 16 hours, then concentrated in vacuo, ethyl acetate and 5% citric acid solution were added, the organic layer was separated and washed with saturated sodium bicarbonate solution and brine, dried with magnesium sulfate, filtered and concentrated to afford 5.7 g of product suitable for the next reaction.

Part B: To a solution of 5.7 g (19 mmol) of product from Part A in 120 mL of methanol and 20 mL of water, was added 38 g (62 mmol) of potassium peroxymonosulfate (OXONE®). After 18 hours, the reaction was filtered, the filter cake was washed with methanol and the filtrate concentrated in vacuo, ethyl acetate and water were added, the layers were separated and the aqueous layer was extracted 2×s with ethyl acetate. The 3 organic extracts were combined and washed with saturated sodium bicarbonate solution and brine, dried with magnesium sulfate, filtered and concentrated to afford 5.5 g of crude product. This was chromatographed on silica gel using 15%–25% ethyl acetate/hexane to yield 4.4 g of methyl 3-[(4-methoxyphenyl)sulfonyl]-octanoic acid, suitable for the next reaction.

Part C: To a solution of 4.4 g (13 mmol) of methyl 3-[(4-methoxyphenyl)sulfonyl]-octanoic acid from Part B in 60 mL of anhydrous THF at zero° C. under nitrogen, was added 14.6 mL (0.5 g, 13 mmol) of a 1.0 M solution of lithium aluminum hydride in THF. After 2 hours, the reaction mixture was cooled to zero° C. and 0.5 mL of water was added, followed by 0.5 mL of 2.5 N sodium hydroxide solution and 1.5 mL of water, the reaction was filtered, the filtrate concentrated in vacuo, ethyl acetate and 5% citric acid solution were added, the organic layer was separated and washed with saturated sodium bicarbonate solution and brine, dried with magnesium sulfate, filtered and concentrated to afford 3.3 grams of pure 3-[(4-methoxyphenyl)sulfonyl]-octan-1-ol, m/z=307 (M+Li).

Part D: To a solution of 3.6 g (14 mmole) of triphenylphosphine in 50 mL of anhydrous THF at zero° C., was added 2.2 mL (2.4 g, 14 mmol) of diethylazodi-carboxylate, followed after 15 min. by a solution of 3.3 g (11 mmol) of 3-[(4-methoxyphenyl)sulfonyl]-octan-1-ol from Part C and 1.0 mL (1.0 g, 14 mM) of thiolacetic acid. After 1 hour, the reaction was concentrated and the residue was chromatographed on silica gel using 10%–20% ethyl acetate/hexane to yield 2.4 g of pure thioacetate, m/z=365 (M+Li).

Part E: To a solution of 2.0 g (6 mmol) of thioacetate, from Part D, in 25 ml of anhydrous methanol, was added 0.5 g (21 mmol) of sodium metal. After 1 hour, the reaction was cooled, 1N HCl solution was added, followed by ethyl acetate and water, the organic layer was separated and washed with water and brine, dried with magnesium sulfate, filtered and concentrated to afford 1.7 g of crude product. This was chromatographed on silica gel using 10%–15% ethyl acetate/hexane to yield 1.0 g of pure 3-[(4-methoxyphenyl)sulfonyl]-octane-1-thiol, m/z=323 (M+Li).

EXAMPLE 23

Preparation of 1-[(4-methoxyphenyl)sulfonyl]-heptane-3-thiol

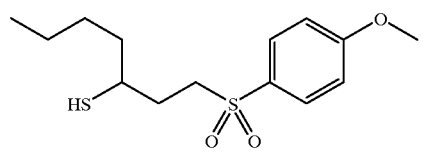

Part A: To a solution of 5.0 g (22 mmol) of 3-[(4-methoxyphenyl)sulfonyl]propan-1-ol from example 13 and 12.1 mL (8.8 g, 87 mmole) of triethylamine in 25 mL of methylene chloride at zero° C., was added a solution of 13.8 g (87 mmol) of sulfur trioxide-pyridine complex in 25 mL of DMSO. After 1 hour, the reaction mixture was added to 300 mL of ice, ethyl acetate was added, the organic layer was separated and washed with water, 5% potassium hydrogen sulfate solution and brine, dried with magnesium sulfate, filtered and concentrated to afford 4.1 g of 3-[(4-methoxyphenyl)sulfonyl]propan-1-al. suitable for the next reaction.

Part B: To 22.3 mL (4.3 g, 37 mM) of a 2.0 M butyl-magnesium chloride solution in THF at zero° C., was added 4.1 g (18 mmol) of 3-[(4-methoxyphenyl)sulfonyl]propan-1-al from Part A in 30 mL of THF. After 3 hours, the reaction mixture was cooled to zero° C. and 40 mL of saturated ammonium chloride solution was added, followed by ethyl acetate and water, the organic layer was separated and washed with 5% potassium hydrogen sulfate solution, saturated sodium bicarbonate solution and brine, dried with magnesium sulfate, filtered and concentrated to afford 4.7 grams of crude product. This was chromatographed on silica gel using 30%–40% ethyl acetate/hexane to yield 3.1 g of pure 1-[(4-methoxyphenyl)sulfonyl]-heptan-3-ol, m/z=324 (M+NH$_4$).

Part C: To a solution of 3.1 g (11 mmol) of 1-[(4-methoxyphenyl)sulfonyl]-heptan-3-ol from Part B and 6.0 g (23 mmole) of triphenylphosphine in 50 mL of anhydrous THF at zero° C., was added 3.6 mL (4.0 g, 23 mmol) of diethylazodicarboxylate, followed after 1 hour by 1.7 mL (1.7 g, 23 mM) of thiolacetic acid. After 1 hour, the reaction was concentrated and the residue was chromatographed on silica gel using 10%–20% ethyl acetate/hexane to yield 1.2 g of thioacetate suitable for the next reaction.

Part D: To a solution of 1.2 g (3 mmol) of thioacetate, from Part C, in 40 mL of anhydrous methanol, was added 0.3 g (13 mmol) of sodium metal. After 1 hour, the reaction was cooled, 1N HCl solution was added, followed by ethyl acetate and water, the organic layer was separated and washed with water and brine, dried with magnesium sulfate, filtered and concentrated to afford 0.9 g of crude product. The crude product was chromatographed on silica gel using 10%–20% ethyl acetate/hexane to yield 0.6 g of pure 1-[(4-methoxyphenyl)sulfonyl]-heptane-3-thiol, m/z=303 (M+H).

EXAMPLE 24

Preparation of 3-[(4-methoxyphenyl)sulfonyl]-1-phenylpropane-1-thiol

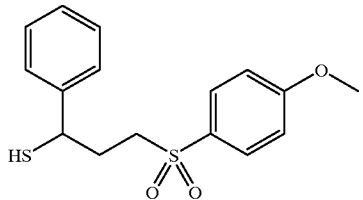

Part A: To a solution of 5.2 g (23 mmol) of 3-[(4-methoxyphenyl)sulfonyl]propan-1-ol from Example 13 and 12.6 mL (9.1 g, 90 mmole) of triethylamine in 25 mL of methylene chloride at zero° C., was added a solution of 14.4 g (90 mmol) of sulfur trioxide-pyridine complex in 25 mL of DMSO. After 1 hour, the reaction mixture was added to 200 mL of ice, ethyl acetate was added, the organic layer was separated and washed with water, 5% potassium hydrogen sulfate solution and brine, dried with magnesium sulfate, filtered and concentrated to afford 4.9 g of 3-[(4-methoxyphenyl)sulfonyl]propan-1-al suitable for the next reaction.

Part B: To 11.4 mL (3.2 g, 23 mM) of a 2.0 M phenyl-magnesium chloride solution in THF at zero° C., was added 2.6 g (11 mmol) of 3-[(4-methoxyphenyl)sulfonyl]propan-1-al from Part A in 20 mL of THF. After 1.5 hours, the reaction mixture was cooled to zero° C. and 20 mL of saturated ammonium chloride solution was added, followed by ethyl acetate and water, the organic layer was separated and washed with 5% potassium hydrogen sulfate solution, saturated sodium bicarbonate solution and brine, dried with magnesium sulfate, filtered and concentrated to afford 2.7 grams of crude product. This was chromatographed on silica gel using 35%–40% ethyl acetate/hexane to yield 1.7 g of pure 3-[(4-methoxyphenyl)sulfonyl]-1-phenylpropan-1-ol, m/z=324 (M+NH$_4$).

Part C: To a solution of 1.7 g (6 mmol) of product from Part B and 3.1 g (12 mmole) of triphenylphosphine in 40 mL of anhydrous THF at zero° C., was added 1.8 mL (2.0 g, 12 mmol) of diethylazodi-carboxylate, followed after 1 hour by 0.9 mL (0.9 g, 12 mM) of thiolacetic acid. After 16 hours, the reaction was concentrated and the residue was chromatographed on silica gel using 15–35% ethyl acetate/hexane to yield 0.8 g of thioacetate, suitable for the next reaction.

Part D: To a solution of 0.8 g (2 mmol) of thioacetate, from Part C, in 15 mL of anhydrous methanol, was added 0.2 g (8 mmol) of sodium metal. After 1 hour, the reaction was cooled, 1N HCl solution was added, followed by ethyl acetate and water, the organic layer was separated and washed with water and brine, dried with magnesium sulfate, filtered and concentrated to afford 0.5 g of crude product. This was chromatographed on silica gel using 10%–30% ethyl acetate/hexane to yield 0.2 g of pure 3-[(4-methoxyphenyl)sulfonyl]-1-phenylpropane-1-thiol, m/z= 340 (M+NH$_4$).

EXAMPLE 25

Preparation of 4-[(4--methoxyphenyl)sulfonyl]butane-1-thiol

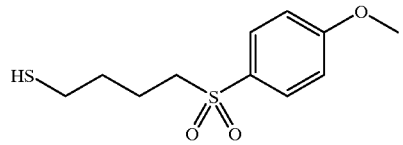

Part A: To a solution of 5.0 g (36 mmol) of 4-methoxybenzenethiol in 50 mL of anhydrous DMF, was added 4.4 mL (4.8 g, 44 mmol) of 3-chloro-1-propanol. After nitrogen gas was bubbled through the solution for 15 min., 17.3 g (125 mM) of powdered potassium carbonate was added. After 66 hours, the DMF was removed in vacuo, ethyl acetate and water were added, the organic layer separated and washed 3×s with brine, dried with magnesium sulfate, filtered and concentrated to afford 8.2 g of product suitable for the next reaction.

Part B: To a solution of 7.6 g (36 mmol) of product from Part A in 250 mL of methanol and 20 mL of water, was added 77 g (125 mmol) of potassium peroxymonosulfate (OXONE®). After 16 hours, the reaction was filtered, the filter cake was washed with methanol and the filtrate concentrated in vacuo, ethyl acetate and water were added, the layers were separated and the aqueous layer was extracted 2×s with ethyl acetate. The 3 organic extracts were combined and washed with saturated sodium bicarbonate solution and brine, dried with magnesium sulfate, filtered and concentrated to afford 8.3 g of the crude product. This was chromatographed on silica gel using 50%–80% ethyl acetate/hexane to yield 5.8 g of pure 4-[(4-methoxyphenyl)sulfonyl]butan-1-ol, m/z =251 (M+Li).

Part C: To a solution of 5.0 g (21 mmol) of 4-[(4-methoxyphenyl)sulfonyl]butan-1-ol from Part B and 5.9 g (23 mmole) of triphenylphosphine in 80 mL of anhydrous THF at zero° C., was added 3.5 mL (3.9 g, 23 mmol) of diethylazodicarboxylate, followed after 5 min. by 1.6 mL (1.7 g, 23 mM) of thiolacetic acid. After 65 hours, the reaction was concentrated and the residue was chromatographed on silica gel using 20%–30% ethyl acetate/hexane to yield 3.9 g of pure thioacetate, m/z=320 (M+NHz).

Part D: To a solution of 2.0 g (7 mmol) of thioacetate, from Part C, in 60 mL of anhydrous methanol, was added 0.6 g (24 mmol) of sodium metal. After 1 hour, the reaction was cooled, 1N HCl solution was added, followed by ethyl acetate and water, the organic layer was separated and washed with saturated sodium bicarbonate solution and brine, dried with magnesium sulfate, filtered and concentrated to afford 1.7 g of crude product. This was chromatographed on silica gel using 15%–25% ethyl acetate/hexane to yield 1.3 g of pure 4-[(4methoxyphenyl)sulfonyl]butane-:L-thiol, m/z=267 (M+Li).

EXAMPLE 26

Preparation of 3-[(4--butoxyphenyl)sulfonyl]propan-1-ol

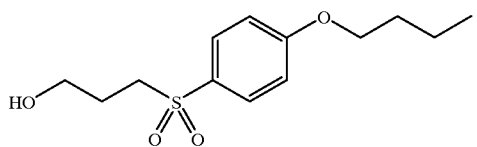

Part A: To a solution of 10.0 g (79 mmol) of 4-hydroxybenzenethiol in 100 mL of anhydrous DMF, was added 7.3 mL (8.2 g, 87 mmol) of 3-chloro-1-propanol. After nitrogen gas was bubbled through the solution for 15 min., 33.0 g (238 mM) of powdered potassium carbonate was added. After 17 hours, the DMF was removed in vacuo, ethyl acetate and water were added, the organic layer separated and washed 3×s with brine, dried with magnesium sulfate, filtered and concentrated to afford 16 g of crude product, m/z=183 (M–H).

Part B: To a solution of 3 g (16 mmol) of product from Part A in 20 mL of anhydrous DMF, was added 6.8 g (49 mmol) of powdered potassium carbonate, followed by 3.3 g (24 mM) of 1-bromobutane. After 65 hours, ethyl acetate and water were added, the organic layer separated and washed 3×s with brine, dried with magnesium sulfate, filtered and concentrated to afford 3.9 g of crude product, m/z=247 (M+Li).

Part C: To a solution of 3.9 g (16 mmol) of product from Part B in 50 mL of methanol and 10 mL of water, was added 32 g (52 mmol) of potassium peroxymonosulfate (OXONE®). After 16 hours, the reaction was filtered, the filter cake was washed with methanol and the filtrate concentrated in vacuo, ethyl acetate and water were added, the layers were separated and the aqueous layer was extracted 2×s with ethyl acetate. The 3 organic extracts were combined and washed with saturated sodium bicarbonate solution and brine, dried with magnesium sulfate, filtered and concentrated to afford 4.3 g of product, identified as 3-[(4-butoxyphenyl)sulfonyl]propan-1-ol m/z=279 (M+Li).

EXAMPLE 27

Preparation of 3-[(4-butoxyphenyl)sulfonyl] propane-1-thiol

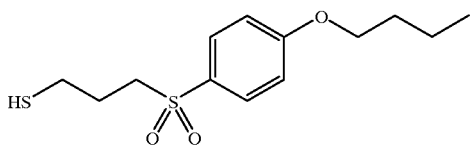

Part A: To a solution of 4.3 g (16 mmol) of 3-[(4-butoxyphenyl)sulfonyl]propan-1-ol from example 27 and 5.1 g (19 mmole) of triphenylphosphine in 50 mL of anhydrous THF at zero° C., was added 3.1 mL (3.4 g, 19 mmol) of diethylazodicarboxylate, followed after 15 min. by 1.4 mL (1.5 g, 19 mM) of thiolacetic acid. After one hour, the reaction was concentrated and the residue was chromatographed on silica gel using 10%–25% ethyl acetate/hexane to yield 4.4 g of pure thioacetate, m/z=348 (M+NH₄).

Part B: To a solution of 2.0 g (6 mmol) of thioacetate, from Part A, in 40 mL of anhydrous methanol, was added 0.5 g (22 mmol) of sodium metal. After one hour, the reaction was cooled, 1N HCl solution was added, followed by ethyl acetate and water, the organic layer was separated and washed with saturated sodium bicarbonate solution and brine, dried with magnesium sulfate, filtered and concentrated to afford the crude product. This was chromatographed on silica gel using 10%–20% ethyl acetate/hexane to yield 1.3 g of pure 3-[(4-butoxyphenyl)sulfonyl]propane-1-thiol, m/z=289 (M+H).

EXAMPLE 28

Preparation of 3-[(4-butoxyphenyl)sulfonyl]-4-phenylbutane-1-thiol

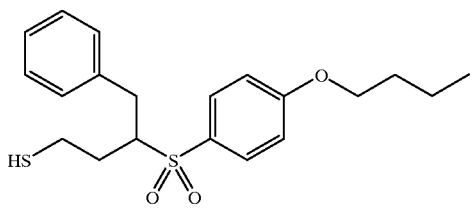

Part A: To a solution of 4.0 g (15 mmol) of 3-[(4-butoxyphenyl)sulfonyl]propan-1-ol from Example 26 and 6 mL of DMPU in 100 mL of anhydrous THF at -70 C under nitrogen, was added 3.9 mL (1.9 g, 29 mmol) of a 10.0 M solution of n-butyllithium in hexane. After stirring for 30 min. at -70 C., 1.6 mL (2.3 g, 13 mmole) of benzyl bromide was added. After 15 hours, the reaction mixture was cooled to zero C. and 25 mL of saturated ammonium chloride solution was added. Ethyl acetate and water were added, the layers were separated and the aqueous layer was extracted 2×s with ethyl acetate. The 3 organic layers were combined and washed with brine, dried with magnesium sulfate, filtered and concentrated to afford 8.4 g of crude product. This was chromatographed on silica gel using 25%–35% ethyl acetate/hexane to yield 4.3 g of pure 3-[(4-butoxyphenyl)sulfonyl]-4-phenylbutan-1-ol.

Part B: To a solution of 4.3 g (12 mmol) of 3-[(4-butoxyphenyl)sulfonyl]-4-phenylbutan-1-ol from Part A and 4.7 g (18 mmole) of triphenylphosphine in 100 mL of anhydrous THF at zero C., was added 2.8 mL (3.1 g, 18 mmol) of diethylazodicarboxylate, followed after 15 min. by 1.3 mL (1.4 g, 18 mM) of thiolacetic acid. After one hour, the reaction was concentrated and the residue was chromatographed on silica gel using 10%–15% ethyl acetate/hexane to yield 4.1 g of pure thioacetate.

Part C: To a solution of 2.0 g (5 mmol) of thioacetate, from Part B, in 30 mL of anhydrous methanol, was added 0.4 g (18 mmol) of sodium metal. After one hour, the reaction was cooled, 1N HCl solution was added, followed by ethyl acetate and water, the organic layer was separated and washed with water and brine, dried with magnesium sulfate, filtered and concentrated to afford 1.9 g of crude product. This was chromatographed on silica gel using 5%–15% ethyl acetate/hexane to yield 1.2 g of pure 3-[(4-butoxyphenyl)sulfonyl]-4-phenylbutane-1-thiol.

EXAMPLE 29

Preparation of 3-[(4-propoxyphenyl)sulfonyl] propanethiol

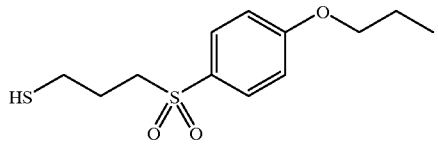

Part A: To a solution of 10.0 g (79 mmol) of 4-hydroxybenzenethiol in 100 ml of anhydrous DMF, was added 7.3 mL (8.2 g, 87 mmol) of 3-chloro-1-propanol. After nitrogen gas was bubbled through the solution for 15 min., 33.0 g (238 mM) of powdered potassium carbonate was added. After 17 hours, the DMF was removed in vacuo, ethyl acetate and water were added, the organic layer separated and washed 3xs with brine, dried with magnesium sulfate, filtered and concentrated to afford 16.1 g of pure product, m/z=183 (M−H).

Part B: To a solution of 2.8 g (15 mmol) of compound from Part A in 20 mL of anhydrous DMF, was added 6.3 g (46 mmol) of powdered potassium carbonate, followed by 2.8 g (23 mM) of 1-bromopropane. After 16 hours, ethyl acetate and water were added, the organic layer separated and washed 3xs with brine, dried with magnesium sulfate, filtered and concentrated to afford 3.4 g of product, m/z=233 (M+Li).

Part C: To a solution of 3.4 g (16 mmol) of compound from Part B in 50 mL of methanol and 10 mL of water, was added 31 g (51 mmol) of potassium peroxymonosulfate (OXONE®). After 18 hours, the reaction was filtered, the filter cake was washed with methanol and the filtrate concentrated in vacuo, ethyl acetate and water were added, the layers were separated and the aqueous layer was extracted 2xs with ethyl acetate. The 3 organic extracts were combined and washed with saturated sodium bicarbonate solution and brine, dried with magnesium sulfate, filtered and concentrated to afford 3.9 g of 3-[(4-propoxyphenyl)sulfonyl]propan-1-ol, m/z=259 (M+H).

Part D: To a solution of 3.9 g (15 mmol) of 3-[(4-propoxyphenyl)sulfonyl]propan-1-ol from Part C and 4.9 g (19 mmole) of triphenylphosphine in 50 mL of anhydrous THF at zero C., was added 2.9 mL (3.2 g, 19 mmol) of diethylazodicarboxylate, followed after 15 min. by 1.4 mL (1.4 g, 19 mM) of thiolacetic acid. After 2 hours, the reaction was concentrated and the residue was chromatographed on silica gel using 15%–25% ethyl acetate/hexane to yield 4.1 g of pure thioacetate, m/z=334 (M+NH$_4$).

Part E: To a solution of 2.0 g (6 mmol) of thioacetate from Part D in 40 mL of anhydrous methanol, was added 0.6 g (23 mmol) of sodium metal. After one hour, the reaction was cooled, 1N HCl solution was added, followed by ethyl acetate and water, the organic layer was separated and washed with water and brine, dried with magnesium sulfate, filtered and concentrated to afford the crude product. This was chromatographed on silica gel using 10%–20% ethyl acetate/hexane to yield 1.2 g of pure 3-[(4-propoxyphenyl)sulfonyl]propane-1-thiol, m/z=275 (M+H).

EXAMPLE 30

Preparation of 3-(phenylsulfonyl)propane-1-thiol

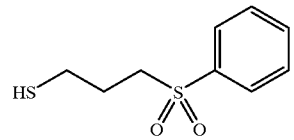

Part A: To a solution of 3.0 g (27 mmol) of thiolphenol in 50 mL of anhydrous DMF, was added 2.4 mL (2.7 g, 28 mmol) of 3-chloro-1-propanol. After nitrogen gas was bubbled through the solution for 15 min., 11.3 g (81 mM) of powdered potassium carbonate was added. After one hour, the DMF was removed in vacuo, ethyl acetate and water were added, the organic layer separated and washed 3xs with brine, dried with magnesium sulfate, filtered and concentrated to afford 4.6 g of product suitable for the next reaction.

Part B: To a solution of 4.6 g (27 mmol) of product from Part A in 80 mL of methanol and 20 mL of water, was added 53 g (87 mmol) of potassium peroxymonosulfate (OXONE®). After 65 hours, the reaction was filtered, the filter cake was washed with methanol and the filtrate concentrated in vacuo, ethyl acetate and water were added, the layers were separated and the aqueous layer was extracted 2xs with ethyl acetate. The 3 organic extracts were combined and washed with saturated sodium bicarbonate solution and brine, dried with magnesium sulfate, filtered and concentrated to afford 4.7 g of 3-(phenylsulfonyl)propan-1-ol, m/e=207 (M+H).

Part C: To a solution of 4.7 g (24 mmol) of 3-(phenylsulfonyl)propan-1-ol from Part B and 7.6 g (29 mmole) of triphenylphosphine in 50 mL of anhydrous THF at zero C., was added 4.6 mL (5.0 g, 29 mmol) of diethylazodicarboxylate, followed after 15 min. by 2.1 mL (2.2 g, 29 mM) of thiolacetic acid. After 1.5 hours, the reaction was concentrated and the residue was chromatographed on silica gel using 10%–30% ethyl acetate/hexane to yield 4.3 g of pure thioacetate, m/z=265 (M+Li).

Part D: To a solution of 2.0 g (8 mmol) of thioacetate, from Part C, in 40 mL of anhydrous methanol, was added 0.7 g (29 mmol) of sodium metal. After one hour, the reaction was cooled, 1N HCl solution was added, followed by ethyl acetate and water, the organic layer was separated and washed with water and brine, dried with magnesium sulfate, filtered and concentrated to afford 1.6 g of crude product. This was chromatographed on silica gel using 10%–20% ethyl acetate/hexane to yield 0.9 g of pure 3-(phenylsulfonyl)propane-1-thiol, m/z=217 (M+H).

EXAMPLE 31

Preparation of

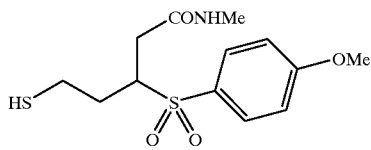

Part A: A 100 mL round bottom flask equipped with magnetic stir bar and $N_2$ inlet was charged with 1.0 g 5,6-Dihydro-2H--pyran-2-one, 1.5 g p-methoxy benzenethiol in 35 mL degassed MeOH. To the stirring solution was added 1.5 mL triethylamine. The reaction was stirred 30 minutes then concentrated in vacuo to remove triethylamine. The crude product was dissolved in 35 mL $MeCl_2$ and treated with 7.6 g MCPBA. The reaction was stirred overnight at room temperature then quenched with 2 eq sodium sulfite. The reaction mixture was diluted with $MeCl_2$ and water. The organic phase was washed with 10% aqueous ammonium hydroxide, brine, and concentrated in vacuo to 2.5 g of an 80:20 ratio of lactone to hydroxy methyl ester, which was used without further purification.

Part B: A 100 mL round bottom flask equipped with magnetic stir bar and $N_2$ inlet was charged with 2.5 g crude from part A, 12.8 mL of 40% aqueous methyl amine (20 eq) in 15 mL MeOH. The reaction was stirred one hour then concentrated in vacuo and purified by chromatography (100% ethyl acetate/10% methanol-ethyl acetate) to yield 1.8 g pure amide.

Part C: To a solution of 1.8 g of hydroxy amide from Part B and 1.65 g of triphenylphosphine in 30 mL of anhydrous THF at zero° C., was added 1.0 mL of diethylazodicarboxylate, followed after 5 min. by 0.5 mL of thiolacetic acid. After 1.5 hours, the reaction was concentrated and the residue was chromatographed on silica gel using 75%–100% ethyl acetate/hexane to yield 1.8 g of crude thioacetate contaminated with triphenyl phosphine oxide. 500 mg of this crude material was deprotected with 2 eq sodium methoxide in methanol. After 20 minutes the reaction was quenched with 1N HCl and extracted with ethyl acetate. The organic phase was washed with brine, and concentrated in vacuo to crude product. Purification was accomplished by preparative-scale reverse phase HPLC to afford pure thiol.

EXAMPLE 32

Preparation of N-[1-(mercaptomethyl)-2-[(4-methoxyphenyl)sulfonyl)ethyl)acetamide

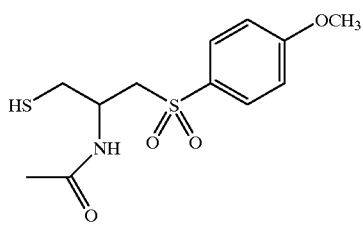

Part A: To a stirred degassed ($N_2$) solution of (20 g, 139 mmol) of N-acetyl-dehydroalanine methyl ester in 400 mL of methanol was added (19.5 g, 139 mmol) of 4-methoxythiophenol followed by 14.0 g, 140 mmol) of triethylamine and the resulting solution stirred for 2 hours. The resulting N-acetyl-β-(4-methoxythio-phenyl)-D,L-alanine methyl ester was oxidized in situ by the addition of 800 mL of methanol, 160 mL of water followed by (250 g, 417 mmol) of OXONE®. The suspension was stirred for 3 hours and then filtered through a fritted glass buchner funnel. The filtrate was concentrated by rotary evaporation and the concentrated material was partitioned between ethyl acetate and sodium bicarbonate. The organic layer was washed with brine, dried over magnesium sulfate, filtered and concentrated to a white solid which was triturated with cold ethyl acetate and filtered to yield 28.5 g of N-acetyl-β-(4-methoxyphenylsulfonyl)-D,L-alanine methyl ester.

Part B: To an ice cooled, stirred solution of (1.6 g, 5 mmol) of N-acetyl-β-(4-methoxyphenylsulfonyl)-D,L-alanine methyl in 20 mL of anhydrous tetrahydrofuran was added (5 mL, 5 mmol) of a 1M lithium aluminum hydride solution in diethyl ether. After 20 minutes the subsequent suspension was quenched by the addition of 2 mL of 2.5 M aqueous sodium hydroxide solution. The resulting suspension was filtered through CELITE® and the filtrate was concentrated by rotory evaporation to yield 530 mg of N-[1-(hydroxymethyl)-2-[(4-methoxphenyl)sulfonyl)ethyl) acetamide.

Part C: (471 mg, 1.8 mmol) of triphenylphosphine and (520 mg, 1.8 mmol) of N-[1-(hydroxymethyl)-2-[(4-methoxyphenyl)sulfonyl)ethyl)acetamide were dissolved in 15 mL of tetrahydrofuran and cooled to zero C. under nitrogen atmosphere. To this was added (313 mg, 1.8 mmol) of diethyldiazodicarboxylate, followed by (140 mg, 1.8 mmol) of thioacetic acid and the solution stirred for 2 hours. The resulting clear solution was concentrated by rotory evaporation and subjected to silica gel chromatography using 15% methanol in ethyl acetate as the eluant to provide a mixture of triphenylphosphine oxide and the desired N-[1-(thioacetylmethyl)-2-[(4-methoxyphenyl)sulfonyl) ethyl)acetamide in equal molar ratios. This mixture was dissolved in 10 ml of methanol and to this was added 1 mL of 25% sodium methoxide in methanol and this stirred for 30 minutes. The solution was acidified with 1N hydrochloric acid and extracted with ethyl acetate. The resulting organics were concentrated and purified by reverse phase $C_{18}$ chromatography to yield 150 mg of N-[1-(mercaptomethyl)-2-[(4-methoxyphenyl)sulfonyl)ethyl)acetamide, m/e=310 (M+Li).

EXAMPLE 33

Preparation of 2-R,S-(N-carbobenzyloxy-glycyl) amino-3-(4-methoxybenzenesulfonyl)propanethiol

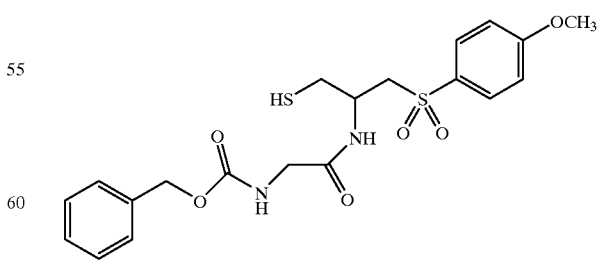

Part A: A solution of (18.13 g, 57 mmol) of N-acetyl-β-(4-methoxyphenylsulfonyl)-D,L-alanine methyl ester in 125 mL concentrated hydrochloric acid and 125 mL of glacial acetic acid was refluxed for several hours under nitrogen atmosphere. The contents were concentrated by rotory evaporation to yield a crude solid which was slurried in dry toluene and filtered to yield 14.3 g of β-(4-methoxyphenylsulfonyl)-D,L-alanine hydrochloride as a white crystalline solid.

Part B: To an ice cooled solution of (8.87 g, 30 mmol) of β-(4-methoxyphenylsulfonyl)-D,L-alanine hydrochloride in 200 mL of dry methanol was added dropwise over 20 minutes (10.7 g, 90 mmol) of thionyl chloride, and the solution was refluxed overnight under nitrogen atmosphere. The contents were cooled to room temperature and concentrated by rotory evaporation and triturated with ether. The product was collected by filtration to yield 6.2 grams of β-(4-methoxyphenylsulfonyl)-D,L-alanine methyl ester hydrochloride.

Part C: To an ice cooled, stirred solution of (6.2 g, 20 mmol) of β-(4-methoxyphenylsulfonyl)-D,L-alanine methyl ester hydrochloride in tetrahydrofuran under nitrogen was added dropwise, (20 mL, 20 mmol) of lithium aluminum hydride in tetrahydrofuran. After 2 hours the ice cooled solution was carefully quenched by the addition of 5 mL of 10% sodium hydroxide and the resulting suspension was filtered through CELITE®. The filtrate was dried over magnesium sulfate filtered and concentrated to yield 2.7 grams of β-(4-methoxyphenyl-sulfonyl)-D,L-alaninol.

Part D: (2.4 g, 10 mmol) of β-(4-methoxyphenylsulfonyl)-D,L-alaninol was added to a solution of dimethylformamide containing (2.0 g, 15 mmol) of hydroxybenzotriazole, (2.0 g, 10 mmol) of EDC and (2.0 g, 10 mmol) of N-carbobenzyloxyglycine and 1.5 g of triethylamine. The reaction stirred overnight at room temperature. The resulting solution was concentrated to an oil and the residue was partitioned between ethyl acetate and saturated sodium bicarbonate. The organic layer was washed with brine, dried over magnesium sulfate, filtered and concentrated to yield a crude material which was purified by column chromatography using 5% methanol in ethyl acetate as the eluant to yield 850 mg of 2-R,S-(N-carbobenzyloxy-glycyl)amino-3-(4-methoxybenzenesulfonyl)propanol.

Part E: To an ice cooled, stirred solution of (650 mg, 1.97 mmol) of 2-R,S-(N-carbobenzyloxy-glycyl)amino-3-(4-methoxybenzenesulfonyl)propanol in 50 mL of anhydrous tetrahydrofuran was added (525 mg, 2.0 mmol) of triphenylphosphine followed by (348 mg, 2.0 mmol) of diethyldiazodicarboxylate,and then (150 mg, 2.0 mol) of thioacetic acid and the clear solution was stirred for several hours. The crude mixture was concentrated on a rotory evaporator and subjected to silica gel chromatography using 100% ethyl acetate as the eluant yielded 600 mg of 2-R,S-(N-carbobenzyloxy-glycyl)amino-3-(4-methoxybenzenesulfonyl)propanethiol as a white solid. m/e=459 (M+Li)

EXAMPLE 34

Preparation of 1-[(4-methoxyphenyl)sulfonyl] ethane-2-thiol

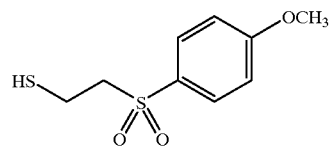

Part A: To a solution of 5.0 mL (6.0 g, 74.9 mmol) of 2-chloroethanol in 100 mL of anhydrous DMF, was added 8.7 mL (10.0 g, 71.3 mmol) of 4-methoxybenzene thiol. After purging with nitrogen for 5 minutes, 31.0 g (224 mmol) of powdered potassium carbonate was added. The temperature of the reaction began to rise, so the reaction was cooled in an ice bath, which was then removed 15 minutes later. After stirring at room temperature for 30 minutes, ethyl acetate and water were added, the organic layer separated and washed with water and brine, dried with magnesium sulfate, filtered and stripped to afford 11.85 g of the desired product, (4-methoxyphenyl)(2-hydroxyethyl)sulfide, m/e= 184 (M+H).

Part B: To a solution of 11.85 g (64 mmol) of the crude product from Part A in 240 mL of methanol and 24 mL of water, was added 118.6 g (193 mmol) of OXONE®, whereupon the temperature began to rise and the reaction was warmed to reflux for 15 minutes. After cooling to room temperature, the solids were filtered off and washed with methanol, the filtrate stripped and redissolved in ethyl acetate. After washing with aqueous sodium bicarbonate and brine, and drying with magnesium sulfate, the solvent was removed to afford 12.8 g of the desired 1-[(4-methoxyphenyl)-sulfonyl]ethan-2-ol, m/e=323 (M+Li).

Part C: To a solution of 2.0 g (9.2 mmol) of product from Part B and 2.67 g (10.2 mmol) of triphenylphosphine in 45 mL of anhydrous THF at zero° C., was added 2.0 mL (10.2 mmol) of diisopropylazodicarboxylate, followed by 0.73 mL (10.2 mmol) of thiolacetic acid. After stirring at room temperature for 15 hours, the reaction was concentrated and the residue chromatographed on 150 g of silica gel using 20–50% ethyl acetate/hexane to afford 2.5 g of the desired product, which was recrystallized from ethyl acetate/hexane to afford 0.55 g of desired pure product, m/e=381 (M+Li).

Part D: To a suspension of 0.54 g (1.95 mmol) of product from Part C above in 5 mL of anhydrous methanol, was added 1.6 mL (7.0 mmol) of 25 weight percent sodium methoxide in methanol. After 30 minutes, the solution was cooled in ice and 2% hydrochloric acid added. Ethyl acetate was added and the organic layer separated and washed with saturated sodium bicarbonate, brine, dried over anhydrous magnesium sulfate, filtered and stripped to afford 0.30 g the desired 1-[(4-methoxyphenyl)sulfonyl]ethane-2-thiol, m/e= 239 (M+Li).

EXAMPLE 35

Preparation of 3-[(4-phenylthio)phenylsulfonyl]propane-1-thiol

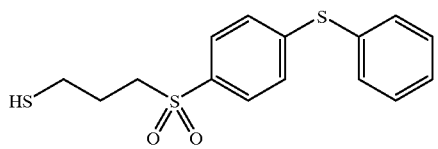

Part A: A 250 mL round bottom flask equipped with magnetic stir bar and $N_2$ inlet was charged with 10 g p-fluorothiophenol and 8.1 g 3-chloro-1-propanol in 80 mL DMF. To this was added 32.4 g $K_2CO_3$ and the reaction was stirred 45 minutes at room temperature. The reaction was concentrated in vacuo and the residue was partitioned between ethyl acetate-$H_2O$, dried, and concentrated in vacuo to yield 14.5 g pure product.

Part B: A 250 mL round bottom flask equipped with magnetic stir bar and $N_2$ inlet was charged with 6.0 g product from part A, 4.2 mL (1.5 eq.) thiophenol and 11.4 g (3 eq.) $K_2CO_3$ in 70 mL DMF. The reaction was heated to 70 C. for 4 hours, then partitioned between ethyl acetate-$H_2O$. The organic phase was washed with 1N HCl, brine, dried, and concentrated in vacuo. Chromatography on silica gel (50% ethyl acetate-hexanes) yielded 6.5 g white solid.

Part C: A 100 mL round bottom flask equipped with magnetic stir bar and $N_2$ inlet was charged with 0.31 g 3-[(4-phenylthio)phenylsulfonyl]propanol, 0.1 mL MsCl (1.25 eq.), 0.2 mL $NEt_3$ in 6 mL $MeCl_2$. The reaction was stirred 20 minutes then concentrated in vacuo and partitioned between ethyl acetate-$H_2O$. The organic phase was concentrated in vacuo and dissolved in 5 mL dry DPF and reacted with 114 mg (1 eq.) potassium thioacetate. The reaction mixture was stirred 24 hours then partitioned between ethyl acetate-$H_2O$. The organic phase was washed with 1N $KHSO_4$, brine, dried, and concentrated in vacuo. Chromatography on silica gel (50% ethyl acetate-hexanes) yielded 195 mg orange oil.

Part D: A 50 mL round bottom flask equipped with magnetic stir bar and $N_2$ inlet was charged with 190 mg product from part C, 0.2 mL (3 eq.) 25% NaOMe in MeOH, and 5 mL MeOH. The reaction was stirred 30 minutes then quenched with 1 N HCl and concentrated in vacuo. The residue was partitioned between ethyl acetate-$H_2O$, dried, and concentrated in vacuo. HPLC showed a 1:1 ratio of product to disulfide. Chromatography on silica gel (50% ethyl acetate-hexanes) yielded 40 mg of pure 3-[(4-phenylthio)phenylsulfonyl]propane-1-thiol.

EXAMPLE 36

Preparation of 3-[(4-phenoxy)phenylsulfonyl]propane-1-thiol

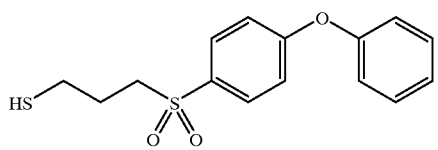

Part A: A 250 mL round bottom flask equipped with magnetic stir bar and $N_2$ inlet was charged with 10 g p-fluorothiophenol and 8.1 g 3-chloro-1-propanol in 80 mL DMF. To this was added 32.4 g $K_2CO_3$ and the reaction was stirred 45 minutes at room temperature. The reaction was concentrated in vacuo and the residue was partitioned between ethyl acetate-$H_2O$, dried, and concentrated in vacuo to yield 14.5 g pure product.

Part B: A 250 mL round bottom flask equipped with magnetic stir bar and $N_2$ inlet was charged with 7.9 g product from part A, 5.1 g phenol, 15.1 g $K_2CO_3$ in 75 mL dry DMF. The reaction was heated to 80° C. for 24 hours then concentrated in vacuo and the residue was partitioned between ethyl acetate-$H_2O$, dried, and concentrated in vacuo to yield 12.3 g red liquid. Chromatography on silica gel (30% to 60% ethyl acetate-hexanes) yielded 6.8 g 64% off white solid.

Part C: A 250 mL round bottom flask equipped with magnetic stir bar and $N_2$ inlet was charged with 1.63 g product from part B, in 35 mL dry THF. The reaction was cooled to zero C. and charged with 1.83 g triphenylphosphine, 1.2 g DEAD and stirred 5 minutes then charged with 0.5 g thioacetic acid. The reaction was stirred 20 minutes then concentrated in vacuo. Chromatography on silica gel (30% to 60% ethyl acetate-hexanes) yielded 1.45 g product. Crystallization from diethyl ether afforded 900 mg white solid.

Part D: A 250 mL round bottom flask equipped with magnetic stir bar and $N_2$ inlet was charged with 870 mg product from part C, 1.6 mL (3 eq.) 25% NaOMe in MeOH, and 25 mL MeOH. The reaction was stirred 30 minutes then quenched with dry ice and concentrated in vacuo. The residue was partitioned between ethyl acetate-$H_2O$, dried, and concentrated in vacuo to yield 670 mg of white 3-[(4-phenoxyphenyl)sulfonyl]propane-1-thiol.

EXAMPLE 37

Preparation of 3-[(4-phenyl)phenylsulfonyl]propane-1-thiol

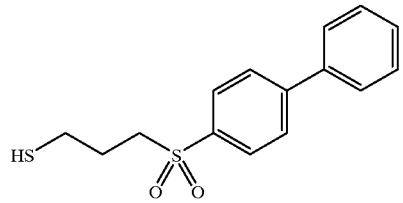

Part A: To a stirred solution of 2.80 g (10 mmol) of 3-(4-bromobenzene)sulfonyl propanol in 75 mL of ethylene glycol dimethyl ether was added 1.35 g (11.15 mmol) of phenylboronic acid followed by 25 mL of 2 M aqueous cesium carbonate and then 1.0 g (1 mmol) of tetrakis-triphenylphosphine palladium and the reaction stirred for 48 hours. The resulting biphasic solution was diluted with ethyl acetate and washed with water 2× 200 mL. The organic layer was dried over magnesium sulfate, filtered and concentrated to a black oil, which was purified by silica gel column chromatography using 2:1 ethyl acetate:hexane as the eluant to yield 1.6 grams, 60% yield of 3-[(4-phenyl)phenylsulfonyl-propanol as a clear oil.

Part B: To an ice-cooled solution of 1.6 g (5.8 mmol) of 3-(4-phenylbenzene)sulfonylpropanol and 1.65 g (6.3 mmol) of triphenylphosphine in 25 mL of dry tetrahydrofuran was added by syringe 1.0 g (6.3 mmol) of diethylazodicarboxylate, followed by 500 mg (6.3 mmol) of thioacetic acid. The reaction was stirred to room temperature over two hours and the resulting solution was concentrated by rotary evaporation and purified by silica gel chromatography to yield 1.93 grams of the desired compound.

Part C: To a suspension of 1.33 g (3.99 mmol) of the product from Part B in 10 mL of methanol was added 3 mL of 25 weight percent sodium methoxide in methanol and the solids dissolved in 5 minutes. After 30 minutes at room temperature the reaction was quenched by the addition of 50 mL of 1N aqueous hydrochloric acid. The suspension was extracted with ethyl acetate and dried over magnesium sulfate, filtered and concentrated to yield 930 mg of a white solid, identified as 3-[(4-phenyl)phenylsulfonyl]propane-1-thiol, m/e=293 (M+H).

EXAMPLE 38

Preparation of (R,S)trans-3-[(phenylthio)phenylsulfonyl]cyclohexanethiol

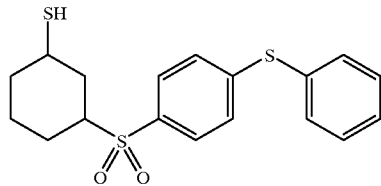

Part A: A 250 mL round bottom flask equipped with magnetic stir bar and N₂ inlet was charged with 5 g p-fluorothiophenol and 3.75 g cyclohexenone in 50 mL degassed MeOH. To this was added 5.5 mL triethylamine. The reaction mixture was stirred one hour at room temperature, then concentrated in vacuo. The residue was dissolved in 60 mL MeOH and treated with 1.6 g (1.2 eq.) NaBH₄. The reaction mixture was stirred 90 minutes at zero° C. The reaction was quenched with concentrated HCl, concentrated in vacuo to remove MeOH and partitioned between ethyl acetate-H₂O. The organic phase was washed with brine and concentrated in vacuo to crude sulfide alcohol which was suspended in 160 mL MeOH/10 mL H₂O and reacted with 72 g (3 eq) OXONE®. The suspension was heated to 65° C. to ensure homogeneity. The reaction was stirred 8 hours then filtered and concentrated in vacuo. The residue was partitioned between ethyl acetate-H₂O, dried, and concentrated in vacuo to 9.5 g of a thick oil. HPLC shows a 78:18 ratio of diastereomers.

Part B: A 250 mL round bottom flask equipped with magnetic stir bar and N₂ inlet was charged with 2.0 g product from part A, 0.87 mL (1.1 eq.) thiophenol and 3.2 g (3 eq.) K₂CO₃ in 70 mL DMF. The reaction was heated to 70° C. for 4 hours then partitioned between ethyl acetate-H₂O. The organic phase was washed with 1N HCl, brine, dried, and concentrated in vacuo. Chromatography on silica gel (30% ethyl acetate-hexanes) yielded 1.7 g pure (R,S) trans-3-[((4-phenylthio)phenyl)sulfonyl]cyclohexanol.

Part C: A 250 mL round bottom flask equipped with magnetic stir bar and N₂ inlet was charged with 1.7 g (R,S)trans-3-[((4-phenylthio)phenyl)sulfonyl]cyclohexanol, 0.4 mL MsCl (1.25 eq.), 1.0 mL NEt₃ in MeCl₂ . The reaction was stirred 20 minutes then concentrated in vacuo and partitioned between ethyl acetate-H₂O. The organic phase was concentrated in vacuo and dissolved in 10 mL dry DMF and reacted with 6.5 g (10 eq.) potassium thioacetate. The reaction mixture was heated to 70° C. for 4 hours then partitioned between ethyl acetate-H₂O. The organic phase was washed with 1N KHSO₄, brine, dried, and concentrated in vacuo. Chromatography on silica gel (30% ethyl acetate-hexanes) yielded 1.1 g orange oil.

Part D: A 250 mL round bottom flask equipped with magnetic stir bar and N₂ inlet was charged with 1.0 g product from part C, 1.7 mL (3 eq.) 25% NaOMe in MeOH, and 25 mL MeOH. The reaction was stirred 30 minutes then quenched with dry ice and concentrated in vacuo. The residue was partitioned between ethyl acetate-H₂O, dried, and concentrated in vacuo to crude thiol. Chromatography on silica gel (30% ethyl acetate-hexanes) yielded 0.9 g pure (R,S)trans-3-[(4-phenylthio)phenylsulfonyl]-cyclohexanethiol.

EXAMPLE 39

Preparation of N1-3-[(4-phenoxyphenyl)sulfonyl]-1sulfanylpropyl-3-morpholinopropanamide

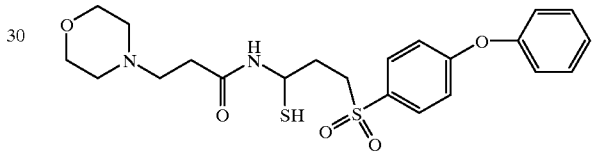

Part A: A solution of 10 g (78 mmol) of 4-fluorothiophenol and 8 g (86 mM) of 3-chloro-1-propanol in 80 mL of anhydrous DMF was purged with nitrogen for 20 min., then treated with 32 g (234 mM) of potassium carbonate. After one hour, the reaction mixture was concentrated in vacuo, and the residue was partitioned between ethyl acetate and water. The layers were separated and the organic layer was washed with brine (3×), dried (MgSO₄), and concentrated to afford 16 g of crude product. The crude product was chromatographed on silica gel using 30–45% ethyl acetate/hexane to yield 12 g of pure 3-[(4-fluorophenyl)thio]propan-1-ol, m/z=203 (M+NH₄).

Part B: A solution of 16 g (78 mmol) of 3-[(4-fluorophenyl)thio]propan-1-ol from Part A in 300 mL of methanol and 60 mL of water was treated with 168 g (273 mM) of potassium peroxyronosulfate (OXONE®). After 72 hours, the reaction was filtered, the filter cake was washed with methanol and the filtrate concentrated in vacuo, ethyl acetate and water were added, the layers were separated and the aqueous layer was extracted with ethyl acetate (2×) The 3 organic extracts were combined and washed with saturated sodium bicarbonate solution and brine, dried with magnesium sulfate, filtered and concentrated to afford 13 g of pure 3-[(fluorophenyl)sulfonyl]propan-1-ol, m/z=225 (M+Li).

Part C: A solution of 13 g (58 mmol) of 3-[(4-fluorophenyl)sulfonyl]propan-1-ol from part B and 16 g (175 mM) of phenol in 100 mL of anhydrous DMF was purged with nitrogen for one-half hour then treated with 24 g (175 mM) of potassium carbonate. The reaction mixture was then placed in a 100° C. oil bath. After 24 hours, the reaction mixture was concentrated in vacuo, and the residue was partitioned between ethyl acetate and water. The layers were separated and the organic layer was washed with 1N HCl solution, saturated sodium bicarbonate solution and brine, dried (MgSO$_4$), and concentrated to afford 29 g of crude product. This was chromatographed on silica gel using 30–45% ethyl acetate/hexane to yield 12 g of pure 3-[(4-phenoxyphenyl)sulfonyl]propan-1-ol, m/z=299 (M+Li).

Part D: A cooled solution of 13 g (44 mmol) of 3-[(4-phenoxyphenyl)sulfonyl]propan-1-ol from Part C in 60 mL of anhydrous CH$_2$Cl$_2$ was treated with 25 mL (18 g, 178 mM) of triethylamine. The reaction mixture was then treated with a slurry of 28 g (178 mM) of pyridine-SO$_3$ complex in 60 mL of methyl sulfoxide added over one-half hour. After stirring for one hour, the reaction mixture was poured over 500 mL of ice and ethyl acetate was added. The layers were separated and the organic layer was washed with 5% KHSO$_4$ solution, water and brine, dried (MgSO$_4$), and concentrated to afford 13 g of 3-[(4-phenoxyphenyl)sulfonyl]propan-1-al, suitable for the next reaction.

Part E: A cooled solution of 13 g (44 mmol) of 3-[(4-phenoxyphenyl)sulfonyl]propan-1-al from Part D in 150 mL of CH$_2$Cl$_2$ was treated with 8.9 mL (6.6 g, 67 mM) of trimethylsilylcyanide (TMSCN), followed by 15.0 g (67 mM) of zinc bromide. After 18 hours, additional TMSCN and zinc bromide were added to drive the reaction to completion. The reaction was concentrated in vacuo and the residue was partitioned between ethyl acetate and 2N HCl solution. The layers were separated and the organic layer was washed with water and brine, dried over MgSO$_4$, and concentrated to yield 13.7 g of crude product. This was chromatographed on silica gel using 25–40% ethyl acetate/hexane to yield 9 g of 1-hydroxy-3-[(3-phenoxybenzyl)sulfonyl]propyl cyanide, suitable for the next reaction.

Part F: A solution of 9 g (28 mmol) of 1-hydroxy-3-[(3-phenoxybenzyl)sulfonyl]propyl cyanide from Part E in 25 mL of glacial acetic acid was treated with 100 mL of concentrated HCl and placed in a 90° C. oil bath for two hours. The reaction was concentrated in vacuo, then aliquots of toluene (1×) and acetonitrile (2×) were added to the crude product and stripped. Drying over P$_2$O$_5$ under vacuum afforded 7.1 g of 2-hydroxy-4-[(3-phenoxybenzyl)sulfonyl]butanoic acid suitable for the next reaction.

Part G: A solution of 3.4 g (10 mmol) of 2-hydroxy-4-[(3-phenoxybenzyl)sulfonyl]butanoic acid from Part F and 2.1 g (15 mM) HOBT in 15 mL of anhydrous DMF was cooled in an ice bath and treated with 2.3 g (12 mM) of EDC. After 2 hours, the reaction was treated with a solution of 1.5 g (12 mM) of 4-(2-aminoethyl)morpholine and 3.3 mL (3.1 g, 30 mM) of N-methylmorpholine in 5 mL anhydrous DMF. After stirring for 66 hours, the reaction was concentrated in vacuo, and the residue was partitioned between ethyl acetate and water. The layers were separated and the organic layer was washed with saturated sodium bicarbonate solution and brine, dried over MgSO$_4$, and concentrated to yield 3.5 g of crude product. The crude product was chromatographed on silica gel using 5% methanol/ethyl acetate followed by 20% ethanol/THF to yield 2.1 g of N1-(2-morpholinoethyl)-2-hydroxy-4-[(3-phenoxybenzyl)sulfonyl]butanamide suitable for the next reaction.

Part H: A cooled solution of 2.1 g (5 mmol) of N1-(2-morpholinoethyl)-2--hydroxy-4-[(3-phenoxybenzyl)sulfonyl]butanamide from Part G in 55 mL of anhydrous CH$_2$Cl$_2$ was treated with 0.5 mL (0.8 g, 7 mM) of methanesulfonyl chloride, followed by 1.0 mL (0.7 g, 7 mM) of triethylamine. After 1 hour, the reaction was concentrated in vacuo, and the residue was partitioned between ethyl acetate and saturated sodium bicarbonate solution. The layers were separated and the aqueous layer was extracted with ethyl acetate (1×). The organic layers were combined and washed with brine, dried (MgSO$_4$) and concentrated to yield 2.5 g of 1-[(2-morpholinoethyl)amino]carbonyl-3-[(3-phenoxybenzyl)sulfonyl]propyl methanesulfonate suitable for the next reaction.

Part I: A solution of 2.5 g (5 mmol) of 1-[(2-morpholinoethyl)amino]carbonyl-3-[(3-phenoxybenzyl)sulfonyl]propyl methanesulfonate from Part H in 20 mL of anhydrous DMF was treated with 0.8 g (7 mM) of potassium thioacetate. After 1 hour, the reaction was partitioned between ethyl acetate and sodium bicarbonate solution. The layers were separated and the organic layer was washed with brine (3×), dried (MgSo$_4$) and concentrated to yield 2.4 g of crude product. This was chromatographed on silica gel using 1–3% methanol/ethyl acetate to yield 1.8 g of 1-[(2-morpholinoethyl)amino]carbonyl-3-[(3-phenoxybenzyl)sulfonyl]propyl ethanethioate suitable for the next reaction.

Part J: A cooled solution of 1.0 g (2 mmol) of 1-[(2-morpholinoethyl)amino]carbonyl-3-[(3-phenoxybenzyl)sulfonyl]propyl ethanethioate from Part I in 8 mL of anhydrous methanol, was treated with a sodium methoxide solution freshly prepared from 0.05 g (2 mmol) of sodium metal and 2 mL anhydrous methanol. After 1 hour, the reaction was quenched with dry ice, then partitioned between ethyl acetate and water. The layers were separated, and the aqueous layer was extracted with ethyl acetate (1×X). The organic layers were combined and washed with brine, dried (MgSO$_4$) and concentrated to yield 0.7 g of crude product. Purification was done using reverse-phase HPLC with 20–30% acetonitrile/water. Ion-exchange treatment gave the free base which was converted to the hydrochloride salt using concentrated HCl solution in CH$_3$CN. Concentration yielded 0.6 g of pure N1-3-[(4-phenoxyphenyl)sulfonyl]-1-sulfanylpropyl-3-morpholinopropanamide, m/z=465 (M+H).

Example 40 to Example 103 were prepared by the procedures presented above, and are tabulated in the following "Example Tables".

EXAMPLE TABLE 1

[Structure: P-S-CH2CH2CH2-S(=O)2-C6H4-O-C6H4-N]

| Example Number | P | N |
|---|---|---|
| 40 | H | o-CH₃ |
| 41 | H | m-CH₃ |
| 42 | CH₃C(=O)- | p-CH₃ |
| 43 | H | p-CH₃ |
| 44 | CH₃C(=O)- | H |
| 45 | Boc-NH-CH(CH₃)-C(=O)- | H |
| 46 | H₂N-CH(CH₃)-C(=O)- · HCl | H |
| 47 | H | m-CF₃ |
| 48 | CH₃C(=O)- | m-CF₃ |

EXAMPLE TABLE 2

[Structure: P-S-CH2CH2CH2-S(=O)2-C6H4-O-C6H4-N]

| Example Number | P | N |
|---|---|---|
| 49 | H | m-Cl |
| 50 | CH₃C(=O)- | m-Cl |
| 51 | Boc-NH-CH(iPr)-C(=O)- | H |
| 52 | H₂N-CH(iPr)-C(=O)- · HCl | H |
| 53 | Boc-NH-CH(CH₂CH(CH₃)₂)-C(=O)- | H |
| 54 | H₂N-CH(CH₂CH(CH₃)₂)-C(=O)- · HCl | H |

EXAMPLE TABLE 3
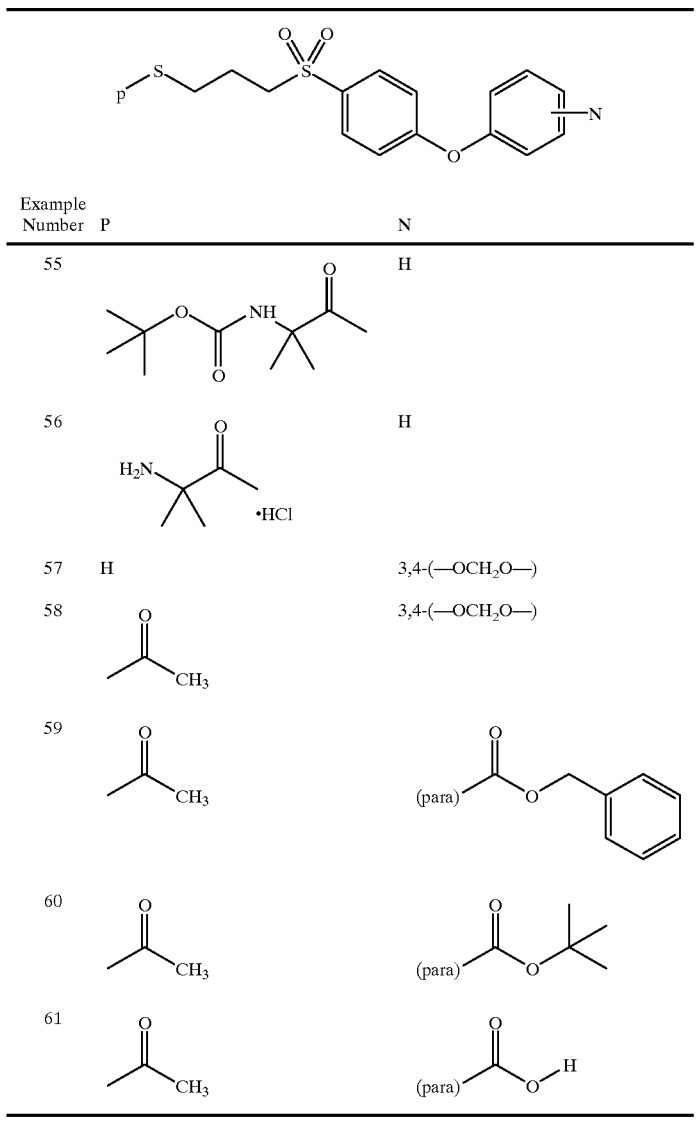
EXAMPLE TABLE 4
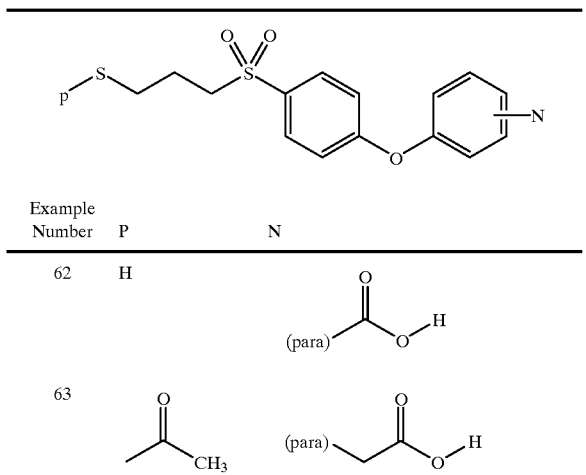
EXAMPLE TABLE 4-continued
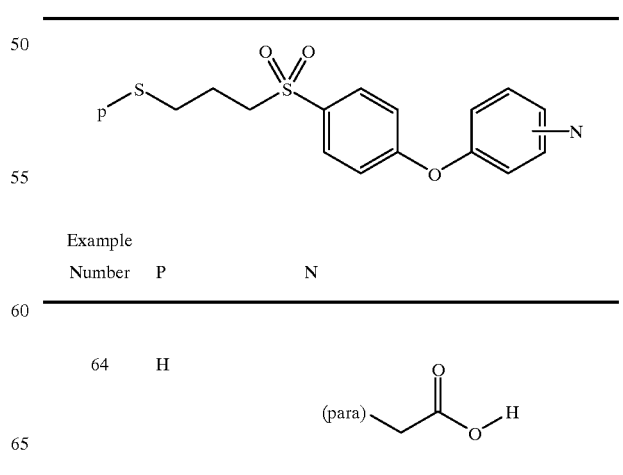

EXAMPLE TABLE 4-continued

[Structure: P-S-(CH2)3-SO2-C6H4-O-C6H4-N]

| Example Number | P | N |
|---|---|---|
| 65 | CH3-C(=O)- | (para) -CH2-C(=O)-O-C(CH3)3 |
| 66 | CH3-C(=O)- | (para) -(CH2)2-C(=O)-O-C(CH3)3 |
| 67 | CH3-C(=O)- | (meta) -CH2-C(=O)-O-C(CH3)3 |

EXAMPLE TABLE 5

[Structure: P-S-(CH2)3-SO2-C6H4-O-C6H4-N]

| Example Number | P | N |
|---|---|---|
| 68 | CH3-C(=O)- | (para) -(CH2)2-C(=O)-OH |
| 69 | CH3-C(=O)- | (meta) -CH2-C(=O)-OH |
| 70 | H | (meta) -CH2-C(=O)-OH |
| 71 | H | (para) -(CH2)2-C(=O)-OH |

EXAMPLE TABLE 6

[Structure: P-S-(CH2)3-SO2-C6H4-N]

| Example Number | P | N |
|---|---|---|
| 72 | CH3-C(=O)- | (p) -S-CH2- pyridine (4-position) |
| 73 | H | (p) -S-CH2- pyridine (4-position) |
| 74 | H | (p) -S-CH2- pyridine (4-position) ·HCl |
| 75 | CH3-C(=O)- | (p) -S-CH2- (1-methylimidazol-2-yl) |
| 76 | H | (p) -S-CH2- (1-methylimidazol-2-yl) |
| 77 | CH3-C(=O)- | (p) -S-CH2- (thiazol-2-yl) |
| 78 | H | (p) -S-CH2- (thiazol-2-yl) |

EXAMPLE TABLE 7
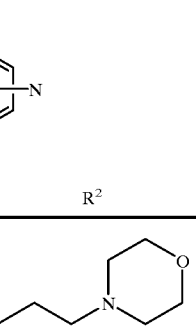
| Example Number | P | N | R² |
|---|---|---|---|
| 79 | H | (p)-OCH₃ | 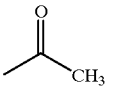 |
| 80 | 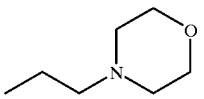 | (p)-OCH₃ | 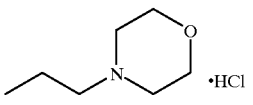 |
| 81 | H | (p)-OCH₃ | 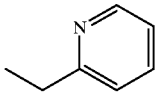 •HCl |
| 82 | H | (p)-O(CH₂)₃CH₃ | 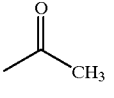 |
| 83 | 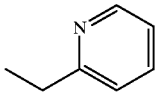 | (p)-O(CH₂)₃CH₃ | 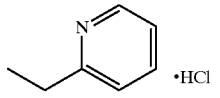 |
| 84 | H | (p)-O(CH₂)₃CH₃ | •HCl |
| 85 | H | (p)-O(CH₂)₃CH₃ | 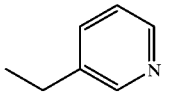 |

EXAMPLE TABLE 8

| Example Number | P | N | R² |
|---|---|---|---|
| 86 | CH₃C(O)– | (p)-O(CH₂)₃CH₃ | 3-pyridyl |
| 87 | H | (p)-O(CH₂)₃CH₃ | 3-pyridyl·HCl |
| 88 | H | (p)-O(CH₂)₃CH₃ | N-propylmorpholine |
| 89 | CH₃C(O)– | (p)-O(CH₂)₃CH₃ | N-propylmorpholine |
| 90 | H | (p)-O(CH₂)₃CH₃ | N-propylmorpholine·HCl |
| 91 | H | (p)-OCH₃ | –C(O)NHCH₂C₆H₅ (ethyl chain) |
| 92 | CH₃C(O)– | (p)-SC₆H₅ (SCH₃ phenyl) | H |

EXAMPLE TABLE 9

[Structure: P-S-CH(R⁶)-CH₂-CH₂-S(=O)(=O)-pyridyl]

| Example Number | P | N | R⁶ |
|---|---|---|---|
| 93 | CH₃-C(=O)- | (p)-O-phenyl | -C(=O)-OH |
| 94 | H | (p)-O-phenyl | -C(=O)-OH |
| 95 | CH₃-C(=O)- | (p)-O-phenyl | -C(=O)-O-C(CH₃)₃ |
| 96 | CH₃-C(=O)- | (p)-O-phenyl | -C(=O)-NH₂ |
| 97 | H | (p)-O-phenyl | -C(=O)-NH₂ |
| 98 | CH₃-C(=O)- | (p)-O-phenyl | -C(=O)-OCH₃ |
| 99 | H | (p)-O-phenyl | -C(=O)-NH-CH₂CH₂-morpholine |

EXAMPLE TABLE 10

| Example Number | Structure |
|---|---|
| 100 | (structure) |
| 101 | (structure) |
| 102 | (structure) |
| 103 | (structure) |

EXAMPLE 104

In Vitro Metalloprotease Inhibition

Most of the compounds prepared in the manner described in Examples 1 to 39 were tested for activity by an in vitro assay. Following the procedures of Knight et al., *FEBS Lett.* 296(3):263 (1992). Briefly, 4-aminophenylmercuric acetate (APMA) or trypsin activated MMPs were incubated with various concentrations of the inhibitor compound at room temperature for 5 minutes (0.02% 2-mercaptoethanol added to buffer for thiol compounds with 5 minutes or overnight incubation).

More specifically, recombinant human MMP-13 and MMP-1 enzymes were prepared in laboratories of the assignee. MMP-13 was expressed in baculovirus as a proenzyme, and purified first over a heparin agarose column and then over a chelating zinc chloride column. The proenzyme was activated by APMA for use in the assay. MMP-1 expressed in transfected HT-1080 cells was provided by Dr. Howard Welgus of Washington University, St. Louis, Mo. The enzyme was also activated using APMA and was then purified over a hydroxamic acid column.

The enzyme substrate is a methoxycoumarin-containing polypeptide having the following sequence:

MCA-ProLeuGlyLeuDpaAlaArgNH$^2$, wherein MCA is methoxycoumarin and Dpa is 3-(2,4--dinitrophenyl)-L-2,3-diaminopropionyl alanine. This substrate is commercially available from Baychem as product M-1895.

The buffer used for assays contained 100 mM Tris-HCl, 100 mM NaCl, 10 mM CaCl$_2$ and 0.05 percent polyethyleneglycol (23) lauryl ether at a pH value of 7.5. Assays were carried out at room temperature, and dimethyl sulfoxide (DMSO) at a final concentration of 1 percent was used to dissolve inhibitor compound.

The assayed inhibitor compound in DMSO/buffer solution was compared to an equal amount of DMSO/buffer with no inhibitor as control using Microfluor™ White Plates (Dynatech). The inhibitor or control solution was maintained in the plate for 10 minutes and the substrate was added to provide a final concentration of 4 µM.

In the absence of inhibitor activity, a fluorogenic peptide was cleaved at the gly-leu peptide bond, separating the highly fluorogenic peptide from a 2,4-dinitrophenyl quencher, resulting in an increase of fluorescence intensity (excitation at 328 nm/emission at 415 nm). Inhibition was measured as a reduction in fluorescent intensity as a function of inhibitor concentration, using a Perkin Elmer L550 plate reader. The IC$_{50}$ values were calculated from those values. The results are set forth in the Inhibition Table below, reported in terms of IC$_{50}$ to three significant: figures. Inhibition Table Inhibition Table

| Example | hMMP 13 (nM) | hMMP 1 (nM) |
|---|---|---|
| 1 | 400 | 4000 |
| 2 | 33 | 8000 |
| 3 | 475 | >10,000 |
| 4 | 1000 | >10,000 |

-continued

Inhibition Table

| Example | hMMP 13 (nM) | hMMP 1 (nM) |
|---|---|---|
| 5 | 400 | >10,000 |
| 6 | >10,000 | >10,000 |
| 7 | 22 | 1000 |
| 8 | 1300 | >10,000 |
| 9 | 500 | >10,000 |
| 10 | 15 | 4000 |
| 11 | >10,000 | >10,000 |
| 13 | 70 | 8000 |
| 14 | 190 | 6500 |
| 15 | 700 | >10,000 |
| 16 | 4 | 600 |
| 17 | 210 | >10,000 |
| 18 | 0.6 | 60 |
| 19 | 200 | 7000 |
| 20 | 7 | 1500 |
| 21 | 1500 | >10,000 |
| 22 | 0.5 | 1100 |
| 23 | 45 | >10,000 |
| 24 | 48 | 3500 |
| 25 | 700 | >10,000 |
| 27 | 40 | >10,000 |
| 28 | 1.5 | 9000 |
| 29 | 55 | 10,000 |
| 30 | 900 | >10,000 |
| 31 | 35 | 4750 |
| 32 | 70 | 4000 |
| 33 | 42 | 900 |
| 34 | 200 | 8000 |
| 35 | 3 | >10,000 |
| 36 | 0.6 | 2400 |
| 37 | 170 | >10,000 |
| 38 | 0.4 | >10,000 |
| 39 | 0.2 | 370 |

EXAMPLE 105

In Vivo Angiogenesis Assay

The study of angiogenesis depends on a reliable and reproducible model for the stimulation and inhibition of a neovascular response. The corneal micropocket assay provides such a model of angiogenesis in the cornea of a mouse. See, *A Model of Angiogenesis in the Mouse Cornea*; Kenyon, BM, et al., Investigative Ophthalmology & Visual Science, July 1996, Vol. 37, No. 8.

In this assay, uniformly sized Hydron™ pellets containing bFGF and sucralfate were prepared and surgically implanted into the stroma mouse cornea adjacent to the temporal limbus. The pellets were formed by making a suspension of 20 μL sterile saline containing 10 μg recombinant bFGF, 10 mg of sucralfate and 10 μL of 12 percent Hydron™ in ethanol. The slurry was then deposited on a 10×10 mm piece of sterile nylon mesh. After drying, the nylon fibers of the mesh was separated to release the pellets.

The corneal pocket was made by anesthetizing a 7 week old C57Bl/6 female mouse, then proptosing the eye with a jeweler's forceps. Using a dissecting microscope, a central, intrastromal linear keratotomy of approximately 0.6 mm in length was performed with a #15 surgical blade, parallel to the insertion of the lateral rectus muscle. Using a modified cataract knife, a lamellar micropocket was dissected toward the temporal limbus. The pocket was extended to within 1.0 mm of the temporal limbus. A single pellet was placed on the corneal surface at the base of the pocket with a jeweler's forceps. The pellet was then advanced to the temporal end of the pocket. Antibiotic ointment was then applied to the eye.

Mice were dosed on a daily basis for the duration of the assay. Dosing of the animals was based on bioavailability and overall potency of the compound. In the case of the compound of Example 39, dosing was 50 mg/kg bid, po. Neovascularization of the corneal stroma began at about day three and was permitted to continue under the influence of the assayed compound until day five. At day five, the degree of angiogenic inhibition was scored by viewing the neovascular progression with a slit lamp microscope.

The mice were anesthetized and the studied eye was once again proptosed. The maximum vessel length of neovascularization, extending from the limbal vascular plexus toward the pellet was measured. In addition, the contiguous circumferential zone of neovascularization was measured as clock hours, where 30 degrees of arc equals one clock hour. The area of angiogenesis was calculated as follows.

$$\text{area} = \frac{(0.4 \times \text{clock hours} \times 3.14 \times \text{vessel length (in mm)})}{2}$$

The studied mice were thereafter compared to control mice and the difference in the area of neovascularization was recorded. The compound of Example 39, N1-3-[(4-phenoxyphenyl)sulfonyl]-1-sulfanylpropyl-3-morpholinopropanamide, exhibited 51 percent inhibition, whereas the vehicle control exhibited zero percent inhibition.

From the foregoing, it will be observed that numerous modifications and variations can be effectuated without departing from the true spirit and scope of the novel concepts of the present invention. It is to be understood that no limitation with respect to the specific example presented is intended or should be inferred. The disclosure is intended to cover by the appended claims all such modifications as fall within the scope of the claims.

What is claimed is:

1. A matrix metalloprotease inhibitor compound corresponding to the formula:

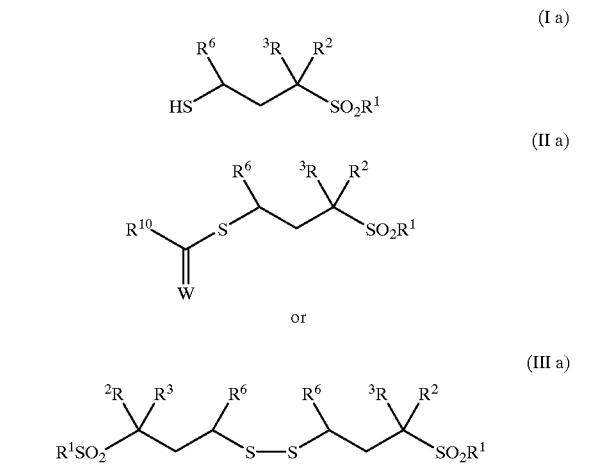

wherein

R$^1$ is a substituted aryl or heteroaryl radical having a length greater than about that of a pentyl group and a length that is less than that of a stearyl group, and when rotated about an axis drawn through the SO$_2$-bonded 1-position and the 4-position of a 6-membered ring or the SO$_2$-bonded position and substituent-bonded 3- or 5-position of a 5-membered ring defines a three-dimensional volume whose widest dimension has the width of about one phenyl ring to about three phenyl rings in a direction transverse to that axis to rotation;

$R^2$ and $R^3$ are radicals independently selected from the group consisting of hydrido, $C_1$–$C_6$ alkyl, single-ringed aralkyl or heteroaralkyl having 1–3 carbons in the alkyl chain, cycloalkylalkyl having 4–8 carbons in the ring and 1–3 carbons in the alkyl chain, and heterocycloalkylalkyl in which 4–8 atoms are in the ring, one or two of which atoms are nitrogen, oxygen or sulfur and in which the alkyl chain contains 1–3 carbons, or wherein $R^2$ and $R^6$ together with the atoms to which they are bonded form a 5- or 6-membered ring;

$R^6$ is a radical selected from the group consisting of an $C_1$–$C_6$ alkyl group, a carboxyl group, a $C_1$–$C_6$ alkoxy carbonyl group, an amino $C_1$–$C_6$ alkanoyl group, a carboxamide group where the amido nitrogen is (i) unsubstituted or substituted with (ii) a $C_1$–$C_4$ alkyl substituted by amino, mono-substituted amino or di-substituted amino, wherein the substituent on the amino nitrogen is selected from the group consisting of $C_1$–$C_6$ alkyl, $C_5$–$C_8$ cycloalkyl and $C_1$–$C_6$ alkanoyl groups, or wherein two amino nitrogen substitutents and the nitrogen to which they are bonded together form a 5- to 8-membered heterocyclic or heteroaryl ring containing zero or one additional hetero atoms that are nitrogen, oxygen or sulfur or (iii) the amido nitrogen is the amine of an amino acid;

W is oxygen (O) or sulfur (S); and $R^{10}$ is aryl or heteroaryl having a single ring or $C_1$–$C_6$ alkoxy.

2. The inhibitor compound according to claim 1 wherein $R^1$ has a length greater than that of a hexyl group and less than that of a lauryl group.

3. The inhibitor compound according to claim 1 wherein $R^1$ is a single-ringed aryl or heteroaryl group that is 5- or 6-membered, and is itself substituted at its own 4-position when a 6-membered ring and at its own 3-position when a 5-membered ring with a substituent selected from the group consisting of one other single-ringed aryl or heteroaryl group, a $C_2$–$C_6$ alkyl group, a $C_1$–$C_6$ alkoxy group, a phenoxy group, a thiophenoxy group, a 4-thiopyridyl group, a phenylazo group and a benzamido group.

4. The inhibitor compound according to claim 1 wherein said $R^1$ is $PhR^{11}$ in which Ph is phenyl substituted with $R^{11}$ at the 4-position, and said $R^{11}$ is a phenoxy group that is itself substituted at the meta- or para-position or both by a single atom or a substituent containing a longest chain of up to five atoms, excluding hydrogen.

5. A matrix metalloprotease inhibitor corresponding to the formula:

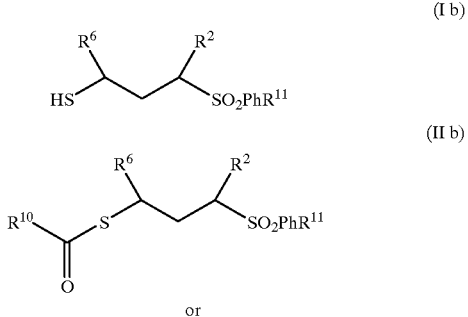

(I b)

(II b)

or

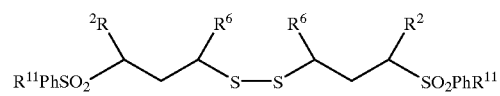

(III b)

wherein

Ph is phenyl substituted with $R^{11}$ at the 4-position;

$R^{11}$ is a substituent selected from the group consisting of $C_1$–$C_6$ alkoxy, $C_3$–$C_6$ alkyl, phenoxy, thiophenoxy, benzamido, phenylazo, and phenyl moieties;

$R^2$ is selected from the group consisting of hydrido, a $C_1$–$C_6$ alkyl group, a $C_2$–$C_3$ alkyl cycloamino group having five or six atoms in the ring and zero or one additional heteroatom that is oxygen or nitrogen, a $C_1$–$C_6$ aminocarbonyl group whose amido nitrogen is unsubstituted or mono- or disubstituted with a $C_2$–$C_3$ alkyl or benzyl radical, and a $C_1$–$C_4$ alkylheteroaryl group having a single heteroaryl ring wherein said single heteroaryl ring contains one or two nitrogen atoms, or wherein $R^2$ and $R^6$ together with the atoms to which they are bonded form a 5- or 6-membered ring;

$R^6$ is a radical selected from the group consisting of an $C_1$–$C_6$ alkyl group, a carboxyl group, a $C_1$–$C_6$ alkoxy carbonyl group, an amino $C_1$–$C_6$ alkanoyl group, a carboxamide group where the amido nitrogen is (i) unsubstituted or (ii) substituted with a $C_1$–$C_4$ alkyl substituted by amino, mono-substituted amino or di-substituted amino, wherein the substituent on the amino nitrogen is selected from the group consisting of $C_1$–$C_6$ alkyl, $C_5$–$C_8$ cycloalkyl and $C_1$–$C_6$ alkanoyl groups, or wherein two amino nitrogen substituents and the nitrogen to which they are bonded together form a 5- to 8-membered heterocyclic or heteroaryl ring containing zero or one additional hetero atoms that are nitrogen, oxygen or sulfur or (iii) the amido nitrogen is the amine of an amino acid; and $R^{10}$ is $C_1$–$C_6$ alkoxy, or a single-ringed aryl or heteroaryl group, with the proviso that only one of $R^2$ or $R^6$ is present unless $R^2$ and $R^6$ together with the atoms to which they are bonded form a 5- or 6-membered ring.

6. The inhibitor compound according to claim 5 wherein $R^{10}$ is selected from the group consisting of phenyl, 2-pyridyl, 3-pyridyl, 4-pyridyl, thiophene-2-yl, 3-thiophene-3-yl, methoxy and ethoxy.

7. The inhibitor compound according to claim 5 wherein the $R^{11}$ substituent group is itself substituted at the meta- or para-position or both with a single atom or a substituent containing a longest chain of up to five atoms, excluding hydrogen.

8. The inhibitor compound according to claim 7 wherein said $R^{11}$ substituent is phenoxy and is substituted at its own para-position with a moiety that is selected from the group consisting of a halogen, a $C_1$–$C_4$ alkoxy group, a $C_1$–$C_4$ alkyl group, a dimethylamino group, a $C_1$–$C_3$ alkyl carboxyl group, a $C_1$–$C_3$ alkylcarbonyl $C_1$–$C_4$ alkoxy group and a $C_1$–$C_3$ alkyl carboxamido group, or is substituted at the meta and para positions by a methylenedioxy group.

9. A matrix metalloprotease inhibitor corresponding to the formula:

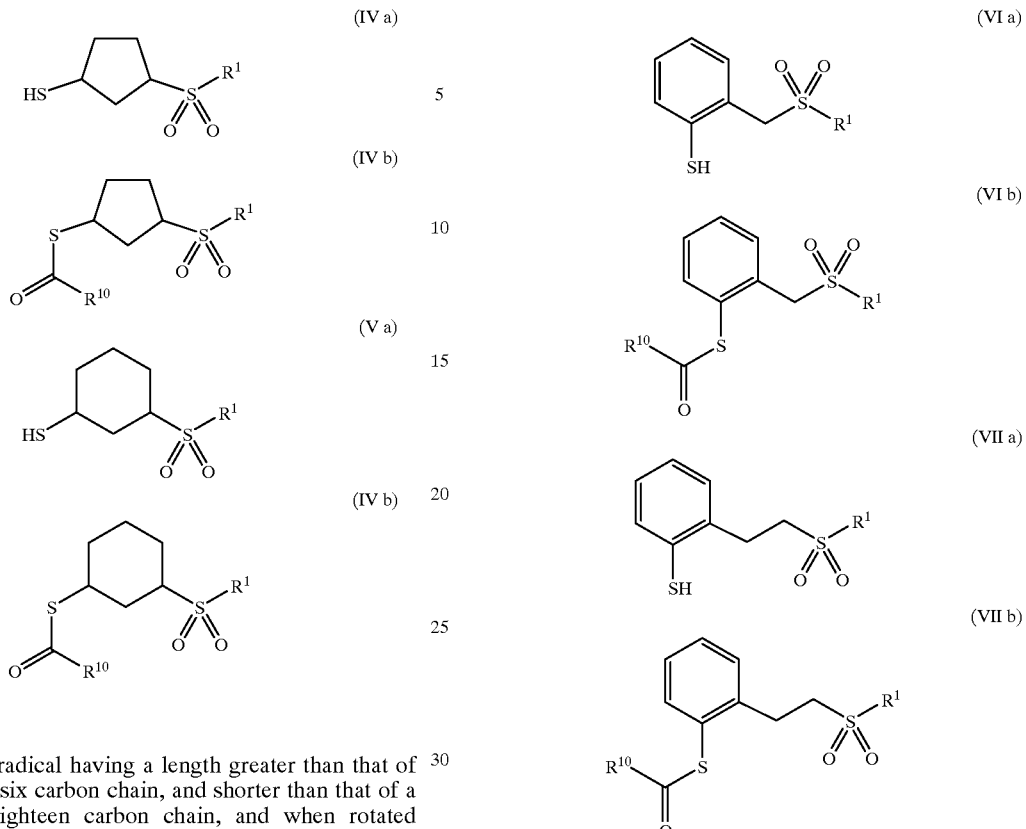

wherein
  R[1] is an aryl radical having a length greater than that of a saturated six carbon chain, and shorter than that of a saturated eighteen carbon chain, and when rotated about an axis drawn through the $SO_2$-bonded 1-position and the 4-position of a 6-membered ring or the $SO_2$-bonded position and substituent-bonded 3- or 5-position of a 5-membered ring defines a three-dimensional volume whose widest dimension has the width of about one phenyl ring to about three phenyl rings in a direction transverse to that axis to rotation; and
  R[10] is aryl or heteroaryl having a single ring or $C_1$–$C_6$ alkoxy.

10. The inhibitor compound according to claim 9 wherein R[1] is a single-ringed aryl or heteroaryl group that is 5- or 6-membered, and is itself substituted at its own 4-position when a 6-membered ring and at its own 3-position when a 5-membered ring with a substituent selected from the group consisting of one other single-ringed aryl or heteroaryl group, a $C_2$–$C_6$ alkyl group, a $C_1$–$C_6$ alkoxy group, a phenoxy group, a thiophenoxy group, a 4-thiopyridyl group, a phenylazo group and a benzamido group.

11. The inhibitor compound according to claim 10 wherein R[1] is PhR[11] in which Ph is phenyl substituted with R[11] at the 4-position, and said R[11] is a phenoxy group that is itself substituted at the meta- or para-position or both by a single atom or a substituent containing a longest chain of up to five atoms, excluding hydrogen.

12. The inhibitor compound according to claim 10 where R[11] is a substituent selected from the group consisting of $C_1$–$C_6$ alkoxy, $C_3$–$C_6$ alkyl, phenoxy, thiophenoxy, benzamido, phenylazo, and phenyl moieties.

13. The inhibitor compound according to claim 12 wherein the R[11] substituent group is itself substituted at the meta- or para-position or both with a single atom or a substituent containing a longest chain of up to five atoms, excluding hydrogen.

14. A matrix metalloprotease inhibitor corresponding to the formula:

wherein
  R[1] is an aryl radical having a length greater than that of a saturated six carbon chain, and shorter than that of a saturated eighteen carbon chain, and when rotated about an axis drawn through the $SO_2$-bonded 1-position and the 4-position of a 6-membered ring or the $SO_2$-bonded position and substituent-bonded 3- or 5-position of a 5-membered ring defines a three-dimensional volume whose widest dimension has the width of about one phenyl ring to about three phenyl rings in a direction transverse to that axis to rotation; and
  R[10] is aryl or heteroaryl having a single ring or $C_1$–$C_6$ alkoxy.

15. The inhibitor compound according to claim 14 wherein R[1] is a single-ringed aryl or heteroaryl group that is 5- or 6-membered, and is itself substituted at its own 4-position when a 6-membered ring and at its own 3-position when a 5-membered ring with a substituent selected from the group consisting of one other single-ringed aryl or heteroaryl group, a $C_2$–$C_6$ alkyl group, a $C_1$–$C_6$ alkoxy group, a phenoxy group, a thiophenoxy group, a 4-thiopyridyl group, a phenylazo group and a benzamido group.

16. The inhibitor compound according to claim 15 wherein said wherein R[1] is PhR[11] in which Ph is phenyl substituted with R[11] at the 4-position, and said R[11] substituent is a phenoxy group that is itself substituted at the meta- or para-position or both by a single atom or a substituent containing a longest chain of up to five atoms, excluding hydrogen.

17. The inhibitor compound according to claim 16 wherein said R[11] phenoxy substituent is itself substituted with a moiety selected from the group consisting of $C_1$–$C_6$ alkoxy, $C_3$–$C_6$ alkyl, phenoxy, methylenedioxy, thiophenoxy, benzamido, phenylazo, and phenyl.

18. The inhibitor compound according to claim 17 wherein $R^{10}$ is selected from the group consisting of phenyl, 2-pyridyl, 3-pyridyl, 4-pyridyl, thiophene-2-yl, 3-thiophene-3-yl, methoxy and ethoxy.

19. A process for treating a host mammal having a condition associated with pathological matrix metalloprotease activity that comprises administering a metalloprotease inhibitor in an effective amount to a mammalian host having such a condition, said metalloprotease inhibitor corresponding in structure to formulas I, II or III below

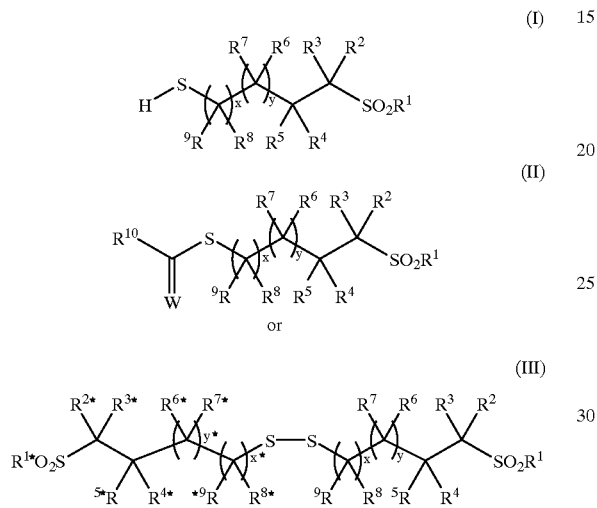

wherein x and y are independently zero, 1 or 2;

W is oxygen or sulfur;

a starred R* group, y* or x* is the same or different from an unstarred R, y or x;

$R^{10}$ is selected from the group consisting of alkyl, aryl, alkoxy, cycloalkyl, aryloxy, aralkoxy, aralkyl, aminoalkyl, heteroaryl and N-monosubstituted or N,N-disubstituted aminoalkyl wherein the substituent on the nitrogen is selected from the group consisting of alkyl, aryl, aralkyl, cycloalkyl, aralkoxycarbonyl, alkoxycarbonyl, and alkanoyl, or wherein the nitrogen and two substituents attached thereto form a 5 to 8 member heterocyclo or heteroaryl ring;

$R^1$ is an aryl or heteroaryl substituent selected from the group consisting of aralkyl, heteroaralkyl, aralkoxy, heteroaralkoxy, aralkoxyalkyl, aryloxyalkyl, aralkanoylalkyl, arylcarbonylalkyl, aralkylaryl, aryloxyalkylaryl, aralkoxyaryl, arylazoaryl, arylhydrazinoaryl, alkylthioaryl, arylthioalkyl, alkylthioaralkyl, aralkylthioalkyl, and aralkylthioaryl, the sulfoxide or sulfone of any of said thio substituents, and a fused ring structure comprising two or more 5- or 6-membered rings selected from the group consisting of aryl, heteroaryl, carbocyclic and heterocyclic, said aryl or heteroaryl substituent of which $R^1$ is comprised being substituted cyano, perfluoroalkyl, trifluoromethylalkyl, hydroxy, with one or more substituents independently selected from among halo, $C_2$–$C_{10}$ alkyl, $C_1$–$C_{10}$ alkoxy, nitro, thiol, hydroxycarbonyl, aryloxy, arylthio, arylamino, aralkyl, aryl, heteroaryloxy, heteroarylthio, heteroarylamino, heteroaralkyl, cycloalkyl, heterocyclooxy, heterocyclothio, heterocycloamino, cycloalkyloxy, cycloalkylthio, cycloalkylamino, heteroaralkoxy, heteroaralkylthio, heteroaralkylamino, aralkoxy, aralkylthio, aralkylamino, heterocyclic, heteroaryl, arylazo, hydroxycarbonylalkoxy, alkoxycarbonylalkoxy, alkanoyl, arylcarbonyl, aralkanoyl, alkanoyloxy, aralkanoyloxy, hydroxyalkyl, hydroxyalkoxy, alkylthio, alkoxyalkylthio, alkoxycarbonyl, aryloxyalkoxyaryl, arylthioalkylthioaryl, aryloxyalkylthioaryl, arylthioalkoxyaryl, hydroxycarbonylalkoxy, hydroxycarbonylalkylthio, alkoxycarbonylalkoxy, alkoxycarbonylalkylthio, amino, alkanoylamino, arylcarbonylamino, aralkanoylamino, heteroarylcarbonylamino, heteroaralkanoylamino, and N-monosubstituted or N,N-disubstituted aminoalkyl wherein the substituent on the amino nitrogen are selected from the group consisting of alkyl, aryl, aralkyl, cycloalkyl, aralkoxycarbonyl, alkoxycarbonyl, and alkanoyl, or wherein the nitrogen and two substituents attached thereto form a 5 to 8 member heterocyclo or heteroaryl ring;

$R^2$ and $R^3$ are independently selected from the group consisting of hydrido, an alkyl, aryl, aralkyl, heteroaryl, heteroaralkyl, alkynylalkyl, alkenylalkyl, thioalkyl, cycloalkyl, cycloalkylalkyl, heterocycloalkylalkyl, alkoxyalkyl, aralkoxyalkyl, aminoalkyl, alkoxyalkoxyalkyl, aryloxyalkyl, hydroxyalkyl, hydroxycarbonylalkyl, hydroxycarbonylaralkyl, or N-monosubstituted or N,N-disubstituted aminoalkyl group wherein the substituent on the amino nitrogen are selected from the group consisting of alkyl, aralkyl, cycloalkyl and alkanoyl, or wherein $R^3$ is hydrido and $R^2$ and another substituent selected from the group consisting of $R^4$, $R^6$ and $R^8$ together with the atoms to which they are bonded form a 4- to 8-membered ring;

$R^4$ and $R^5$ are independently selected from the group consisting of hydrido, alkyl, cycloalkyl, cycloalkylalkyl, alkoxyalkyl, hydroxyalkyl, aryloxyalkyl, aralkoxyalkyl, aralkyl, aryl, heteroaryl, heteroaralkyl, hydroxycarbonylalkyl, alkoxycarbonylalkyl, aralkoxycarbonylalkyl, hydroxycarbonyl, alkoxycarbonyl, perfluoroalkyl, trifluoromethylalkyl, thioalkyl, alkylthioalkyl, arylthioalkyl, aralkylthioalkyl, heteroaralkylthioalkyl, or a sulfoxide or sulfone of any of said thio substituents, aminocarbonyl, aminocarbonylalkyl and N-monosubstituted or N,N-disubstituted aminocarbonyl or aminocarbonylalkyl wherein the substituent on the amino nitrogen are independently selected from among alkyl, aralkyl, cycloalkyl and alkanoyl, or $R^5$ is hydrido and $R^4$ and another substituent selected from the group consisting of $R^2$, $R^6$ and $R^8$ together with the atoms to which they are bonded form a 4- to 8-membered ring;

$R^6$ and $R^7$ are independently selected from the group consisting of hydrido, an $C_1$–$C_6$ alkyl group, a cycloalkyl, cycloalkylalkyl, alkoxyalkyl, hydroxyalkyl, aryloxyalkyl, aralkoxyalkyl, aralkyl, aryl, heteroaryl, heteroaralkyl, hydroxycarbonylalkyl, alkoxycarbonylalkyl, aralkoxycarbonylalkyl, hydroxycarbonyl, alkoxycarbonyl, perfluoroalkyl, trifluoromethylalkyl, thioalkyl, alkylthioalkyl, arylthioalkyl, aralkylthioalkyl, heteroaralkylthioalkyl, or a sulfoxide or sulfone of any of said thio substituents, a carboxyl group, a $C_1$–$C_6$ alkoxy carbonyl group, an amino $C_1$–$C_6$ alkanoyl group, a carboxamide group where the amido nitrogen is (i) unsubstituted or (ii) substituted with a $C_1$–$C_4$ alkyl substituted by amino, mono-substituted amino or di-substituted amino, wherein the substituent on the amino nitrogen is selected from the group consisting of $C_1$–$C_6$ alkyl, $C_5$–$C_8$ cycloalkyl and $C_1$–$C_6$ alkanoyl groups, or wherein two amino nitrogen substitutents and the nitrogen to which they are bonded together form a 5- to 8-membered heterocyclic or heteroaryl ring containing zero or one additional hetero atoms that are nitrogen, oxygen or sulfur or (iii) the amido nitrogen is the amine of an amino acid, or $R^7$ is hydrido and $R^6$ and another substituent selected from the group consisting of $R^2$, $R^4$ and $R^8$ together with the atoms to which they are bonded form a 4- to 8-membered ring;

$R^8$ and $R^9$ are independently selected from the group consisting of hydrido, alkyl, cycloalkyl, cycloalkylalkyl, alkoxyalkyl, hydroxyalkyl, aryloxyalkyl, aralkoxyalkyl, aralkyl, aryl, heteroaryl, heteroaralkyl, hydroxycarbonylalkyl, alkoxycarbonylalkyl, aralkoxycarbonylalkyl, hydroxycarbonyl, alkoxycarbonyl, perfluoroalkyl, trifluoromethylalkyl, thioalkyl, alkylthioalkyl, arylthioalkyl, aralkylthioalkyl, heteroaralkylthioalkyl, or a sulfoxide or sulfone of any of said thio substituents, aminocarbonyl, aminocarbonylalkyl and N-monosubstituted or N,N-disubstituted aminocarbonyl or aminocarbonylalkyl wherein the substituent on the anino nitrogen are independently selected from among alkyl, aralkyl, cycloalkyl and alkanoyl, or $R^9$ is hydrido and $R^8$ and another substituent selected from the group consisting of $R^2$, $R^4$ and $R^6$ together with the atoms to which they are bonded form a 4- to 8-membered ring;

provided that no carbon atom is geminally substituted with more than one sulfhydryl group.

20. The process according to claim 19 wherein x is zero and y is 1.

21. The process according to claim 20 wherein:

$R^4$, $R^5$ and $R^7$ are each hydrido;

$R^1$ is a substituted aryl or heteroaryl radical having a length greater than about that of a pentyl group and a length that is less than that of a stearyl group, and when rotated about an axis drawn through the $SO_2$-bonded 1-position and the 4-position of a 6-membered ring or the $SO_2$-bonded position and substituent-bonded 3- or 5-position of a 5-membered ring defines a three-dimensional volume whose widest dimension has the width of about one phenyl ring to about three phenyl rings in a direction transverse to that axis to rotation;

$R^2$ and $R^3$ are radicals independently selected from the group consisting of hydrido, $C_1$–$C_6$ alkyl, single-ringed aralkyl or heteroaralkyl having 1–3 carbons in the alkyl chain, cycloalkylalkyl having 4–8 carbons in the ring and 1–3 carbons in the alkyl chain, and heterocycloalkylalkyl in which 4–8 atoms are in the ring, one or two of which atoms are nitrogen, oxygen or sulfur and in which the alkyl chain contains 1–3 carbons, or wherein $R^2$ and $R^6$ together with the atoms to which they are bonded form a 5- or 6-membered ring;

$R^6$ is a radical selected from the group consisting of an $C_1$–$C_6$ alkyl group, a carboxyl group, a $C_1$–$C_6$ alkoxy carbonyl group, an amino $C_1$–$C_6$ alkanoyl group, a carboxamide group where the amido nitrogen is (i) unsubstituted or (ii) substituted with a $C_1$–$C_4$ alkyl substituted by amino, mono-substituted amino or di-substituted amino, wherein the substituent on the amino nitrogen is selected from the group consisting of $C_1$–$C_6$ alkyl, $C_5$–$C_8$ cycloalkyl and $C_1$–$C_6$ alkanoyl groups, or wherein two amino nitrogen substitutents and the nitrogen to which they are bonded together form a 5- to 8-membered heterocyclic or heteroaryl ring containing zero or one additional hetero atoms that are nitrogen, oxygen or sulfur or (iii) the amido nitrogen is the amine of an amino acid;

W is oxygen (O) or sulfur (S); and $R^{10}$ is aryl or heteroaryl having a single ring or $C_1$–$C_6$ alkoxy.

22. The process according to claim 21 wherein $R^1$ is a single-ringed aryl or heteroaryl group that is 5- or 6-membered, and is itself substituted at its own 4-position when a 6-membered ring and at its own 3-position when a 5-membered ring with a substituent selected from the group consisting of one other single-ringed aryl or heteroaryl group, a $C_2$–$C_6$ alkyl group, a $C_1$–$C_6$ alkoxy group, a phenoxy group, a thiophenoxy group, a 4-thiopyridyl group, a phenylazo group and a benzamido group.

23. The process according to claim 22 wherein said $R^1$ is $PhR^{11}$ in which Ph is phenyl substituted with $R^{11}$ at the 4-position, and said $R^{11}$ substituent is a phenoxy group that is itself substituted at the meta- or para-position or both by a single atom or a substituent containing a longest chain of up to five atoms, excluding hydrogen.

24. A process for treating a host mammal having a condition associated with pathological matrix activity that comprises administering a metalloprotease inhibitor in an effective amount to a mammalian host having such a condition, said metalloprotease inhibitor corresponding in structure to a formula shown below

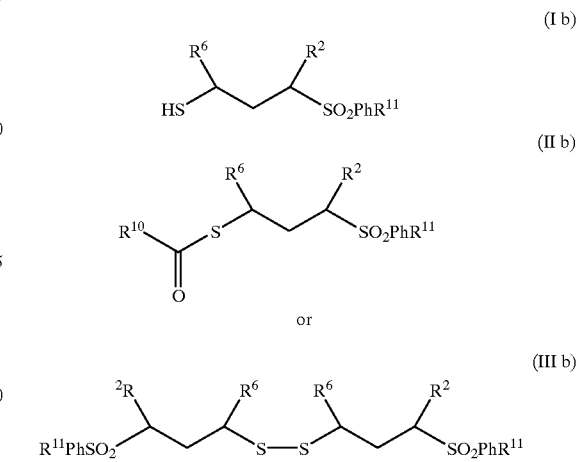

wherein

Ph is phenyl substituted with $R^{11}$ at the 4-position;

$R^{11}$ is a substituent selected from the group consisting of $C_1$–$C_6$ alkoxy, $C_3$–$C_6$ alkyl, phenoxy, thiophenoxy, benzamido, phenylazo, and phenyl moieties;

$R^2$ is selected from the group consisting of hydrido, a $C_1$–$C_6$ alkyl group, a $C_2$–$C_3$ alkyl cycloamino group having five or six atoms in the ring and zero or one additional heteroatom that is oxygen or nitrogen, a $C_1$–$C_6$ aminocarbonyl group whose amido nitrogen is unsubstituted or mono- or disubstituted with a $C_2$–$C_3$ alkyl or benzyl radical, and a $C_1$–$C_4$ alkylheteroaryl group having a single heteroaryl ring wherein said single heteroaryl ring contains one or two nitrogen atoms, or wherein $R^2$ and $R^6$ together with the atoms to which they are bonded form a 5- or 6-membered ring;

$R^6$ is a radical selected from the group consisting of an $C_1$–$C_6$ alkyl group, a carboxyl group, a $C_1$–$C_6$ alkoxy carbonyl group, an amino $C_1$–$C_6$ alkanoyl group, a carboxamide group where the amido nitrogen is (i) unsubstituted or (ii) substituted with (a $C_1$–$C_4$ alkyl substituted by amino, mono-substituted amino or di-substituted amino, wherein the substituent on the amino nitrogen is selected from the group consisting of $C_1$–$C_6$ alkyl, $C_5$–$C_8$ cycloalkyl and $C_1$–$C_6$ alkanoyl groups, or wherein two amino nitrogen substitutents and the nitrogen to which they are bonded together form a 5- to 8-membered heterocyclic or heteroaryl ring containing zero or one additional hetero atoms that are nitrogen, oxygen or sulfur or (iii) the amido nitrogen is the amine of an amino acid; and $R^{10}$ is $C_1$–$C_6$ alkoxy, or a single-ringed aryl or heteroaryl group, with the proviso that only one of $R^2$ or $R^6$ is present unless $R^2$ and $R^6$ together with the atoms to which they are bonded form a 5- or 6-membered ring.

25. The process according to claim 24 wherein the $R^{11}$ substituent group is itself substituted at the meta- or para-position or both with a single atom or a substituent containing a longest chain of up to five atoms, excluding hydrogen.

26. The process according to claim 25 wherein said $R^{11}$ substituent is phenoxy and is substituted at its own para-position with a moiety that is selected from the group consisting of a halogen, a $C_1$–$C_4$ alkoxy group, a $C_1$–$C_4$ alkyl group, a dimethylamino group, a $C_1$–$C_3$ alkyl carboxyl group, a $C_1$–$C_3$ alkylcarbonyl, $C_1$–$C_4$ alkoxy group and a $C_1$–$C_3$ alkyl carboxamido group, or at the meta and para positions by a methylenedioxy group.

* * * * *